(12) United States Patent
Lee et al.

(10) Patent No.: US 9,000,169 B2
(45) Date of Patent: *Apr. 7, 2015

(54) COMPOUNDS AND ORGANIC ELECTRONIC DEVICE USING THE SAME

(71) Applicant: LG Chem, Ltd., Seoul (KR)

(72) Inventors: Dong Hoon Lee, Daejeon (KR); Tae Yoon Park, Daejeon (KR); Jungi Jang, Daejeon (KR); Song Kil Hong, Daejeon (KR); Seong So Kim, Gyeonggi-do (KR); Boonjae Jang, Daejeon (KR); Sangbin Lee, Seoul (KR); Kidong Koo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 59 days.

This patent is subject to a terminal disclaimer.

(21) Appl. No.: 13/725,170

(22) Filed: Dec. 21, 2012

(65) Prior Publication Data

US 2013/0181196 A1 Jul. 18, 2013

Related U.S. Application Data

(63) Continuation of application No. PCT/KR2012/004864, filed on Jun. 20, 2012.

(30) Foreign Application Priority Data

Jul. 8, 2011 (KR) ........................ 10-2011-0067965

(51) Int. Cl.
*C07D 471/12* (2006.01)
*H01L 51/50* (2006.01)
*H01L 51/00* (2006.01)
*C07D 471/04* (2006.01)
*C07D 471/14* (2006.01)

(52) U.S. Cl.
CPC .......... *H01L 51/0072* (2013.01); *C07D 471/04* (2013.01); *H01L 51/0052* (2013.01); *H01L 51/0073* (2013.01); *H01L 51/0074* (2013.01); *C07D 471/14* (2013.01); *H01L 51/0054* (2013.01); *H01L 51/0058* (2013.01); *H01L 51/5016* (2013.01); *Y02E 10/549* (2013.01)

(58) Field of Classification Search
USPC .................................. 546/36, 41, 52; 313/504
See application file for complete search history.

(56) References Cited

U.S. PATENT DOCUMENTS 8,368,062 B2 * 2/2013 Lee et al. ........................ 257/40
2011/0127513 A1 6/2011 Lee et al.

FOREIGN PATENT DOCUMENTS

| EP | 2311826 A2 | 4/2011 |
| JP | 2010-120893 A | 6/2010 |
| KR | 2010-0099459 A | 9/2010 |

* cited by examiner

*Primary Examiner* — Charanjit Aulakh

(74) *Attorney, Agent, or Firm* — McKenna Long & Aldridge LLP

(57) ABSTRACT

The present invention provides a new compound and an organic electronic device using the same. The organic electronic device according to the present invention exhibits excellent properties in views of efficiency, driving voltage and a life span.

22 Claims, 5 Drawing Sheets

COMPOUNDS AND ORGANIC ELECTRONIC DEVICE USING THE SAME

This application is a continuation application of PCT/KR2012/004864, filed on Jun. 20, 2012, which claims priority from Korean Patent Application No. 10-2011-0067965, filed on Jul. 8, 2011, in the Korean Intellectual Patent Office, all of which are incorporated herein by reference in their entirety.

TECHNICAL FIELD

This application claims priority from Korean Patent Application No. 10-2011-0067965 filed on Jul. 8, 2011, in the KIPO, the disclosure of which is incorporated herein by reference in its entirety.

The present invention relates to a new compound and an organic electronic device using the same.

BACKGROUND ART

An organic electronic device means a device that requires exchanging of electric charges between an electrode using holes and/or electrons and an organic material. The organic electronic device may be largely divided into the following two categories according to an operation principle. The first device is an electric device in which an exciton is formed in an organic material layer by a photon flowing from an external light source to the device, the exciton is separated into electrons and holes, and the electrons and the holes are transferred to the different electrodes and used as current sources (voltage sources). The second device is an electronic device in which holes and/or electrons are injected into an organic material semiconductor forming an interface in respects to the electrode by applying a voltage or a current to two or more electrodes and the device is operated by the injected electrons and holes.

Examples of the organic electronic device include an organic light emitting device, an organic solar cell, an organic photoconductor (OPC), an organic transistor and the like, and all of the examples require a hole injection or transport material, an electron injection or transport material or a light emitting material in order to drive the device. Hereinafter, an organic light emitting device will be mainly described in detail. However, in the organic electronic devices, the hole injection or transport material, the electron injection or transport material or the light emitting material are operated based on a similar principle.

In general, an organic light emitting phenomenon means a phenomenon converting electric energy into light energy by using an organic material. The organic light emitting device using the organic light emitting phenomenon has a structure generally comprising an anode, a cathode, and an organic material layer interposed therebetween. Herein, most organic material layers have a multilayered structure comprising different materials in order to increase efficiency and stability of the organic light emitting device, and for example, the organic material layer may be formed of a hole injection layer, a hole transport layer, a light emitting layer, an electron transport layer, an electron injection layer and the like. In the organic light emitting device structure, if a voltage is applied between two electrodes, holes are injected from an anode and electrons are injected from a cathode to the organic material layer, and when the injected holes and electrons meet each other, an exciton is formed, and light is emitted when the exciton falls to a bottom state. It is known that this organic light emitting device has properties such as magnetic light emission, high brightness, high efficiency, low driving voltage, a wide viewing angle, high contrast and high response speed.

In the organic light emitting device, the material used as the organic material layer may be classified into a light emitting material and an electric charge transport material, for example, a hole injection material, a hole transport material, an electron transport material, an electron injection material and the like, according to a function thereof. In addition, the light emitting material may be classified into blue, green, and red light emitting materials and yellow and orange light emitting materials in order to implement better natural colors according to the emission color. Meanwhile, in the case where only one material is used as a light emitting material, since there are problems in that a maximum light emitting wavelength moves to a long wavelength or color purity is lowered due to interaction between molecules, or efficiency of the device is reduced due to reduced effect of light emission, host/dopant systems may be used as the light emitting material in order to increase color purity and increase light emitting efficiency through transferring of energy.

A material constituting the organic material layer in the device, for example, the hole injection material, the hole transport material, the light emitting material, the electron transport material, the electron injection material or the like, should be supported in advance by stable and efficient materials in order to sufficiently exhibit the aforementioned excellent properties of the organic light emitting device. However, the development of a stable and efficient organic material layer material for organic light emitting devices has not been yet sufficiently made. Therefore, there is a demand for developing a novel material, and the demand for developing the material is similarly applied to the aforementioned other organic electronic devices.

DISCLOSURE

Technical Problem

The present inventors found a nitrogen-containing heterocyclic compound having a new structure. Further, the present inventors found the fact that in the case where an organic material layer of an organic electronic device is formed by using the new nitrogen-containing heterocyclic compound, effects of an increase in efficiency of the device, a reduction in driving voltage, and an increase in stability can be exhibited.

Accordingly, the present invention has been made in an effort to provide a new compound and an organic electronic device using the same.

Technical Solution

An exemplary embodiment of the present invention provides a new compound.

Another exemplary embodiment of the present invention provides an organic electronic device comprising: a first electrode, a second electrode, and one or more organic material layers interposed between the first electrode and the second electrode, wherein one or more layers of the organic material layers comprise the new compound.

Advantageous Effects

The new compound according to the present invention may be used as a material of an organic material layer of an organic electronic device comprising an organic light emitting device, and the organic electronic device comprising the organic light emitting device using the same exhibits excellent properties in view of efficiency, driving voltage, a life span and the like. In particular, the new compound according to the present invention has excellent thermal stability, a deep HOMO level, a high triplet state and hole stability, thus exhibiting excellent properties. The compound may be used alone or as a mixture with impurity in the organic electronic device comprising the organic light emitting device, improve light efficiency, and improve a life span property of the device by thermal stability of the compound.

DESCRIPTION OF REFERENCE NUMERALS AND SIGNS

Figure 1:
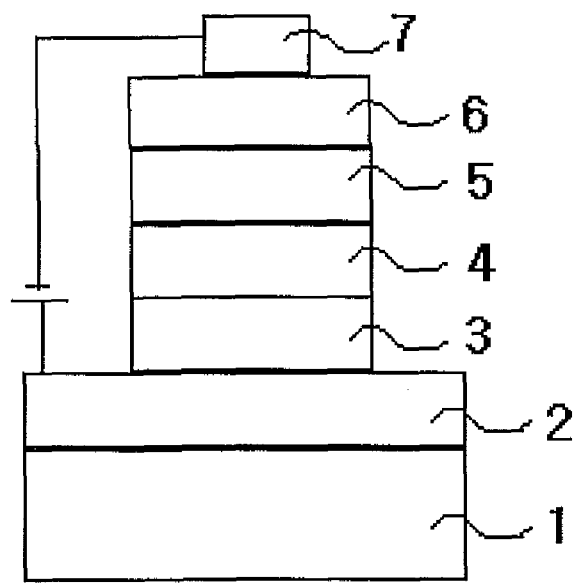
FIGS. 1 to 5 are cross-sectional views illustrating a structure of an organic electronic device according to an exemplary embodiment of the present invention.

1: Substrate
2: Anode
3: Hole injection layer
4: Hole transport layer
5: Light emitting layer
6: Electronic transport layer
7: Cathode

BEST MODE

Hereinafter, the present invention will be described in more detail.

The present invention provides a new compound represented by the following Formula 1.

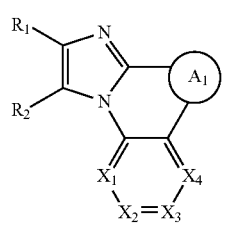

[Formula 1]

In Formula 1,
$X_1$ is N or $CR_3$, $X_2$ is N or $CR_4$, $X_3$ is N or $CR_5$, $X_4$ is N or $CR_6$, and all of $X_1$ to $X_4$ are not simultaneously N, $R_3$ to $R_6$ are each independently $-(L_1)p-(Y_1)q$ where p is an integer of 0 to 10, q is an integer of 1 to 10, two or more adjacent groups of $R_3$ to $R_6$ may form a monocycle or a polycycle, $L_1$ is oxygen; sulfur; substituted or unsubstituted nitrogen; substituted or unsubstituted phosphorus; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, $Y_1$ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms, $R_1$ and $R_2$ may be connected to each other to form or not to form a substituted or unsubstituted aliphatic, aromatic or heteroaromatic monocycle or polycycle, and in the case where $R_1$ and $R_2$ do not form a cycle, $R_1$ and $R_2$ are the same as or different from each other, and each independently hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms, the aromatic or heteroaromatic monocycle and polycycle formed by connecting $R_1$, $R_2$, and $R_1$ and $R_2$ to each other may be each independently substituted by $-(L_1)p-(Y_1)q$, in the case where two or more $L_1$ and two or more $Y_1$ are present in Formula 1, $L_1$ and $Y_1$ are each independently the same as or different from each other, a $A_1$ cycle is represented by Formula 2,

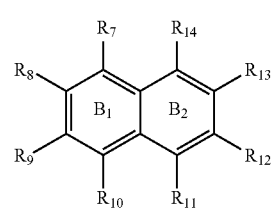

[Formula 2]

in Formula 2,
$R_7$ and $R_8$, $R_8$ and $R_9$, or $R_9$ and $R_{10}$ are groups connected to Formula 1, the group that is not used in connection to Formula 1 among $R_7$ to $R_{10}$, $R_{11}$, $R_{12}$, $R_{13}$ and $R_{14}$ are each independently $-(L_2)r-(Y_2)s$ where r is an integer of 0 to 10, s is an integer of 1 to 10, and two or more adjacent groups of the group that is not used in connection to Formula 1 among $R_7$ to $R_{10}$, $R_{11}$, $R_{12}$, $R_{13}$ and $R_{14}$ may form a monocycle or a polycycle, $L_2$ is oxygen; sulfur; substituted or unsubstituted nitrogen; substituted or unsubstituted P; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, $Y_2$ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms, aromatic or hetero aromatic monocycle and polycycle formed by connecting two or more adjacent groups of the group that is not used in connection to Formula 1 among $R_7$ to $R_{10}$, $R_{11}$, $R_{12}$, $R_{13}$ and $R_{14}$ to each other may be each independently substituted by $-(L_2)r-(Y_2)s$, in the case where two or more $L_2$ and two or more $Y_2$ are present in Formula 2, $L_2$ and $Y_2$ are each independently the same as or different from each other, $B_1$ is an aryl group where one or more carbons constituting a cycle may be further substituted by nitrogen, and $B_2$ is an aryl group where one or more carbons constituting a cycle may be substituted by nitrogen.

In Formula 1, unsubstituted nitrogen means that nitrogen does not have a substituent group other than hydrogen bonded to nitrogen, and unsubstituted phosphorus means that phosphorus does not have a substituent group other than hydrogen bonded to phosphorus.

Formula 2 may be represented by any one of the following Formulas 2-1 to 2-7.

[Formula 2-1]

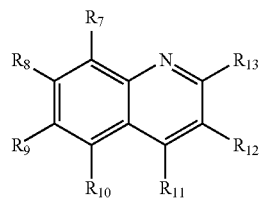

In Formula 2-1, $R_7$ and $R_8$ are a group connected to Formula 1, and the remains are the same as definitions of Formula 2.

[Formula 2-2]

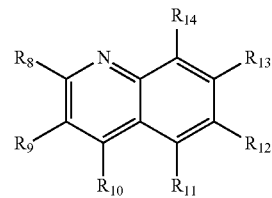

In Formula 2-2, $R_8$ and $R_9$ are a group connected to Formula 1, and the remains are the same as definitions of Formula 2.

[Formula 2-3]

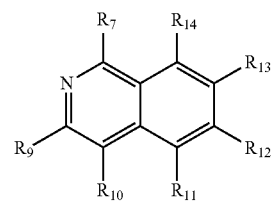

In Formula 2-3, $R_9$ and $R_{10}$ are a group connected to Formula 1, and the remains are the same as definitions of Formula 2.

[Formula 2-4]

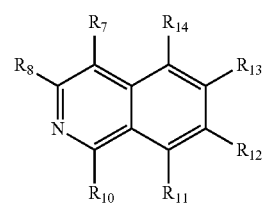

In Formula 2-4, $R_7$ and $R_8$ are a group connected to Formula 1, and the remains are the same as definitions of Formula 2.

[Formula 2-5]

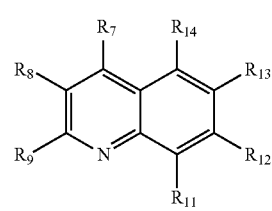

In Formula 2-5, $R_8$ and $R_9$ are a group connected to Formula 1, and the remains are the same as definitions of Formula 2.

[Formula 2-6]

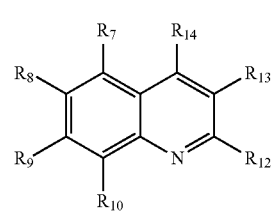

In Formula 2-6, $R_9$ and $R_{10}$ are a group connected to Formula 1, and the remains are the same as definitions of Formula 2.

[Formula 2-7]

In Formula 2-7, $R_7$ to $R_{14}$ are the same as definitions of Formula 2.

Further, the compound represented by Formula 1 of the present invention may be represented by any one of the following Formulas 1-1 to 1-4.

[Formula 1-1]

[Formula 1-2]

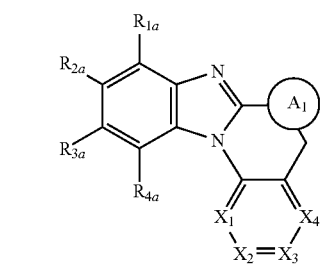

[Formula 1-3]

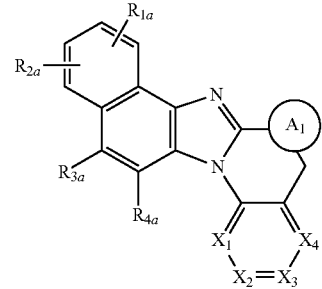

[Formula 1-4]

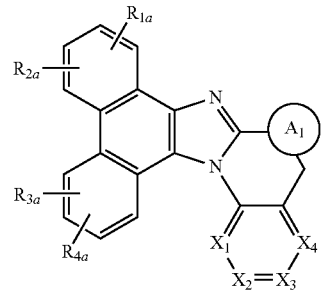

In Formula 1-1 to Formula 1-4, $R_{1a}$ to $R_{4a}$ are the same as definitions of $R_1$ to $R_2$ of Formula 1, and $A_1$, and $X_1$ to $X_4$ are the same as definitions of Formula 1.

Further, the compound represented by Formula 1 of the present invention may be represented by any one of the following Formulas 3-1 to 3-18.

[Formula 3-1]

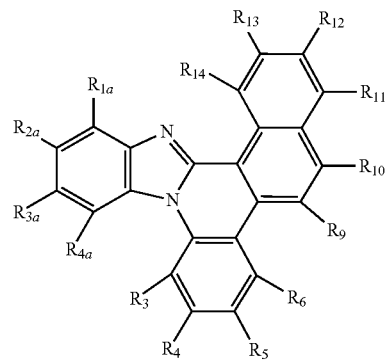

[Formula 3-2]

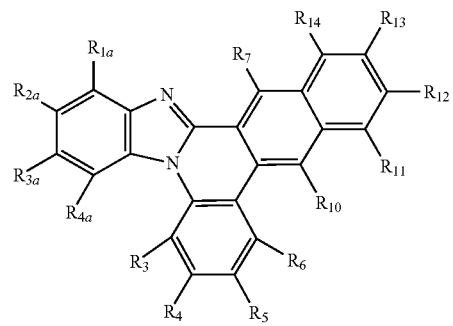

[Formula 3-3]

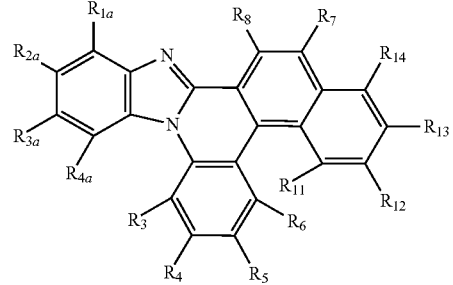

[Formula 3-4]
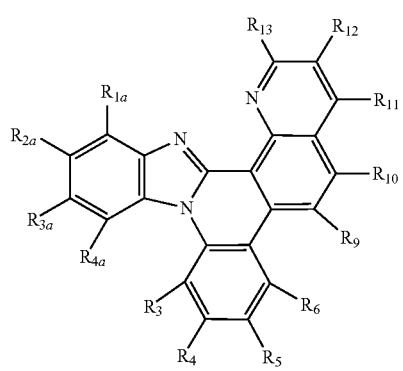
[Formula 3-5]
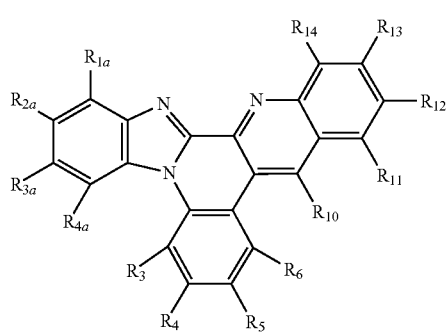
[Formula 3-6]
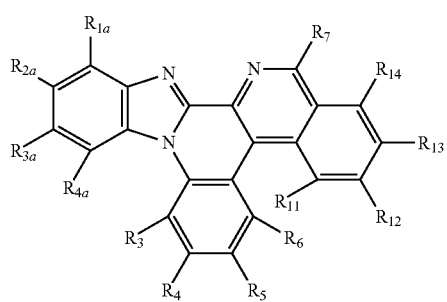
[Formula 3-7]
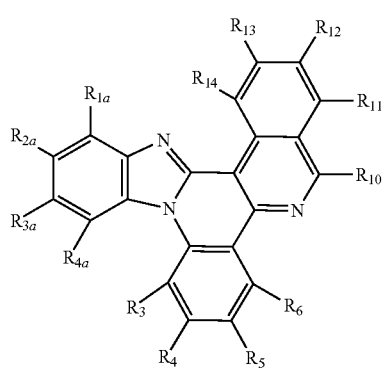
[Formula 3-8]
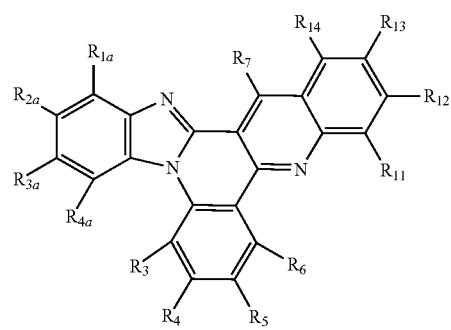
[Formula 3-9]
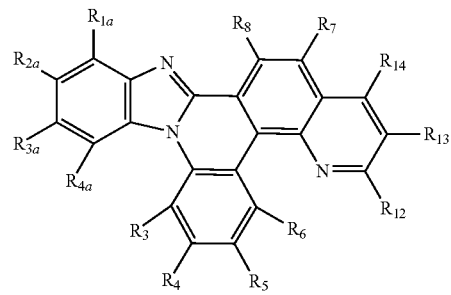
[Formula 3-10]
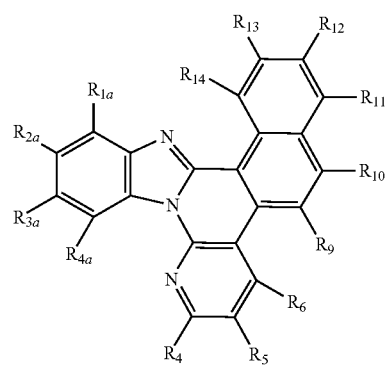
[Formula 3-11]
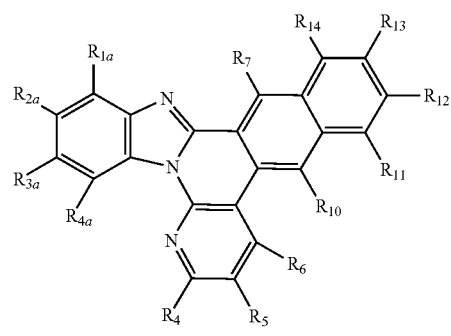

[Formula 3-12]
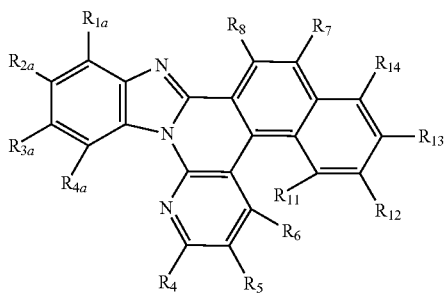

[Formula 3-13]
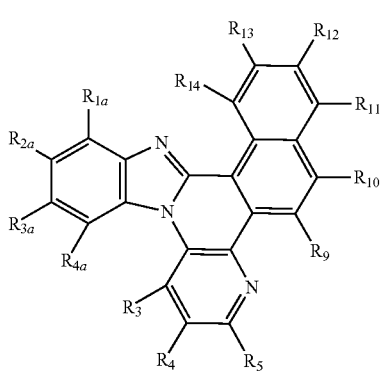

[Formula 3-14]
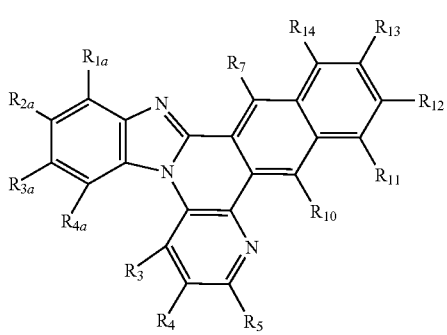

[Formula 3-15]
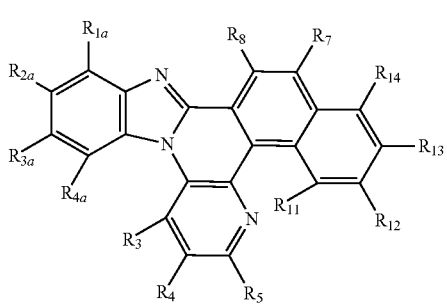

[Formula 3-16]
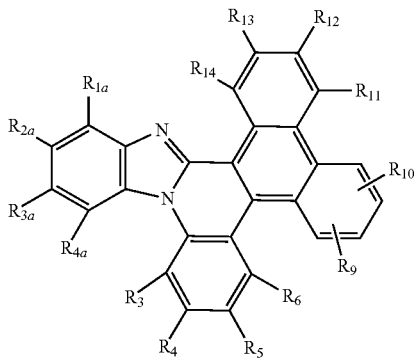

[Formula 3-17]
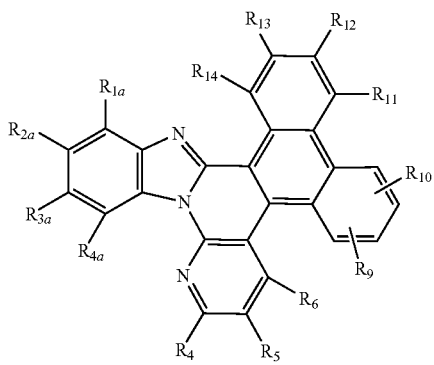

[Formula 3-18]
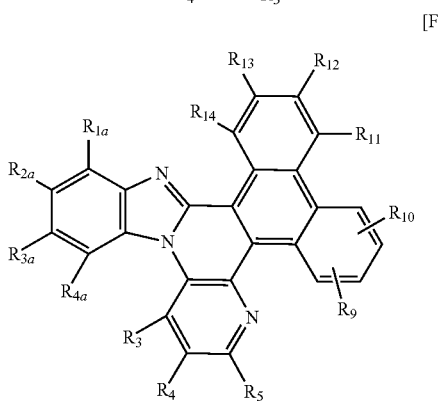

In Formula 3-1 to Formula 3-18, $R_{1a}$ to $R_{4a}$ are the same as definitions of $R_1$ to $R_2$ of Formula 1, $R_3$ to $R_6$ are the same as definitions of Formula 1, and $R_7$ to $R_{14}$ are the same as definitions of Formula 2.

Particularly, in Formula 3-1, Formula 3-2, Formula 3-3 and Formula 3-16, it is more preferable that $R_{1a}$ to $R_{4a}$, $R_3$, $R_6$ and $R_7$ to $R_{14}$ be hydrogen, and $R_4$ or $R_5$ be each independently -$(L_2)r$-$(Y_2)s$. Herein, $L_2$, $Y_2$, r and s are the same as definitions of Formula 2. In this case, in the case where $L_2$ is an arylene group, it is preferable that the arylene group be a phenylene group or a naphthalene group, and in the case where $Y_2$ is an aryl group, it is preferable that the aryl group be a phenyl group, a naphthyl group, a phenanthrenyl group, a fluorene group, a dimethylfluorene group, a triphenylene group, a benzocrycene group or a fluoranthrene group.

Further, the new compound represented by Formula 1 of the present invention may be represented by any one of the following Formulas 4-1 to 4-4.

[Formula 4-1]

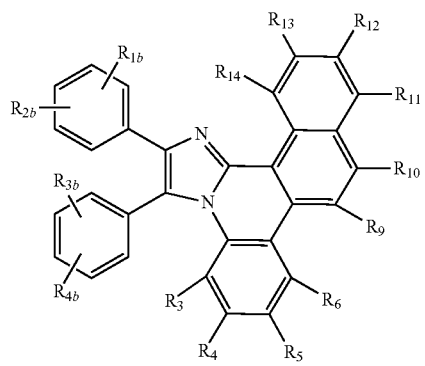

[Formula 4-2]

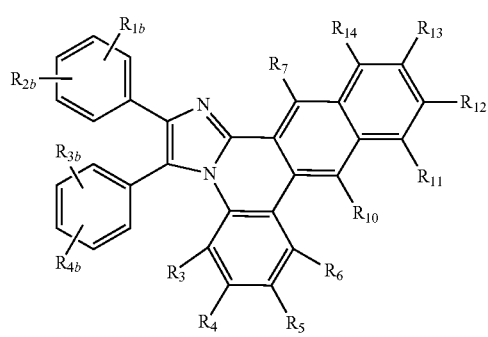

[Formula 4-3]

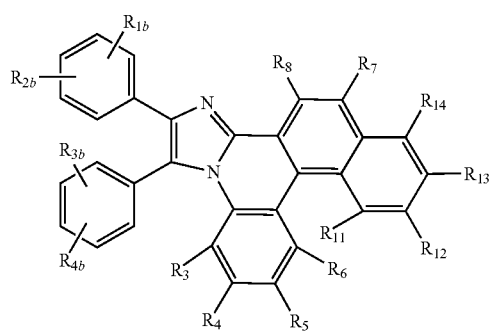

[Formula 4-4]

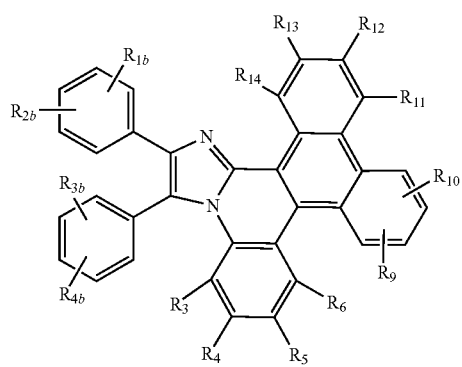

In Formula 4-1 to Formula 4-4, $R_{1b}$ to $R_{4b}$ are the same as definitions of $R_1$ to $R_2$ of Formula 1, $R_3$ to $R_6$ are the same as definitions of Formula 1, $R_7$ to $R_{14}$ are the same as definitions of Formula 2, and $R_{15}$ to $R_{18}$ are the same as definitions of $R_7$ to $R_{14}$ of Formula 2.

Further, the new compound represented by Formula 1 of the present invention may be represented by any one of the following Formulas 5-1 to 5-25.

[Formula 5-1]

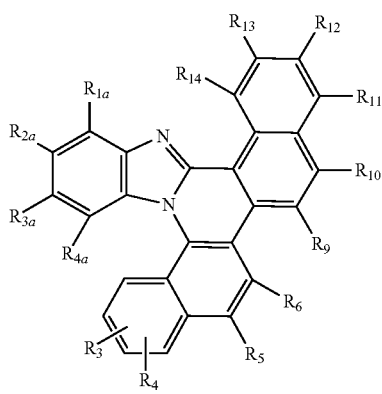

[Formula 5-2]

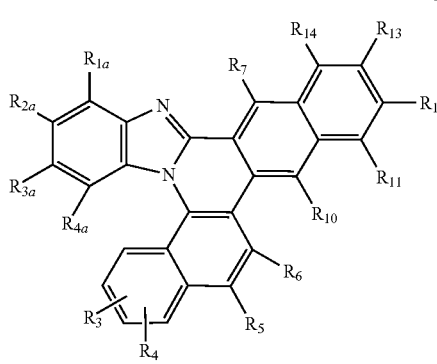

[Formula 5-3]

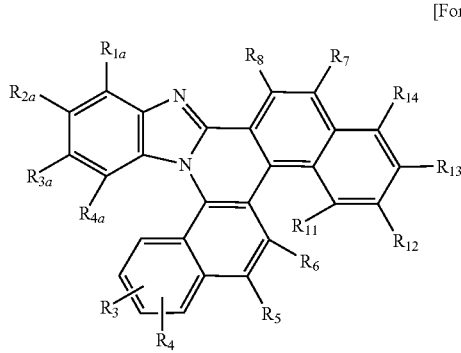

[Formula 5-4]

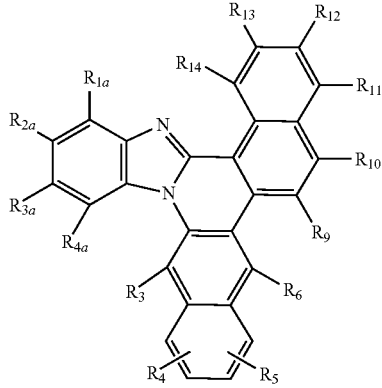

-continued
[Formula 5-5]
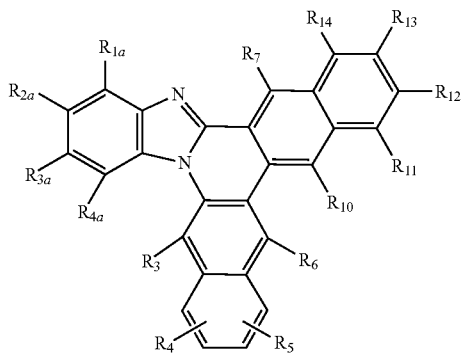
[Formula 5-6]
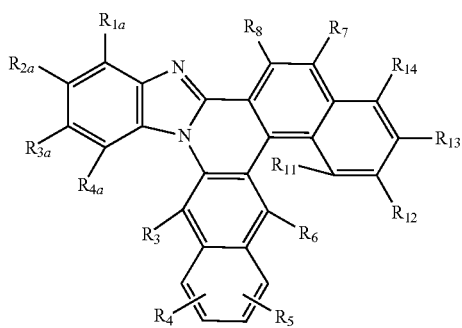
[Formula 5-7]
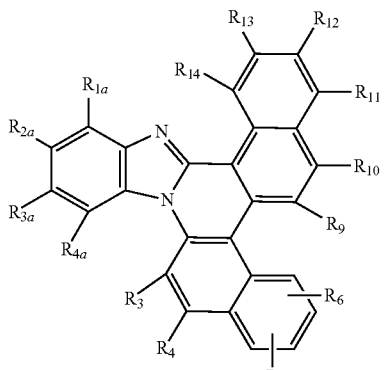
[Formula 5-8]
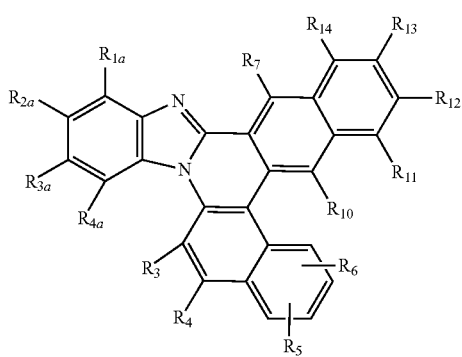
[Formula 5-9]
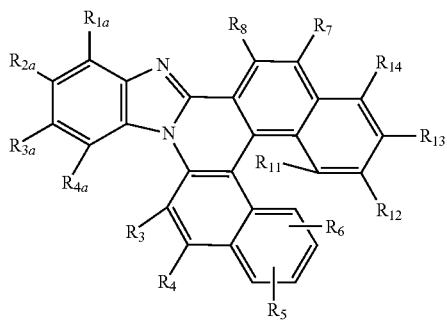
[Formula 5-10]
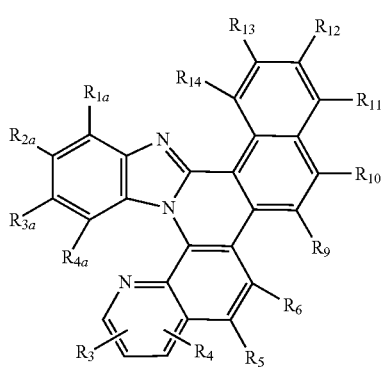
[Formula 5-11]
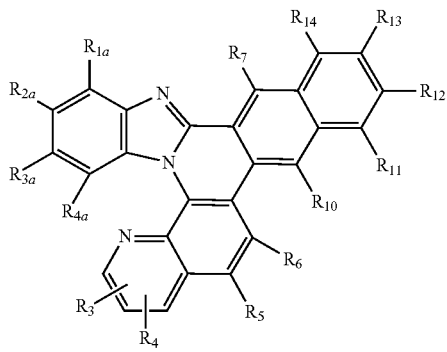
[Formula 5-12]
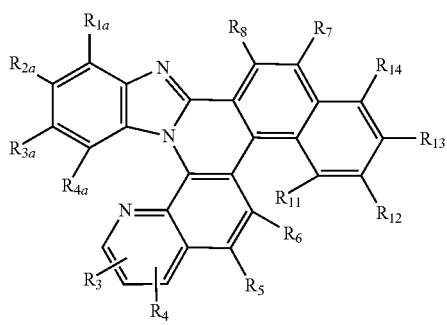

[Formula 5-13]
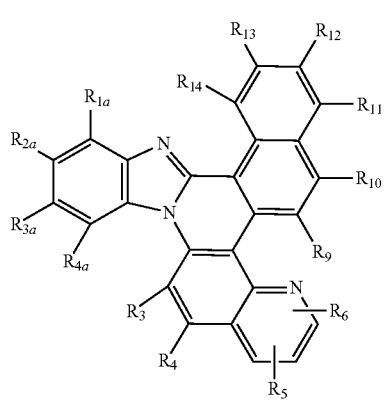
[Formula 5-14]
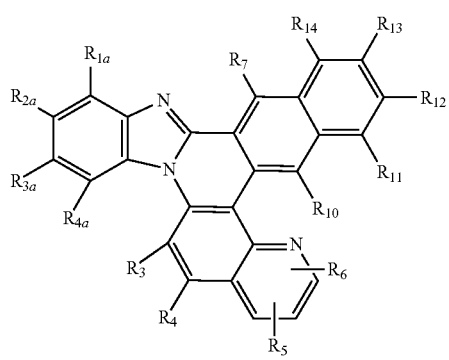
[Formula 5-15]
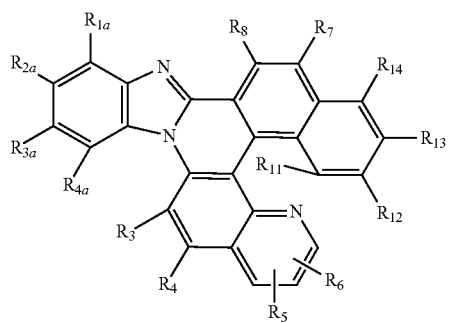
[Formula 5-16]
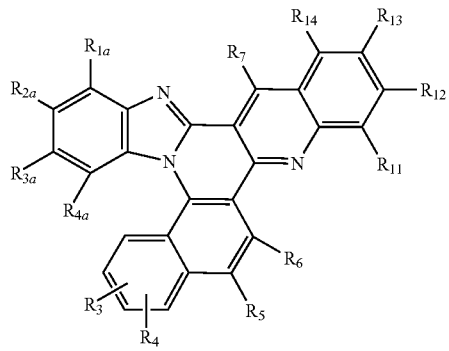
[Formula 5-17]
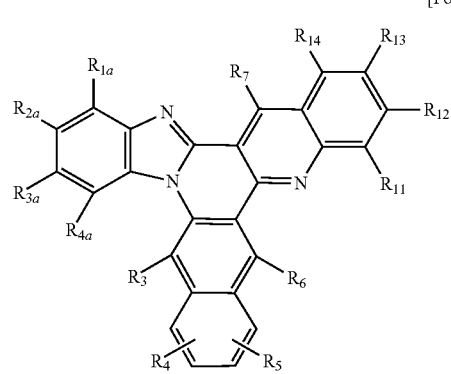
[Formula 5-18]
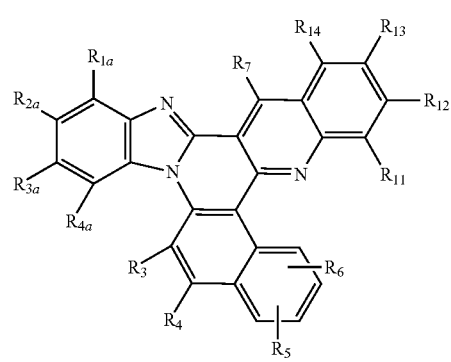
[Formula 5-19]
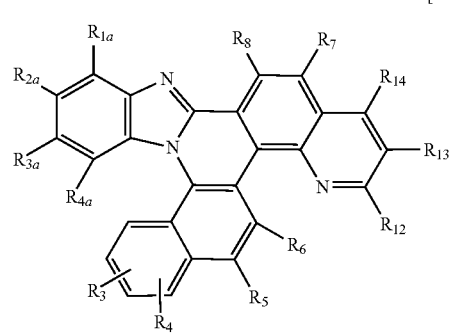
[Formula 5-20]
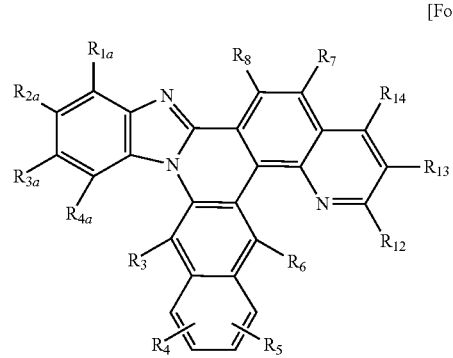

[Formula 5-21]

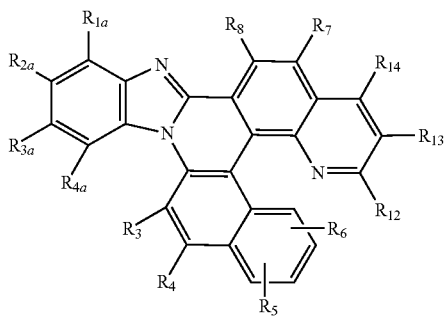

[Formula 5-22]

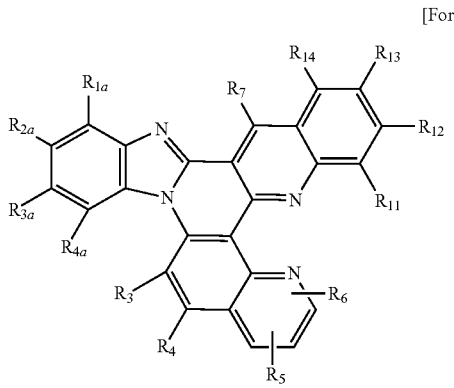

[Formula 5-23]

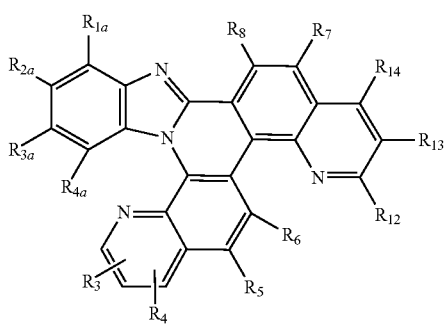

[Formula 5-24]

[Formula 5-25]

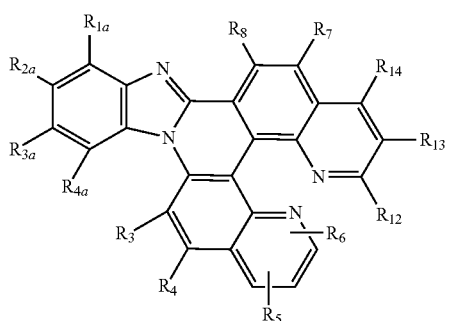

In Formula 5-1 to Formula 5-25, $R_{1a}$ to $R_{4a}$ are the same as definitions of $R_1$ to $R_2$ of Formula 1, $R_3$ to $R_6$ are the same as definitions of Formula 1, and $R_7$ to $R_{14}$ are the same as definitions of Formula 2.

Further, the new compound represented by Formula 1 of the present invention may be represented by any one of the following Formulas 6-1 to 6-8.

[Formula 6-1]

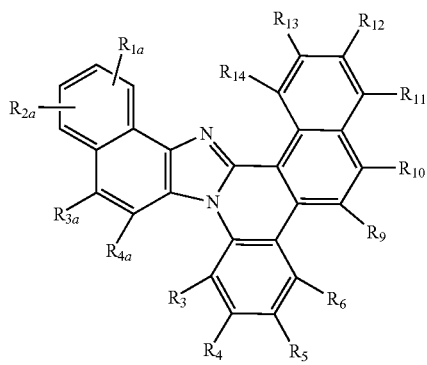

[Formula 6-2]

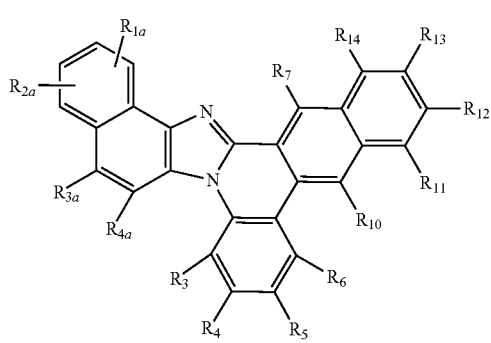

21
-continued

[Formula 6-3]
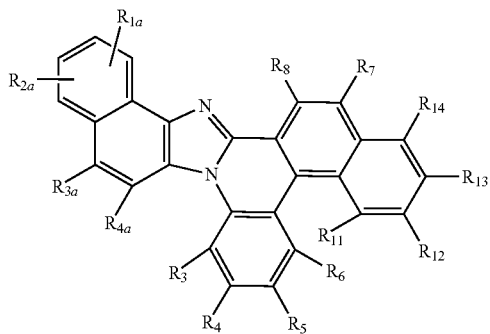

[Formula 6-4]
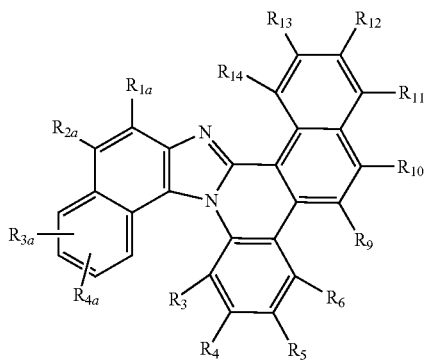

[Formula 6-5]
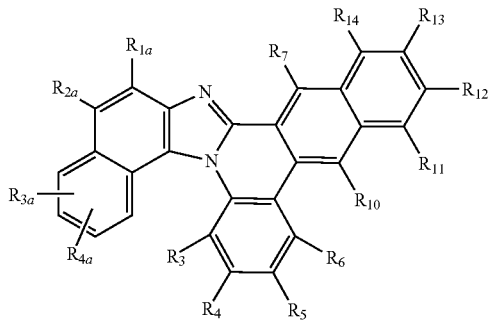

[Formula 6-6]
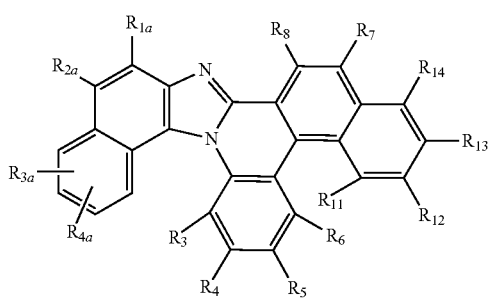

22
-continued

[Formula 6-7]
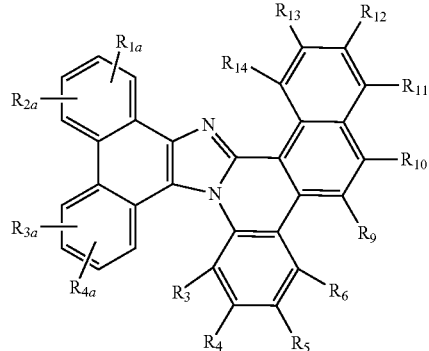

[Formula 6-8]
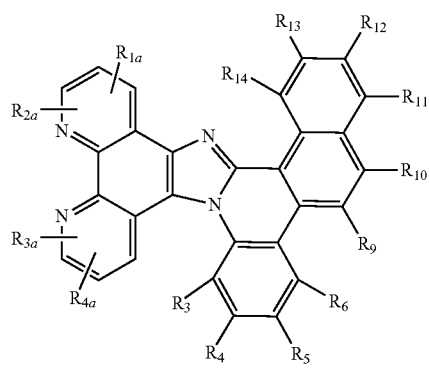

In Formula 6-1 to Formula 6-8, $R_{1a}$ to $R_{4a}$ are the same as definitions of $R_1$ to $R_2$ of Formula 1, $R_3$ to $R_6$ are the same as definitions of Formula 1, and $R_7$ to $R_{14}$ are the same as definitions of Formula 2.

Examples of the substituent groups will be described below, but are not limited thereto.

In the present invention, it is preferable that the alkyl group do not cause steric hindrance of 1 to 30 carbon atoms. Specific examples thereof comprise a methyl group, an ethyl group, a propyl group, an isopropyl group, a butyl group, a t-butyl group, a pentyl group, a hexyl group, a heptyl group and the like, but are not limited thereto.

In the present invention, the alkoxy group may be a straight chain or a branched chain. The number of carbon atoms of the alkoxy group is not particularly limited, but it is preferable that it is in the range of 1 to 30, which does not provide sterical hindrance. For example, in Formula 1, in the case where Y of $-(L_1)p-(Y_1)q$ is the alkoxy group, since the number of carbon atoms of the alkoxy group does not affect a conjugation length of the compound but affects an application method of the compound to the organic electronic device, for example, a vacuum deposition method or a solution coating method, the number of carbon atoms of the alkoxy group is not particularly limited.

In the present invention, the alkenyl group may be a straight chain or a branched chain, is preferably an alkenyl group having 2 to 40 carbon atoms, and specifically preferably an alkenyl group substituted by an aryl group, such as a stylbenzyl group and a styrenyl group, but is not limited thereto.

In the present invention, the aryl group may be a monocycle or a polycycle, and the number of carbon atoms thereof is not particularly limited but is preferably 6 to 60. Examples of the monocyclic aryl group include a phenyl group, a biphenyl group, a terphenyl group, a stilben group and the like, and examples of the polycyclic aryl group include a naphthyl group, an anthracenyl group, a phenanthrenyl group, a pyrenyl group, a perylenyl group, a tetracenyl group, a cryxenyl group, a fluorenyl group, an acenaphthacenyl group, a triphenylene group, a fluoranthrene group and the like, but the scope of the present invention is not limited thereto.

In the present invention, the heterocyclic group is a heterocyclic group comprising O, N or S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzthiazol group, a benzcarbazole group, a benzthiophene group, a dibenzothiophene group, a benzfuranyl group, a dibenzofuranyl group and the like, but are not limited thereto.

In the present invention, the cycloalkyl group is not particularly limited, the number of carbon atoms thereof is preferably 3 to 60, and a cyclopentyl group and a cyclohexyl group are particularly preferable.

In the present invention, examples of the halogen group include fluorine, chlorine, bromine or iodine.

In the present invention, the fluorenyl group has a structure where two cyclic organic compounds are connected through one atom, and examples thereof include

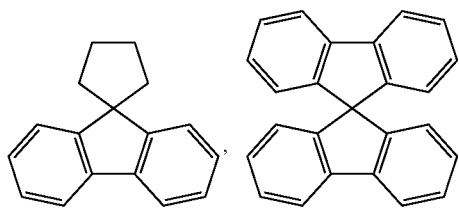

and the like.

In the present invention, the fluorenyl group comprises a structure of an opened fluorenyl group, the opened fluorenyl group has a structure where two cyclic organic compounds are connected through one atom and connection of one cyclic compound is broken, and examples thereof include

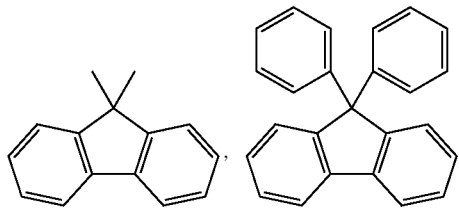

and the like.

In the present invention, examples of the arylamine group mean a substituted or unsubstituted monocyclic diarylamine group, a substituted or unsubstituted polycyclic diarylamine group or a substituted or unsubstituted monocyclic and polycyclic diarylamine group.

In the present invention, the term "substituted or unsubstituted" means that a matter is substituted or unsubstituted by at least one substituent group of heavy hydrogen; a halogen group; a nitrile group; a nitro group; a hydroxy group; an alkyl group; a cycloalkyl group; an alkoxy group; an aryloxy group; an alkylthioxy group; an arylthioxy group; an alkylsulfoxy group; an arylsulfoxy group; an alkenyl group; a silyl group; a boron group; an alkylamine group; an aralkylamine group; an arylamine group; an aryl group; a fluorenyl group; a carbazole group; and a heterocyclic group comprising one or more of N, O and S atoms.

In the compound according to the present invention, in the case where p of -($L_1$)p-($Y_1$)q is 0, at least one of $Y_1$ is preferably heavy hydrogen, a nitrile group, a halogen group, a substituted or unsubstituted boron group, a substituted or unsubstituted aryl group, a substituted or unsubstituted heterocyclic group or the like.

In the present invention, in the case where p of -($L_1$)p-($Y_1$)q is 1 or more, $L_1$ is preferably a substituted or unsubstituted arylene group, a substituted or unsubstituted heteroarylene group or the like, and $Y_1$ is preferably a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms.

In Formula 1, in the case where $L_1$ is an arylene group or a heteroarylene group and $Y_1$ is an aryl group or a heteroaryl group, p+q is preferably 2 or more.

In the case where p of -($L_1$)p-($Y_1$)q is 2 or more, $L_1$ are the same as or different from each other, and in the case where q of -($L_1$)p-($Y_1$)q is 2 or more, $Y_1$ are the same as or different from each other.

In the present invention, it is preferable that at least one of $R_3$ to $R_{14}$ be heavy hydrogen, a nitrile group, a halogen group, an aryl group, a substituted arylene group, a heterocyclic group, a substituted heterocyclic group, a fluorenyl group, a carbazole group or the like.

In the present invention, the substituted arylene group means that a phenyl group, a biphenyl group, a naphthalene group, a fluorenyl group, a pyrenyl group, a phenanthrenyl group, a perylen group, a tetracenyl group, an anthracenyl group and the like are substituted by other substituent groups.

In the present invention, the substituted heteroarylene group means that a pyridyl group, a thiophenyl group, a triazine group, a quinoline group, a phenanthroline group, an imidazole group, a thiazole group, an oxazole group, a carbazole group and a condensed heterocyclic group thereof, for example, a benzquinoline group, a benzimidazole group, a benzoxazole group, a benzthiazole group, a benzcarbazole group, a dibenzothiophenyl group, a dibenzofurane group and the like are substituted by other substituent groups.

In the present invention, in the case where $R_1$ and $R_2$ are a substituted or unsubstituted aryl group or a substituted or unsubstituted heteroaryl group, it is preferable that $R_1$ and $R_2$ be the same as each other.

Further, $R_1$ to $R_2$ may be each independently the same as or different from each other, and is preferably substituted by phenyl, biphenyl, naphthyl group, pyridinyl or phenyl substituted by nitrile.

In the present invention, $R_1$ to $R_{14}$ of Formula 1 may be further substituted by an additional substituent group, and examples thereof may include heavy hydrogen, a halogen group, an alkyl group, an alkenyl group, an alkoxy group, a silyl group, an arylalkenyl group, an aryl group, a heteroaryl group, a carbazole group, an arylamine group, a fluorenyl group substituted or unsubstituted by an aryl group, a nitrile group and the like, but are not limited thereto.

Since the compound of Formula 1 has a high glass transition temperature (Tg), thermal stability is excellent. Such increase in thermal stability is an important factor providing driving stability to the device.

The present invention provides a new compound represented by the following Formula 1. The compound may be used as an organic material layer in the organic electronic device because of structural peculiarity thereof.

Preferable specific examples of the compound according to the present invention include the following compounds, but are not limited thereto.

[Formula 3-1-1-1]

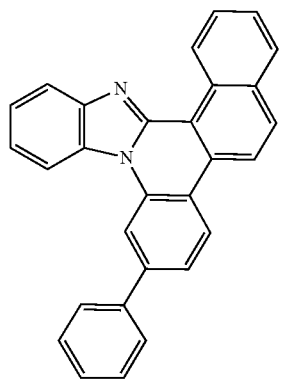

[Formula 3-1-1-2]

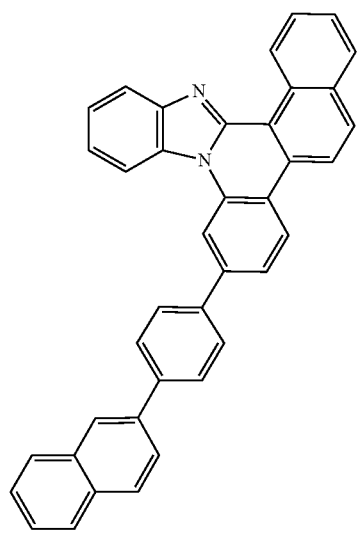

[Formula 3-1-1-3]

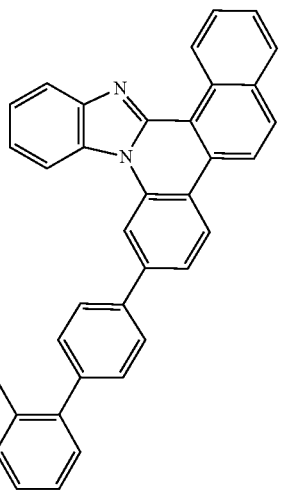

[Formula 3-1-1-4]

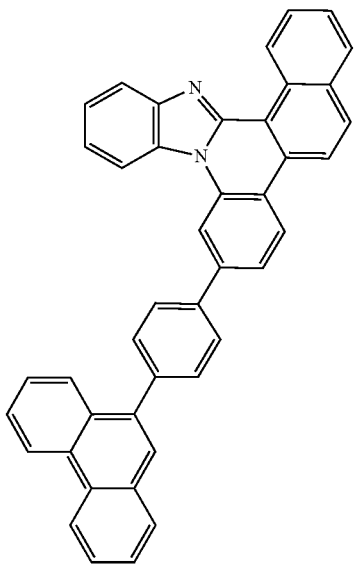

[Formula 3-1-1-5]

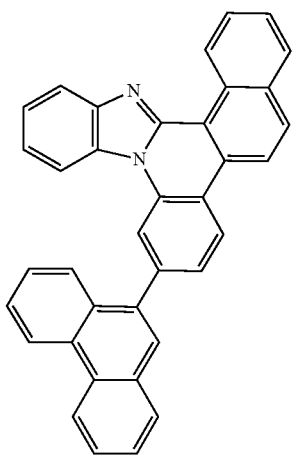

[Formula 3-1-1-6]
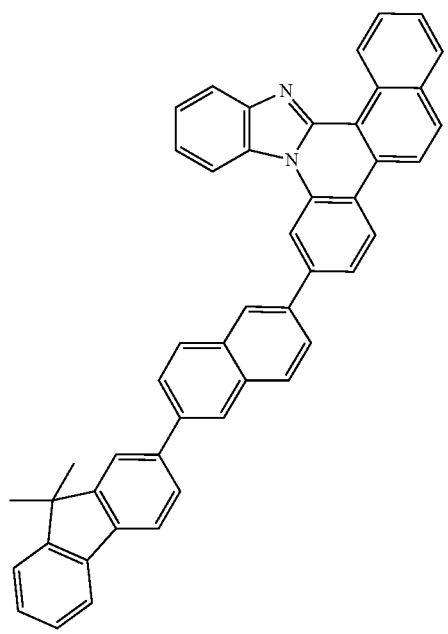
[Formula 3-1-1-7]
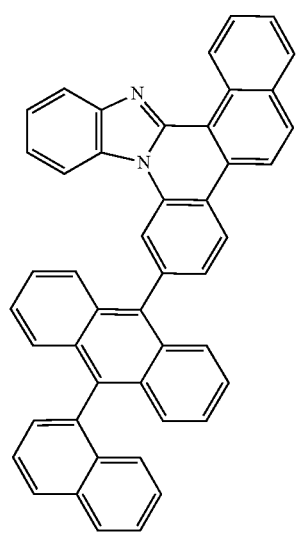
[Formula 3-1-1-8]
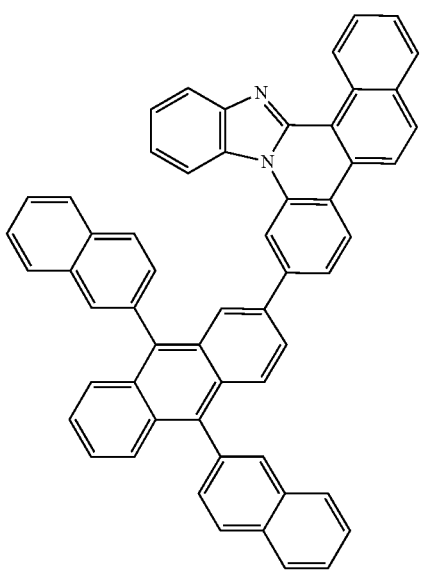
[Formula 3-1-1-9]
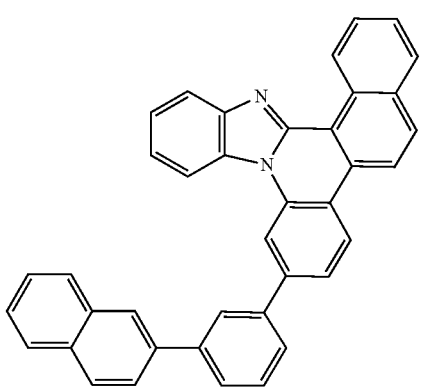
[Formula 3-1-1-10]
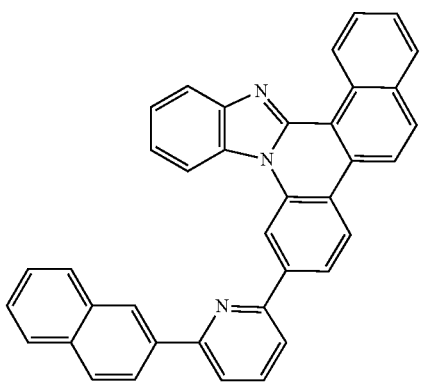

-continued
[Formula 3-1-1-11]
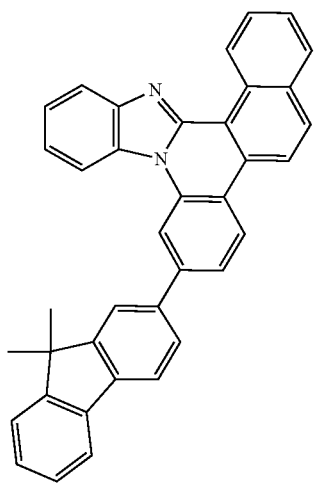
[Formula 3-1-1-12]
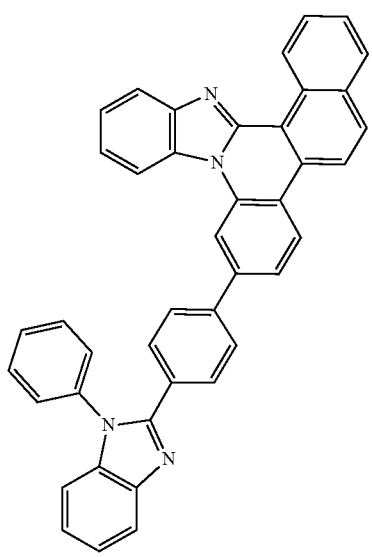
[Formula 3-1-1-13]
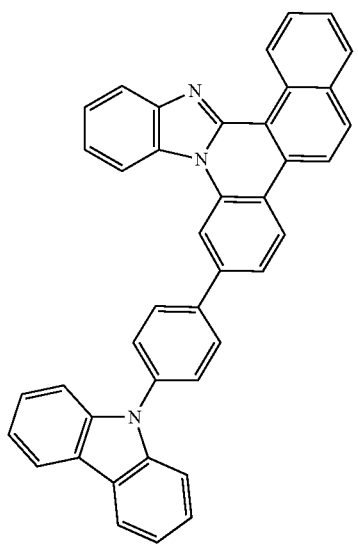
[Formula 3-1-1-14]
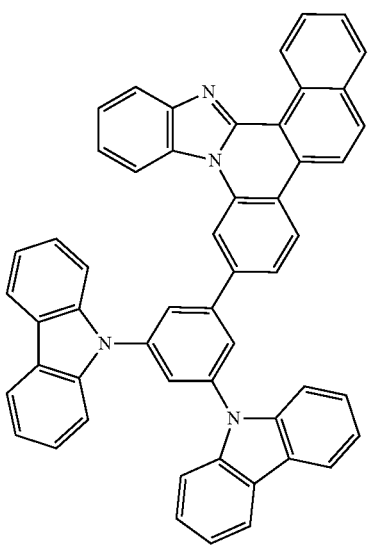
[Formula 3-1-1-15]
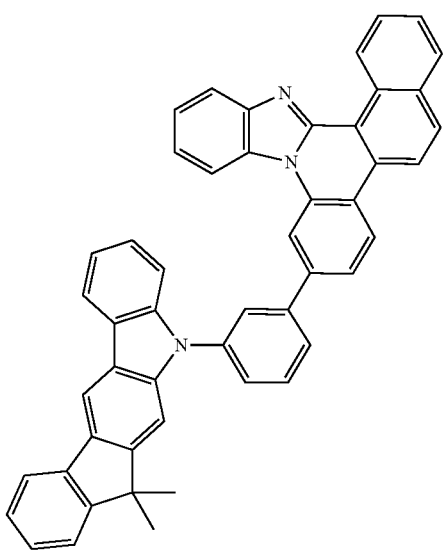
[Formula 3-1-1-16]
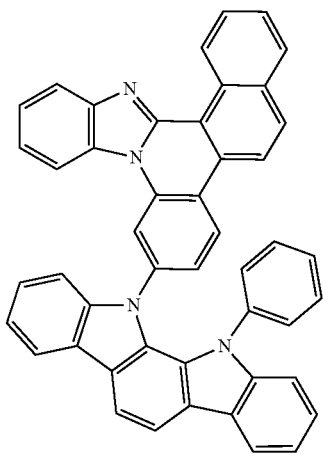

[Formula 3-1-1-17]
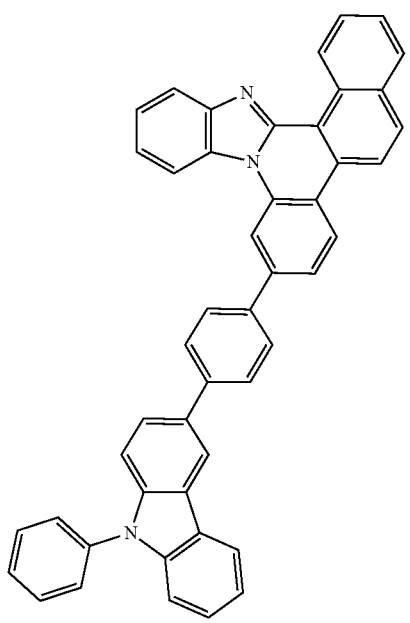
[Formula 3-1-1-18]
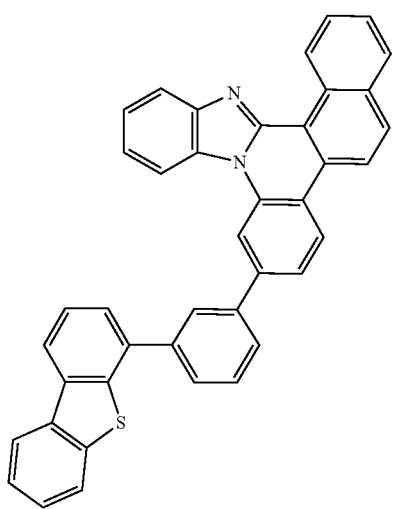
[Formula 3-1-1-19]
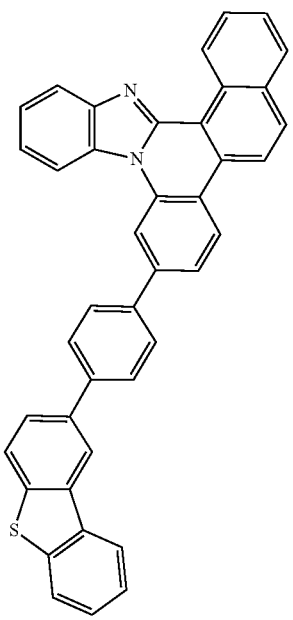
[Formula 3-1-1-20]
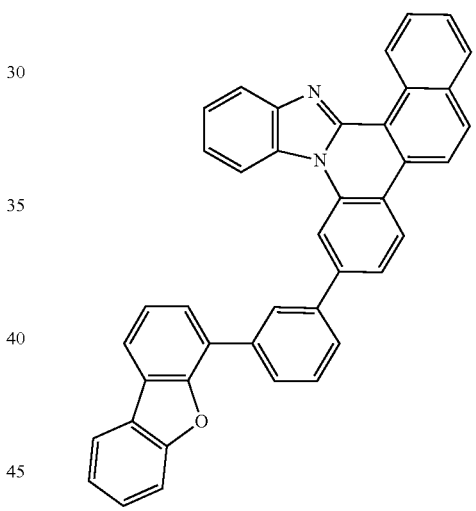
[Formula 3-1-1-21]
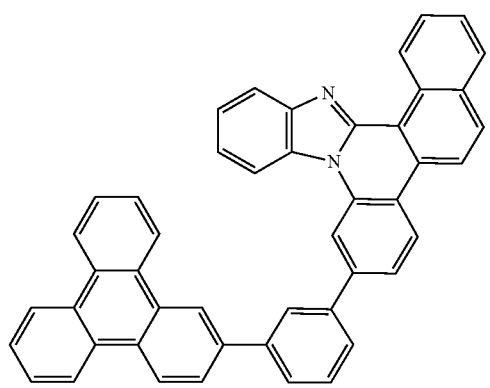

[Formula 3-1-1-22]
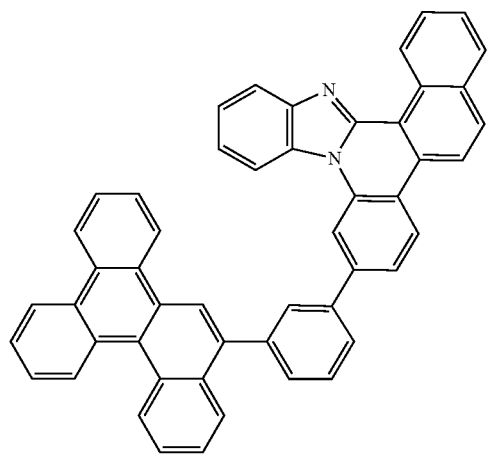
[Formula 3-1-1-23]
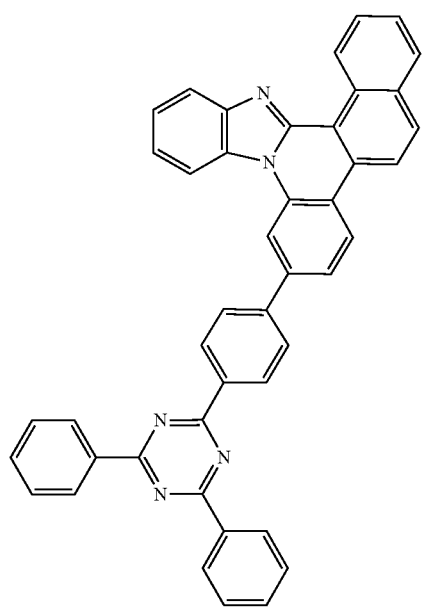
[Formula 3-1-1-24]
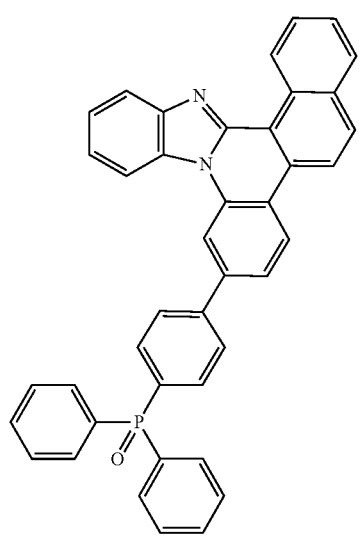
[Formula 3-1-1-25]
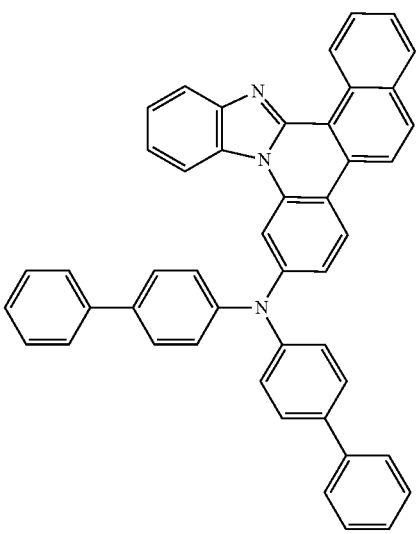
[Formula 3-1-1-26]
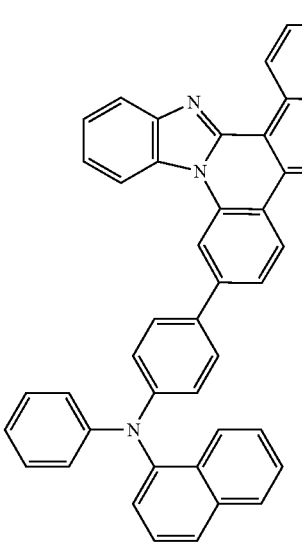
[Formula 3-1-1-27]
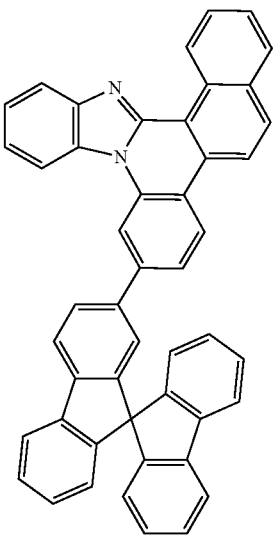

[Formula 3-1-1-28]
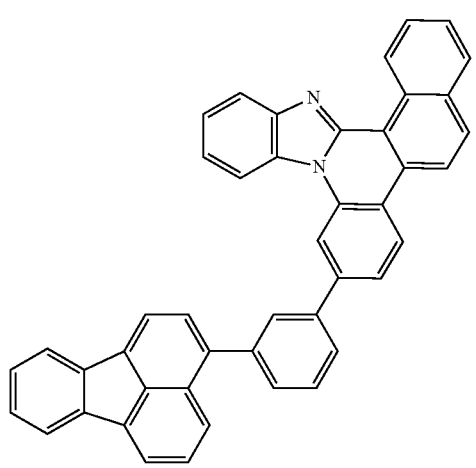
[Formula 3-1-1-29]
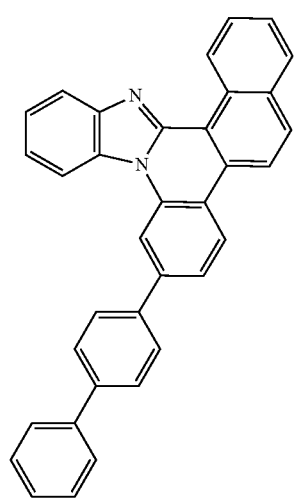
[Formula 3-1-1-30]
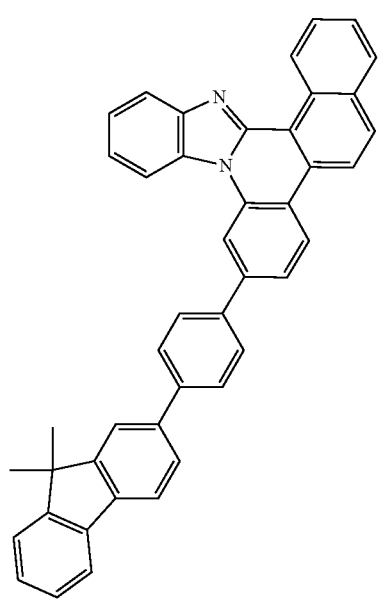
[Formula 3-1-1-31]
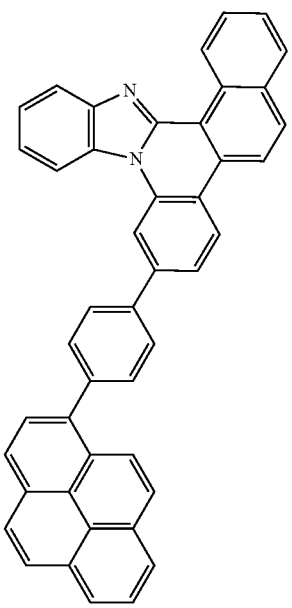
[Formula 3-1-1-32]
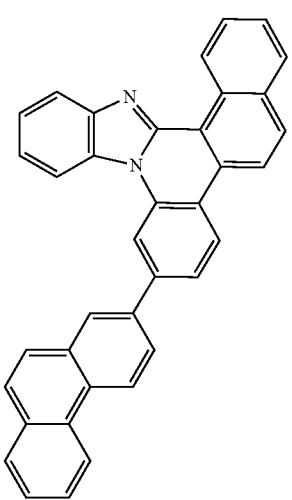

[Formula 3-1-1-33]
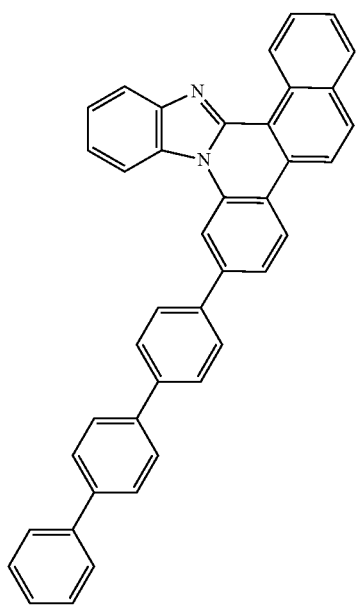
[Formula 3-1-1-34]
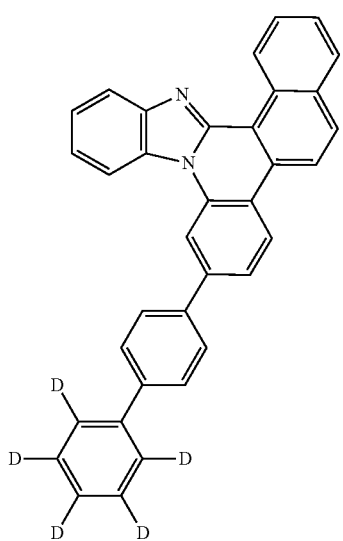
{Formula 3-1-1-35}
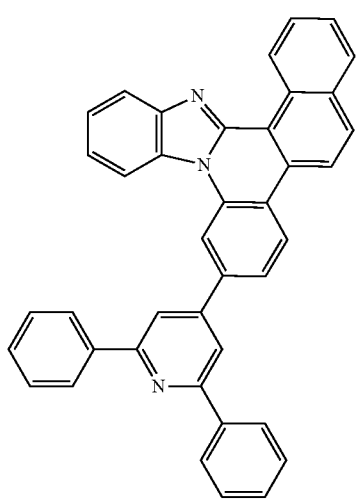
[Formula 3-1-1-36]
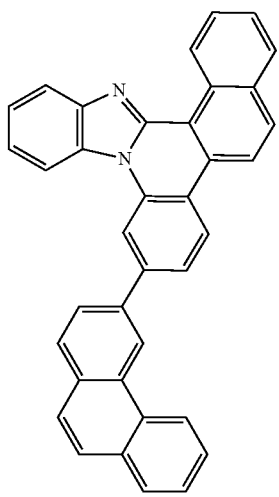
[Formula 3-1-2-1]
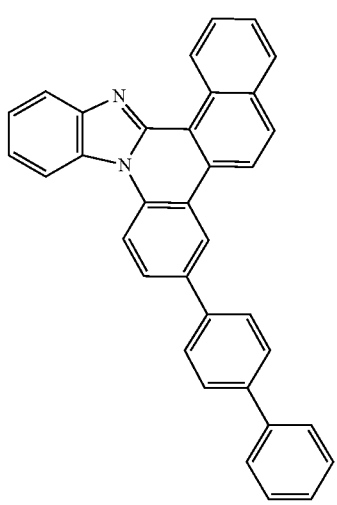
[Formula 3-1-2-2]
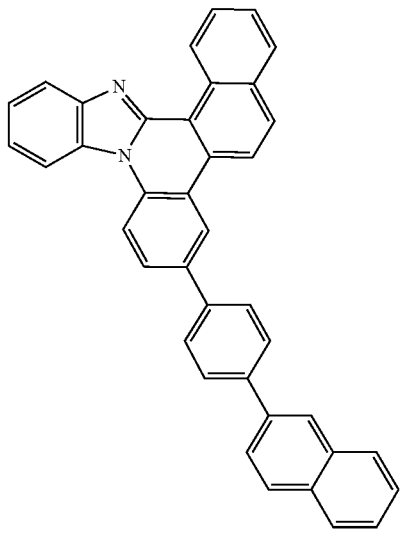

[Formula 3-1-2-3]
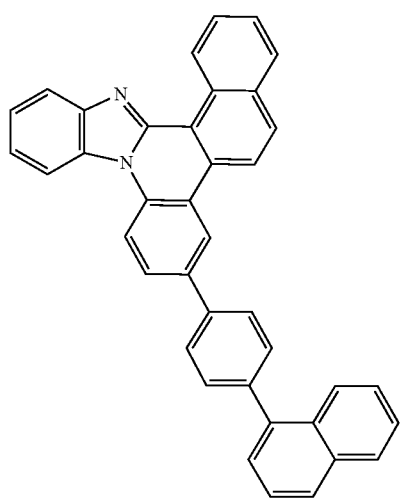
[Formula 3-1-2-4]
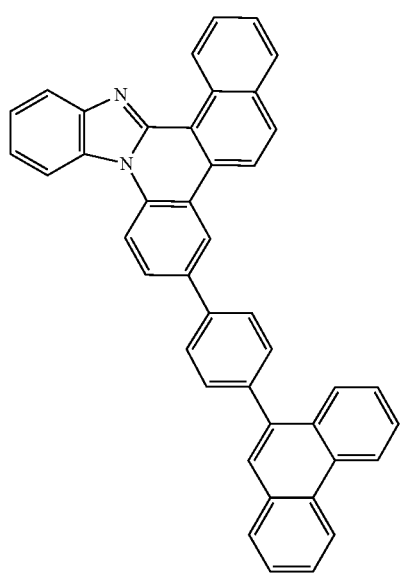
[Formula 3-1-2-5]
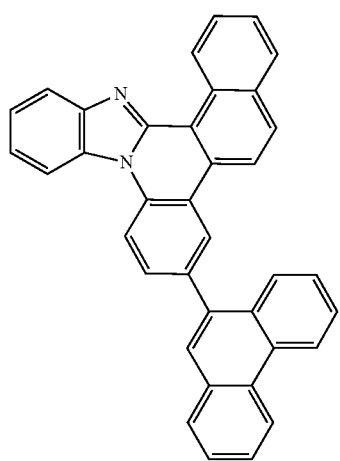
[Formula 3-1-2-6]
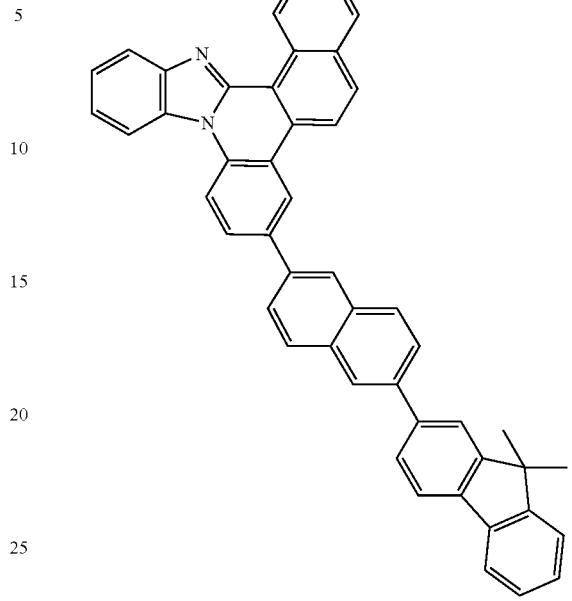
[Formula 3-1-2-7]
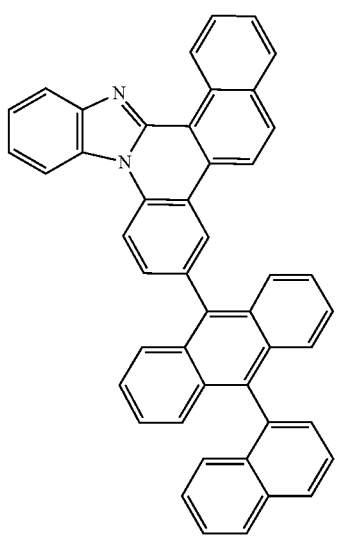

[Formula 3-1-2-8]
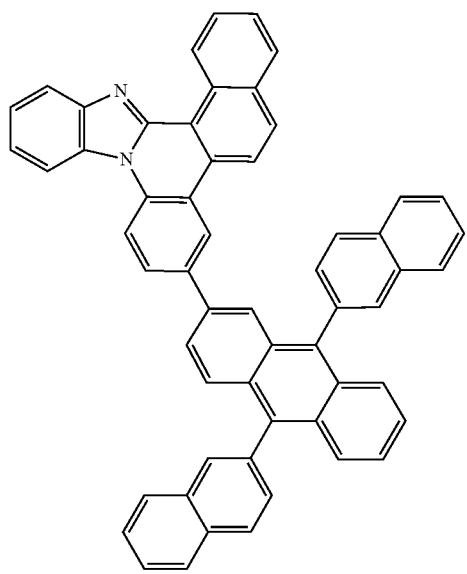
[Formula 3-1-2-9]
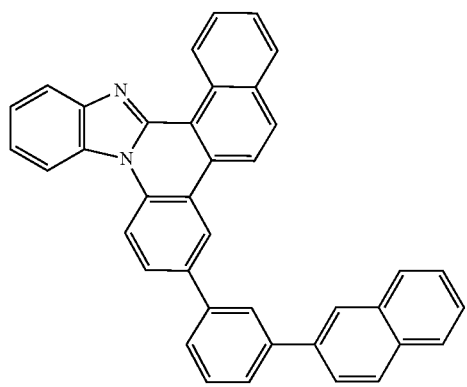
[Formula 3-1-2-10]
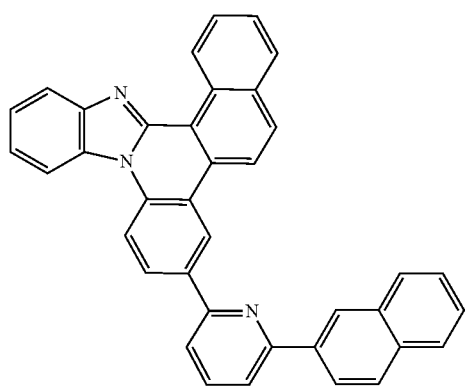
[Formula 3-1-2-11]
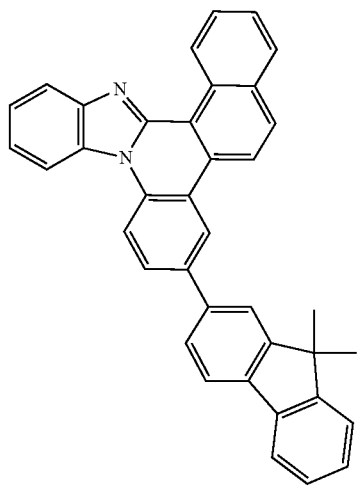
[Formula 3-1-2-12]
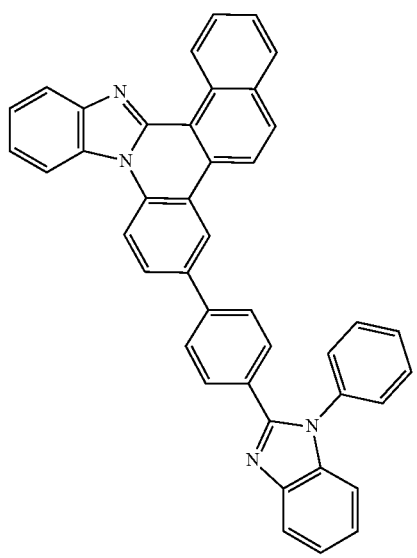
[Formula 3-1-2-13]
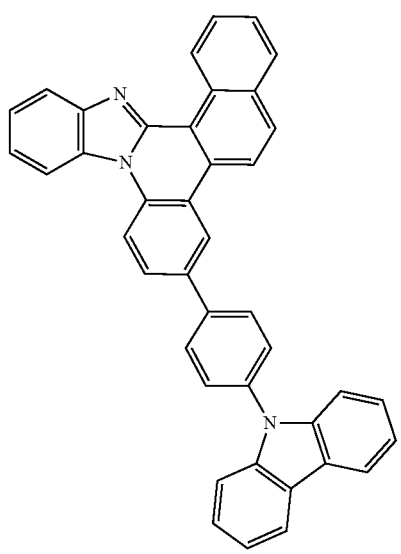

[Formula 3-1-2-14]
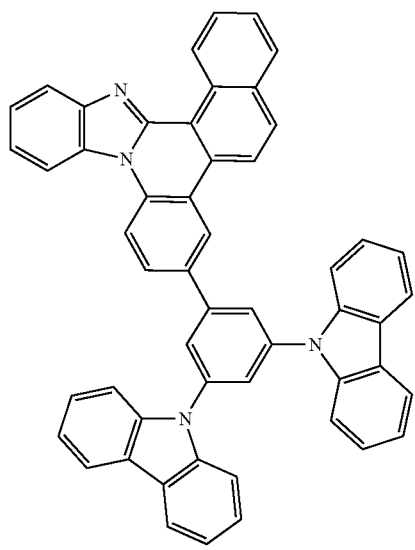
[Formula 3-1-2-15]
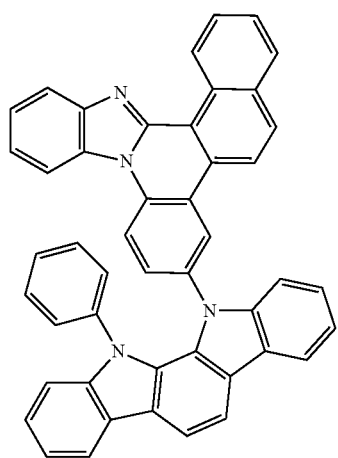
[Formula 3-1-2-16]
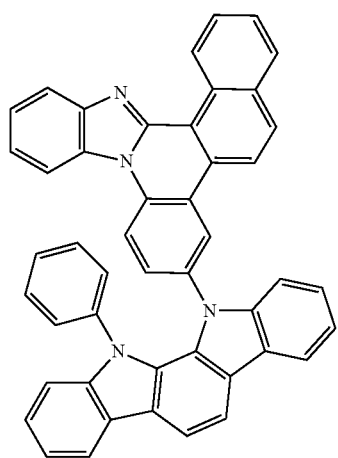
[Formula 3-1-2-17]
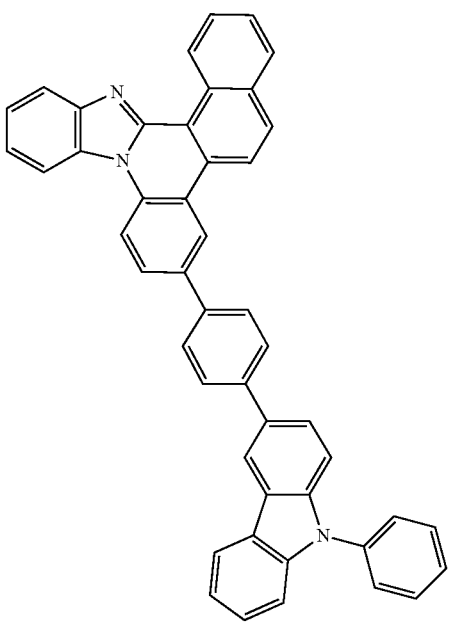
[Formula 3-1-2-18]
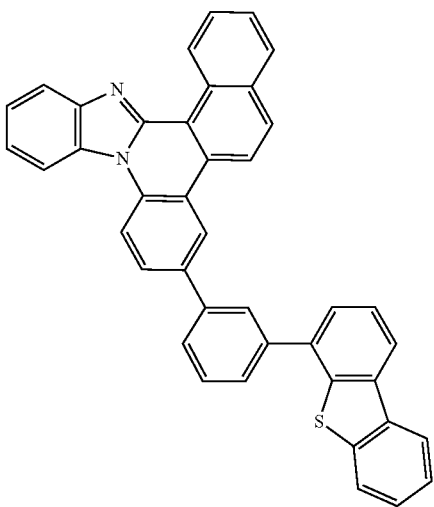

[Formula 3-1-2-19]
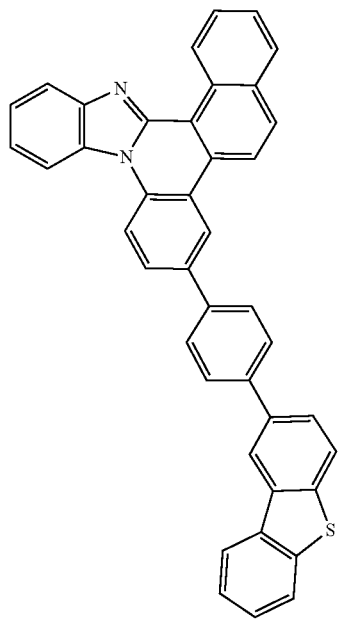
[Formula 3-1-2-20]
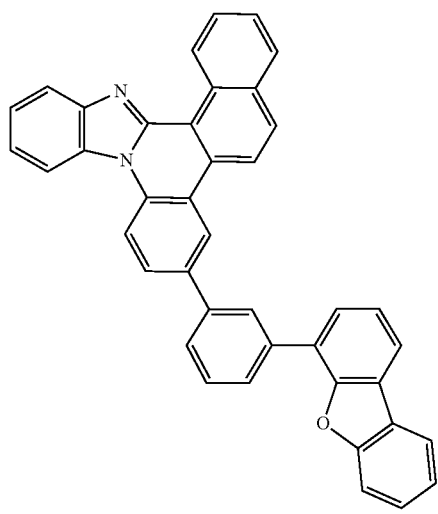
[Formula 3-1-2-21]
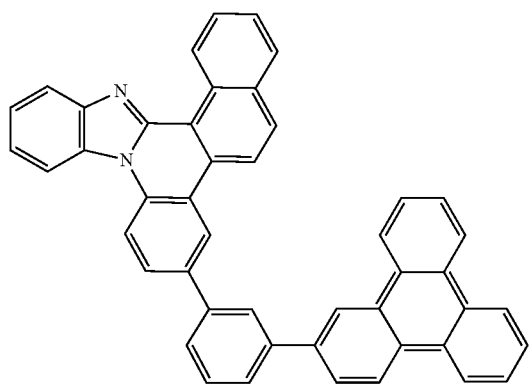
[Formula 3-1-2-22]
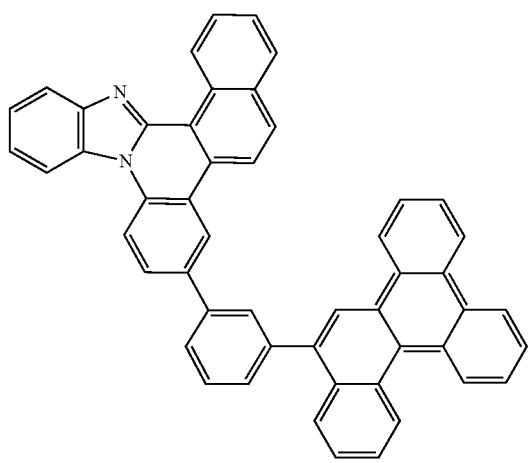
[Formula 3-1-2-23]
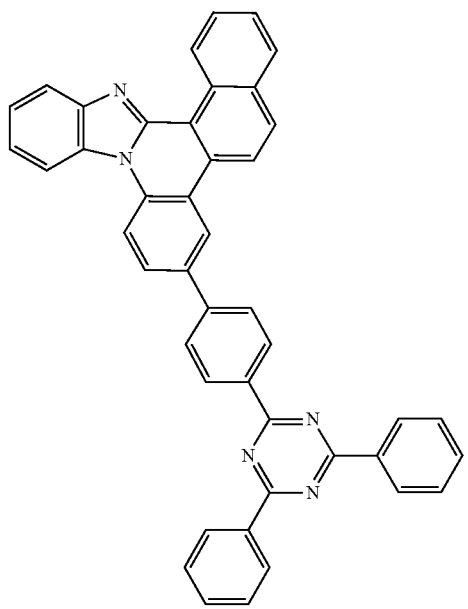
[Formula 3-1-2-24]
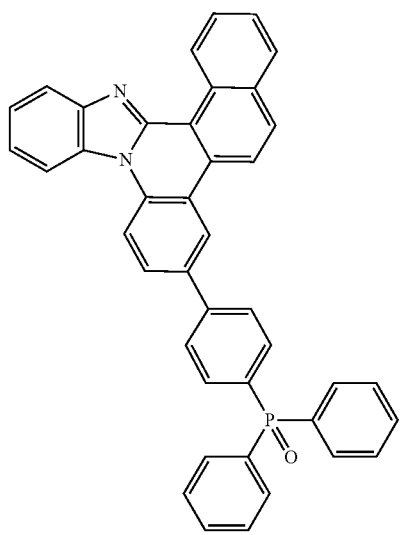

[Formula 3-1-2-25]
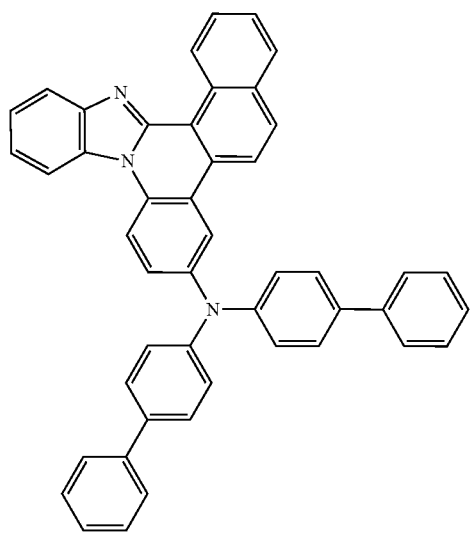
[Formula 3-1-2-26]
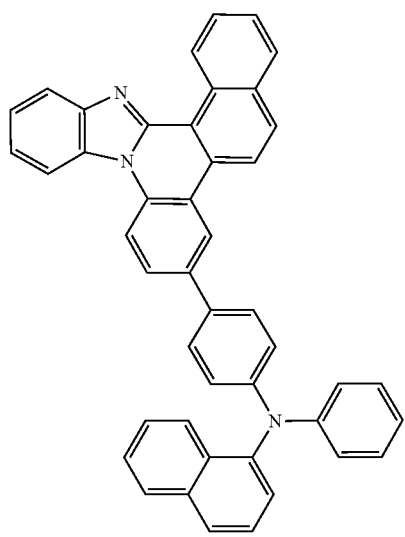
[Formula 3-1-2-27]
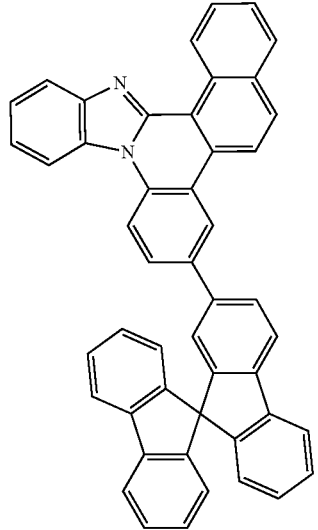
[Formula 3-1-2-28]
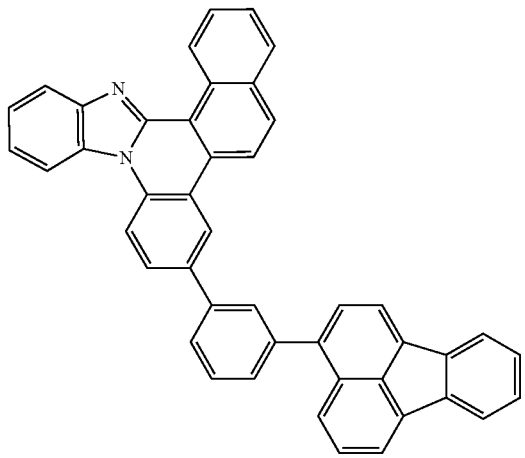
[Formula 3-1-2-29]
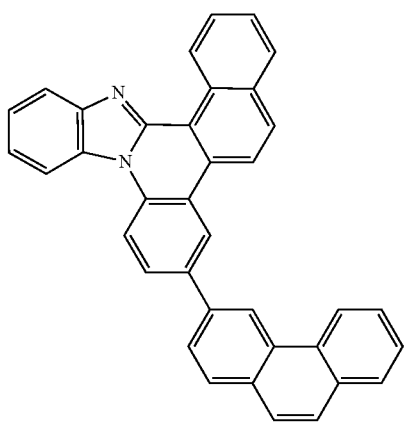
[Formula 3-1-2-30]
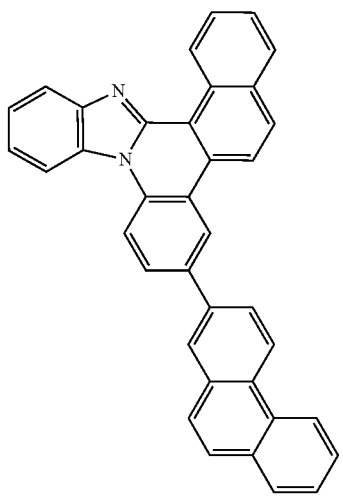

[Formula 3-1-2-31]
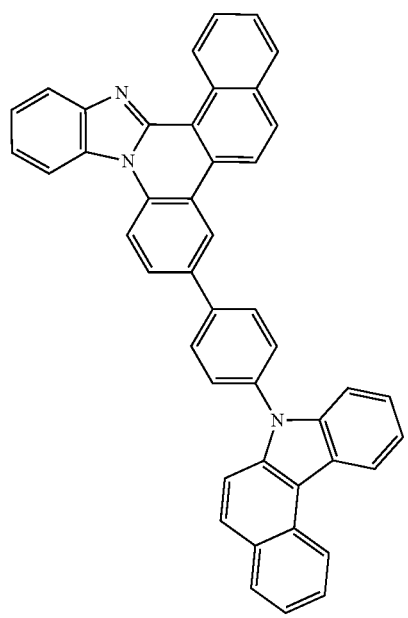
[Formula 3-1-2-33]
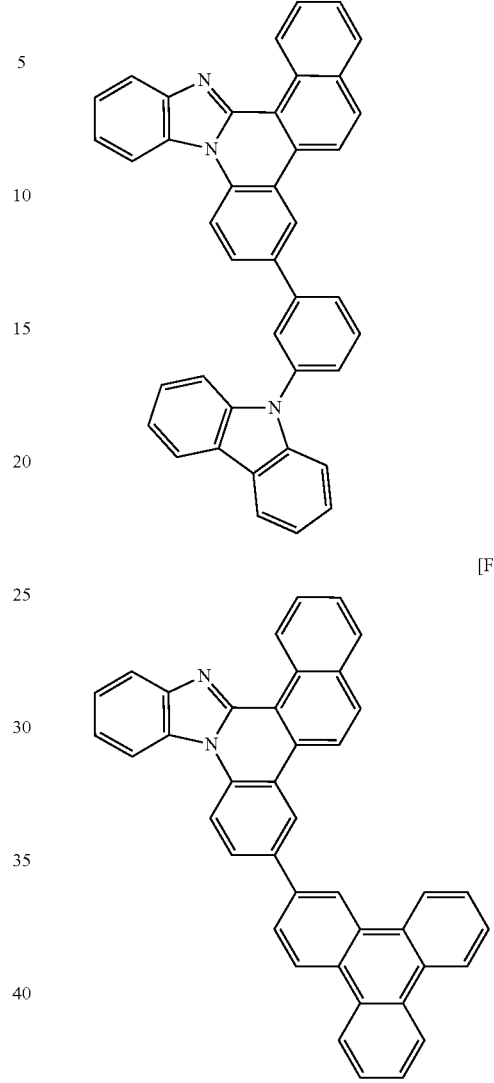
[Formula 3-1-2-34]
[Formula 3-1-2-32]
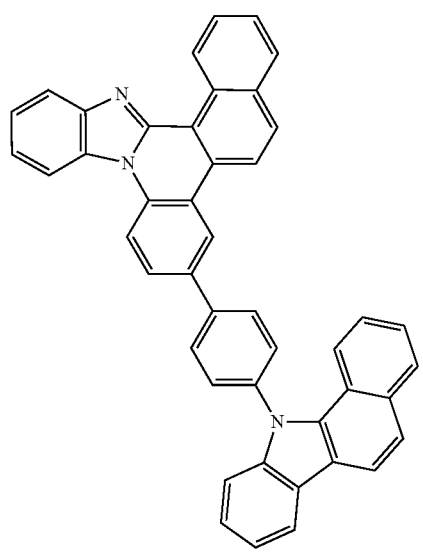
[Formula 3-1-2-35]
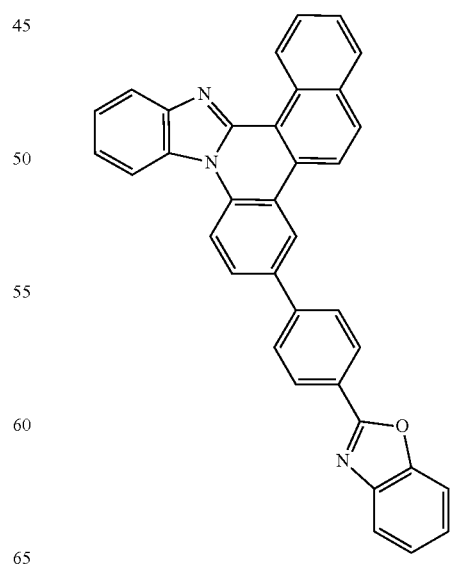

[Formula 3-1-2-36]
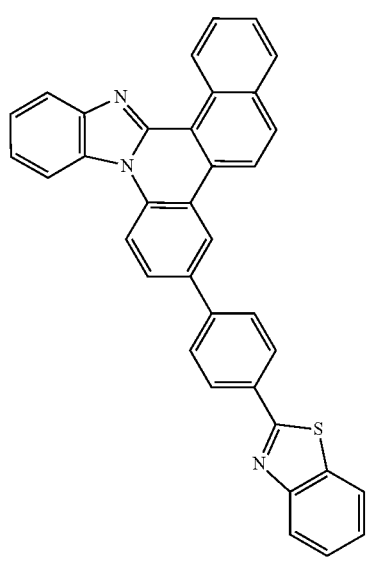
[Formula 3-2-1-1]
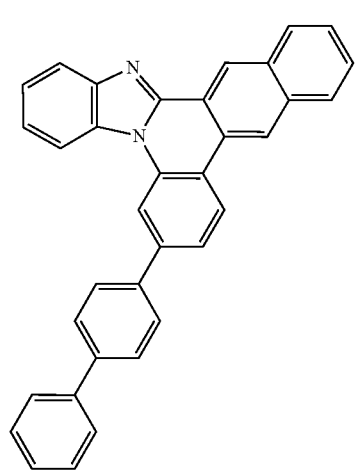
[Formula 3-2-1-2]
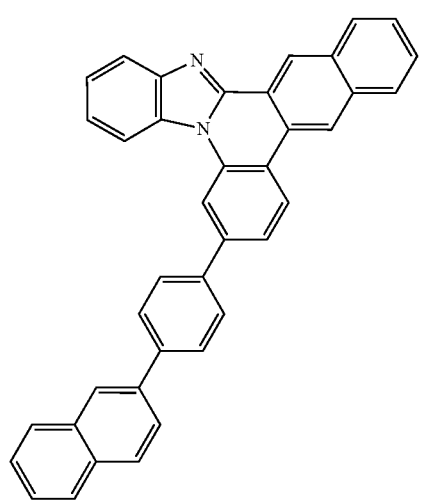
[Formula 3-2-1-3]
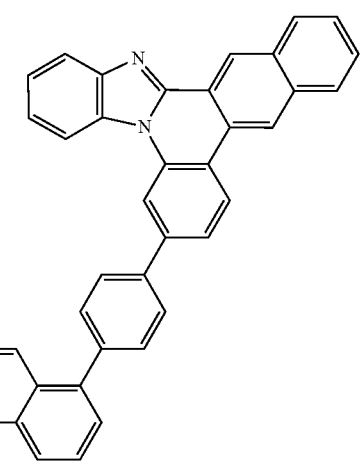
[Formula 3-2-1-4]
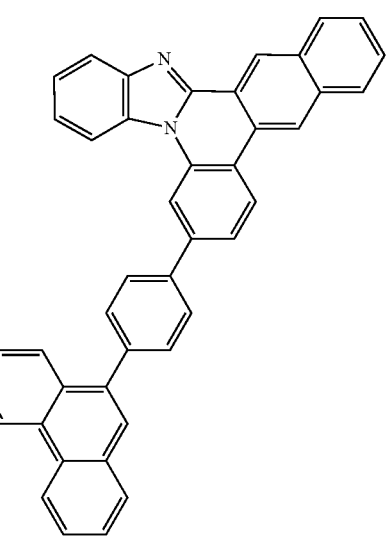
[Formula 3-2-1-5]
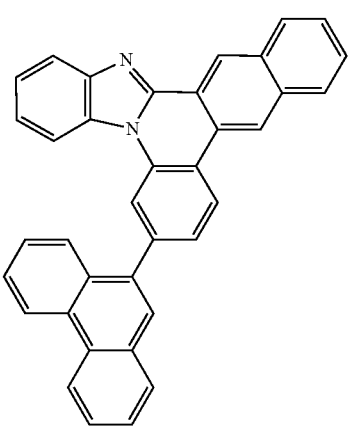

[Formula 3-2-1-6]
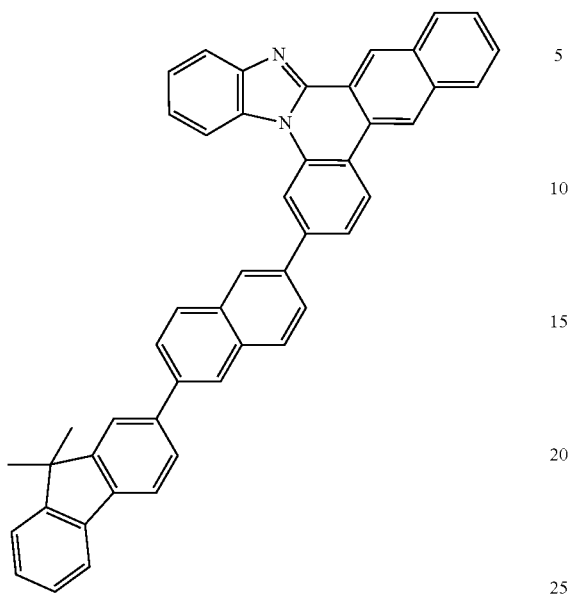
[Formula 3-2-1-7]
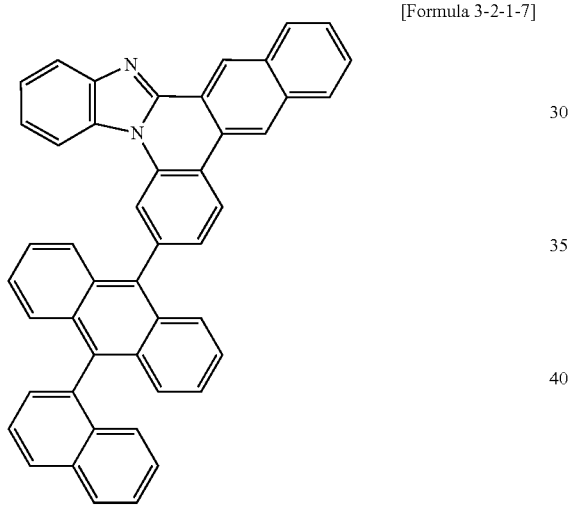
[Formula 3-2-1-8]
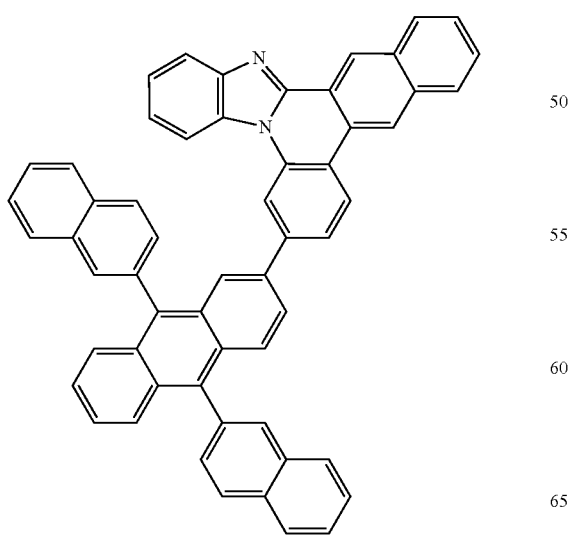
[Formula 3-2-1-9]
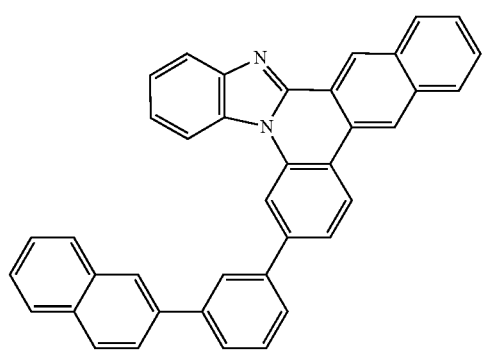
[Formula 3-2-1-10]
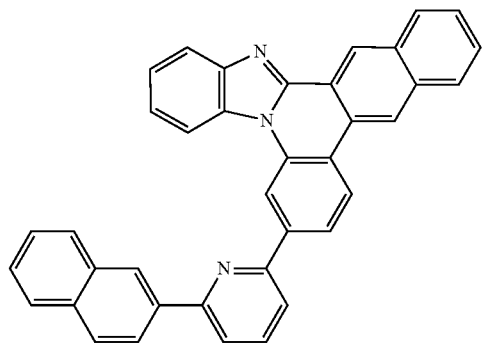
[Formula 3-2-1-11]
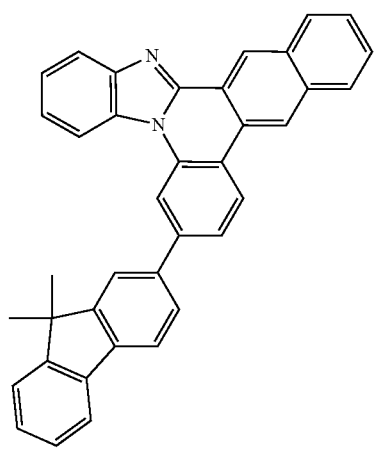

[Formula 3-2-1-12]
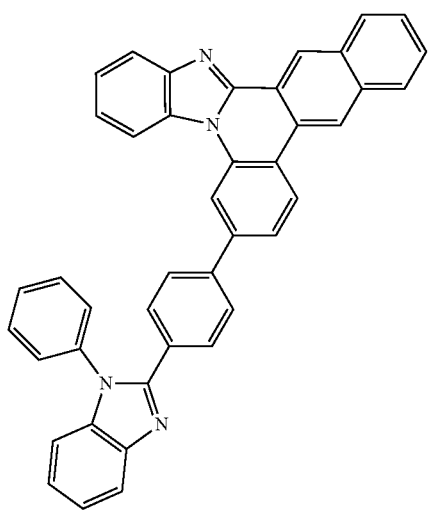
[Formula 3-2-1-13]
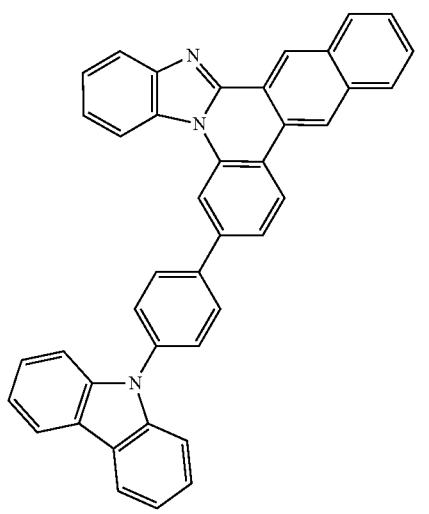
[Formula 3-2-1-14]
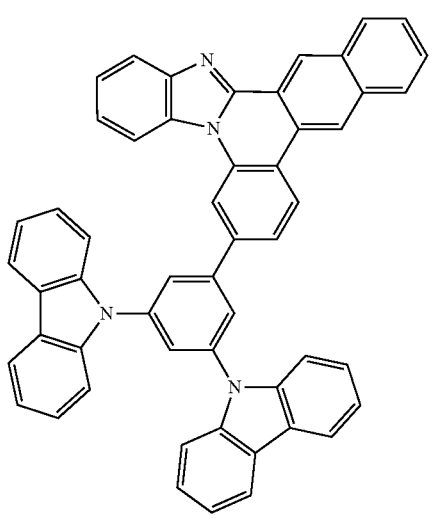
[Formula 3-2-1-15]
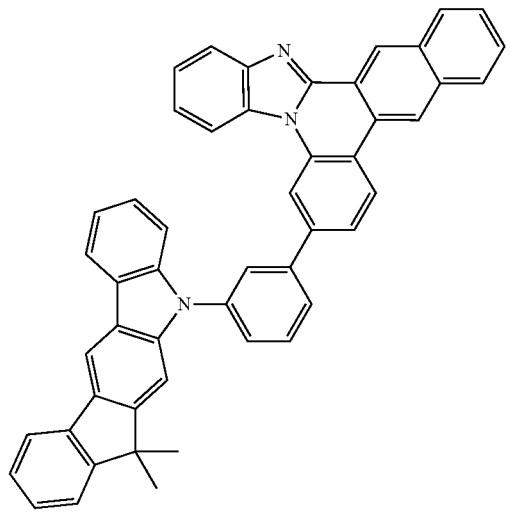
[Formula 3-2-1-16]
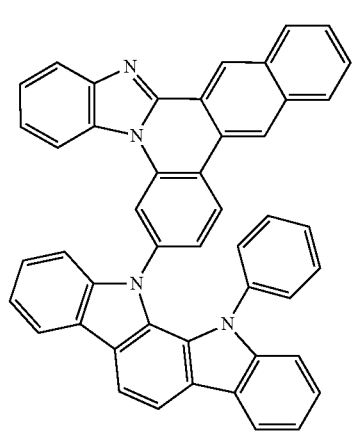
[Formula 3-2-1-17]
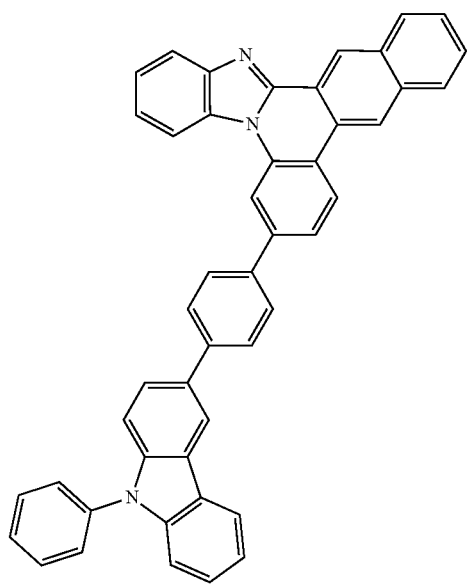

[Formula 3-2-1-18]
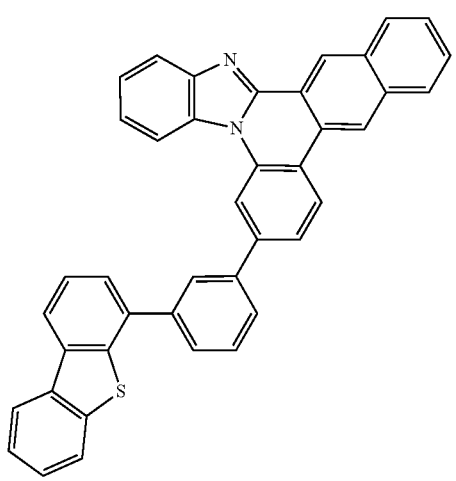
[Formula 3-2-1-19]
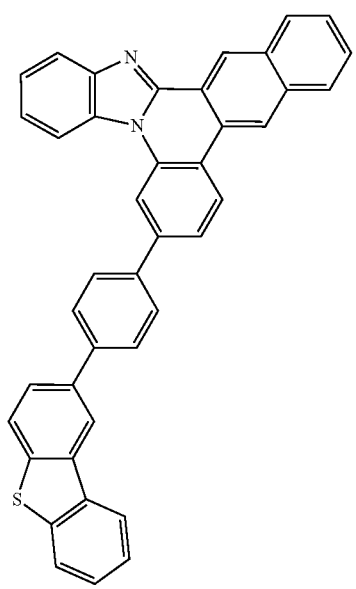
[Formula 3-2-1-20]
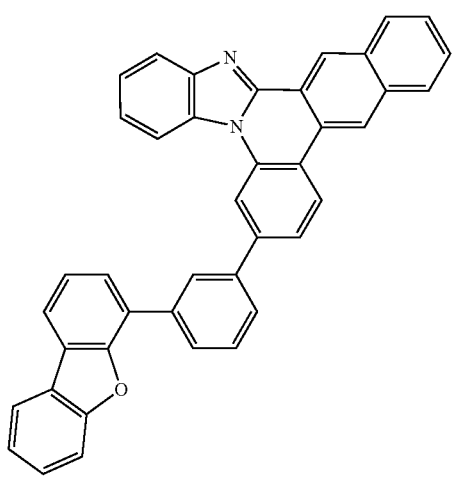
[Formula 3-2-1-21]
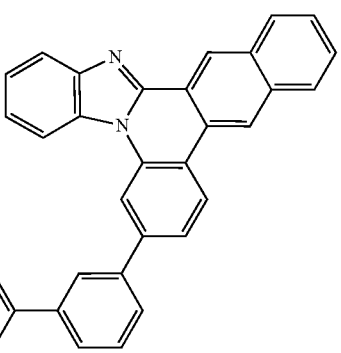
[Formula 3-2-1-22]
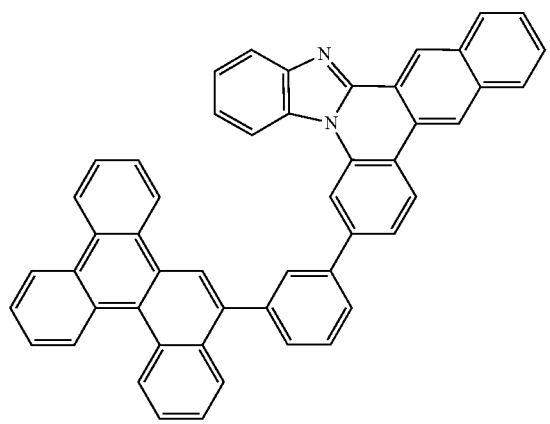
[Formula 3-2-1-23]
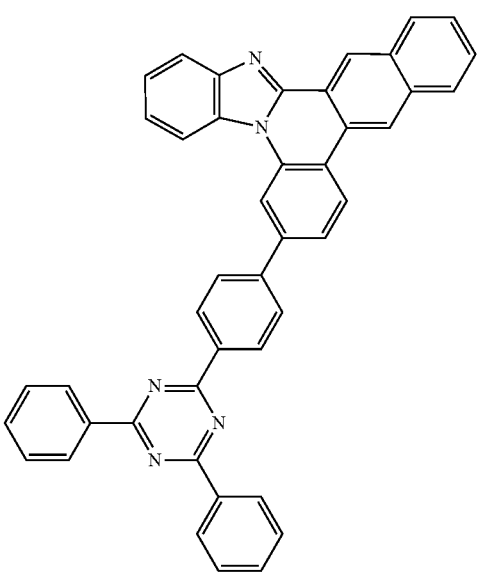

[Formula 3-2-1-24]
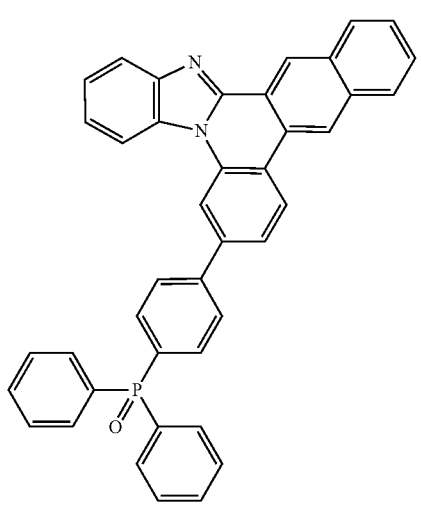
[Formula 3-2-1-27]
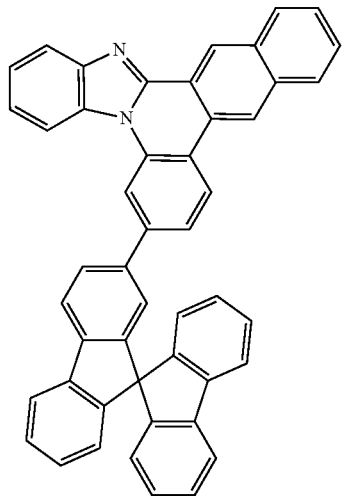
[Formula 3-2-1-25]
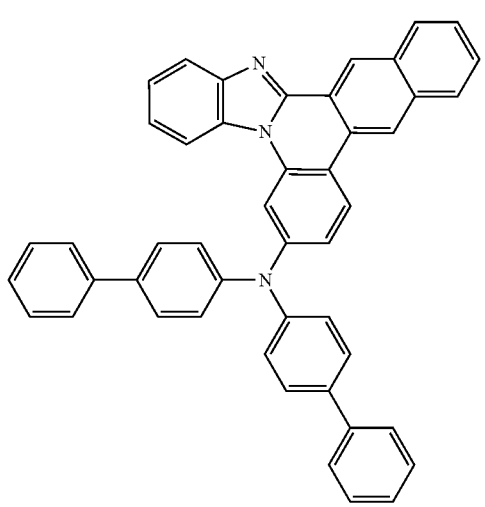
[Formula 3-2-1-28]
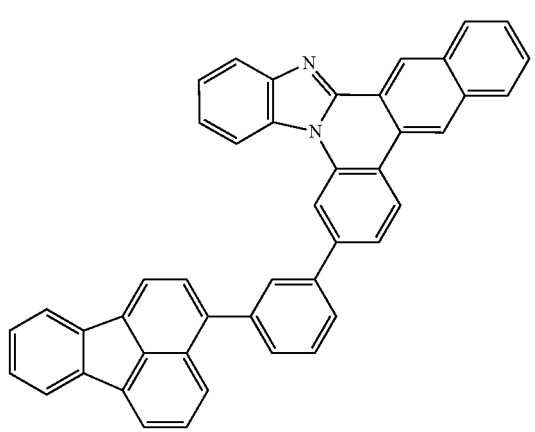
[Formula 3-2-1-26]
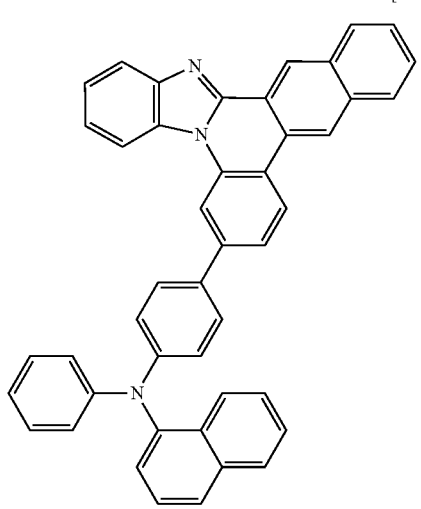
[Formula 3-2-2-1]
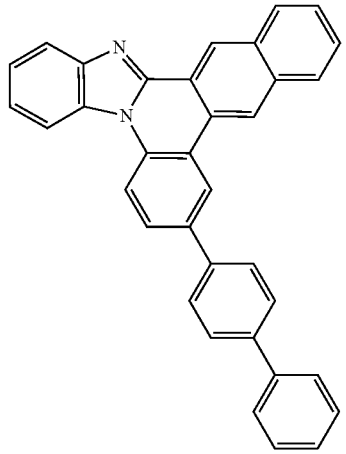

-continued
[Formula 3-2-2-2]
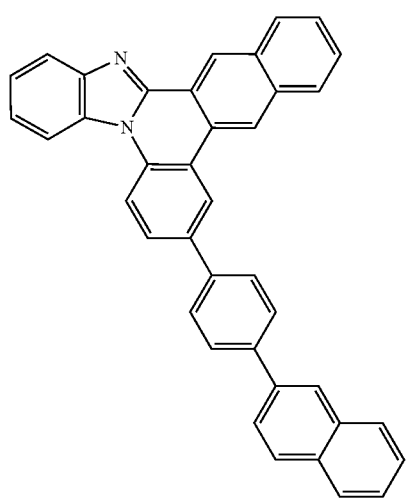
[Formula 3-2-2-3]
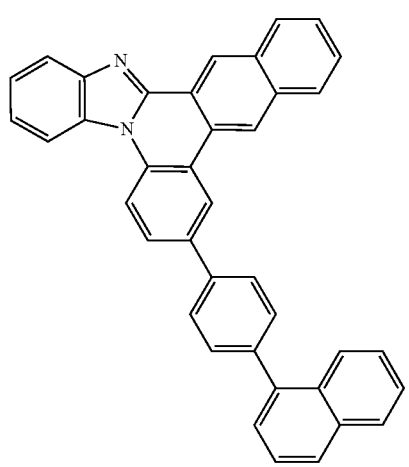
[Formula 3-2-2-4]
-continued
[Formula 3-2-2-5]
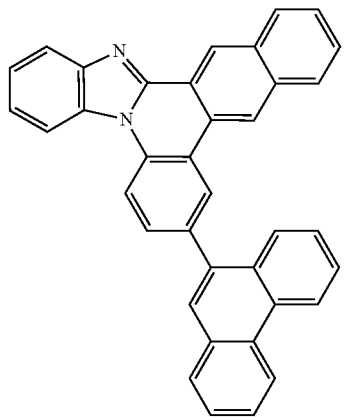
[Formula 3-2-2-6]
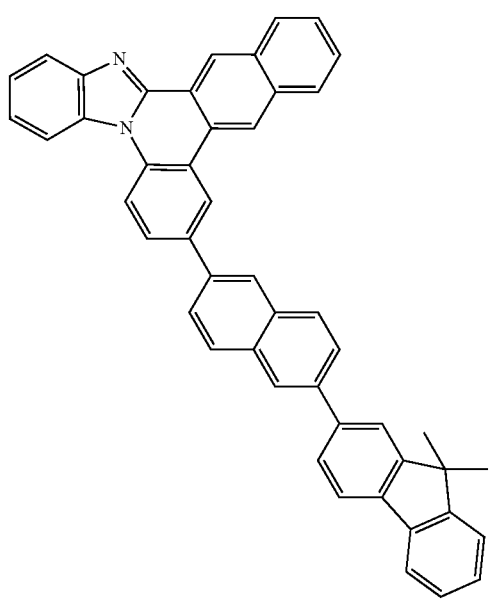
[Formula 3-2-2-7]

[Formula 3-2-2-8]
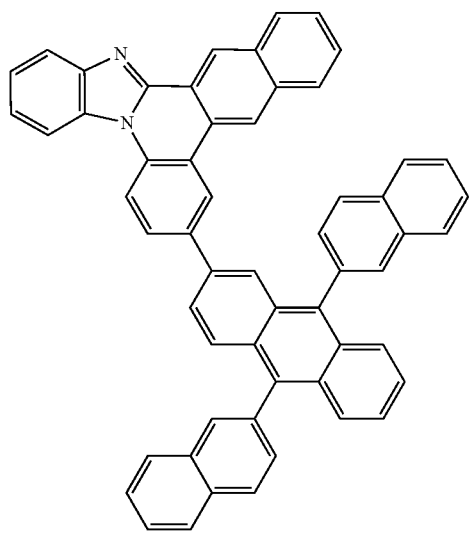
[Formula 3-2-2-9]
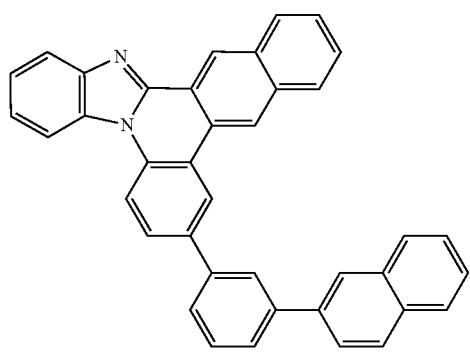
[Formula 3-2-2-10]
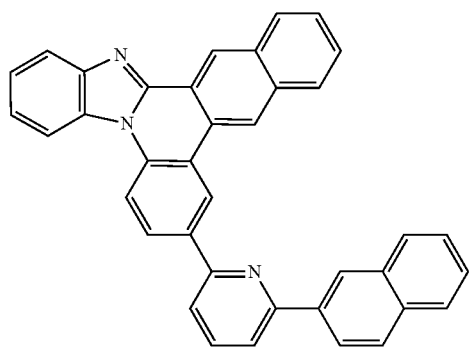
[Formula 3-2-2-11]
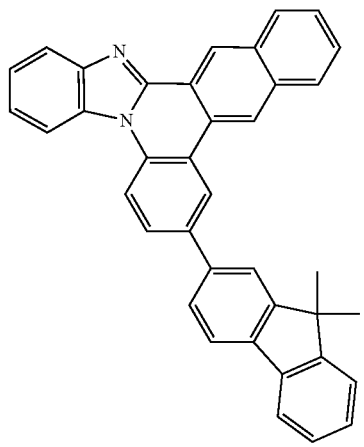
[Formula 3-2-2-12]
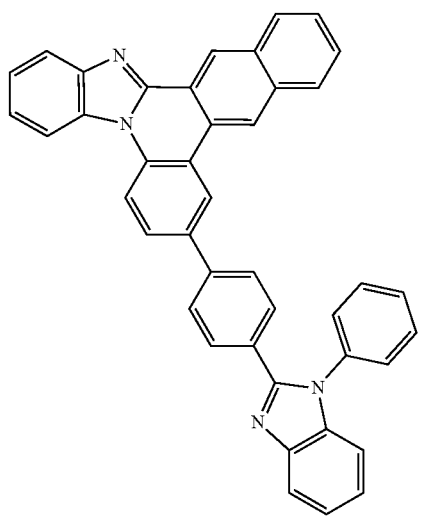
[Formula 3-2-2-13]
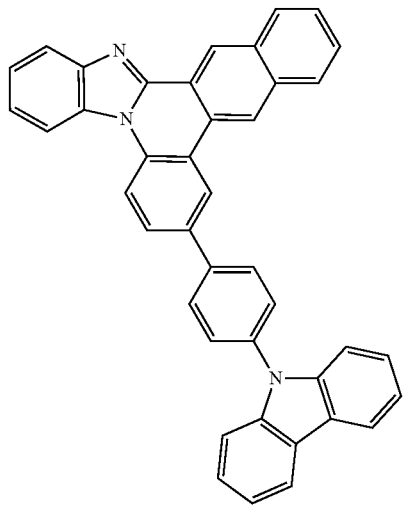

[Formula 3-2-2-14]
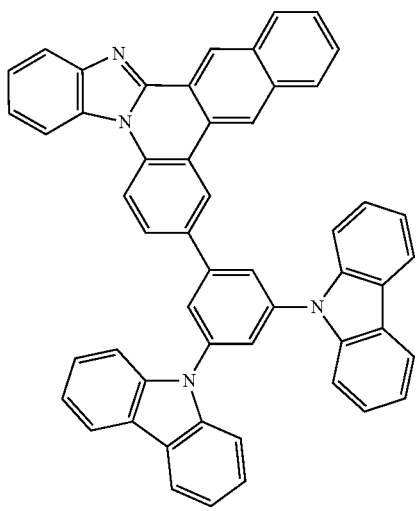
[Formula 3-2-2-15]
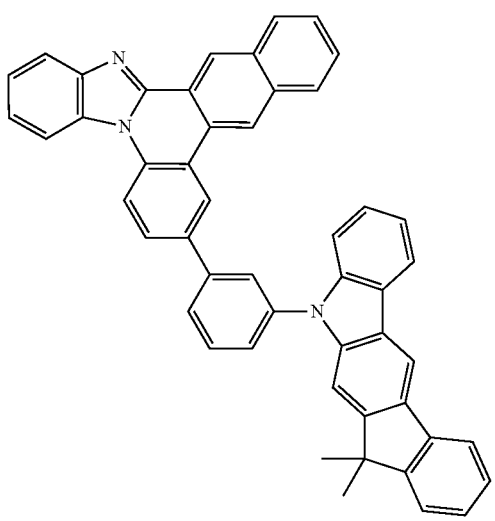
[formula 3-2-2-16]
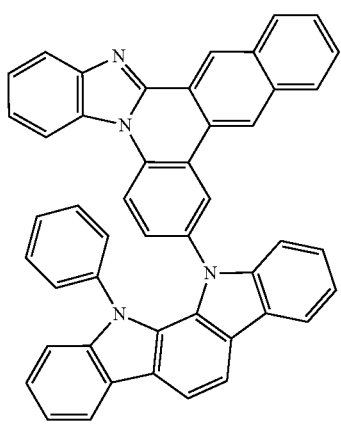
[Formula 3-2-2-17]
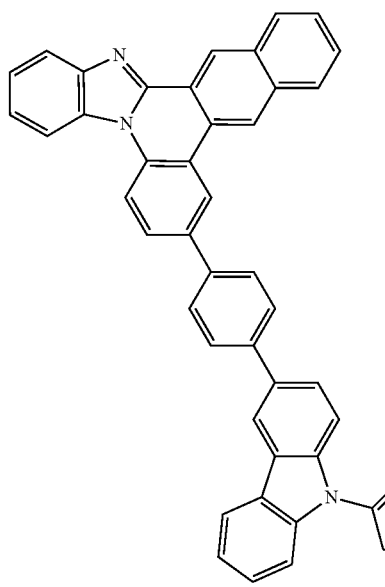
[Formula 3-2-2-18]
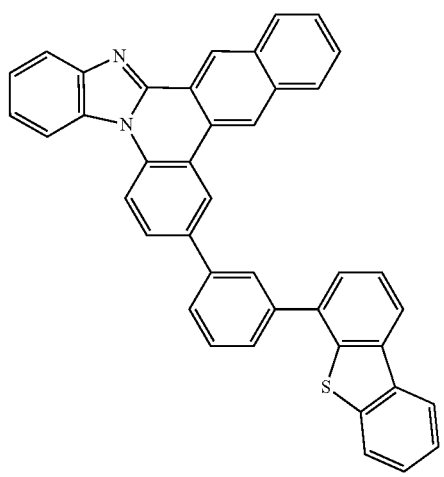
[Formula 3-2-2-19]
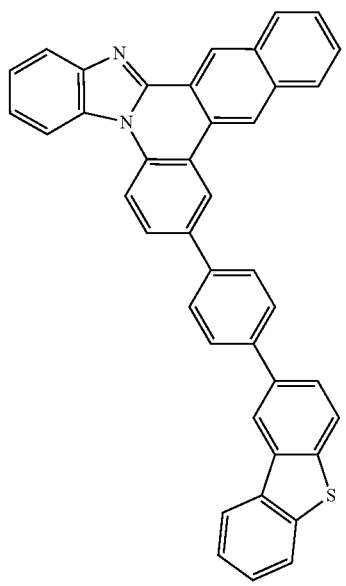

[Formula 3-2-2-20]
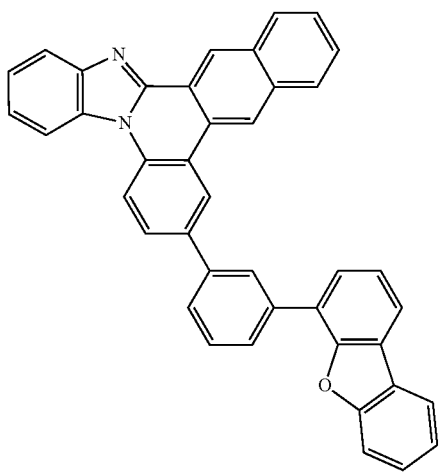
[Formula 3-2-2-21]
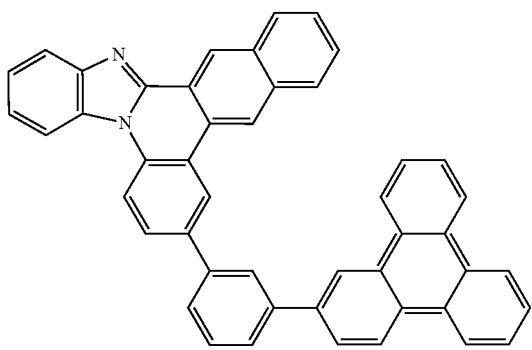
[Formula 3-2-2-22]
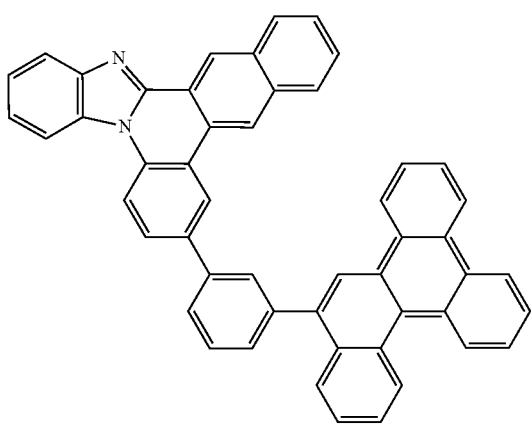
[Formula 3-2-2-23]
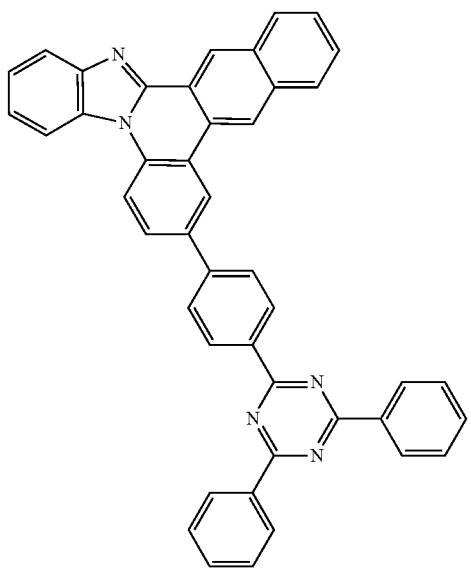
[Formula 3-2-2-24]
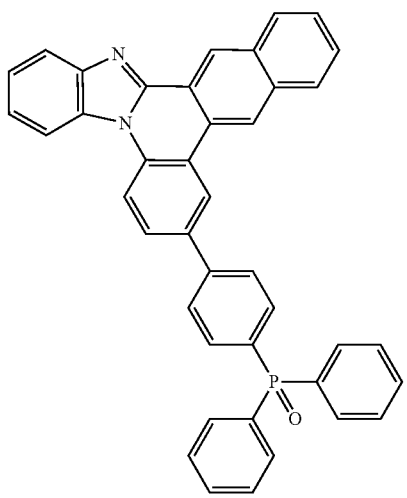
[Formula 3-2-2-25]
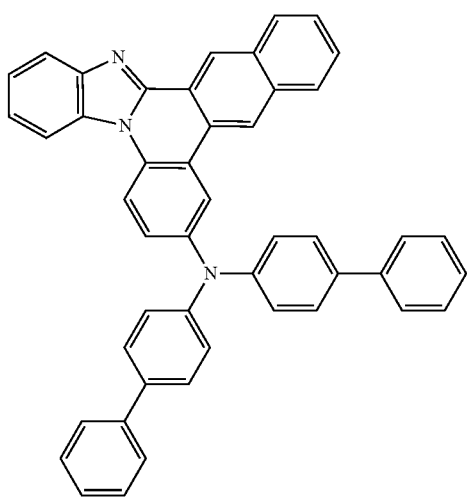

[Formula 3-2-2-26]
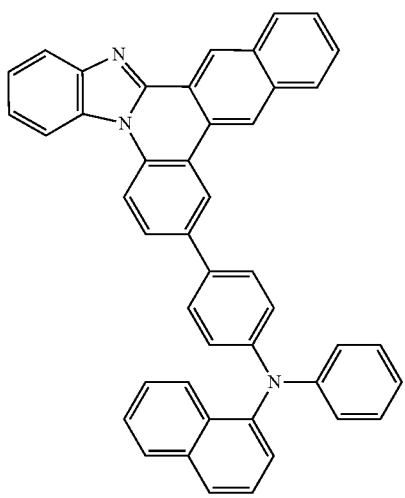
[Formula 3-3-1-1]
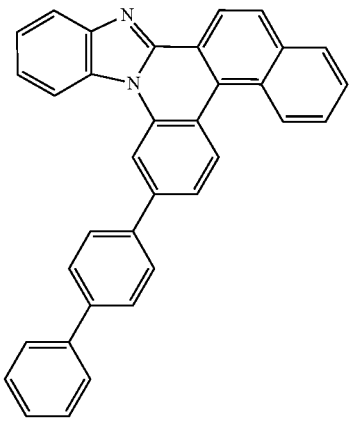
[Formula 3-2-2-27]
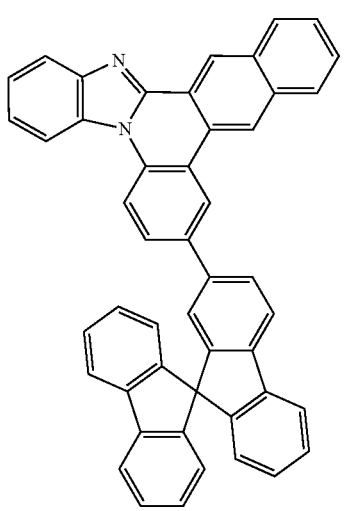
[Formula 3-3-1-2]
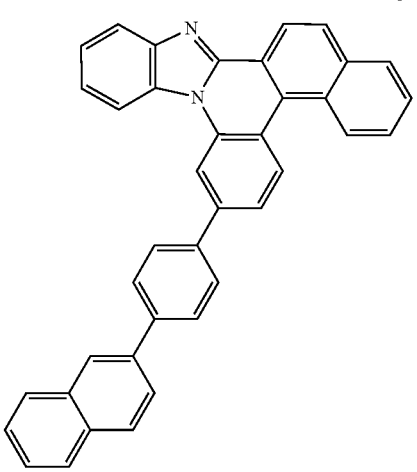
[Formula 3-2-2-28]
[Formula 3-3-1-3]
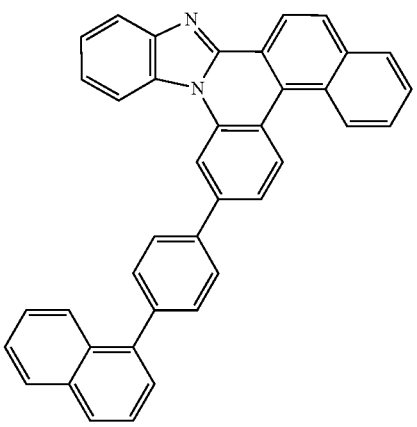

[Formula 3-3-1-4]
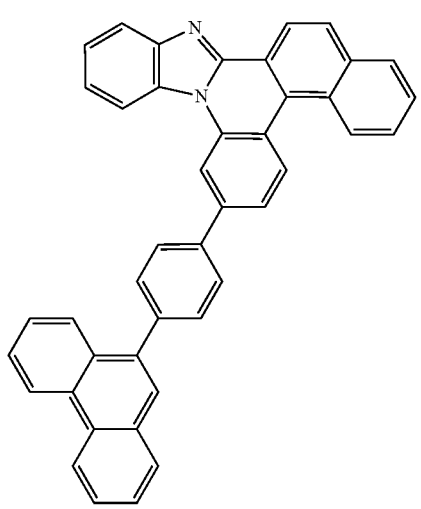
[Formula 3-3-1-5]
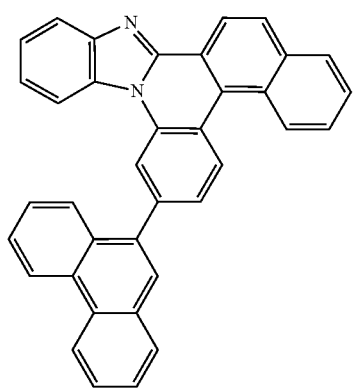
[Formula 3-3-1-6]
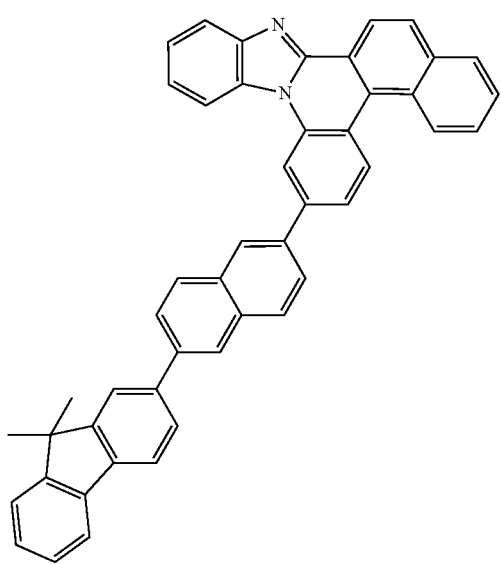
[Formula 3-3-1-7]
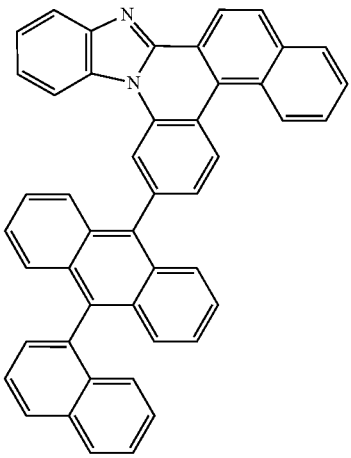
[Formula 3-3-1-8]
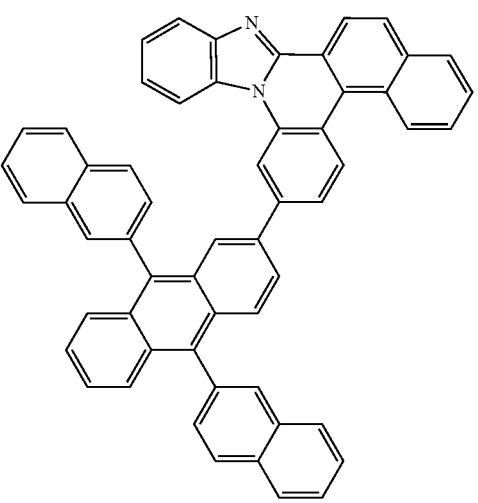
[Formula 3-3-1-9]
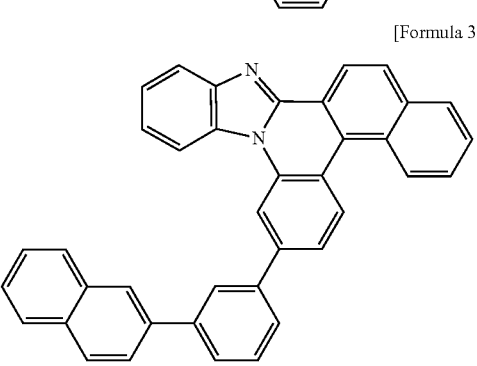
[Formula 3-3-1-10]
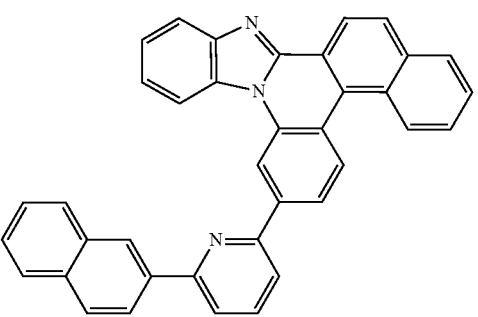

[Formula 3-3-1-11]
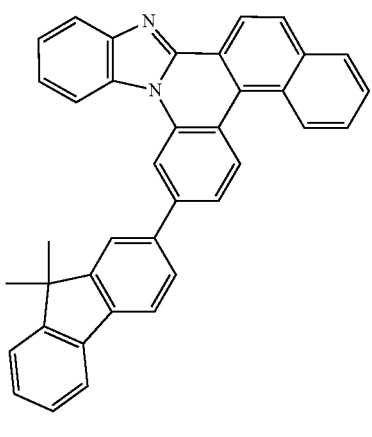
[Formula 3-3-1-14]
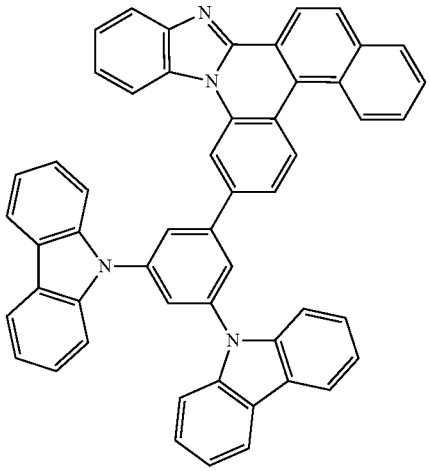
[Formula 3-3-1-12]
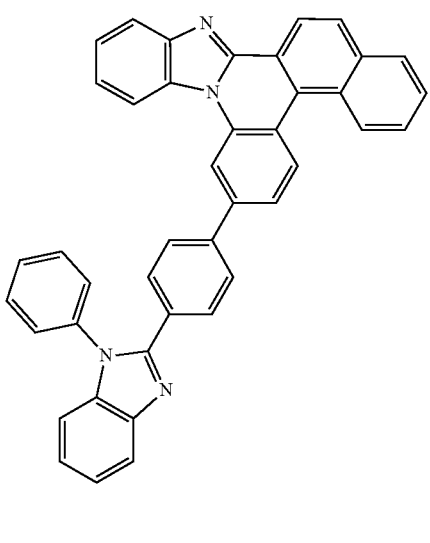
[Formula 3-3-1-15]
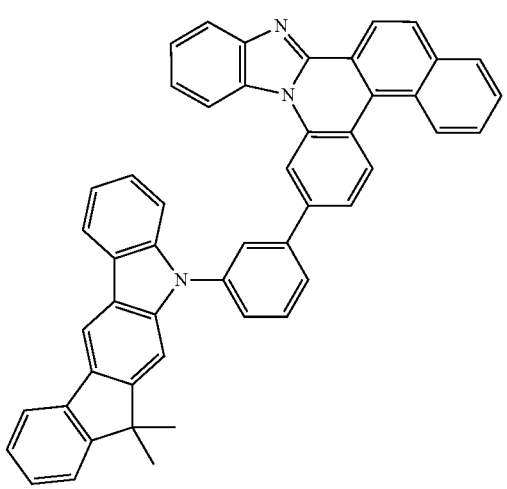
[Formula 3-3-1-13]
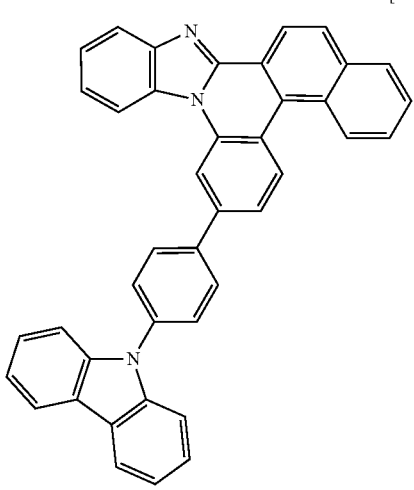
[Formula 3-3-1-16]
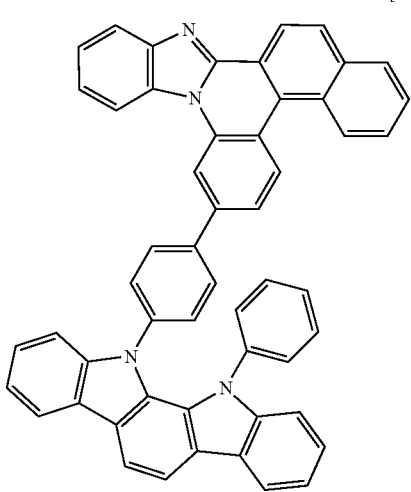

[Formula 3-3-1-17]
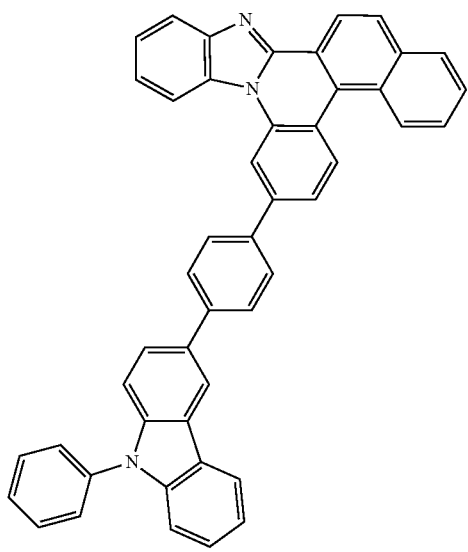
[Formula 3-3-1-18]
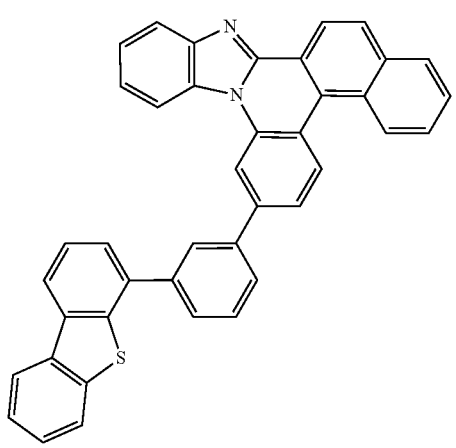
[Formula 3-3-1-19]
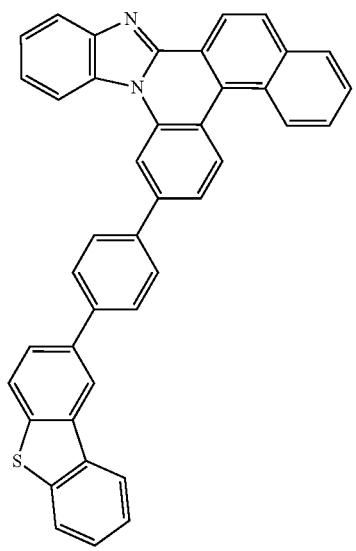
[Formula 3-3-1-20]
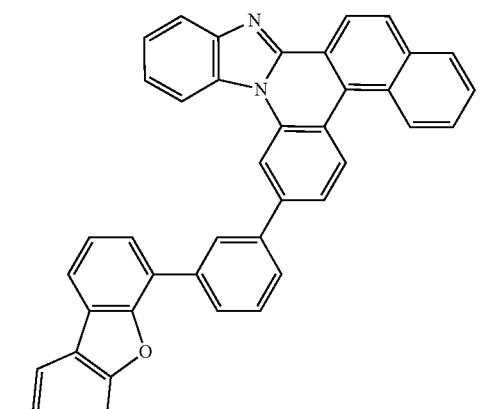
[Formula 3-3-1-21]
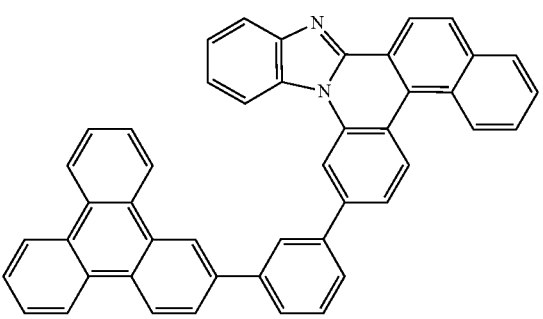
[Formula 3-3-1-22]
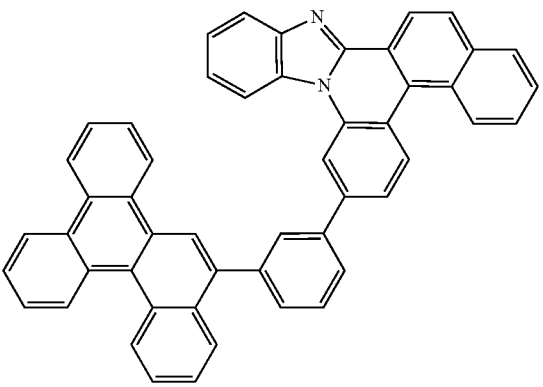

[Formula 3-3-1-23]
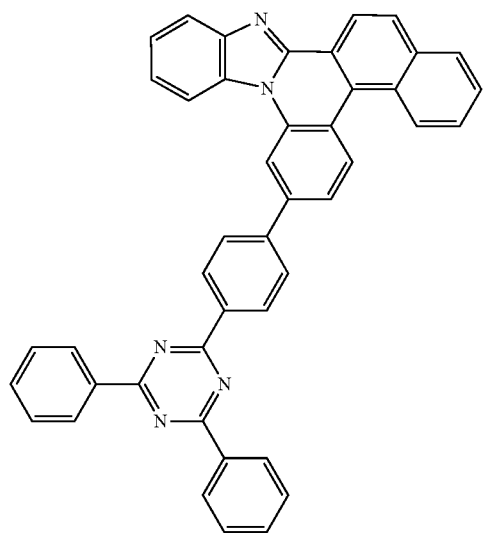
[Formula 3-3-1-24]
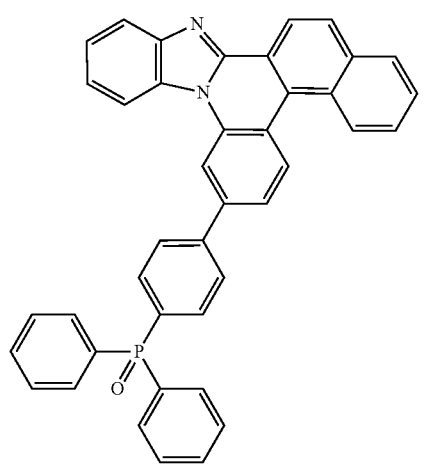
[Formula 3-3-1-25]
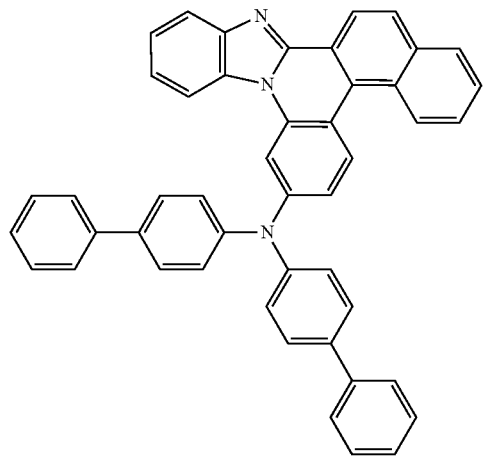
[Formula 3-3-1-26]
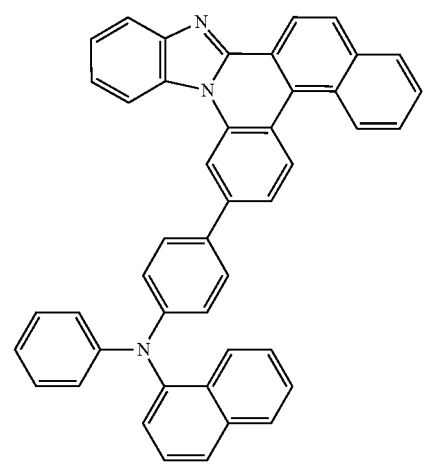
[Formula 3-3-1-27]
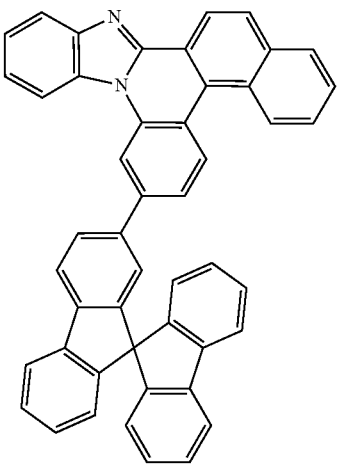
[Formula 3-3-1-28]
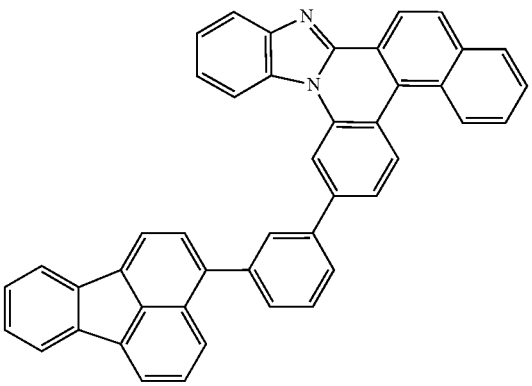

[Formula 3-3-2-1]
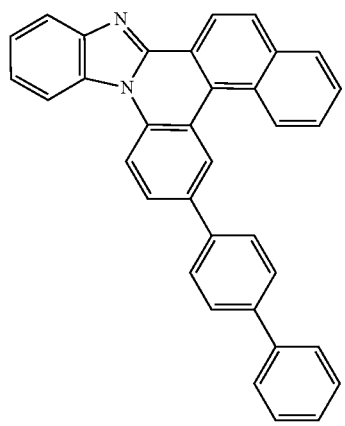
[Formula 3-3-2-2]
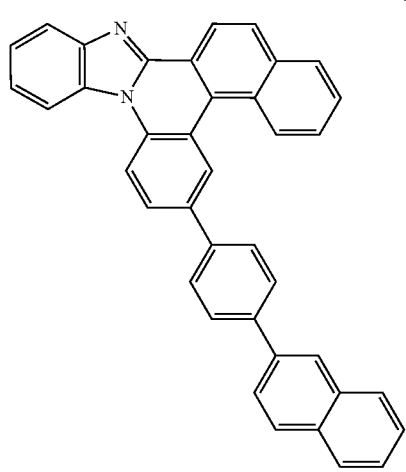
[Formula 3-3-2-3]
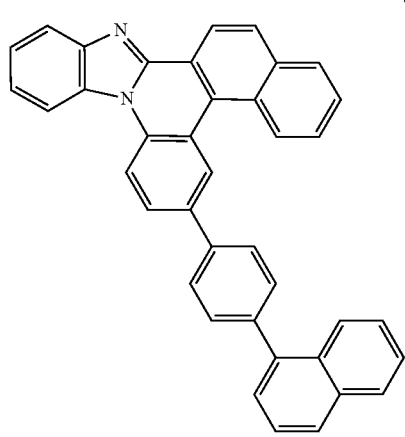
[Formula 3-3-2-4]
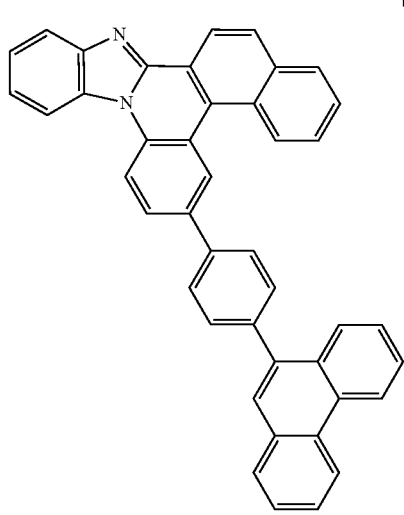
[Formula 3-3-2-5]
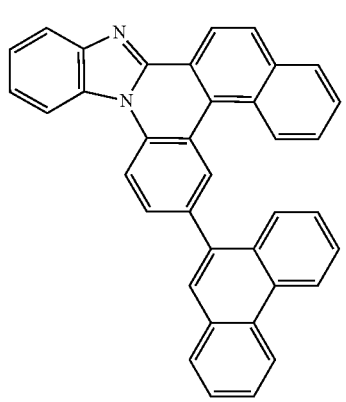
[Formula 3-3-2-6]
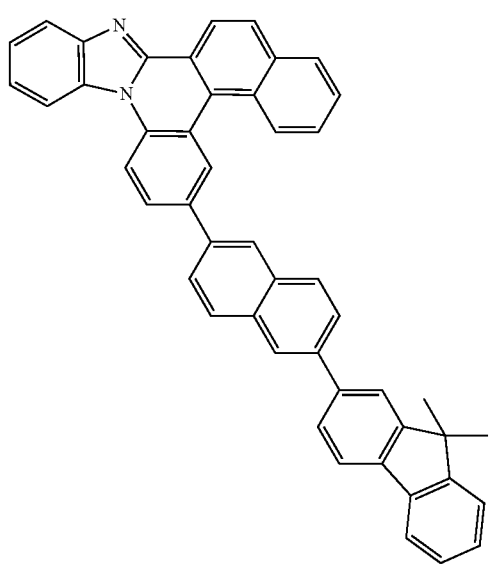

[Formula 3-3-2-7]
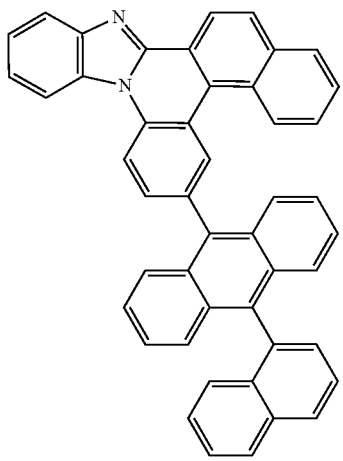
[Formula 3-3-2-8]
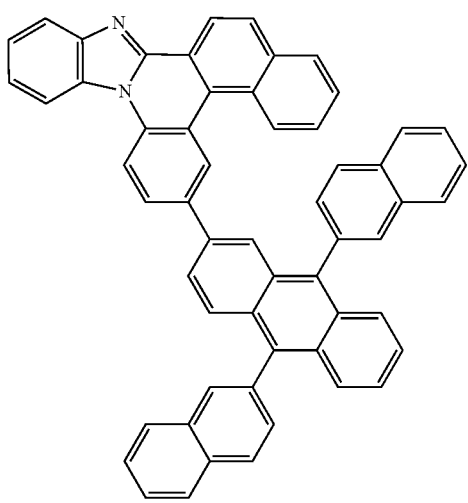
[Formula 3-3-2-9]
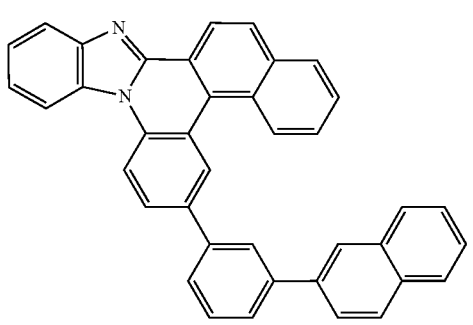
[Formula 3-3-2-10]
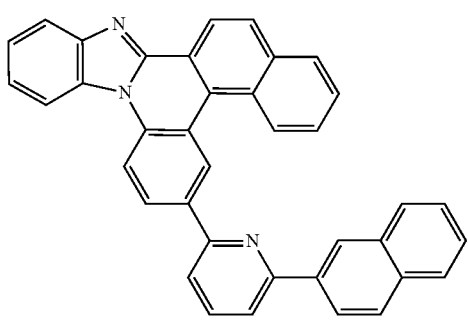
[Formula 3-3-2-11]
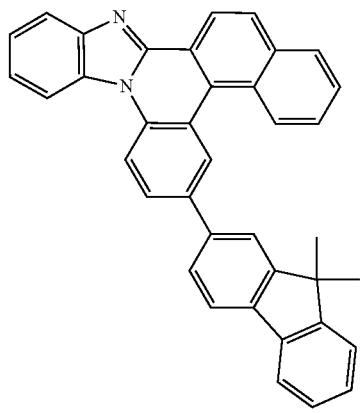
[Formula 3-3-2-12]
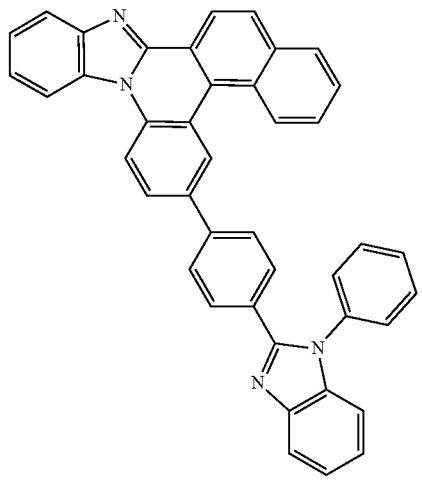
[Formula 3-3-2-13]
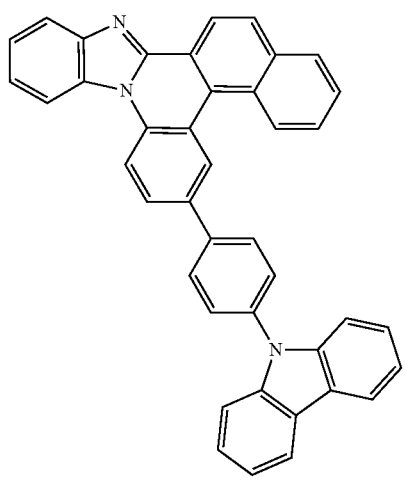

[Formula 3-3-2-14]
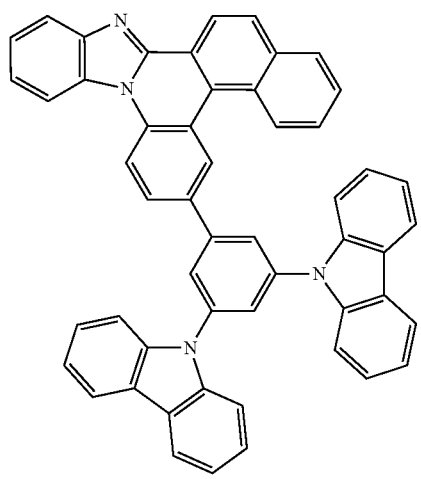
[Formula 3-3-2-15]
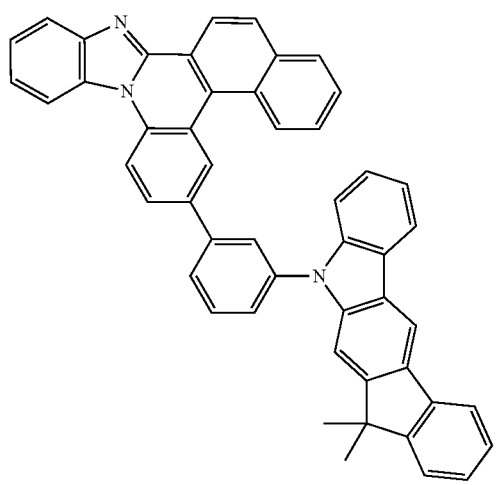
[Formula 3-3-2-16]
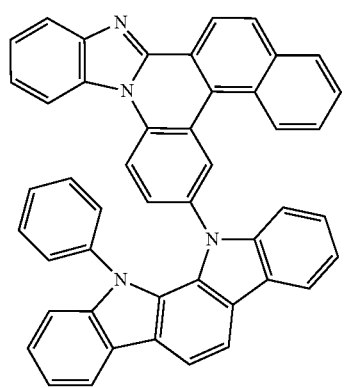
[Formula 3-3-2-17]
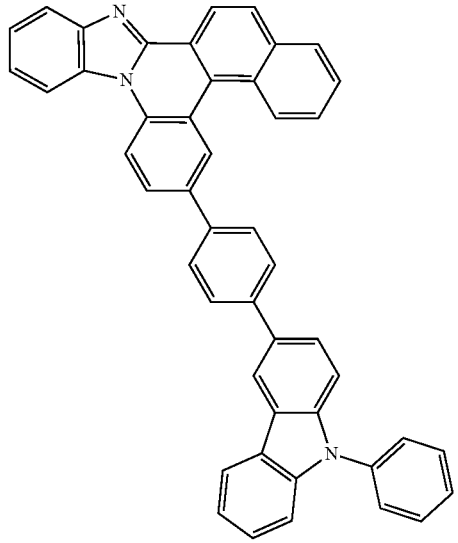
[Formula 3-3-2-18]
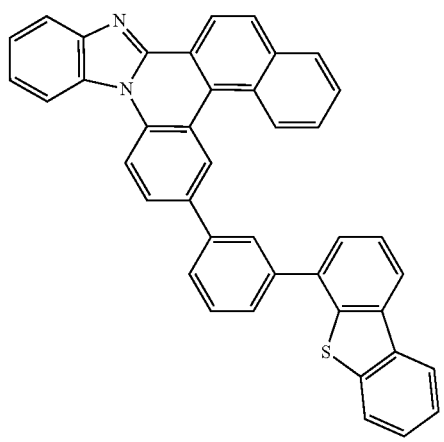
[Formula 3-3-2-19]
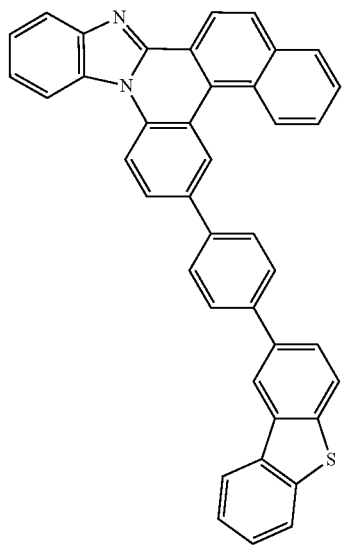

[Formula 3-3-2-20]
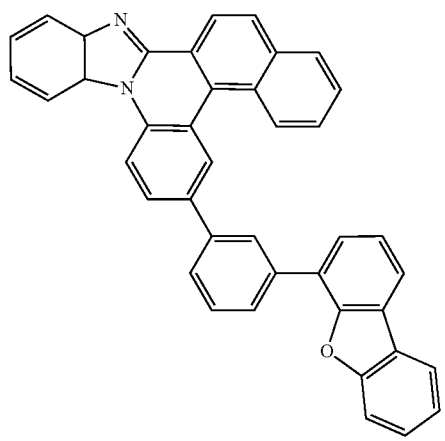
[Formula 3-3-2-21]
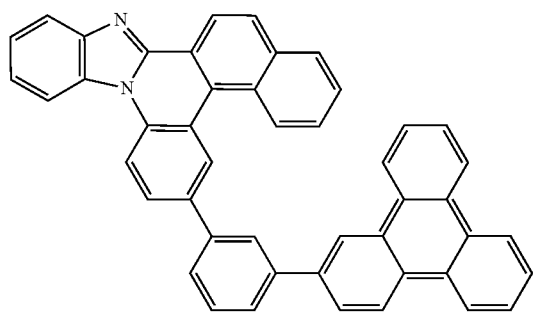
[Formula 3-3-2-22]
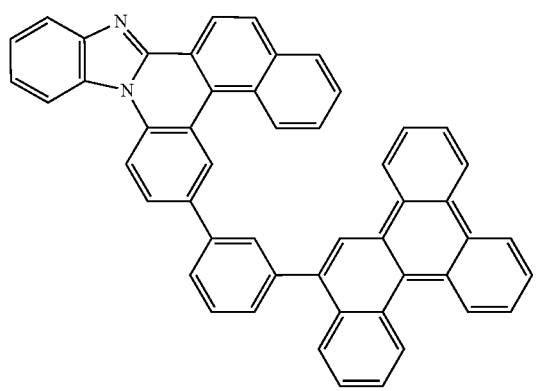
[Formula 3-3-2-23]
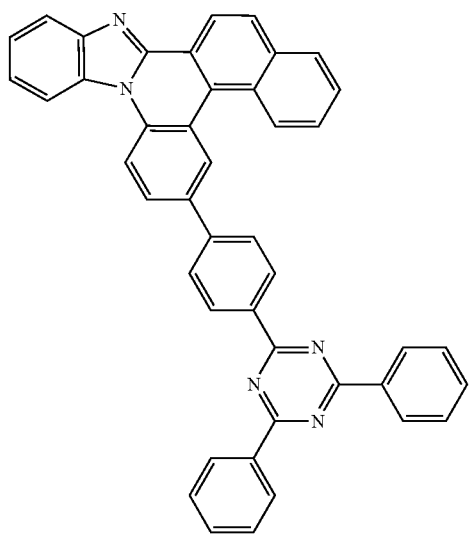
[Formula 3-3-2-24]
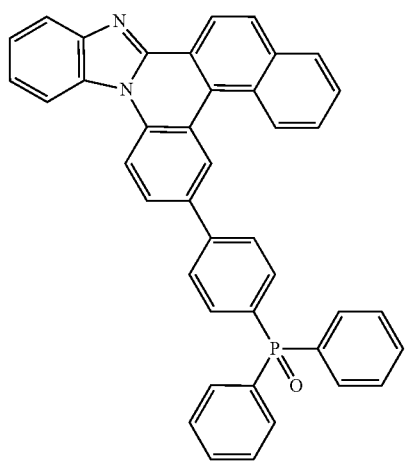
[Formula 3-3-2-25]
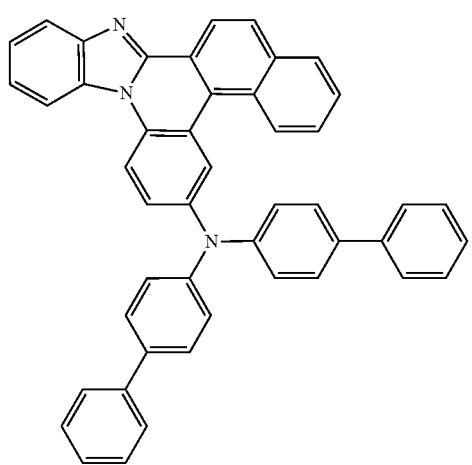

[Formula 3-3-2-26]
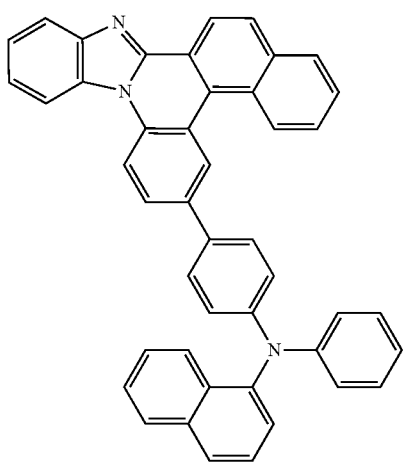
[Formula 3-4-1-1]
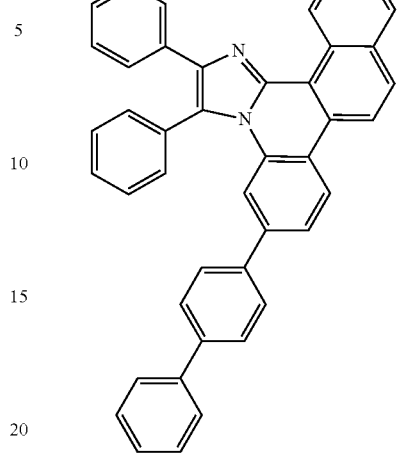
[Formula 3-3-2-27]
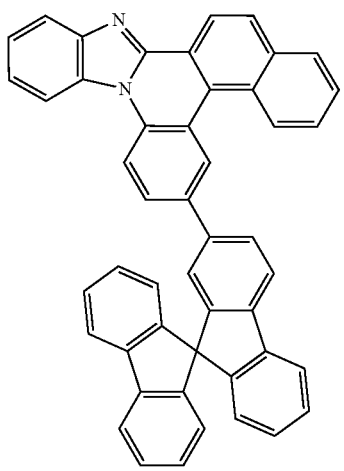
[Formula 3-4-1-2]
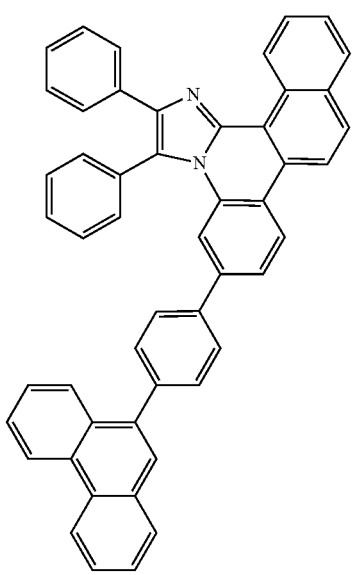
[Formula 3-3-2-28]
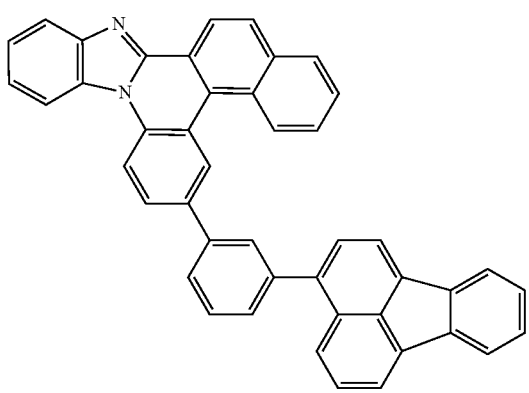
[Formula 3-4-1-3]
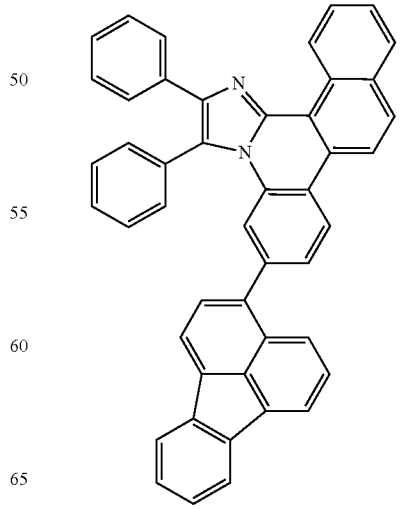

[Formula 3-4-1-4]
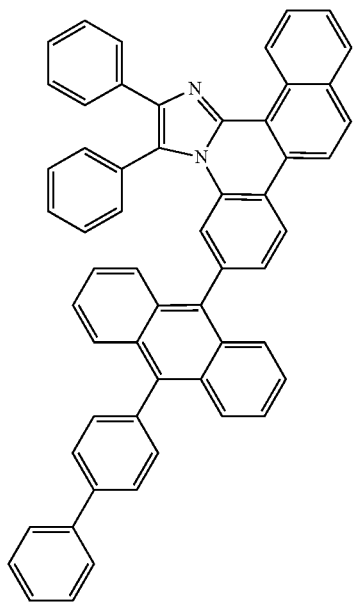
[Formula 3-2-1-6]
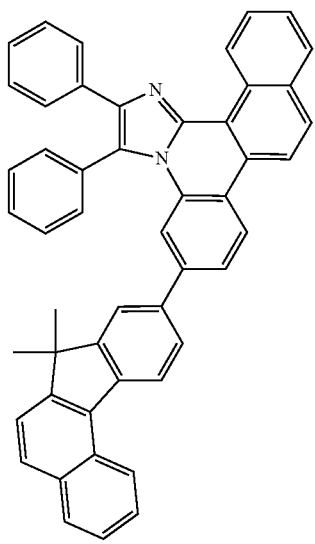
[Formula 3-4-1-5]
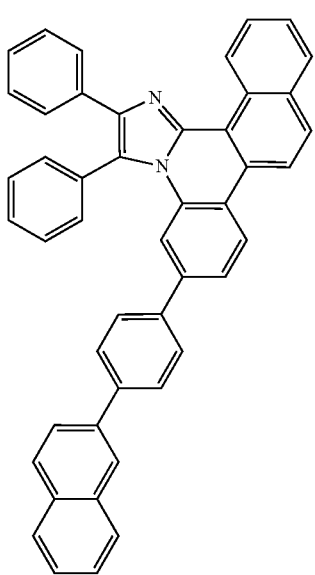
[Formula 3-4-1-7]
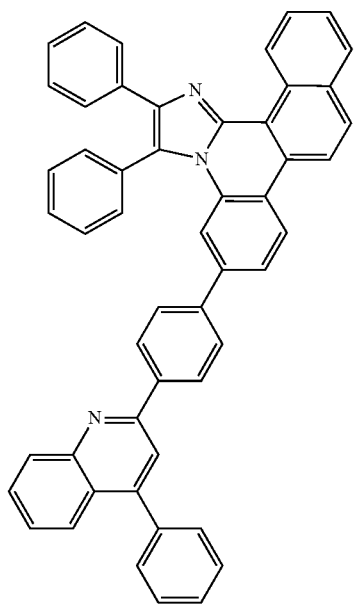

[Formula 3-4-1-8]
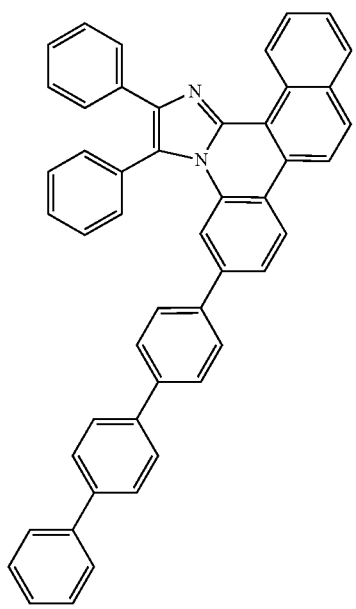
[Formula 3-4-1-9]
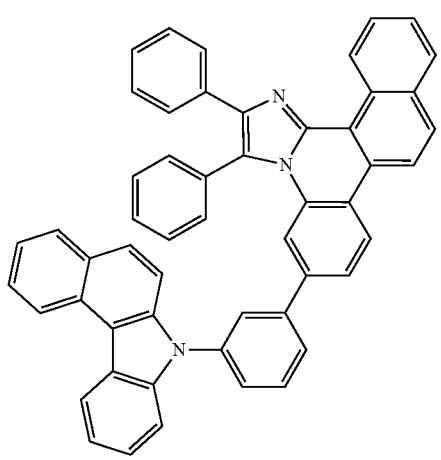
[Formula 3-4-1-10]
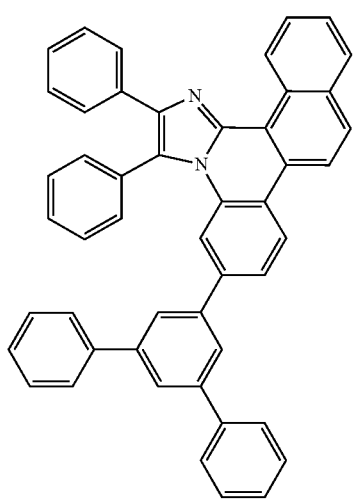
[Formula 3-4-1-11]
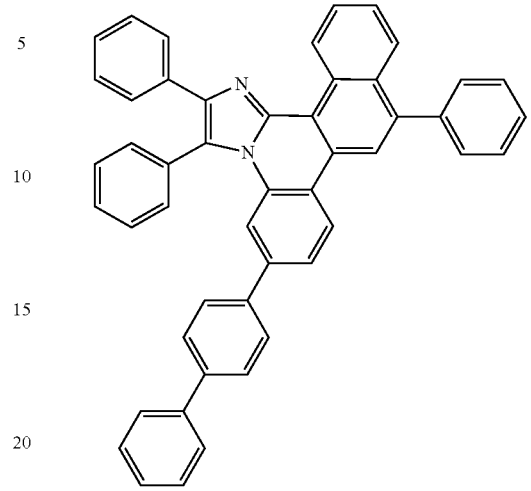
[Formula 3-4-1-12]
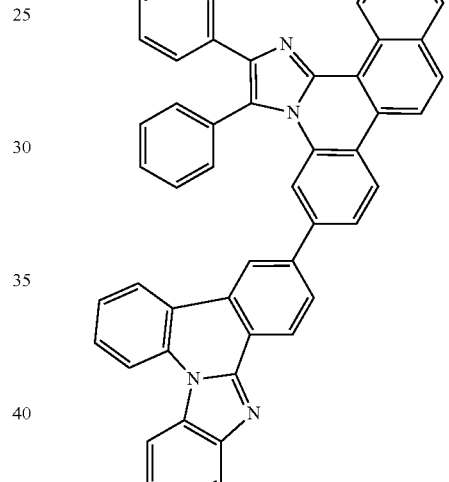
[Formula 3-5-1-1]
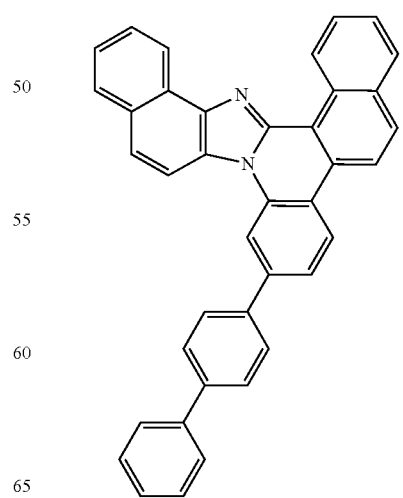

-continued
[Formula 3-5-1-2]
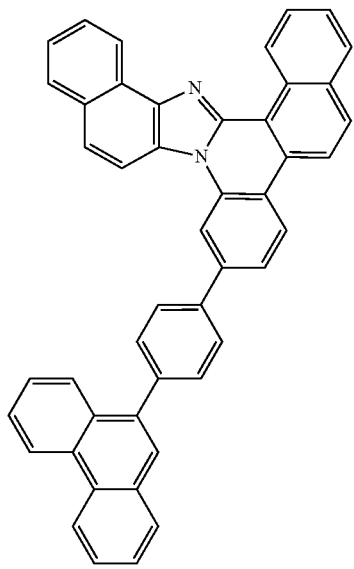
[Formula 3-5-1-3]
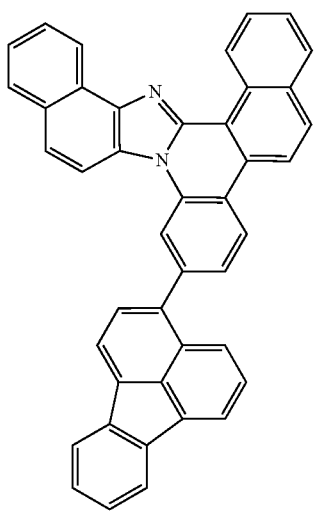
-continued
[Formula 3-5-1-4]
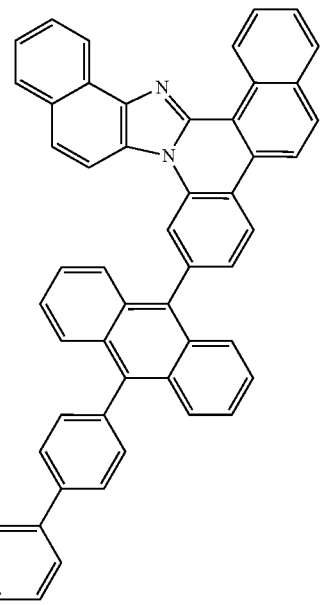
[Formula 3-5-1-5]
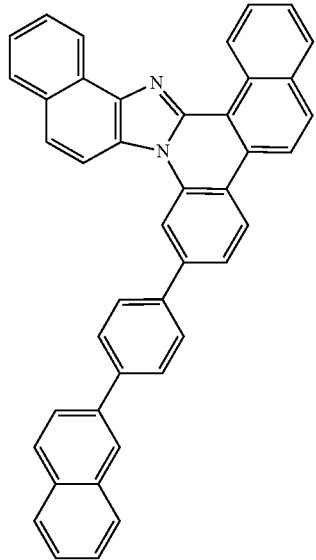

[Formula 3-5-1-6]
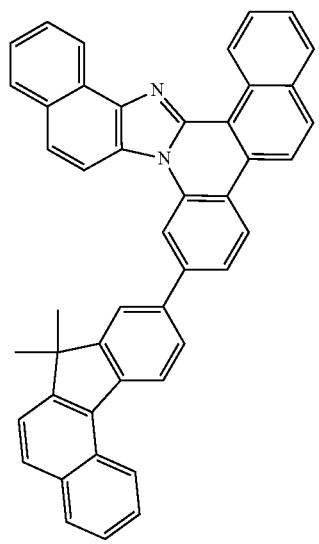
[Formula 3-5-1-8]
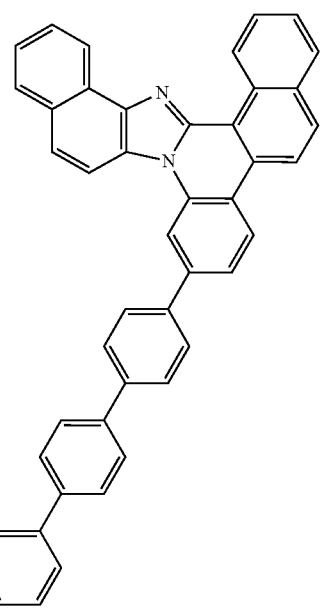
[Formula 3-5-1-9]
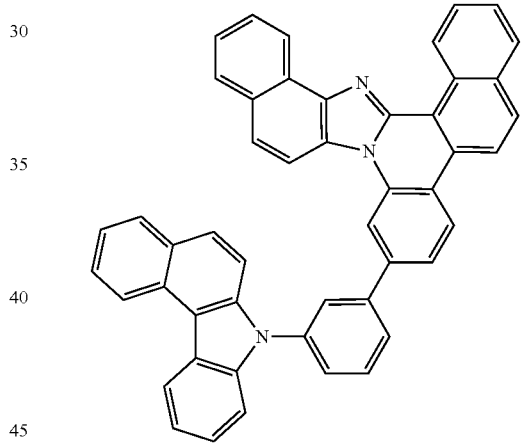
[Formula 3-5-1-7]
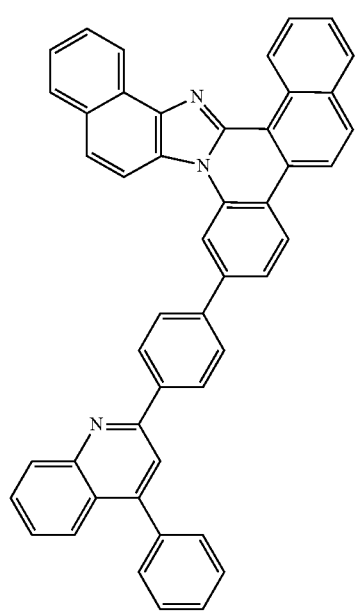
[Formula 3-5-1-10]
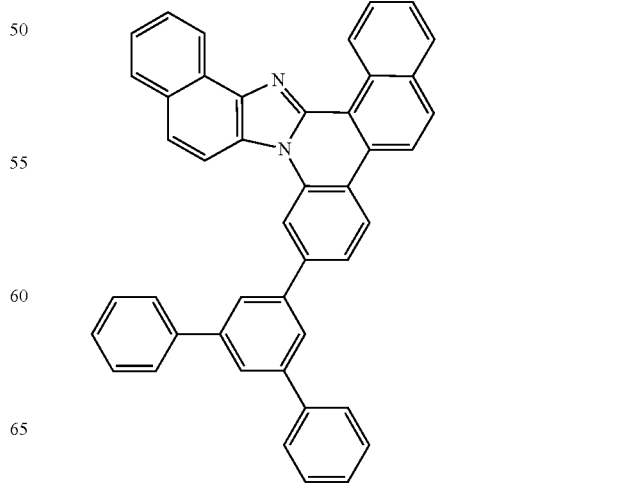

97
-continued
[Formula 3-5-1-11]
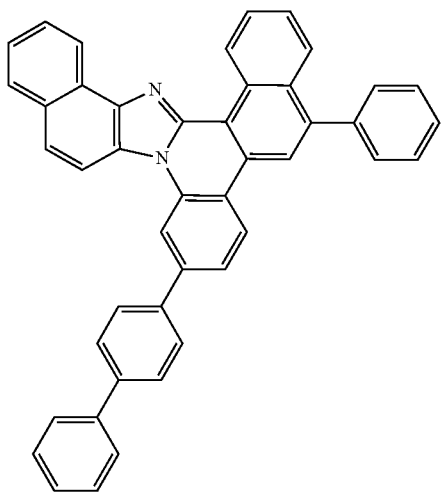
[Formula 3-5-1-12]
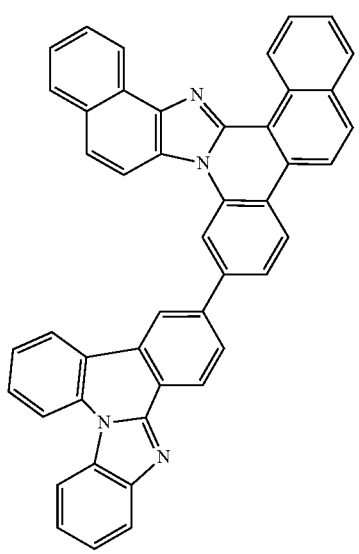
[Formula 3-6-1-1]
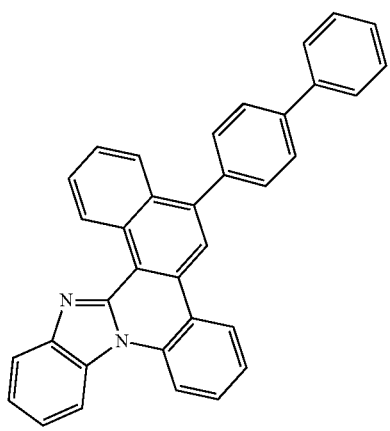
98
-continued
[Formula 3-6-1-2]
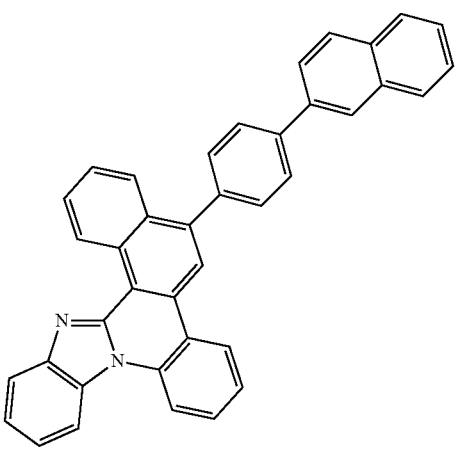
[Formula 3-6-1-3]
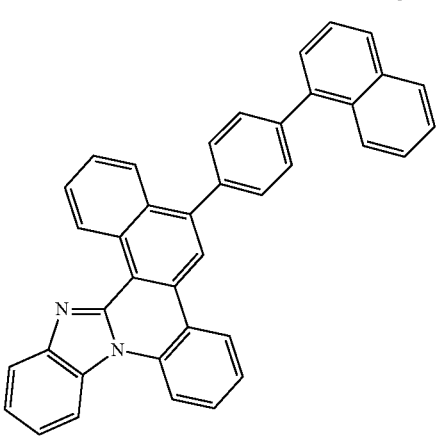
[Formula 3-6-1-4]
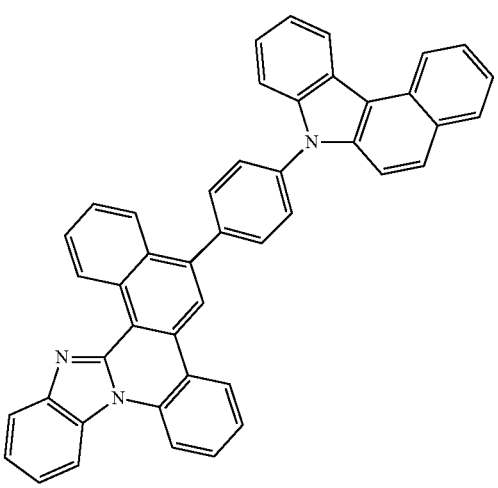

[formula 3-6-1-5]
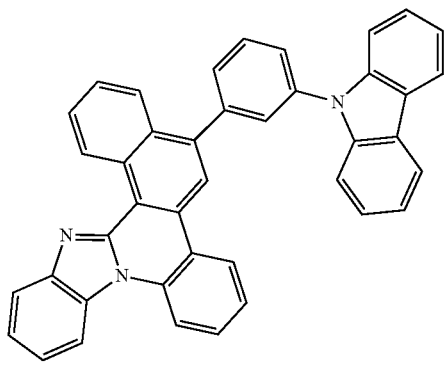
[Formula 3-6-1-6]
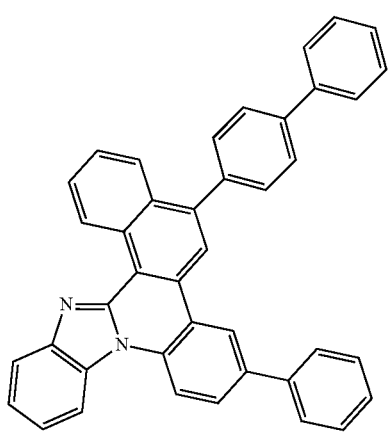
[Formula 3-6-1-7]
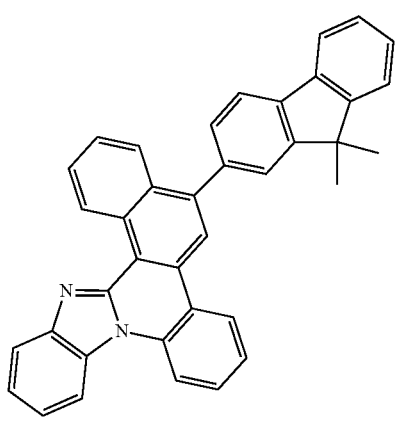
[Formula 3-6-1-8]
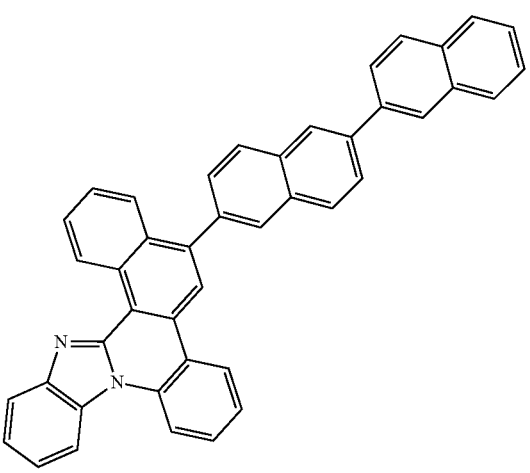
[Formula 3-6-1-9]
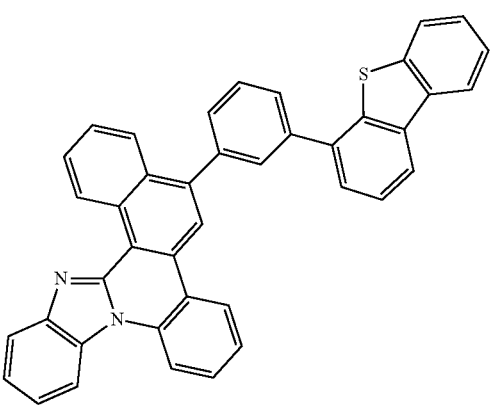
[Formula 3-6-1-10]
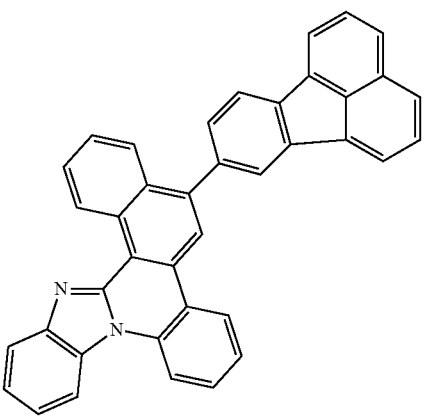

[Formula 3-6-1-11]
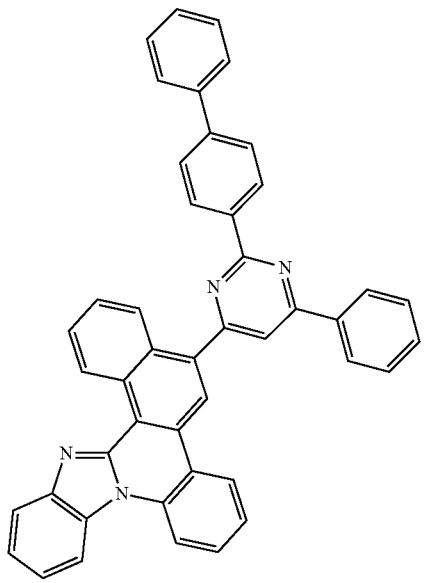
[Formula 3-6-1-12]
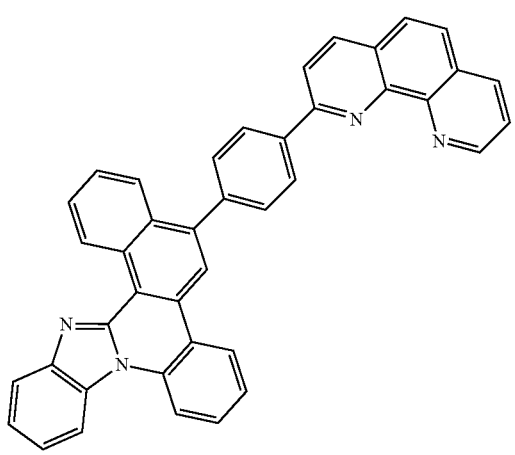
[Formula 3-6-2-1]
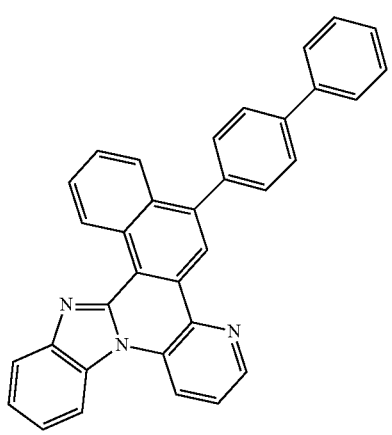
[Formula 3-6-2-2]
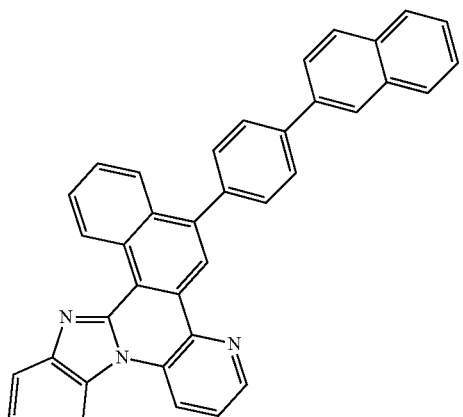
[Formula 3-6-2-3]
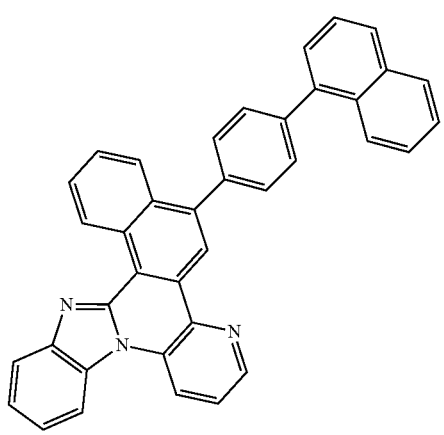
[Formula 3-6-2-4]
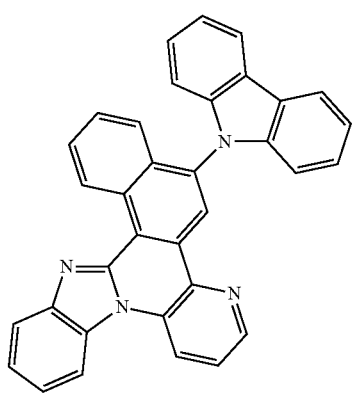

[Formula 3-6-2-5]
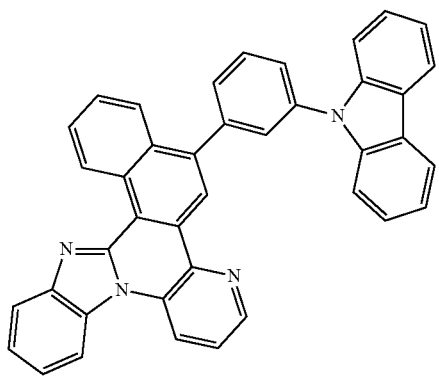
[Formula 3-6-2-6]
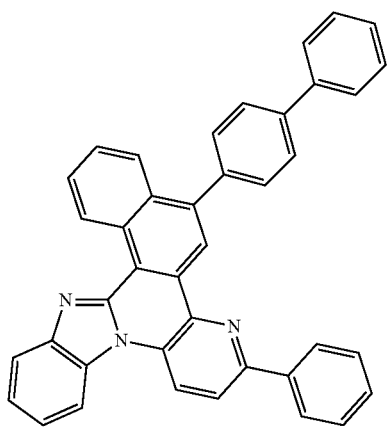
[Formula 3-6-2-7]
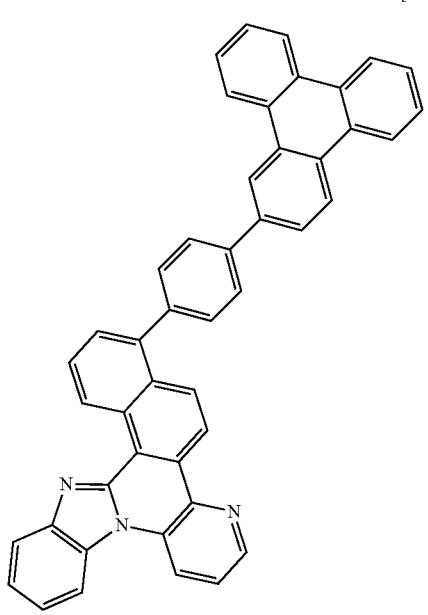
[Formula 3-6-2-8]
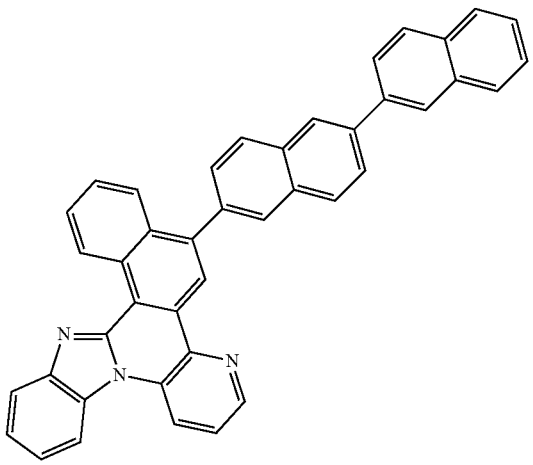
[Formula 3-6-2-9]
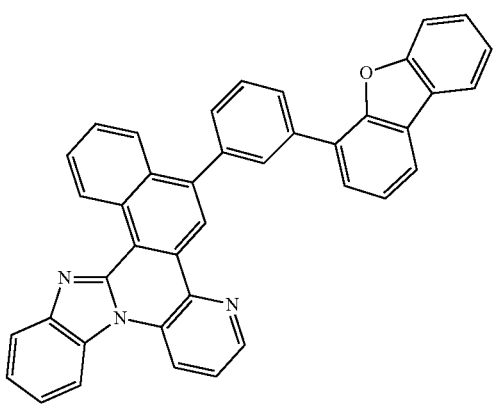
[Formula 3-6-2-10]
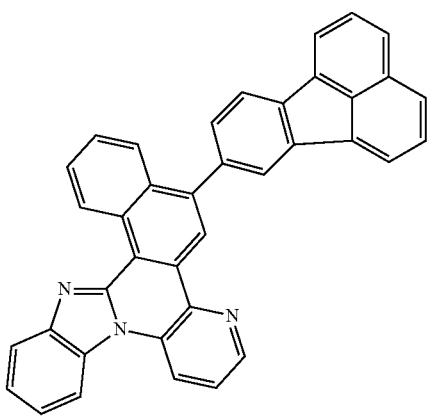

[Formula 3-6-2-11]
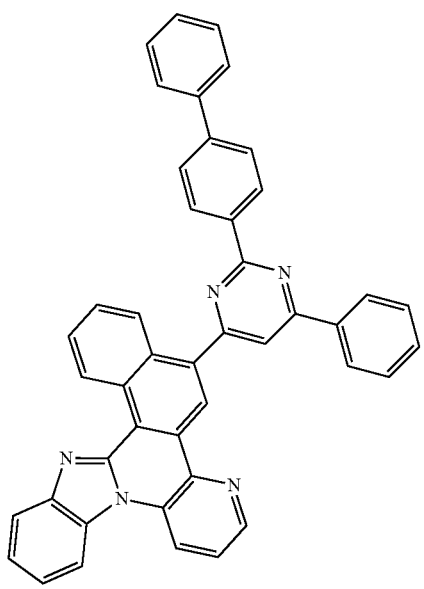
[Formula 3-6-2-12]
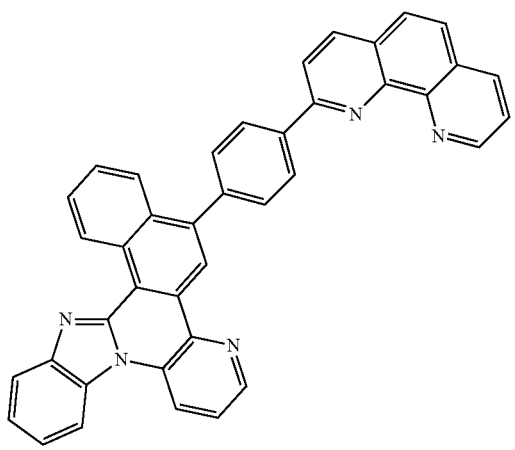
[Formula 3-7-1-1]
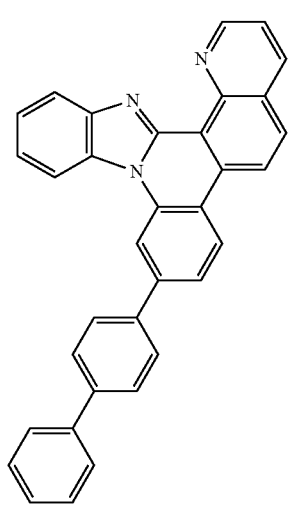
[Formula 3-7-1-2]
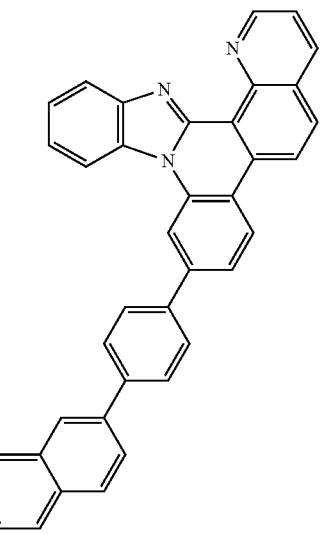
[Formula 3-7-1-3]
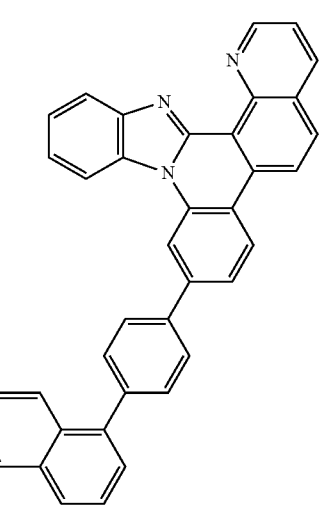
[Formula 3-7-1-4]
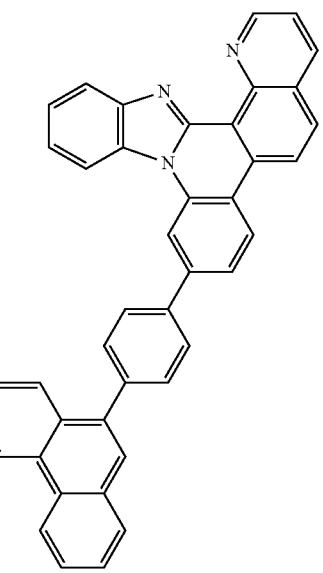

[Formula 3-7-1-5]
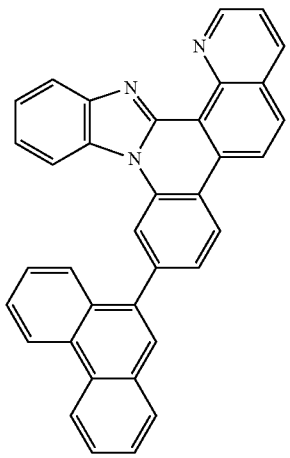
[Formula 3-7-1-6]
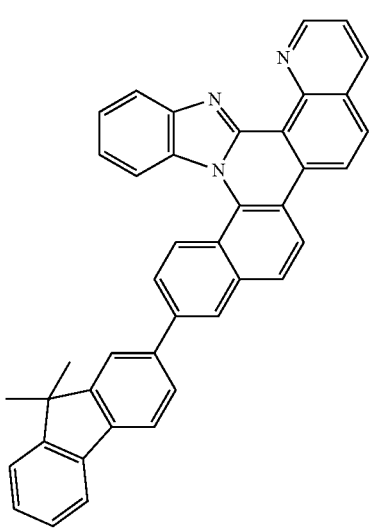
[Formula 3-7-1-7]
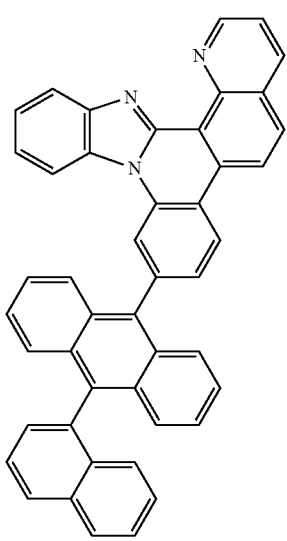
[Formula 3-7-1-8]
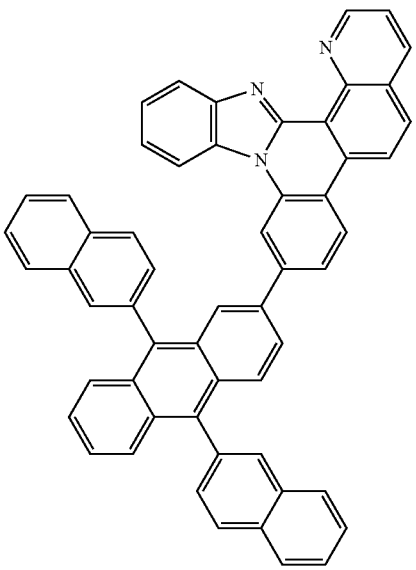
[Formula 3-7-1-9]
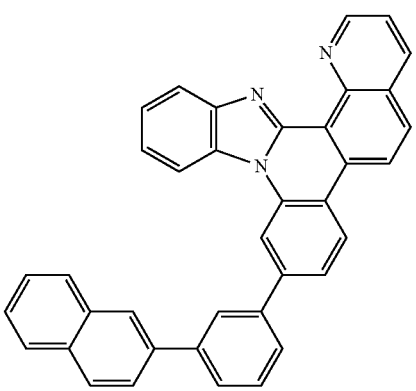
[Formula 3-7-1-10]
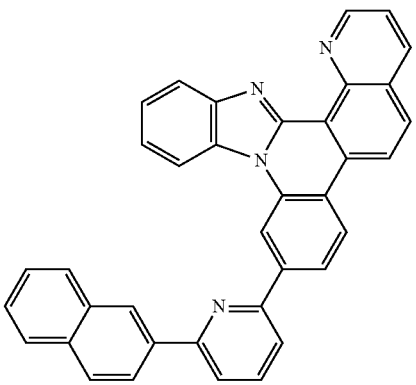

-continued
[Formula 3-7-1-11]
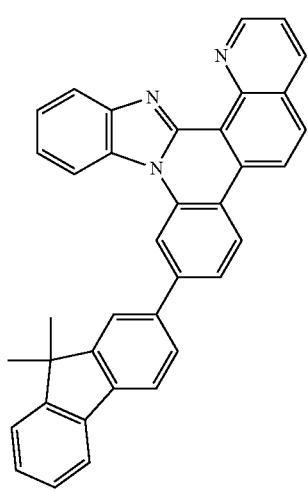
[Formula 3-7-1-12]
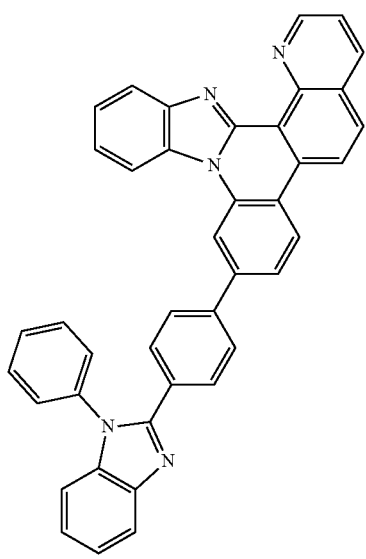
[Formula 3-7-1-13]
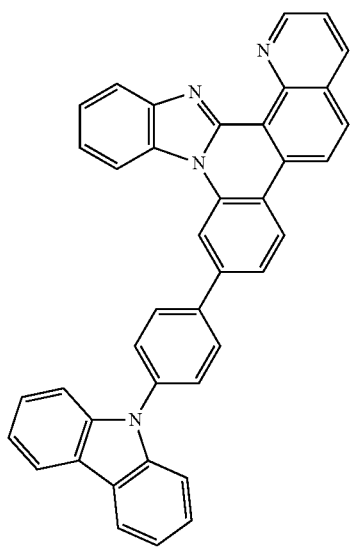
[Formula 3-7-1-14]
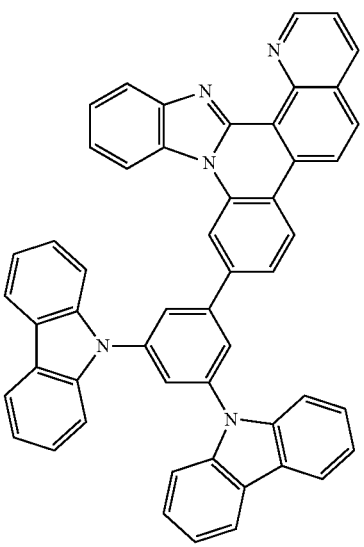
[Formula 3-7-1-15]
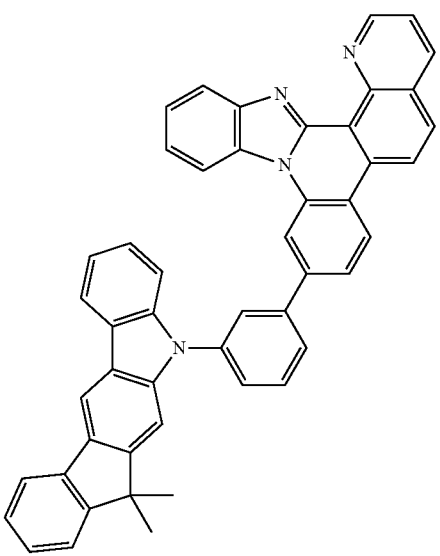

-continued
[Formula 3-7-1-16]
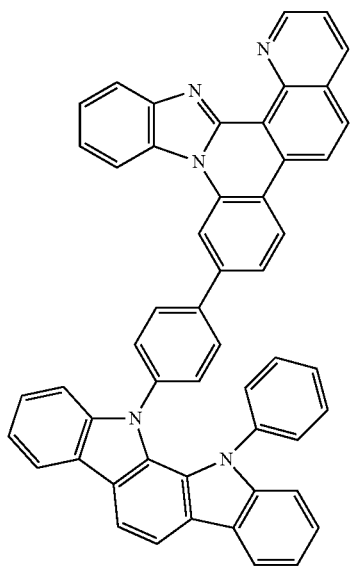
[Formula 3-7-1-17]
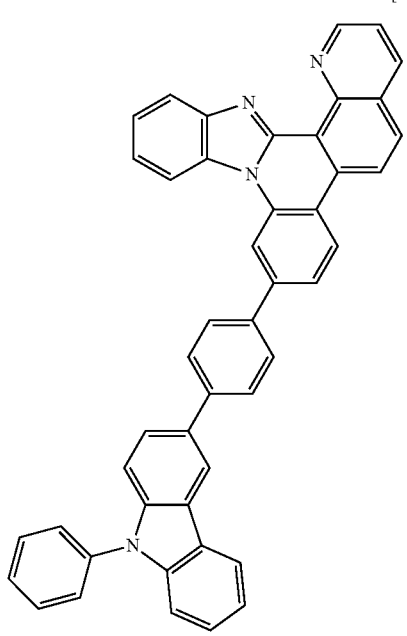
-continued
[Formula 3-7-1-18]
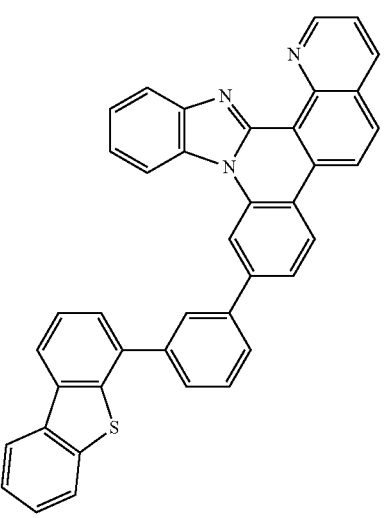
[Formula 3-7-1-19]
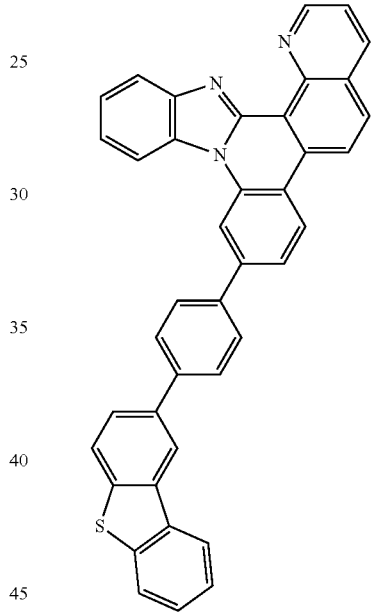
[Formula 3-7-1-20]
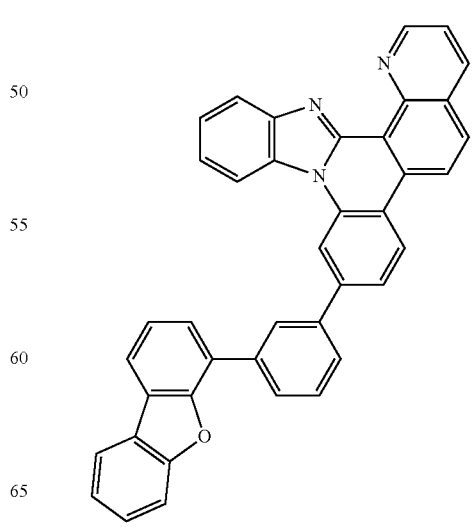

[Formula 3-7-1-21]
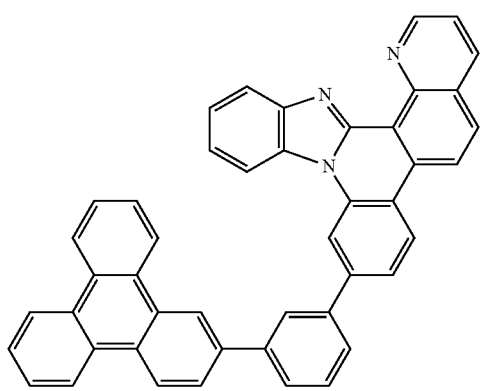
[Formula 3-7-1-22]
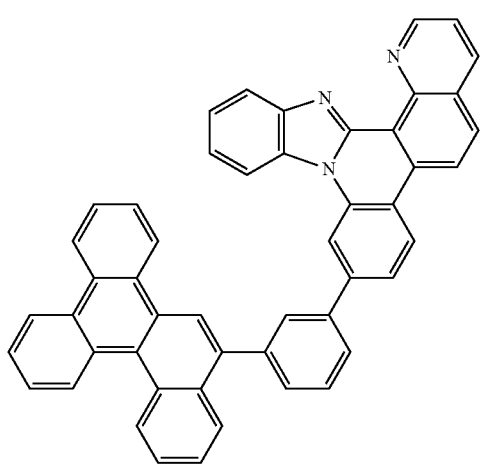
[Formula 3-7-1-23]
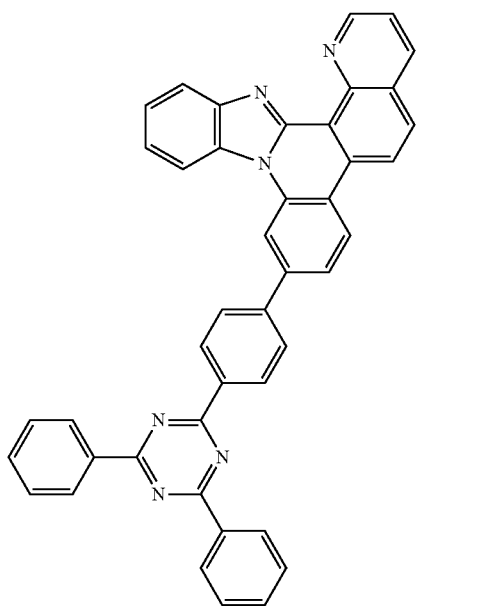
[Formula 3-7-1-24]
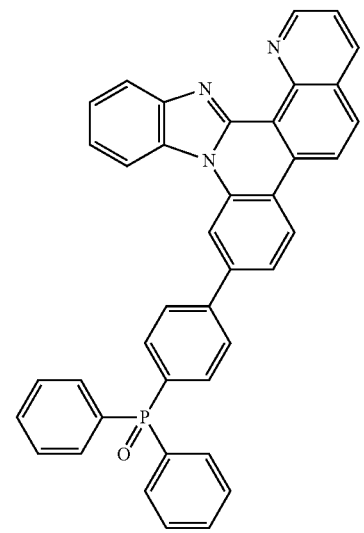
[Formula 3-7-1-25]
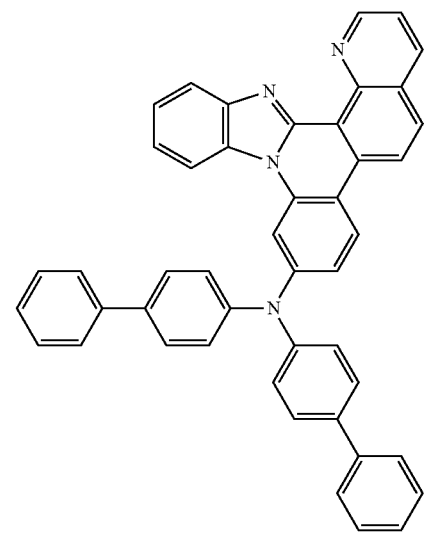
[Formula 3-7-1-26]
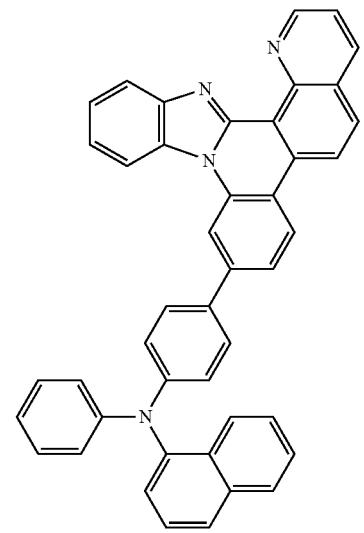

[Formula 3-7-1-27]
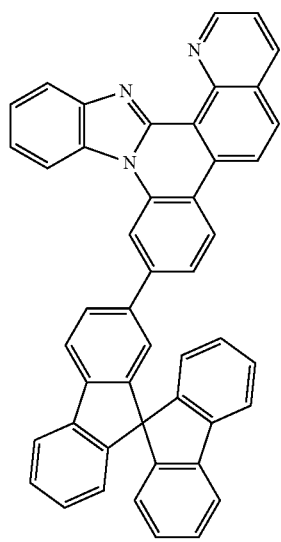
[Formula 3-7-1-28]
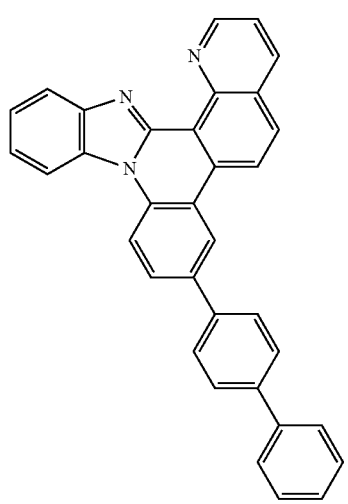
[Formula 3-7-2-1]
[Formula 3-7-2-2]
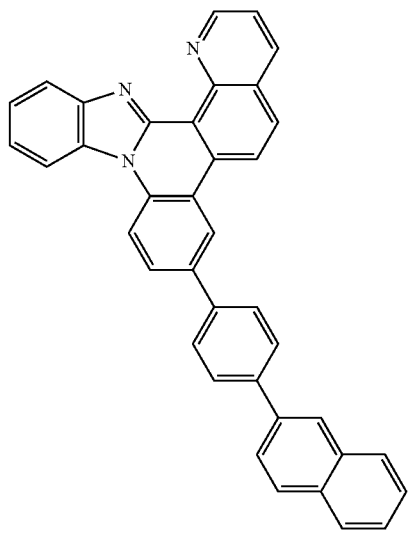
[Formula 3-7-2-3]
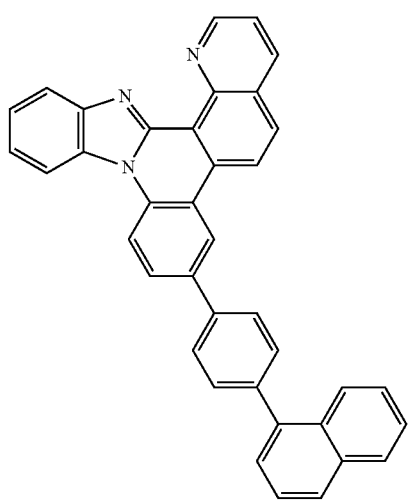
[Formula 3-7-2-4]
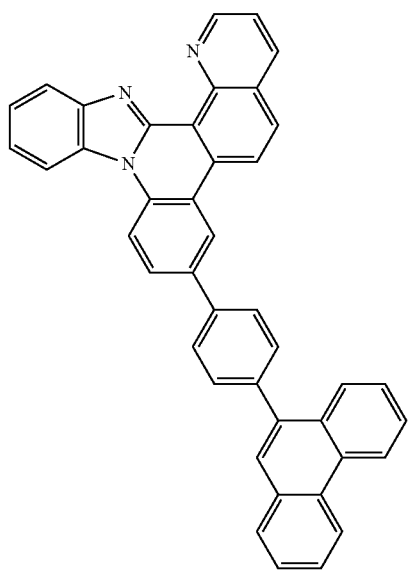

[Formula 3-7-2-5]
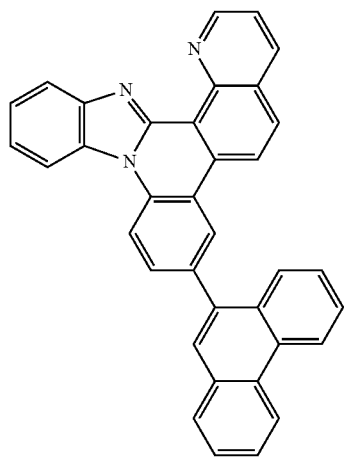
[Formula 3-7-2-6]
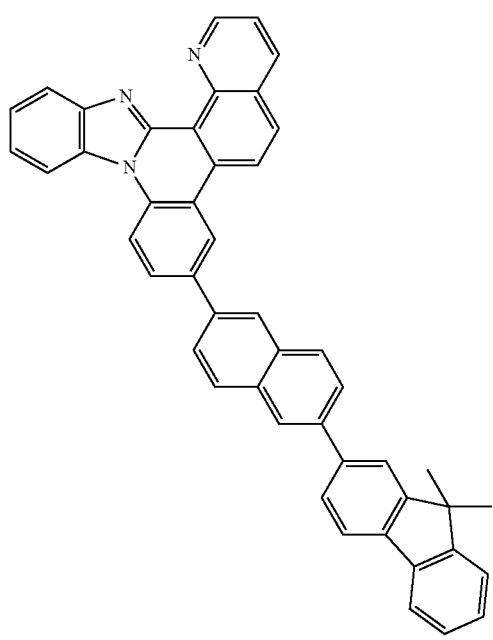
[Formula 3-7-2-7]
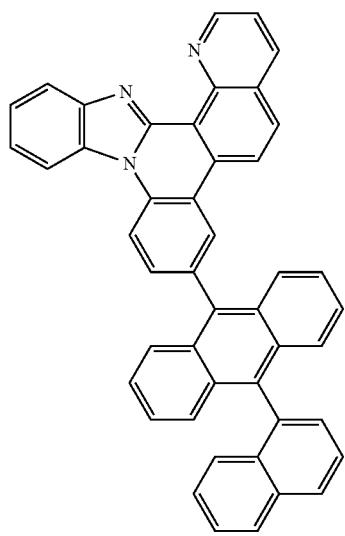
[Formula 3-7-2-8]
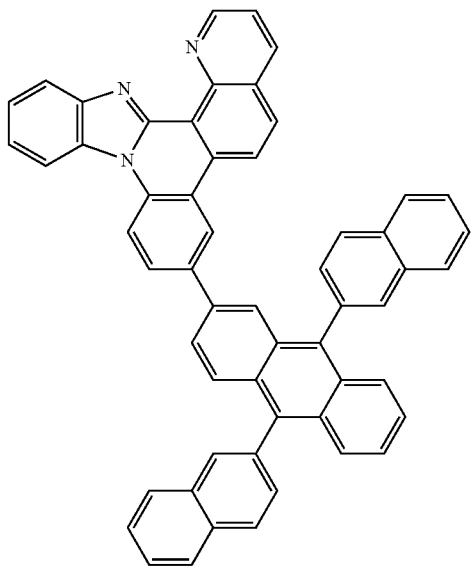
[Formula 3-7-2-9]
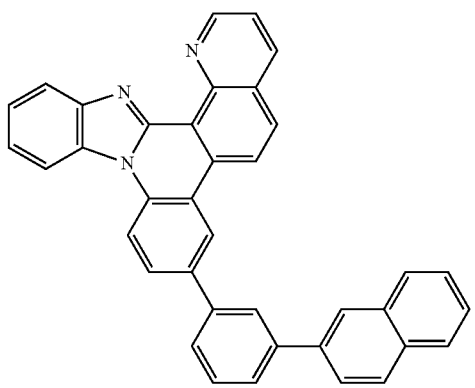
[Formula 3-7-2-10]
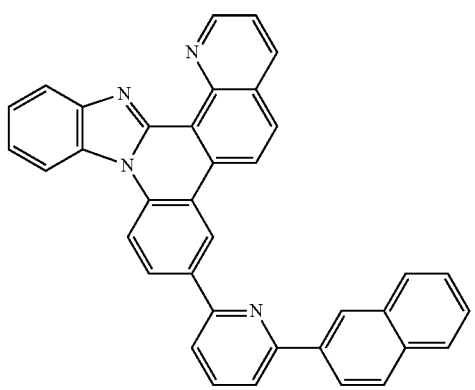

[Formula 3-7-2-11]
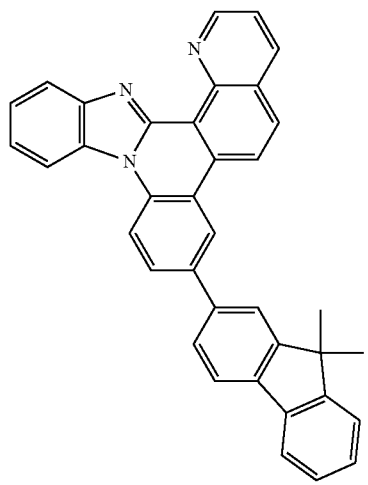
[Formula 3-7-2-12]
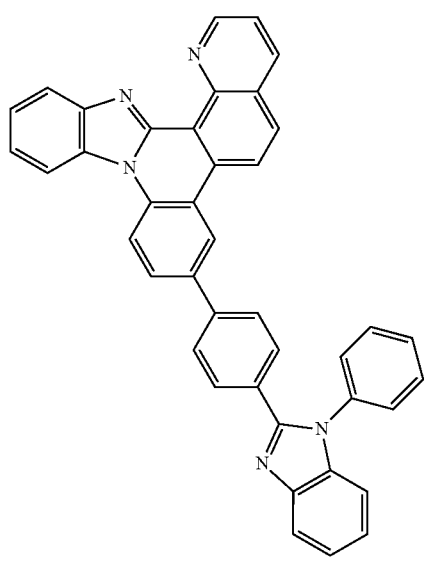
[Formula 3-7-2-13]
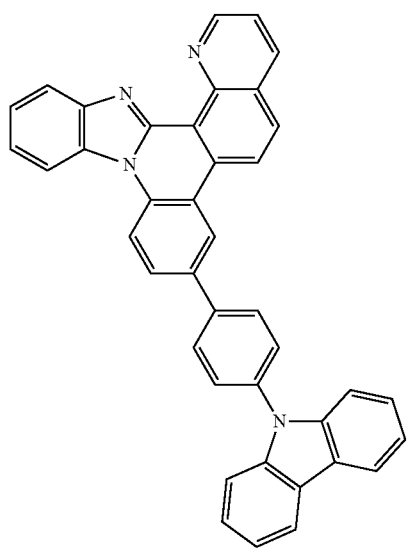
[Formula 3-7-2-14]
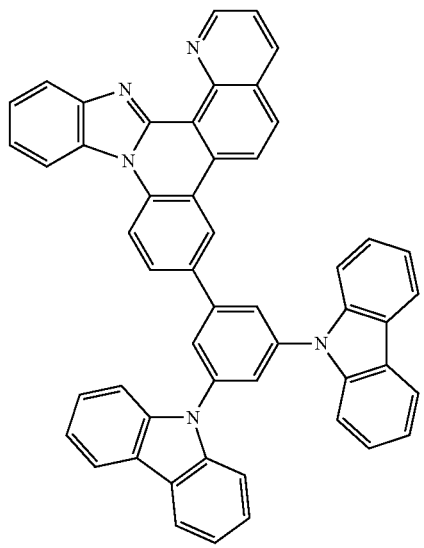
[Formula 3-7-2-15]
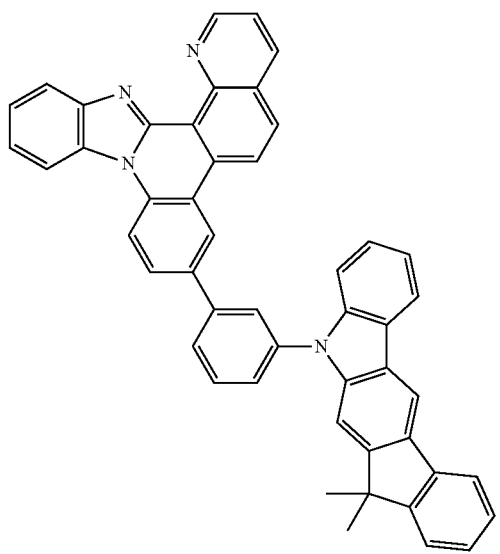
[Formula 3-7-2-16]
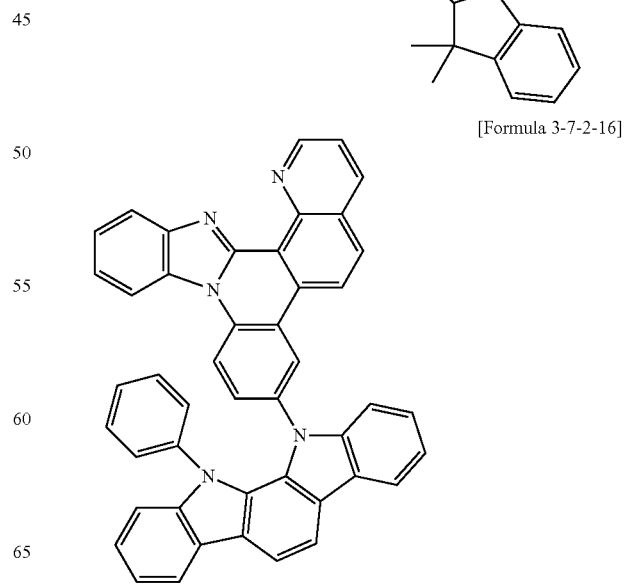

[Formula 3-7-2-17]
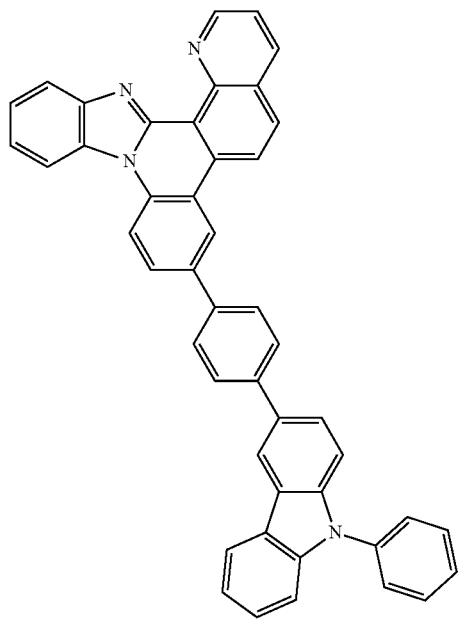
[Formula 3-7-2-18]
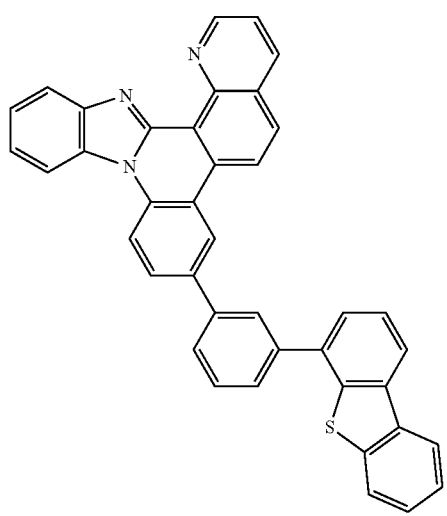
[Formula 3-7-2-19]
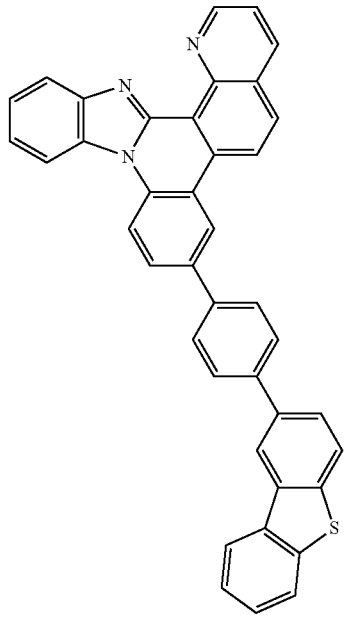
[Formula 3-7-2-20]
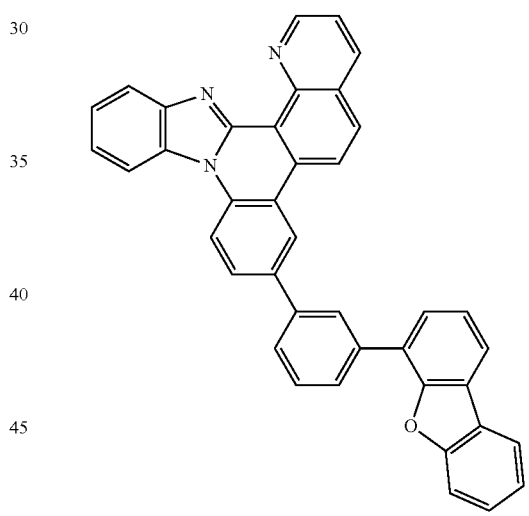
[Formula 3-7-2-21]
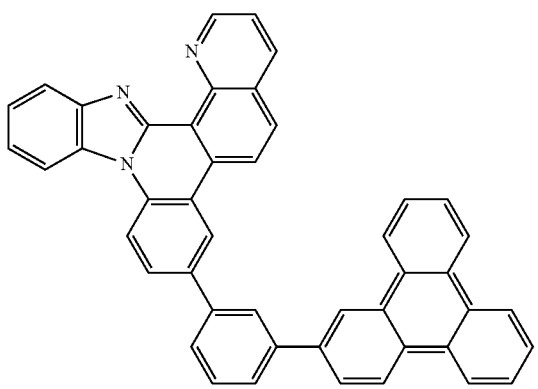

123
-continued
[Formula 3-7-2-22]
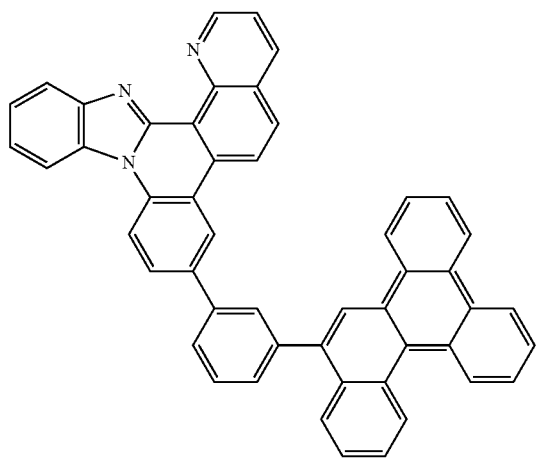
[Formula 3-7-2-23]
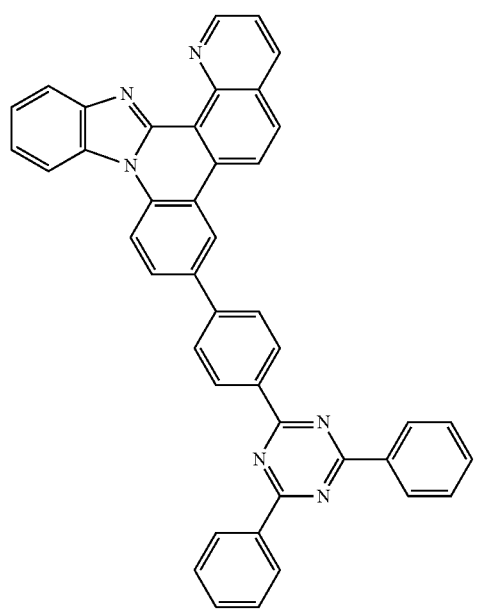
[Formula 3-7-2-24]
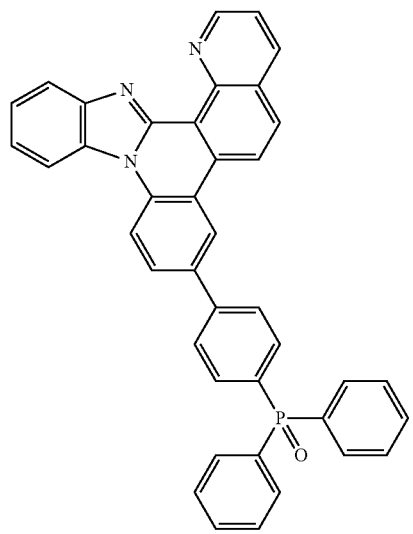
124
-continued
[Formula 3-7-2-25]
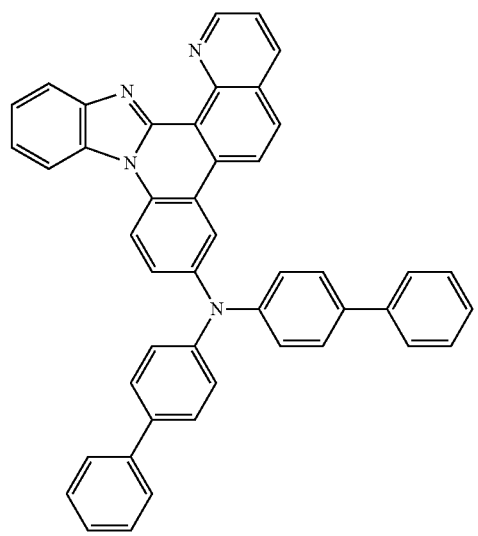
[Formula 3-7-2-26]
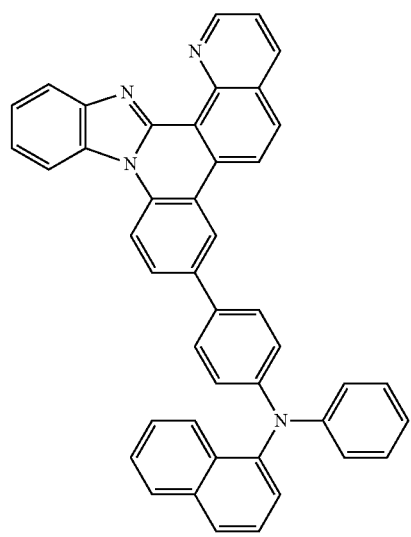
[Formula 3-7-2-27]
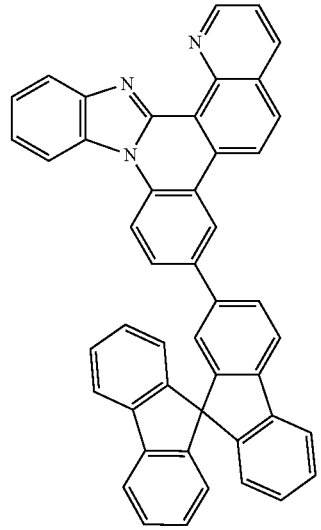

[Formula 3-7-2-28]
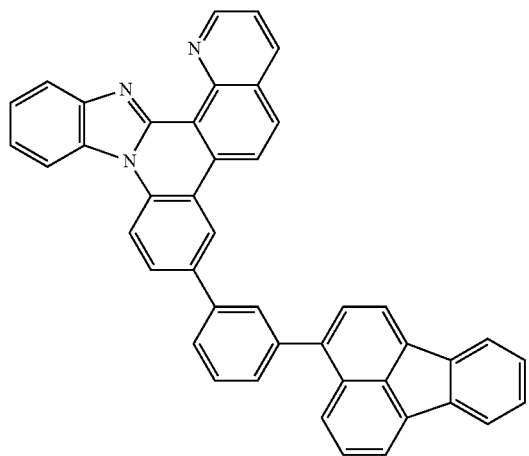
[Formula 3-8-1-3]
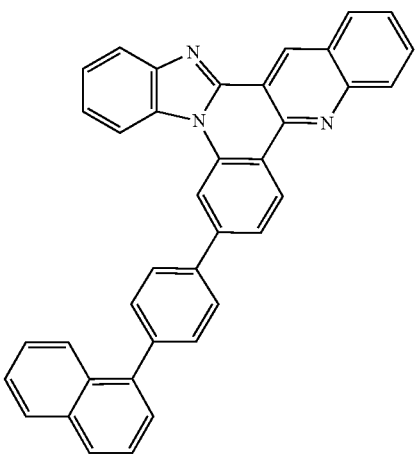
[Formula 3-8-1-1]
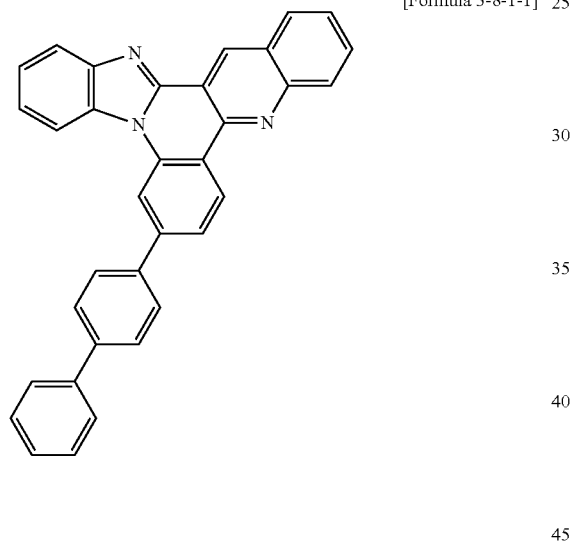
[Formula 3-8-1-4]
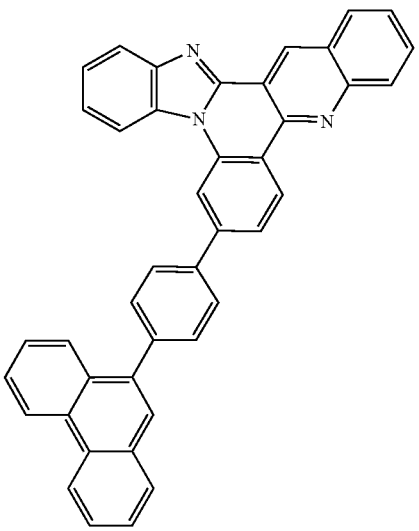
[Formula 3-8-1-2]
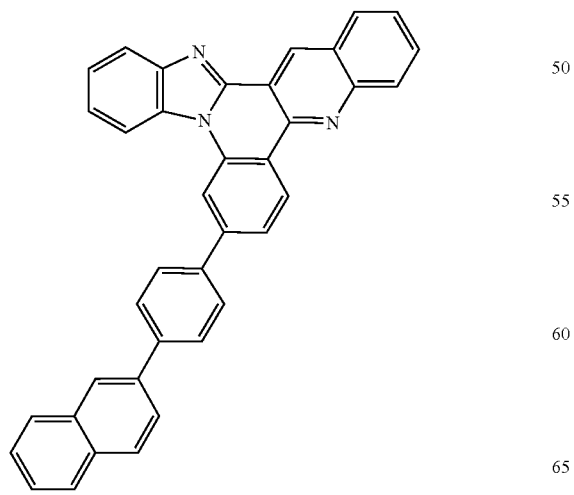
[Formula 3-8-1-5]
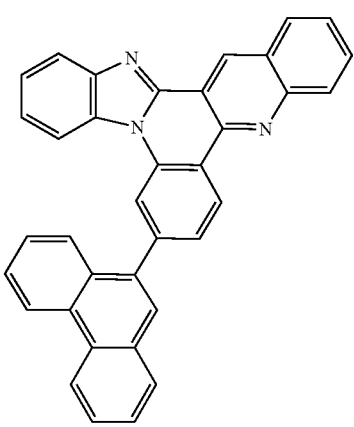

[Formula 3-8-1-6]
[Formula 3-8-1-9]
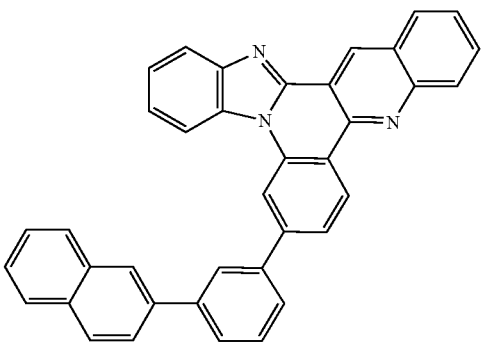
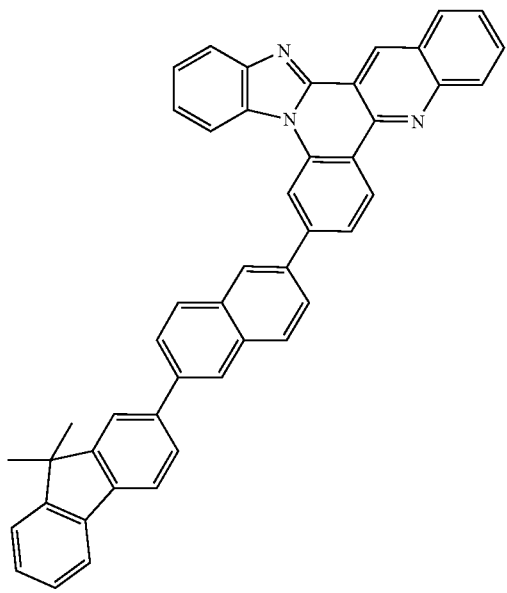
[Formula 3-8-1-7]
[Formula 3-8-1-10]
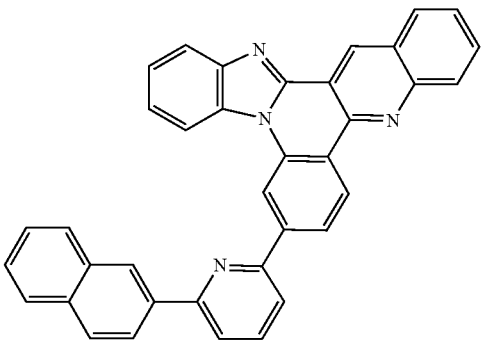
[Formula 3-8-1-8]
[Formula 3-8-1-11]
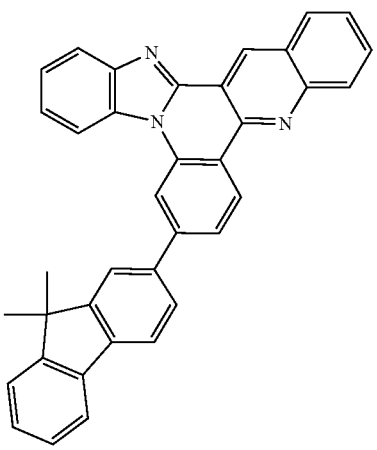

-continued
[Formula 3-8-1-12]
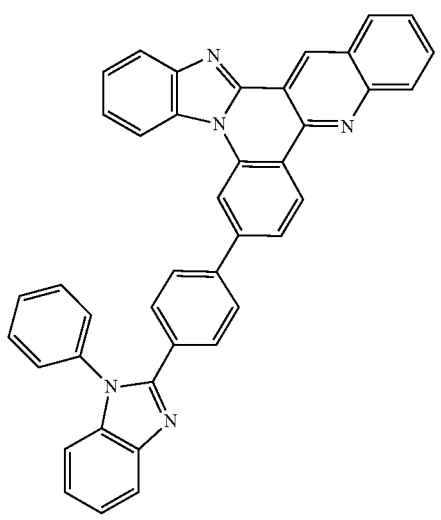
[Formula 3-8-1-13]
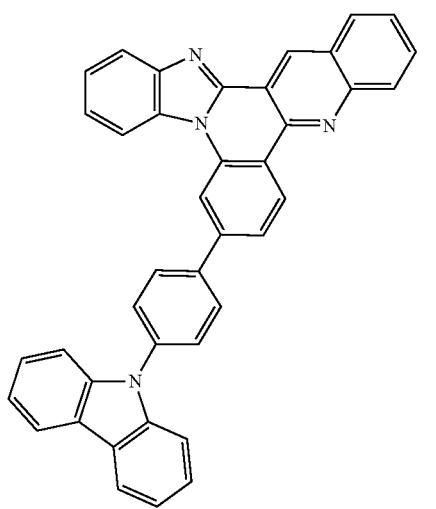
[Formula 3-8-1-14]
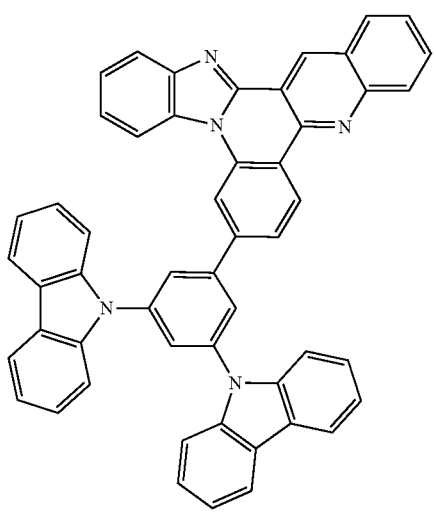
-continued
[Formula 3-8-1-15]
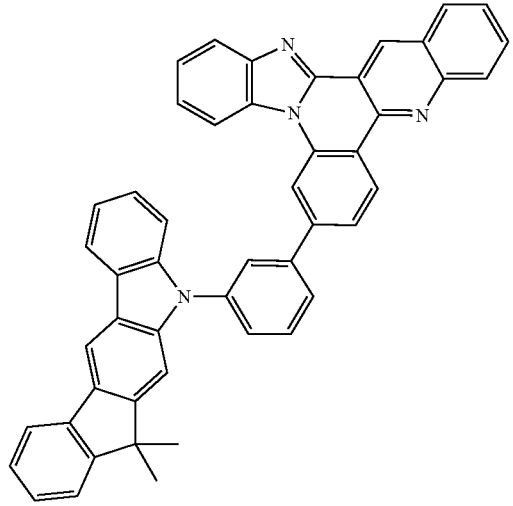
[Formula 3-8-1-16]
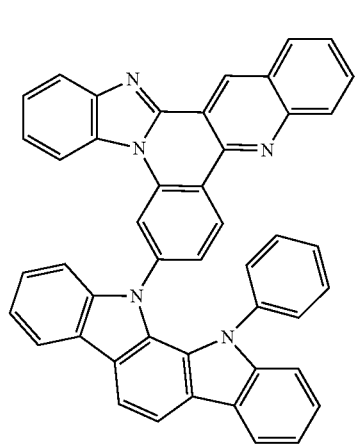
[Formula 3-8-1-17]
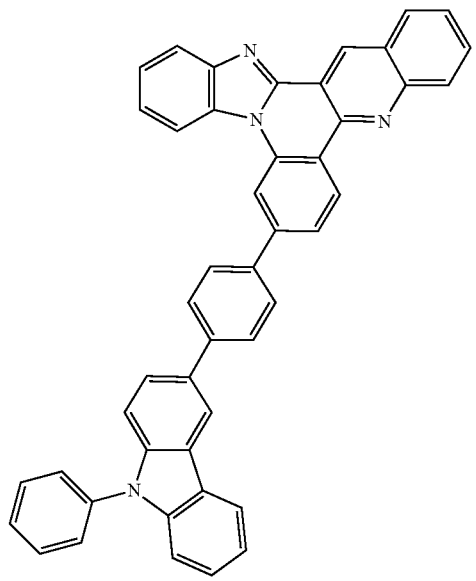

[Formula 3-8-1-18]
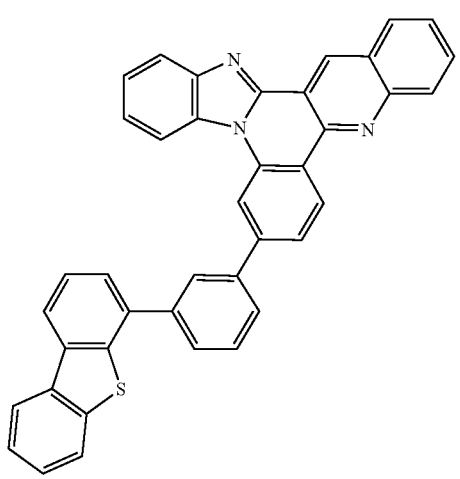
[Formula 3-8-1-19]
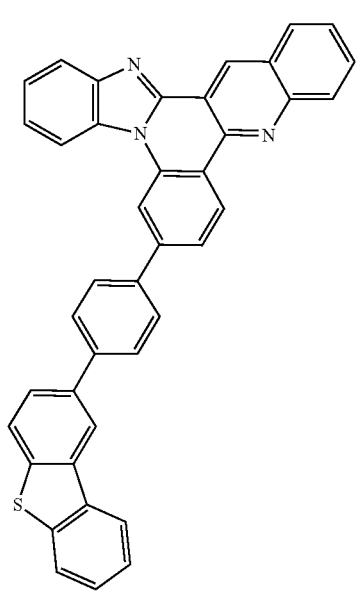
[Formula 3-8-1-20]
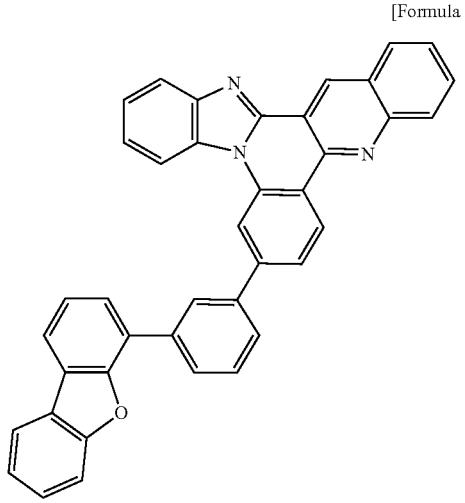
[Formula 3-8-1-21]
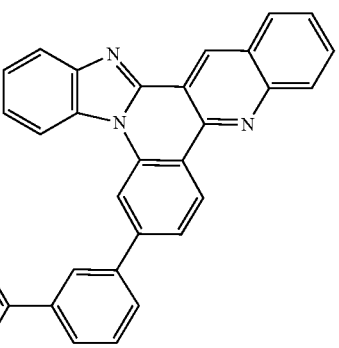
[Formula 3-8-1-22]
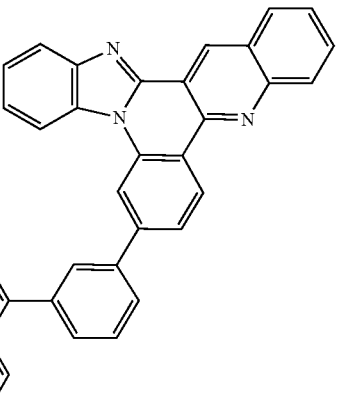
[Formula 3-8-1-23]
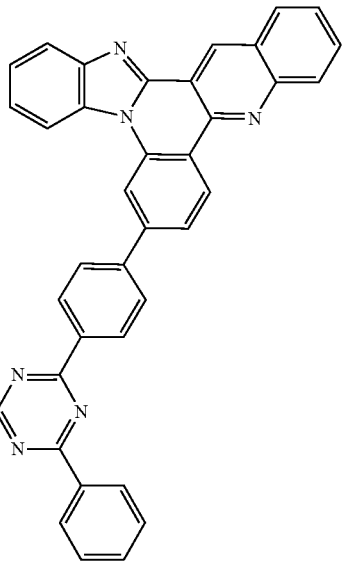

[Formula 3-8-1-24]
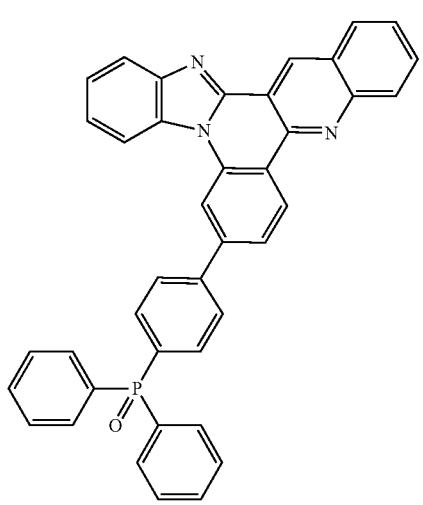
[Formula 3-8-1-25]
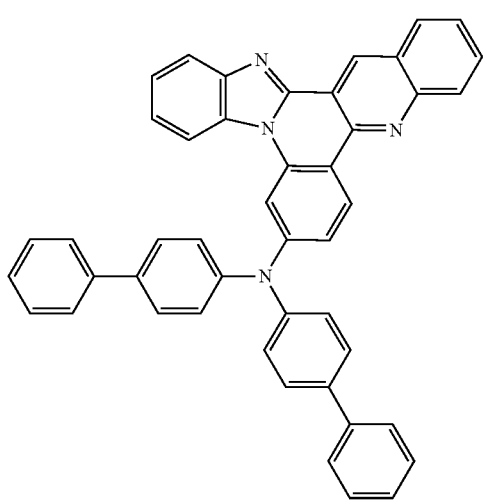
[Formula 3-8-1-26]
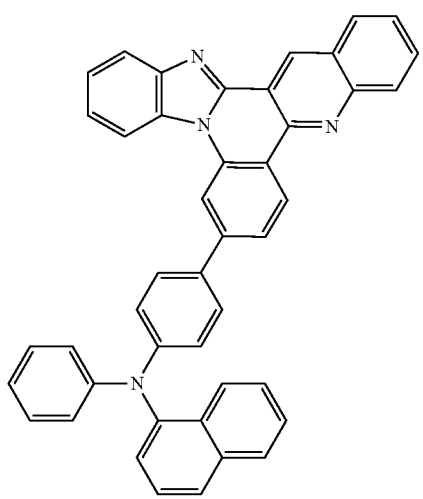
[Formula 3-8-1-27]
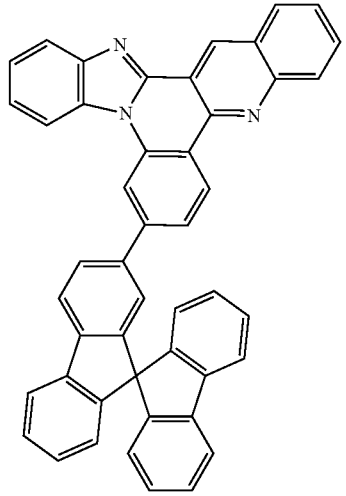
[Formula 3-8-1-28]
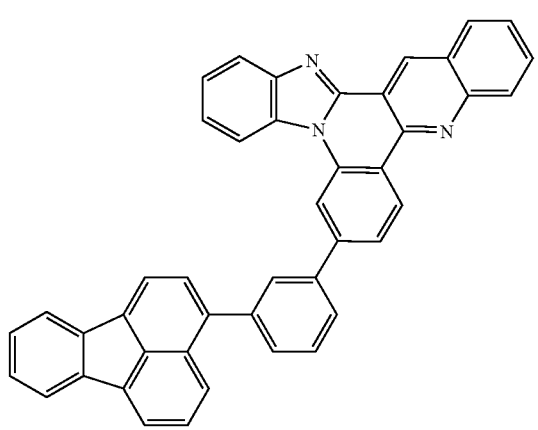
[Formula 3-8-2-1]
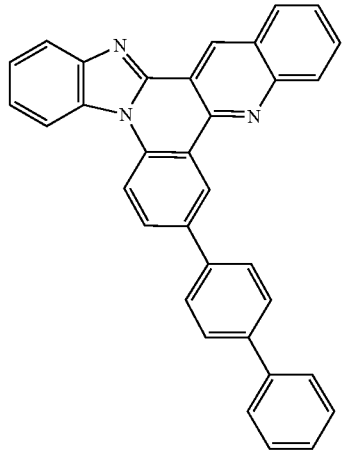

[Formula 3-8-2-2]
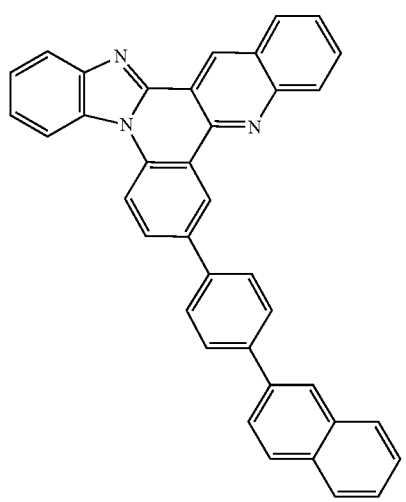
[Formula 3-8-2-3]
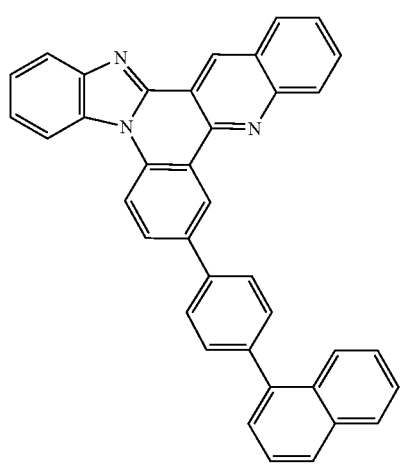
[Formula 3-8-2-4]
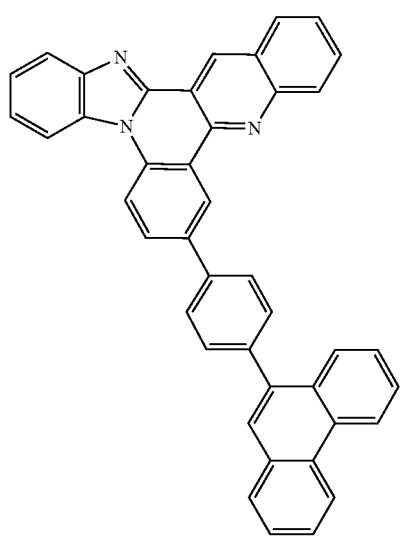
[Formula 3-8-2-5]
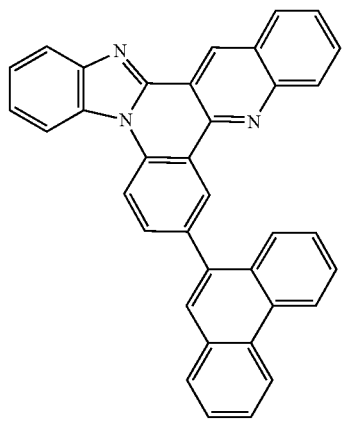
[Formula 3-8-2-6]
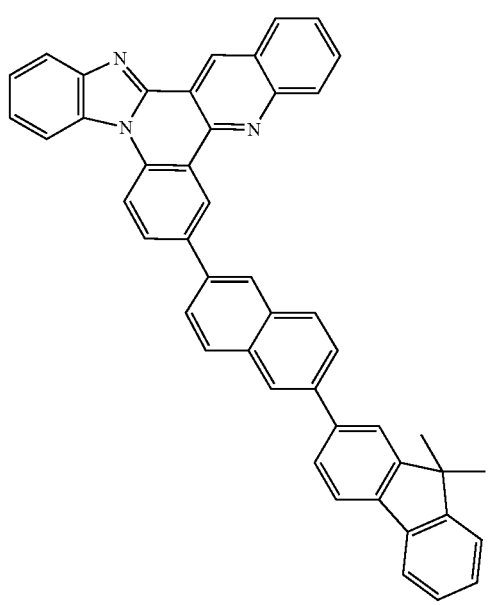
[Formula 3-8-2-7]
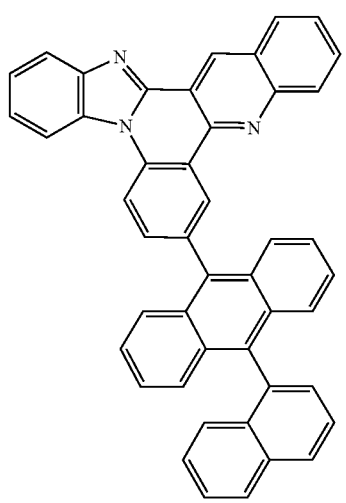

[Formula 3-8-2-8]
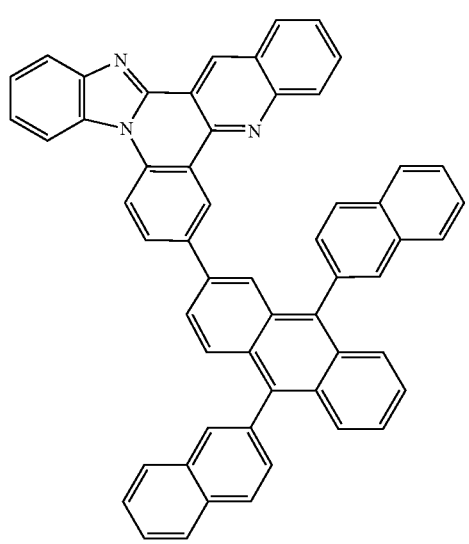
[Formula 3-8-2-9]
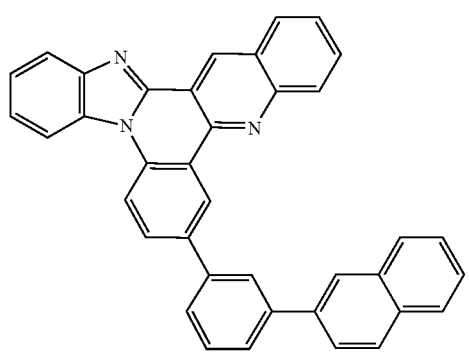
[Formula 3-8-2-10]
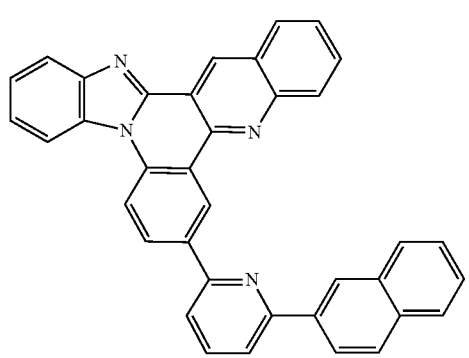
[Formula 3-8-2-11]
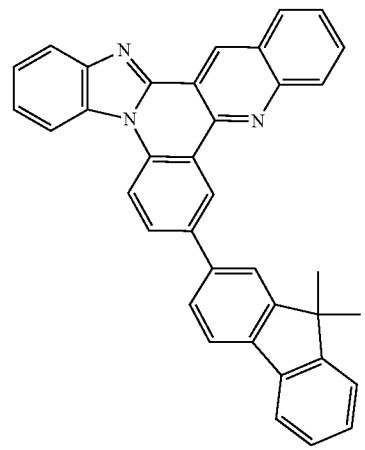
[Formula 3-8-2-12]
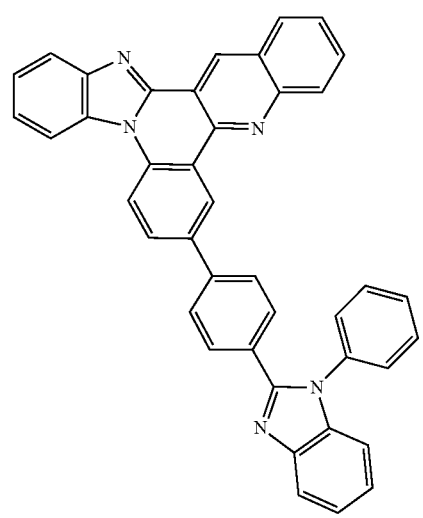
[Formula 3-8-2-13]
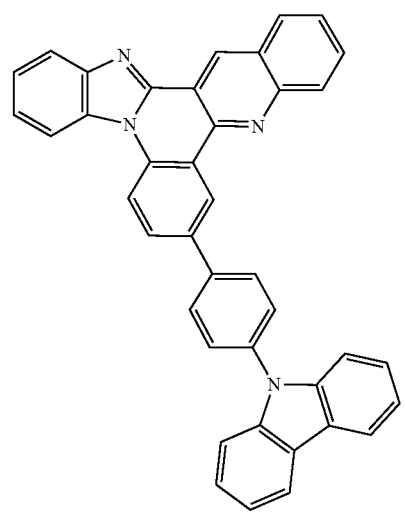

[Formula 3-8-2-14]
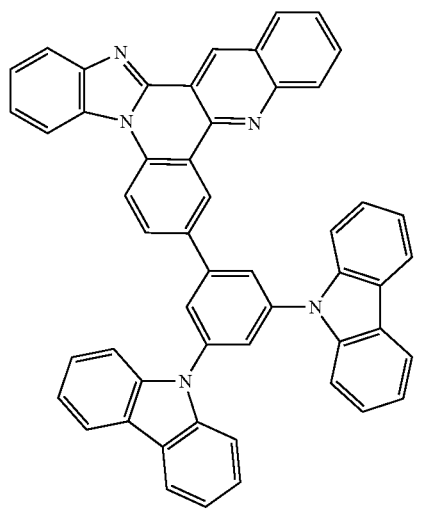
[Formula 3-8-2-15]
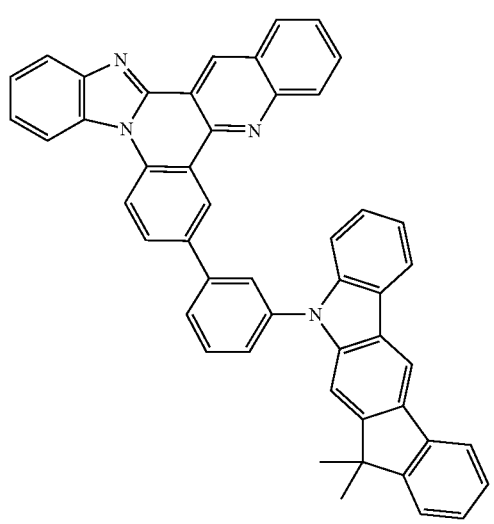
[Formula 3-8-2-16]
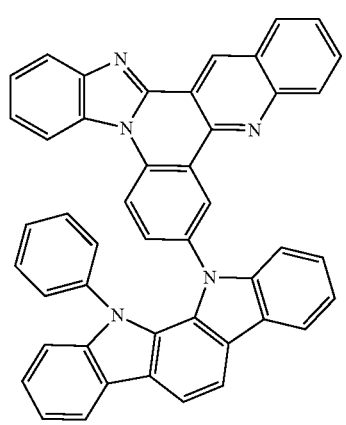
[Formula 3-8-2-17]
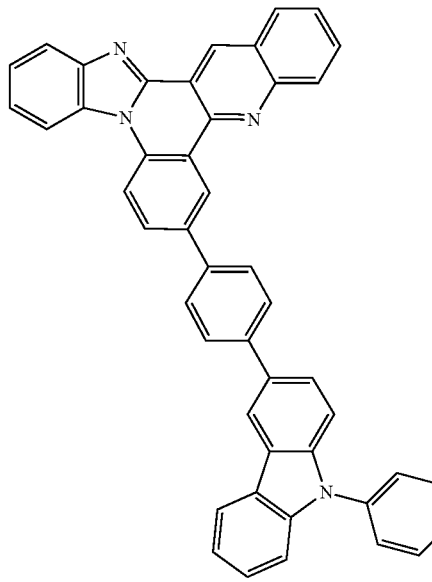
[Formula 3-8-2-18]
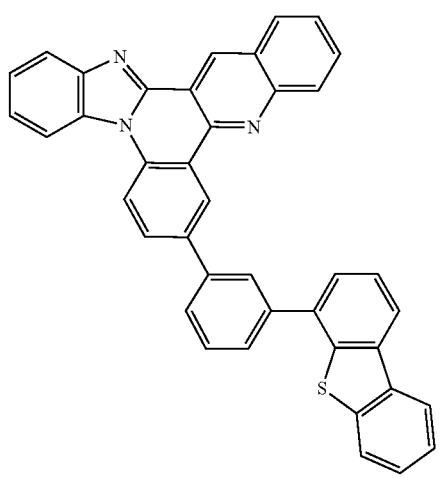
[Formula 3-8-2-19]
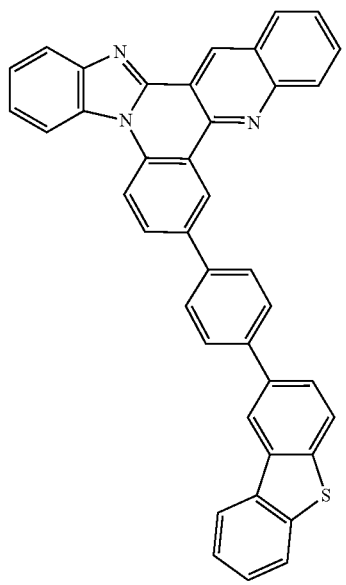

[Formula 3-8-2-20]
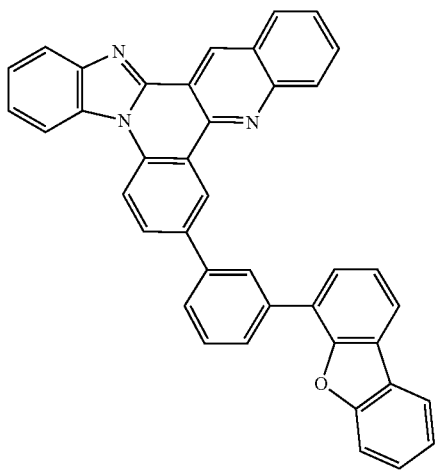
[Formula 3-8-2-21]
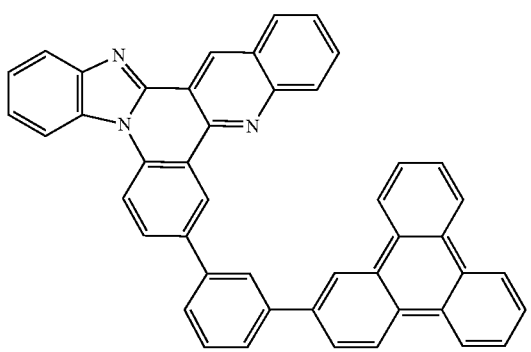
[Formula 3-8-2-22]
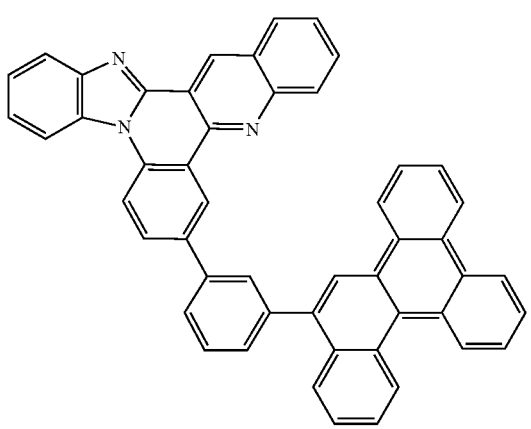
[Formula 3-8-2-23]
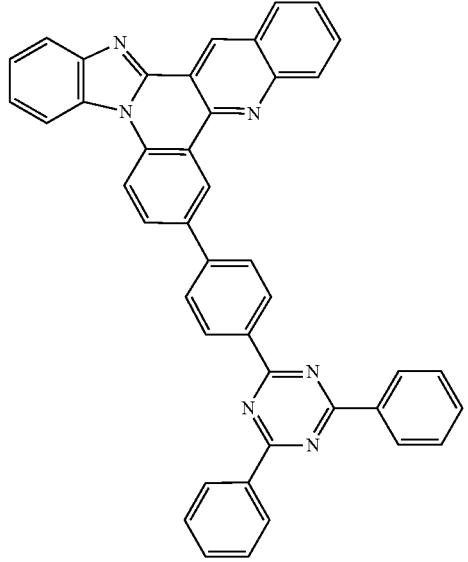
[Formula 3-8-2-24]
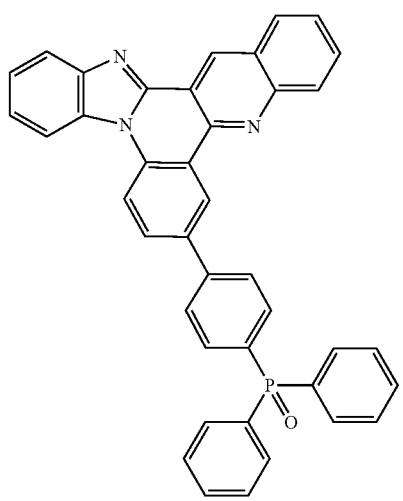
[Formula 3-8-2-25]
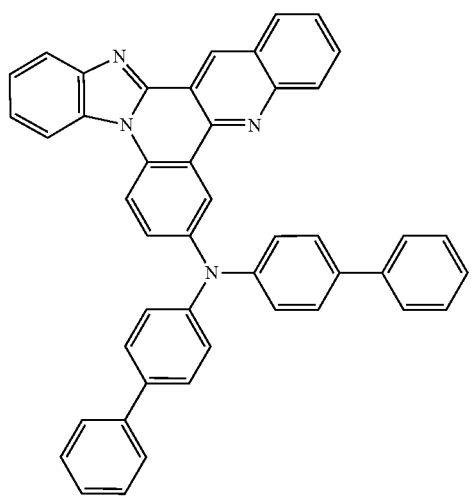

[Formula 3-8-2-26]
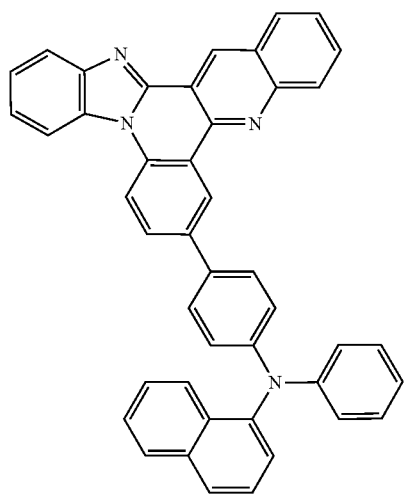
[Formula 3-9-1-1]
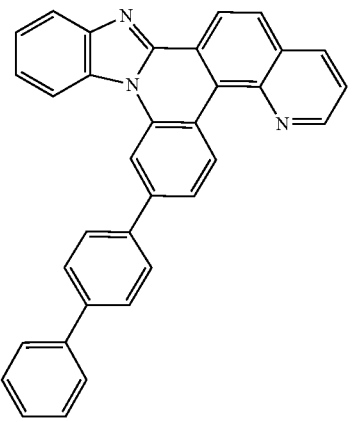
[Formula 3-8-2-27]
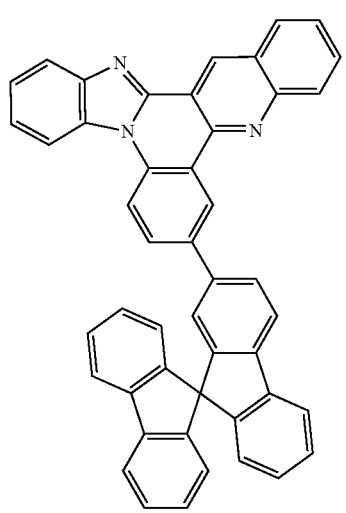
[Formula 3-9-1-2]
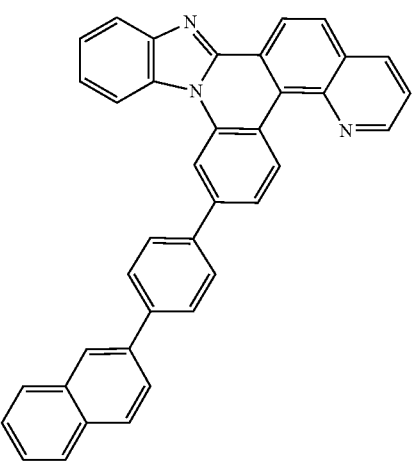
[Formula 3-8-2-28]
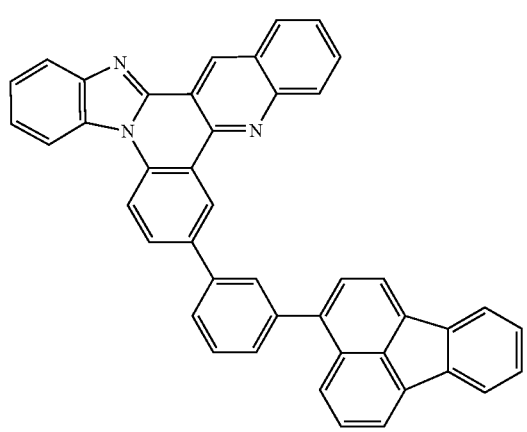
[Formula 3-9-1-3]
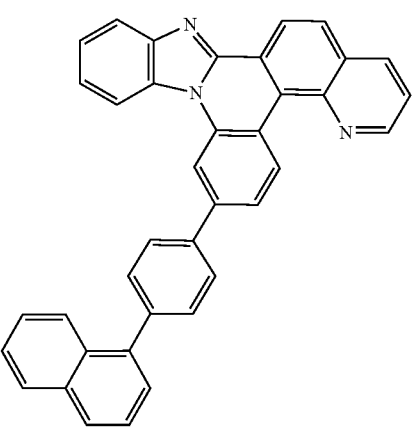

[Formula 3-9-1-4]
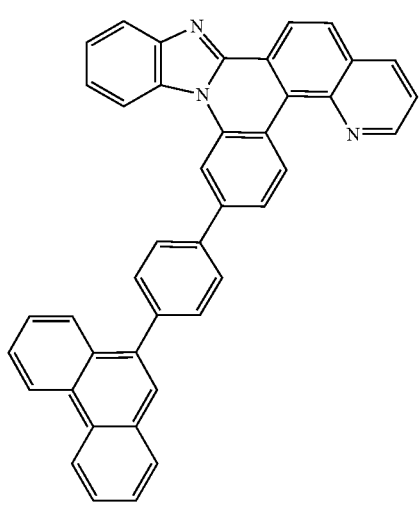
[Formula 3-9-1-5]
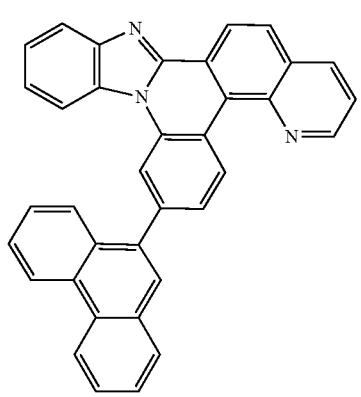
[Formula 3-9-1-6]
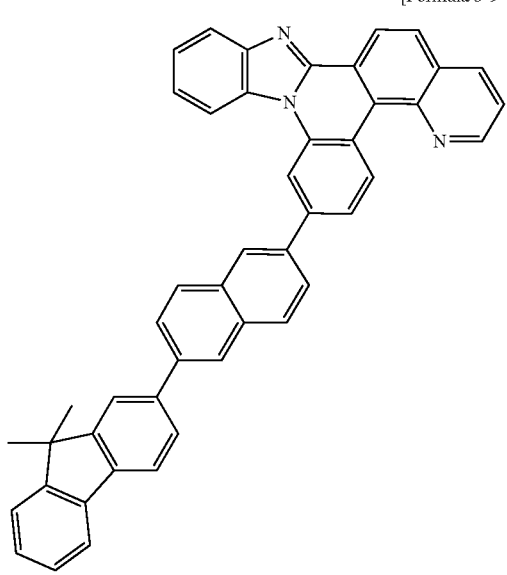
[Formula 3-9-1-7]
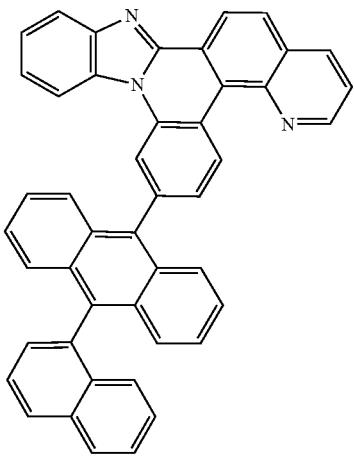
[Formula 3-9-1-8]
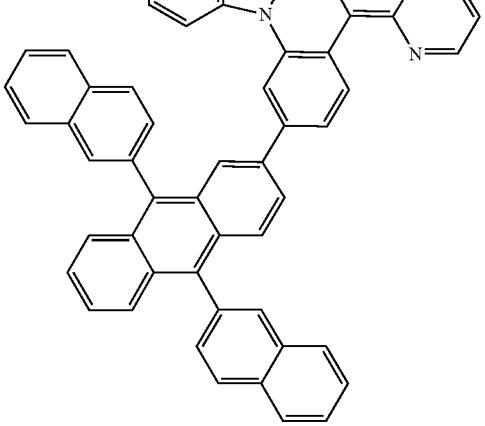
[Formula 3-9-1-9]
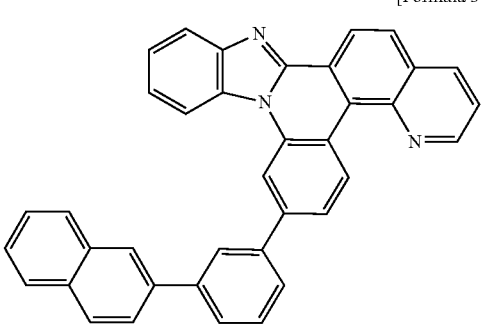
[Formula 3-9-1-10]
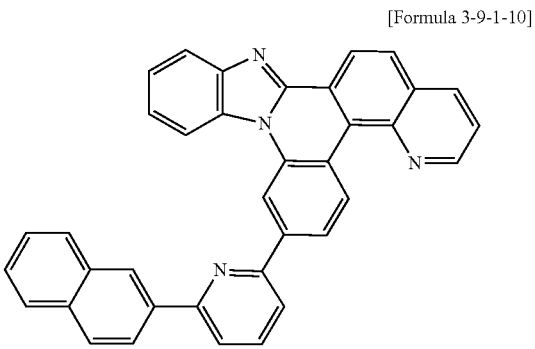

[Formula 3-9-1-11]
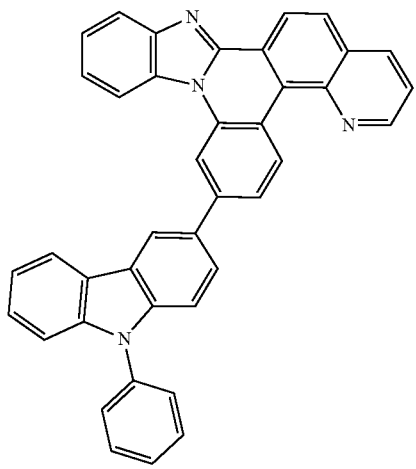
[Formula 3-9-1-12]
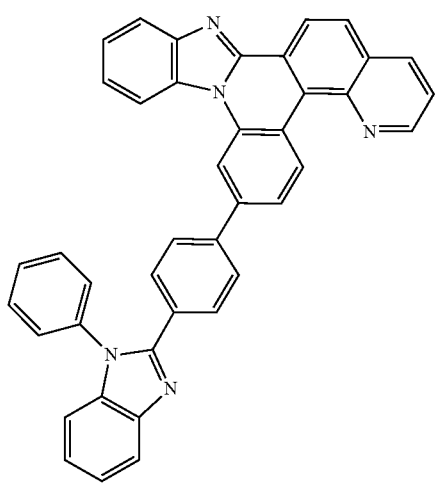
[Formula 3-9-1-13]
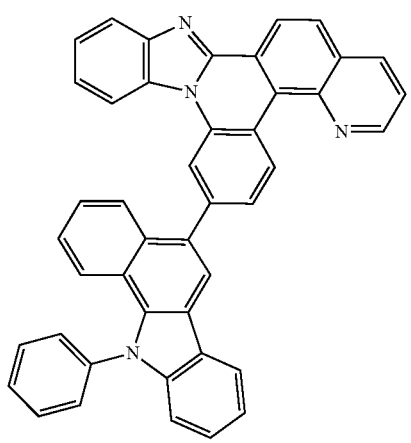
[Formula 3-9-1-14]
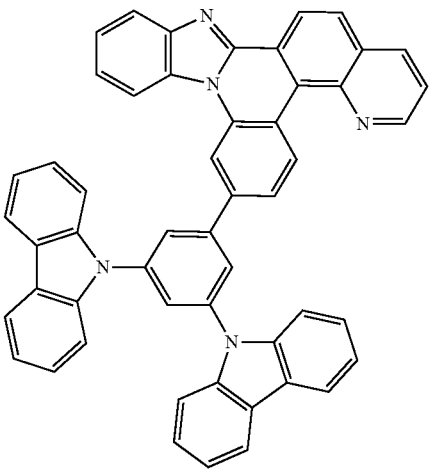
[Formula 3-9-1-15]
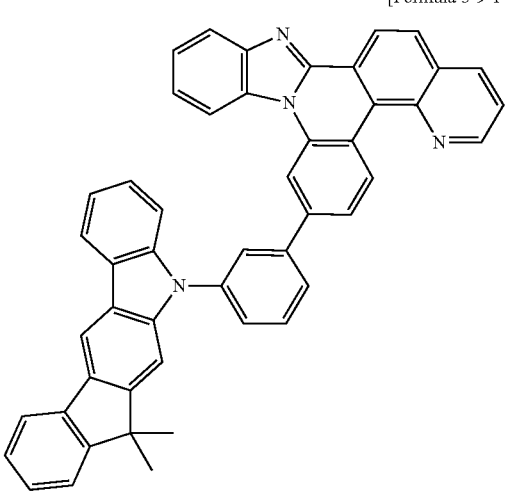
[Formula 3-9-1-16]
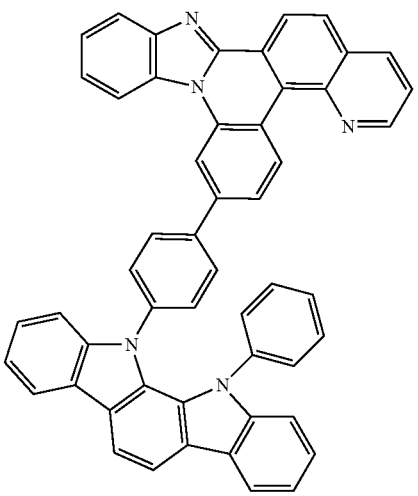

[Formula 3-9-1-17]
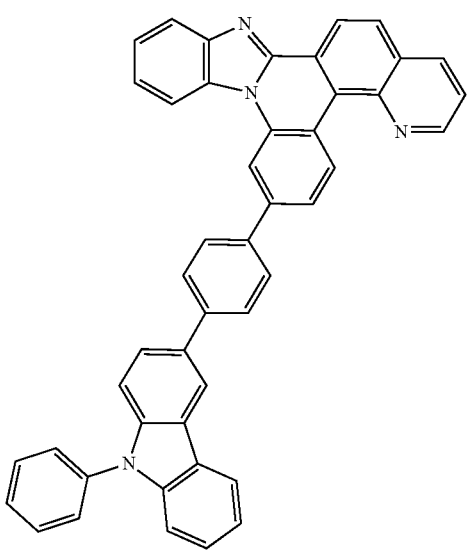
[Formula 3-9-1-18]
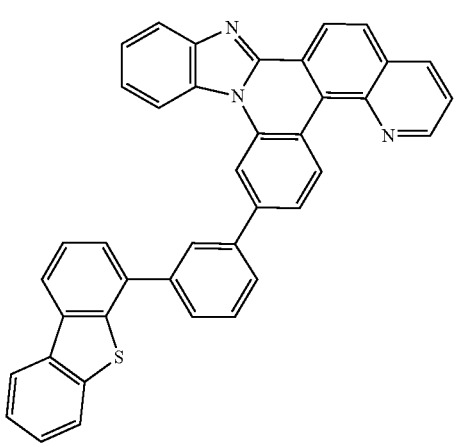
[Formula 3-9-1-19]
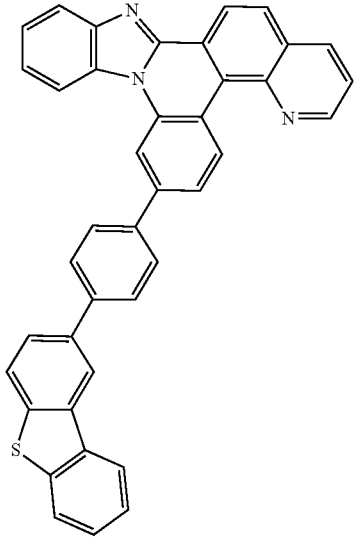
[Formula 3-9-1-20]
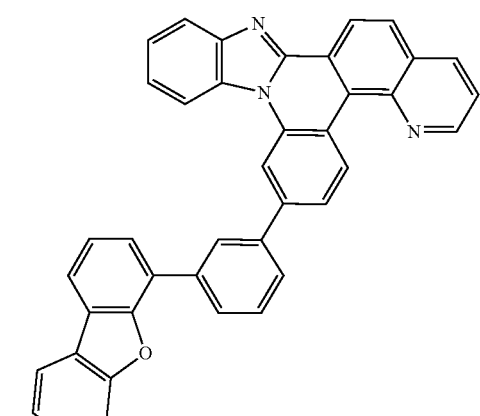
[Formula 3-9-1-21]
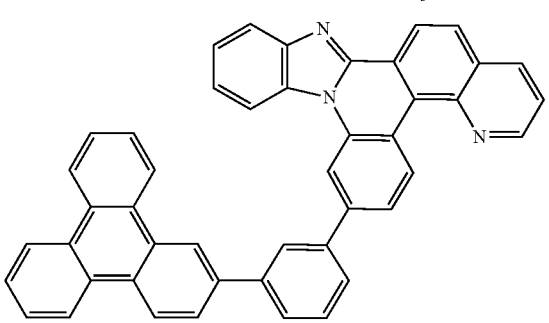
[Formula 3-9-1-22]
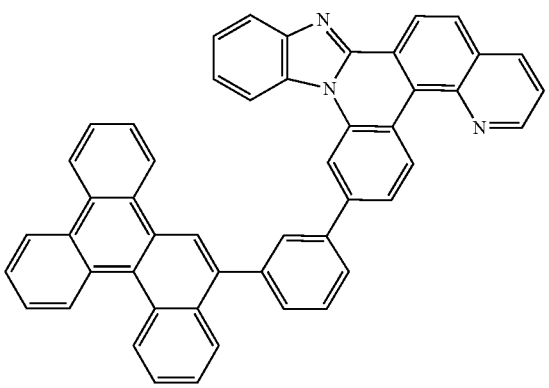

[Formula 3-9-1-23]
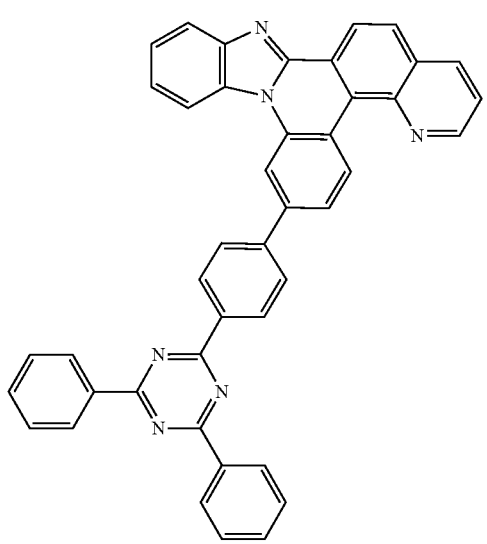
[Formula 3-9-1-24]
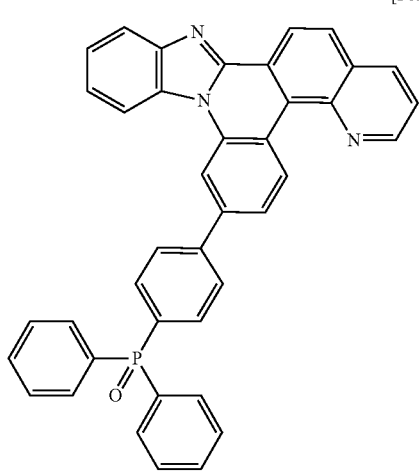
[Formula 3-9-1-25]
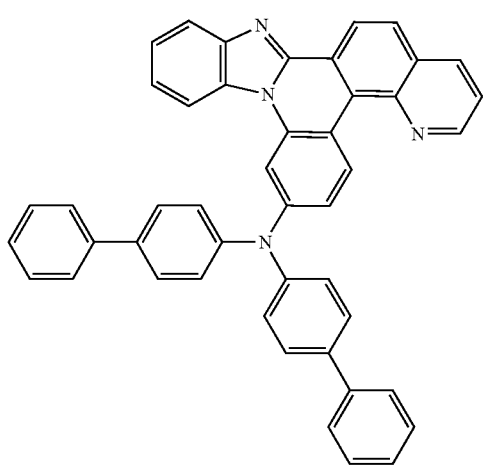
[Formula 3-9-1-26]
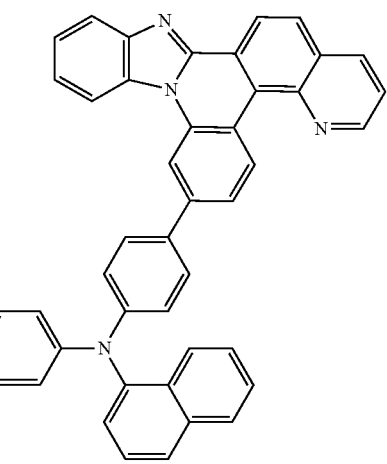
[Formula 3-9-1-27]
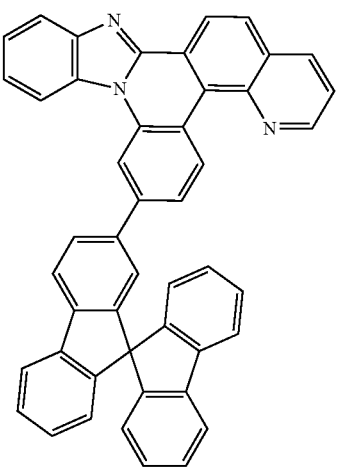
[Formula 3-9-1-28]
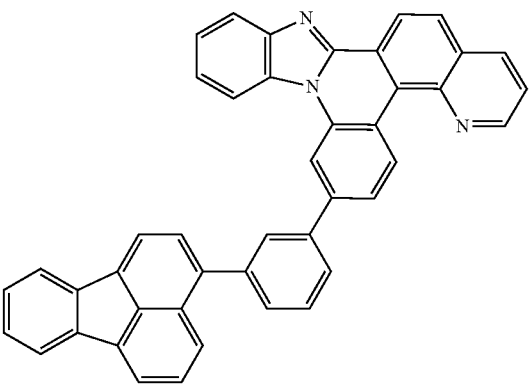

153
-continued
[Formula 3-9-2-1]
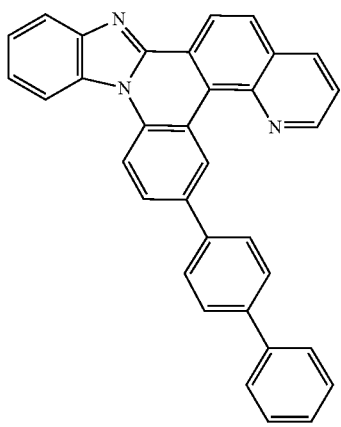
[Formula 3-9-2-2]
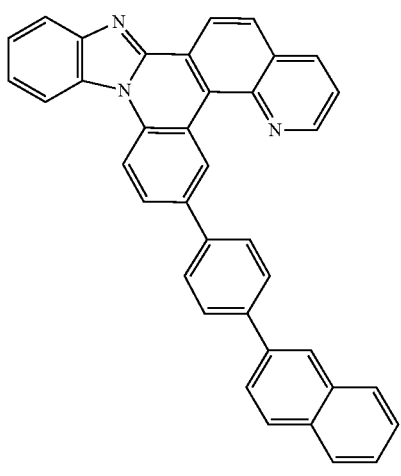
[Formula 3-9-2-3]
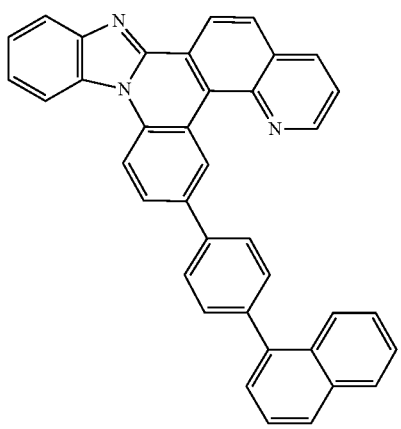
154
-continued
[Formula 3-9-2-4]
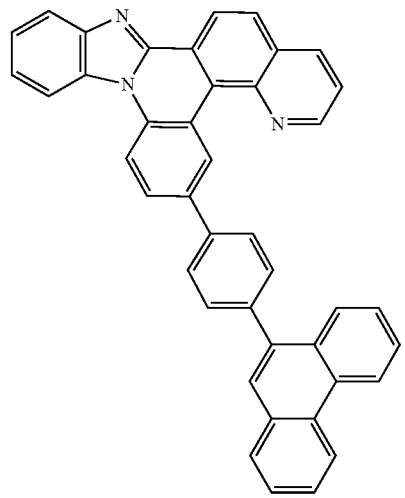
[Formula 3-9-2-5]
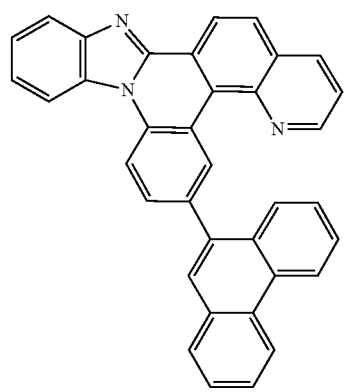
[Formula 3-9-2-6]
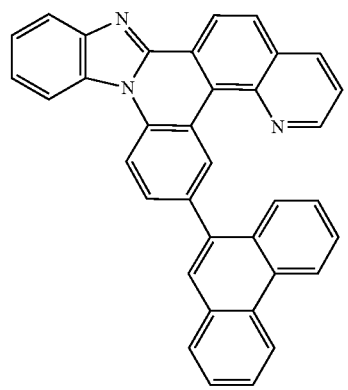

[Formula 3-9-2-7]
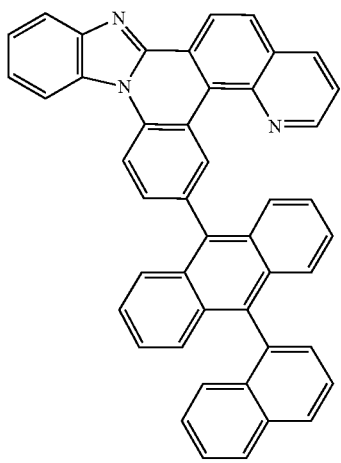
[Formula 3-9-2-8]
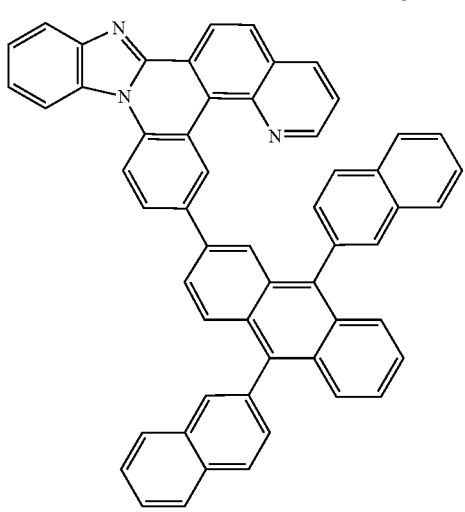
[Formula 3-9-2-9]
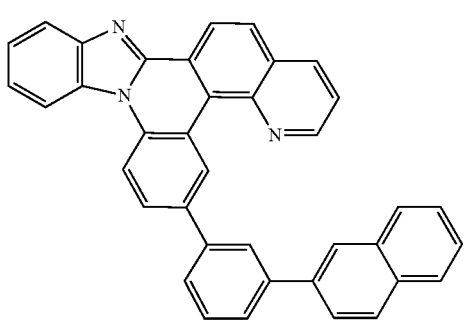
[Formula 3-9-2-10]
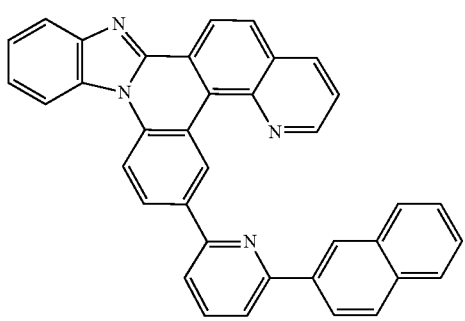
[Formula 3-9-2-11]
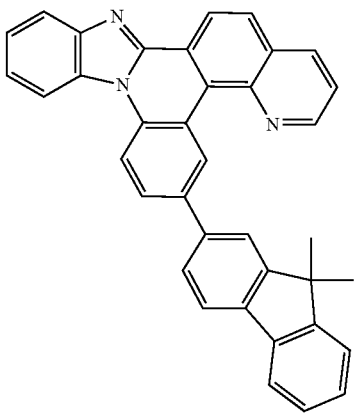
[Formula 3-9-2-12]
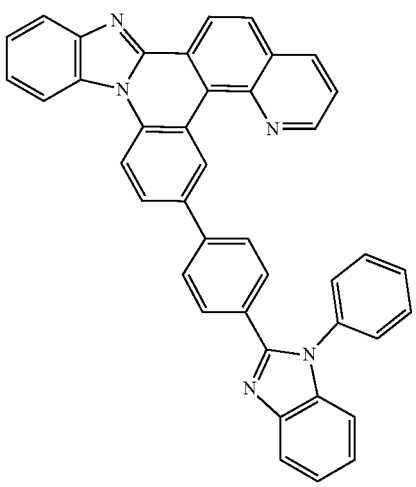
[Formula 3-9-2-13]
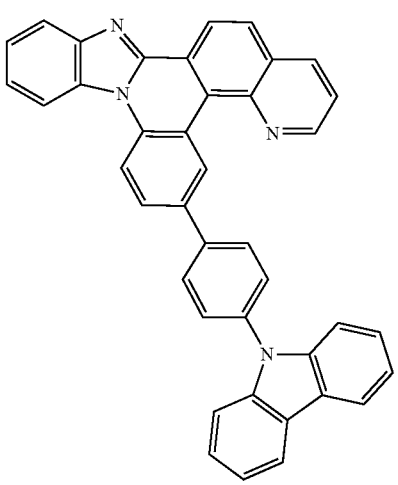

-continued
[Formula 3-9-2-14]
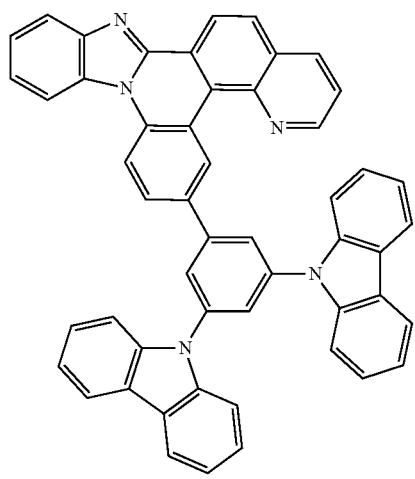
[Formula 3-9-2-15]
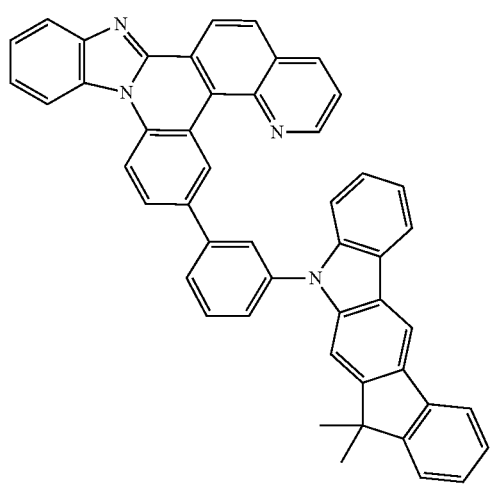
[Formula 3-9-2-16]
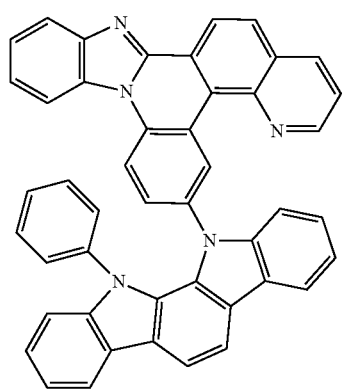
-continued
[Formula 3-9-2-17]
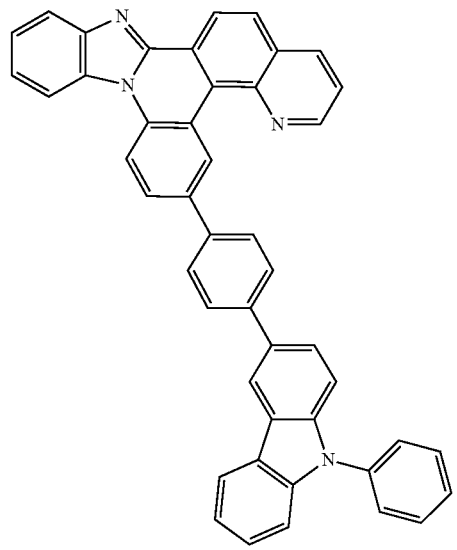
[Formula 3-9-2-18]
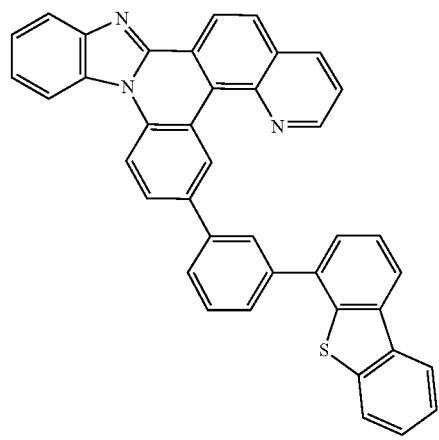
[Formula 3-9-2-19]
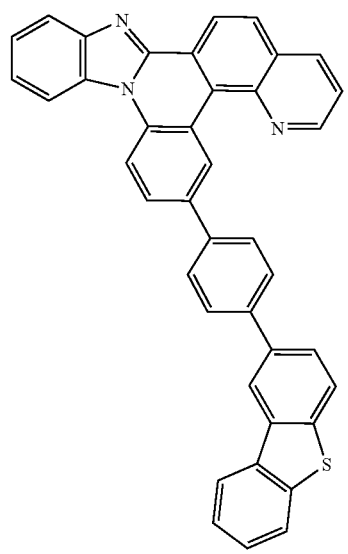

[Formula 3-9-2-20]
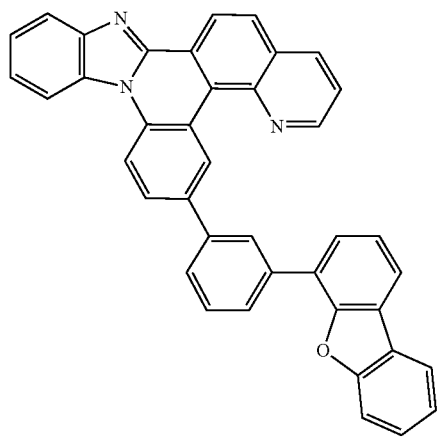
[Formula 3-9-2-21]
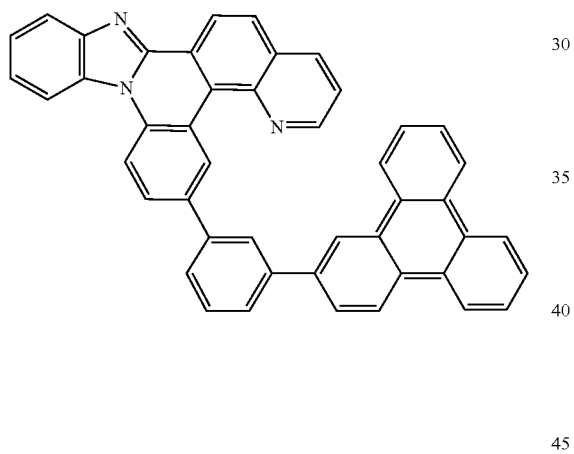
[Formula 3-9-2-22]
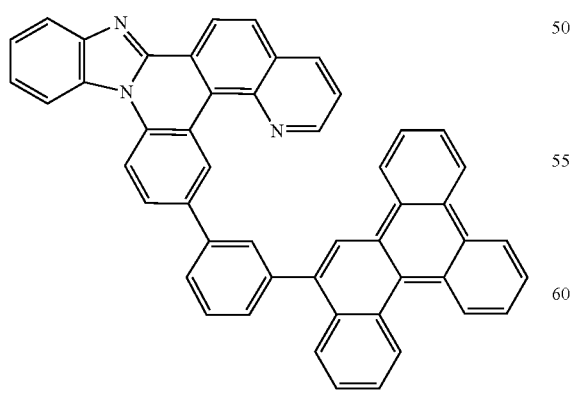
[Formula 3-9-2-23]
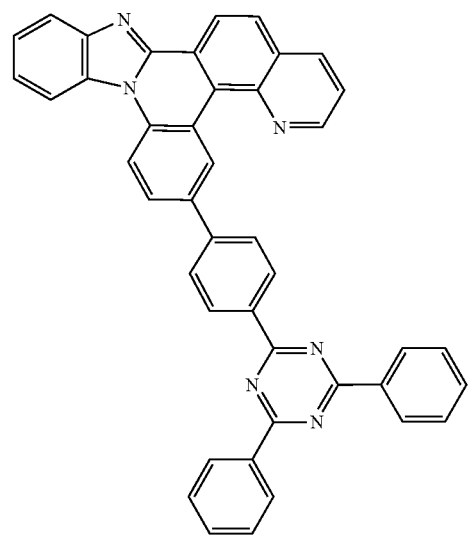
[Formula 3-9-2-24]
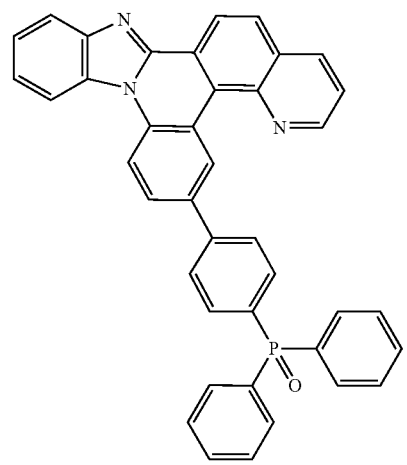
[Formula 3-9-2-25]
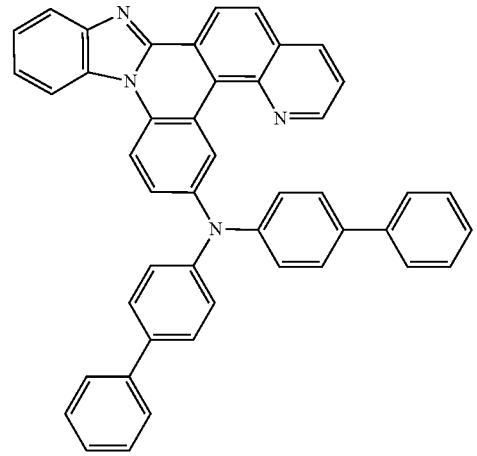

[Formula 3-9-2-26]

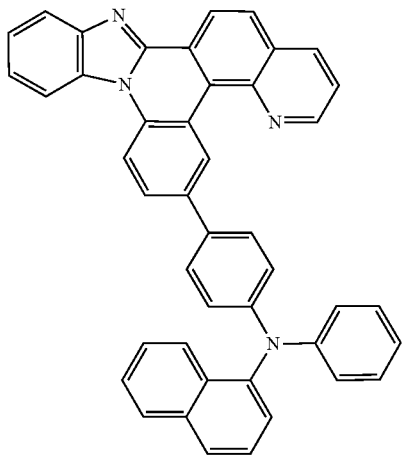

[Formula 3-9-2-27]

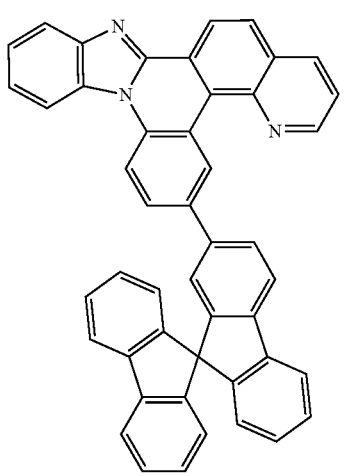

[Formula 3-9-2-28]

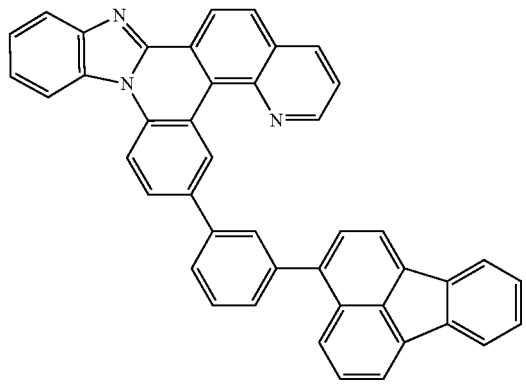

In addition, the present invention provides a method of manufacturing a new compound represented by Formula 1. The compound (Cpd C) represented by Formula 1 may be prepared by the following procedure. First, after a compound Cpd A is prepared through a Suzuki bonding reaction under a Pd catalyst, an imidazole derivative Cpd B may be prepared by reacting the compound to which 1,2-diaminobenzene and a formyl group are introduced. Subsequently, the structure of Formula 1 may be prepared through a cyclization reaction of —NH of the imidazole group and the aryl group or the heteroaryl group comprising the chloro (Cl) group in a molecule.

Specifically, the compound represented by Cpd A may be prepared through 1) a Suzuki bonding reaction of compound Cpd 1 substituted by halogen and boronic acid Cpd 2 or boron ester Cpd 3 substituted by the formyl group under the Pd catalyst. Alternatively, the compound may be prepared through the Suzuki bonding reaction of boronic acid Cpd 4 or boron ester Cpd 5 substituted by halogen and the compound Cpd 6 substituted by the formyl group under the Pd catalyst.

The preparation method may be represented by the following Reaction Equation 1.

[Reaction Equation 1]

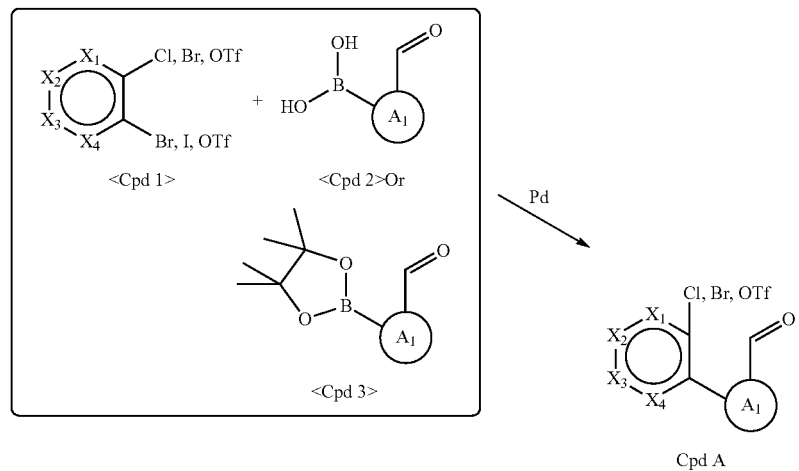

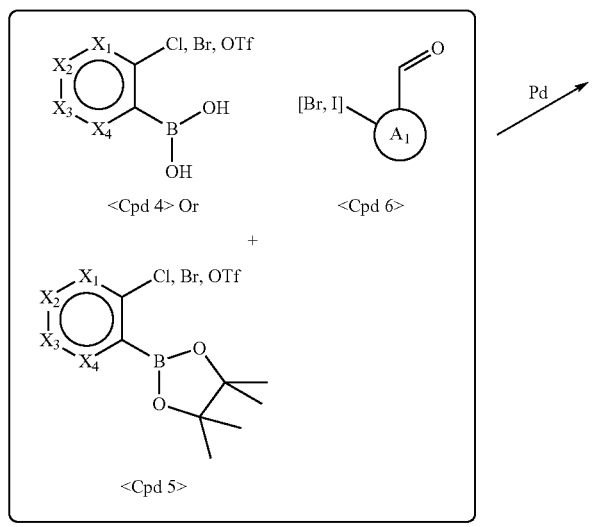

Specifically, the compound represented by Cpd B may be prepared as described below.

2) an imidazole group may be manufactured through an acid catalyst by mixing Cpd A substituted by the halogen group and the formyl group, a diketo derivative (Cpd 7) having $R_1$ and $R_2$ substituents, and ammonium acetate. Alternatively, the imidazole group may be manufactured through an acid catalyst by mixing Cpd A substituted by the halogen group and the formyl group and a diamine derivative (Cpd 8) having $R_1$ and $R_2$ substituents.

The preparation method may be represented by the following Reaction Equation 2.

[Reaction Equation 2]

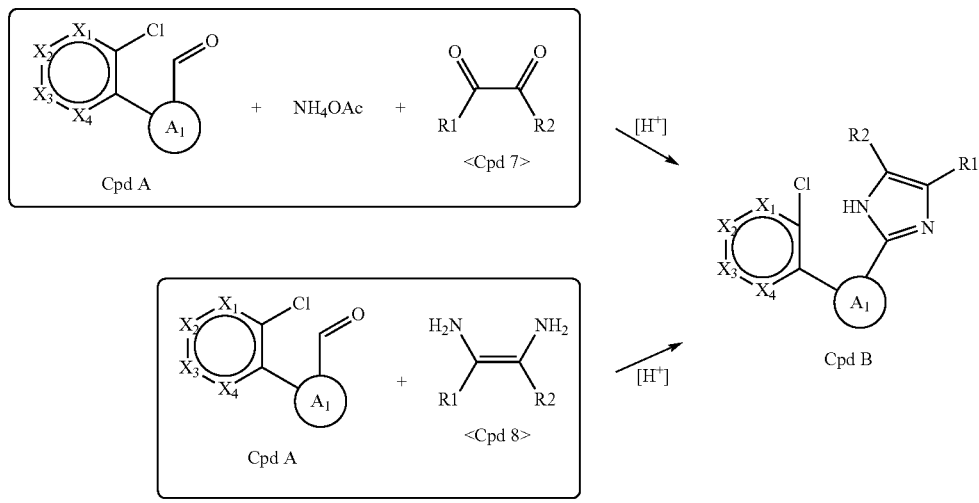

Specifically, the compound represented by Cpd C (Formula 1) may be prepared through 3) a cyclization reaction of Cpd B substituted by the halogen group and the imidazole group by using a Pd catalyst in a molecule.

The preparation method may be represented by the following Reaction Equation 3.

[Reaction Equation 3]

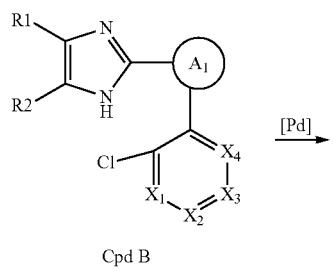

Cpd B

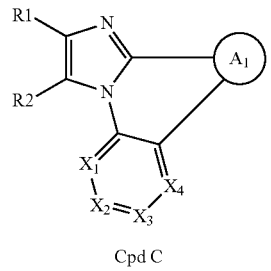

Cpd C

In addition, compounds having intrinsic properties of the introduced substituent groups may be synthesized by introducing various substituent groups to the aforementioned core structure. For example, it is possible to manufacture a material satisfying conditions required in each organic material layer by introducing the substituent group used in a hole injection layer material, a hole transport layer material, a light emitting layer material and an electron transport layer material used to manufacture the organic light emitting device and the organic electronic device to the aforementioned structure. The compound of the present invention may be applied to the organic electronic device according to a general method of manufacturing the organic electronic device.

In an exemplary embodiment of the present invention, the organic electronic device may be constituted by a structure comprising a first electrode, a second electrode, and an organic material layer interposed therebetween, and may be manufactured by using the general method of manufacturing the organic electronic device and a general material thereof, except that the compound according to the present invention is used in the organic material layer of the organic electronic device.

The organic material layer of the organic electronic device of the present invention may be constituted by a single layer structure, but by a multilayered structure in which two or more organic material layers are laminated. For example, the organic electronic device of the present invention may have a structure comprising a hole injection layer, a hole transport layer, a light emitting layer, an electron transport layer, an electron injection layer and the like as an organic material layer. However, the structure of the organic electronic device is not limited thereto, but may comprise the smaller number of organic material layers.

Accordingly, in the organic electronic device of the present invention, the organic material layer may comprise one or more layers of the hole injection layer, the hole transport layer, and a layer injecting and transporting holes simultaneously, and one or more layers of the layers may comprise the compound represented by Formula 1.

In addition, the organic material layer may comprise the light emitting layer, and the light emitting layer may comprise the compound represented by Formula 1. Herein, the compound represented by Formula 1 may be comprised as a host material in the light emitting layer. In the case where the compound represented by Formula 1 is comprised as the host material in the light emitting layer, the light emitting layer may comprise one or more kinds of phosphorescent dopants.

In the present invention, the phosphorescent dopant applied to the organic electronic device is not particularly limited, but is preferably selected from the phosphorescent dopant compounds represented by the following Formula 7.

$$M_1 L_{10} L_{11} L_{12}$$ [Formula 7]

In Formula 7, $M_1$ is Ir or Os, $L_{10}$, $L_{11}$ and $L_{12}$ are ligands bonded to $M_1$, and are each independently selected from the following structures,

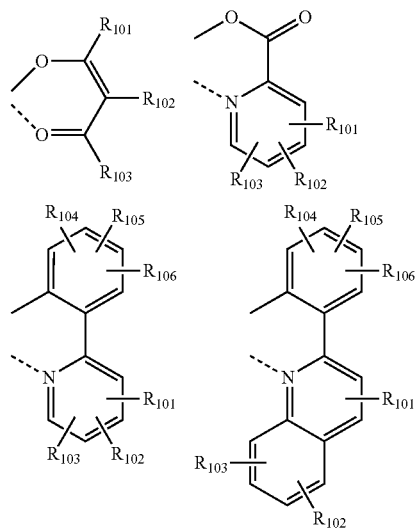

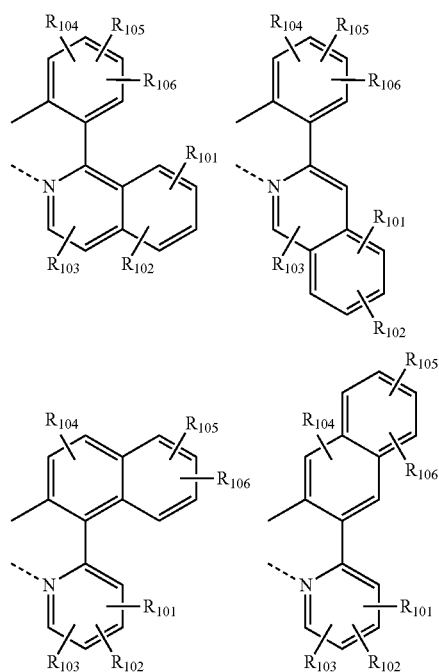

-continued

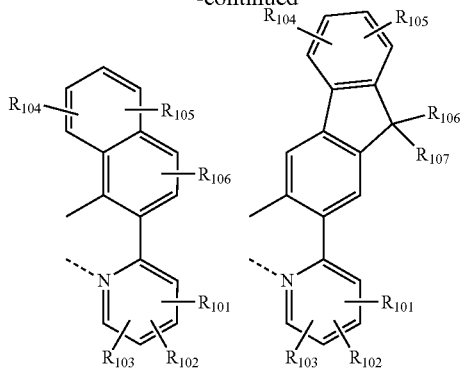

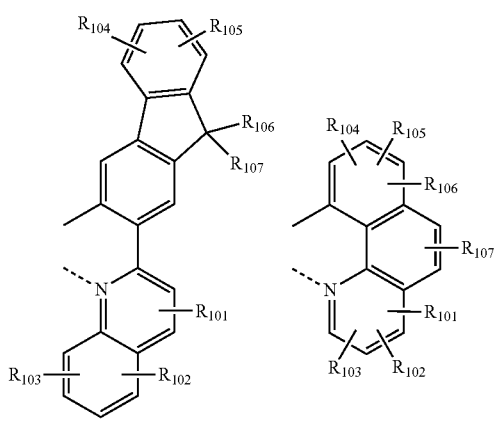

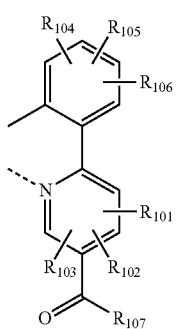

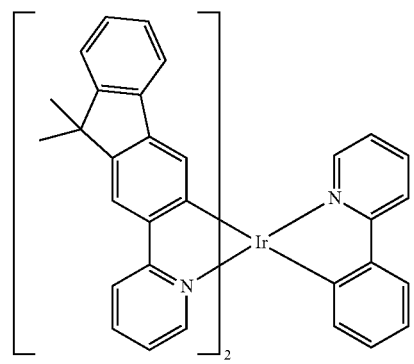
PD-1

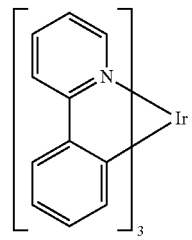
PD-2

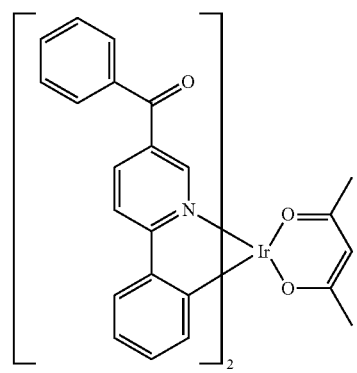
PD-3

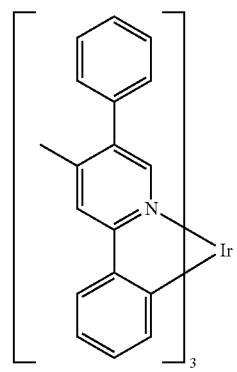
PD-4

$R_{101}$ to $R_{107}$ are the same as or different from each other, and are each independently selected from the group consisting of hydrogen, heavy hydrogen, a halogen group, a cyano group, a substituted or unsubstituted alkylsilyl group having 2 to 10 carbon atoms, a substituted or unsubstituted arylsilyl group having 6 to 30 carbon atoms, a substituted or unsubstituted alkyl group having 1 to 10 carbon atoms, a substituted or unsubstituted alkenyl group having 2 to 10 carbon atoms, a substituted or unsubstituted alkoxy group having 1 to 10 carbon atoms, a substituted or unsubstituted aryl group having 6 to 20 carbon atoms, and a substituted or unsubstituted heteroaryl group having 5 to 20 carbon atoms, and the adjacent groups may be bonded to form an aromatic condensed ring group or a heteroaromatic condensed ring group.

The compound represented by Formula 7 may be preferably selected from the group consisting of the following Structural Formulas, but is not limited thereto.

PD-5
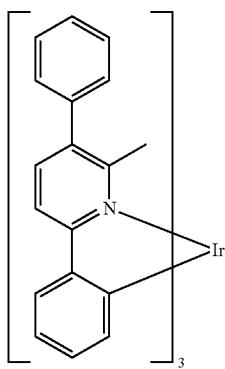
PD-6
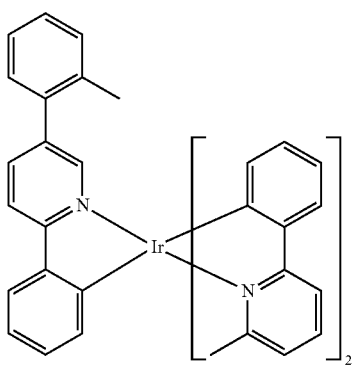
PD-7
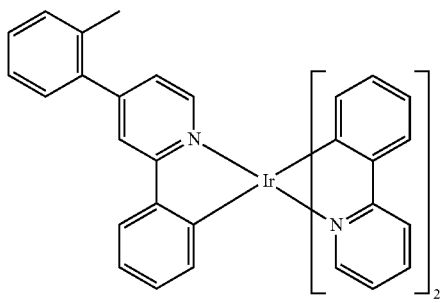
PD-8
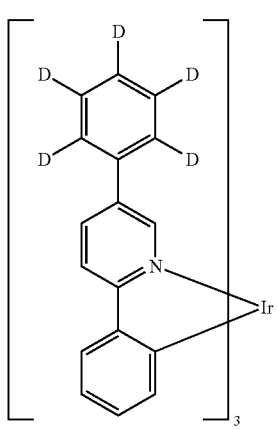
PD-9
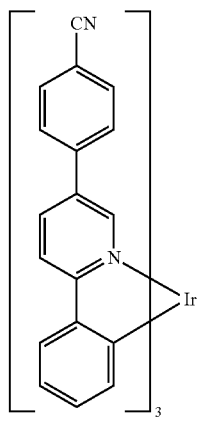
PD-10
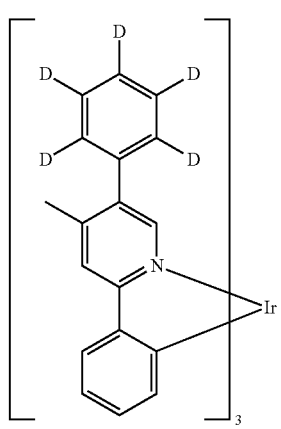
PD-11
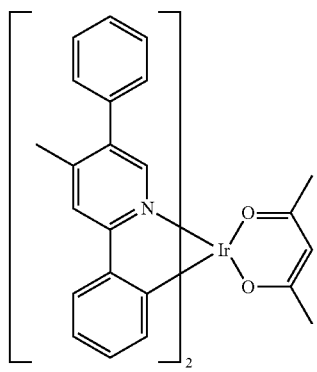
PD-12
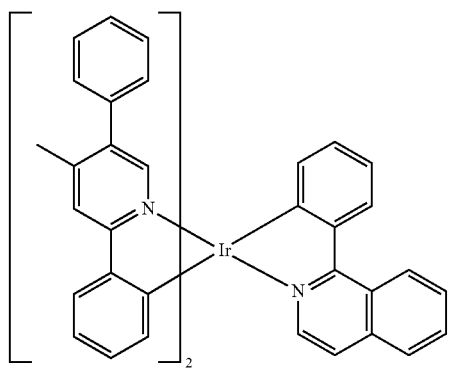

PD-13

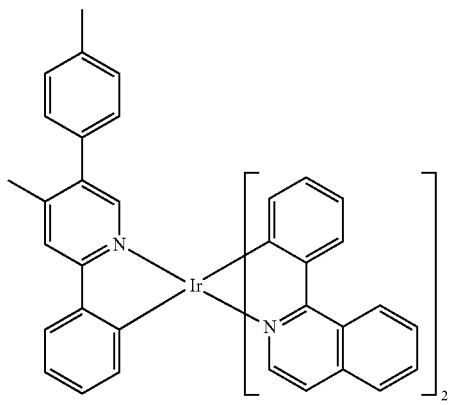

PD-14

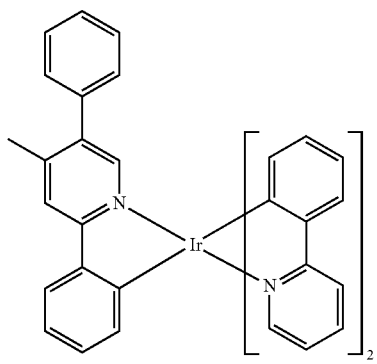

PD-15

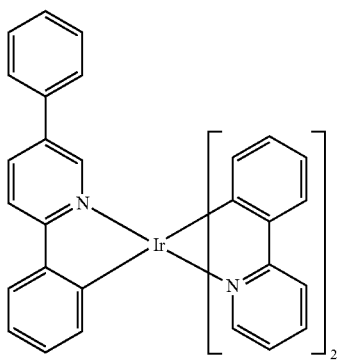

PD-16

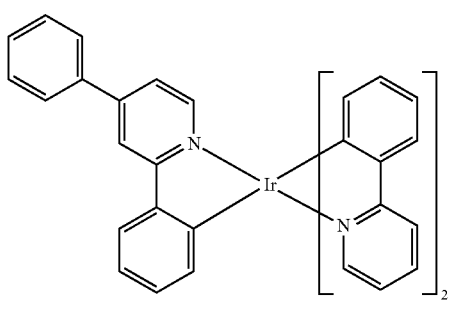

PD-17

PD-18

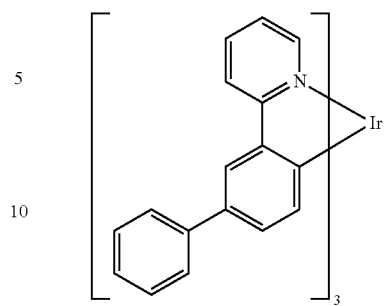

PD-19

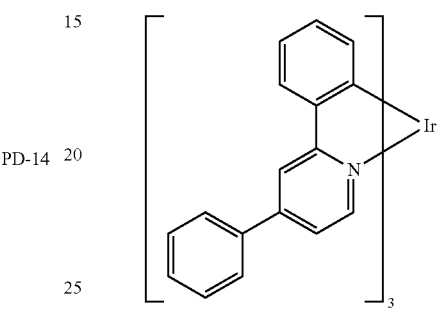

PD-20


The content of the phosphorescent dopant may be 1 to 50 wt % based on the total weight of the material constituting the light emitting layer, but is not limited thereto.

Further, the organic material layer may comprise one or more layers of an electron transport layer, an electron injection layer, and a layer transporting and injecting electrons simultaneously, and one or more layers of the layers may comprise the compound represented by Formula 1. Herein, the layer comprising the compound represented by Formula 1 may further comprise alkali metal, an alkali metal compound, alkali earth metal, an alkali earth metal compound or a combination thereof that is an n-type dopant. In the present invention, the n-type dopant applied to the organic electronic device is not particularly limited, and is preferably selected from Li, Na, K, Rb, Cs, Mg, Ca, Sr, Ba, La, Nd, Sm, Eu, Tb, Yb, LiF, Li$_2$O, CsF or the following compounds.

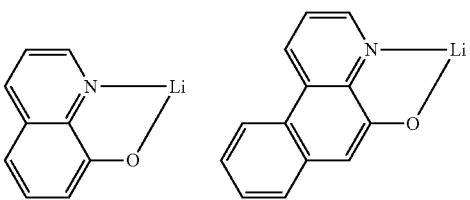

-continued

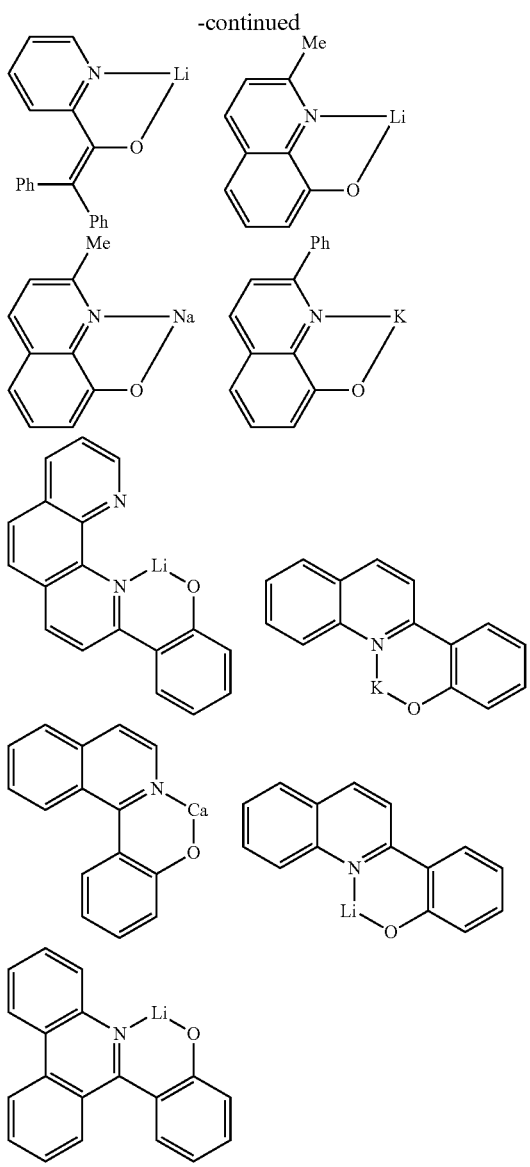

In the case where the electronic transport layer, the electronic injection layer, the layer transporting and injecting electrons simultaneously and the like are formed by using the n-type dopant and the compound represented by Formula 1, an electronic injection characteristic may be improved to exhibit effects of an increase in efficiency of the device, a reduction in driving voltage, and an increase in stability. It is preferable that the n-type dopant be present at the weight ratio of 1 to 70%.

In the organic material layer having the multilayered structure, the compound represented by Formula 1 may be comprised in a light emitting layer, a layer performing hole injection/hole transport and light emitting simultaneously, a layer performing hole transport and light emitting simultaneously, a layer performing electron transport and light emitting simultaneously or the like.

For example, the structure of the organic electronic device according to the present invention is illustrated in FIGS. 1 to 5.

FIG. 1 illustrates an organic electronic device having a structure where an anode 2, a hole injection layer 3, a hole transport layer 4, a light emitting layer 5, an electron transport layer 6 and a cathode 7 are sequentially laminated on a substrate 1. In the aforementioned structure, the compound represented by Formula 1 may be comprised in the hole injection layer 3, the hole transport layer 4, the light emitting layer 5 or the electron transport layer 6.

Figure 2:
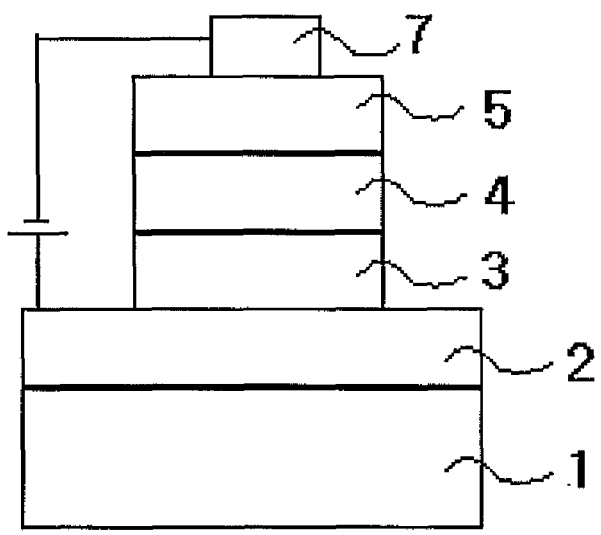

FIG. 2 illustrates an organic electronic device having a structure where an anode 2, a hole injection layer 3, a hole transport layer 4, a light emitting layer 5, and a cathode 7 are sequentially laminated on a substrate 1. In the aforementioned structure, the compound represented by Formula 1 may be comprised in the hole injection layer 3, the hole transport layer 4, or the electron transport layer 6.

Figure 3:
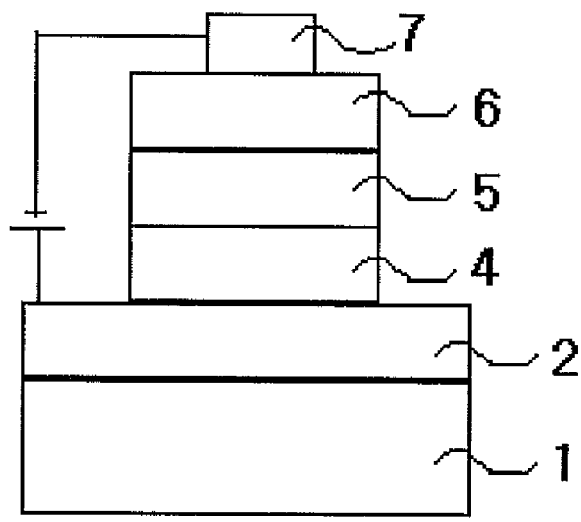

FIG. 3 illustrates an organic electronic device having a structure where an anode 2, a hole transport layer 4, a light emitting layer 5, an electron transport layer 6 and a cathode 7 are sequentially laminated on a substrate 1. In the aforementioned structure, the compound represented by Formula 1 may be comprised in the hole transport layer 4, the light emitting layer 5 or the electron transport layer 6.

Figure 4:
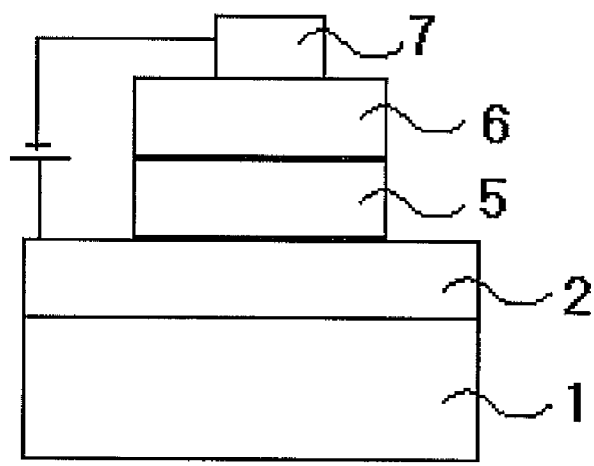

FIG. 4 illustrates an organic electronic device having a structure where an anode 2, a light emitting layer 5, an electron transport layer 6 and a cathode 7 are sequentially laminated on a substrate 1. In the aforementioned structure, the compound represented by Formula 1 may be comprised in the light emitting layer 5 or the electron transport layer 6.

Figure 5:
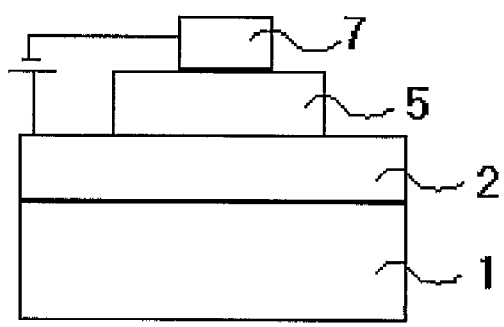
Figure 6:
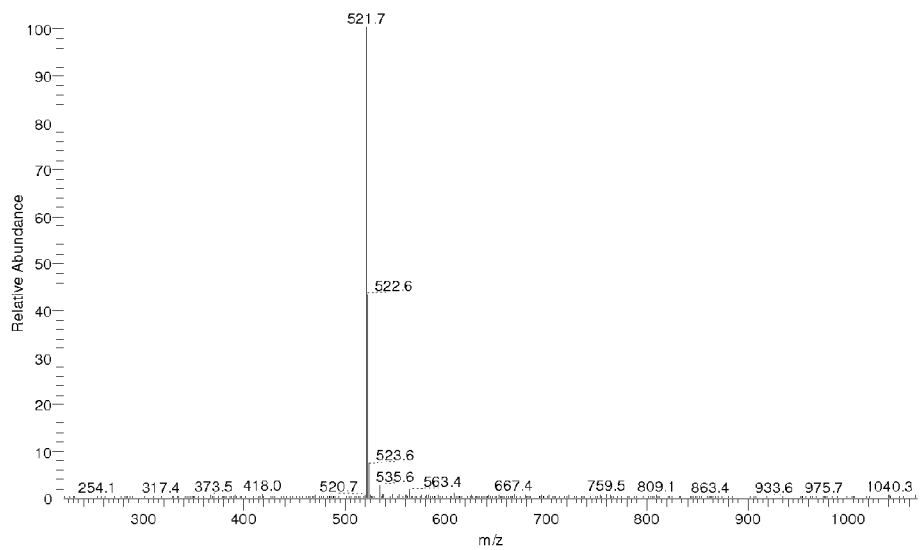
FIG. 6 is a view illustrating a mass spectrum of a compound of Formula 3-1-1-2 according to the exemplary embodiment of the present invention.
Figure 7:
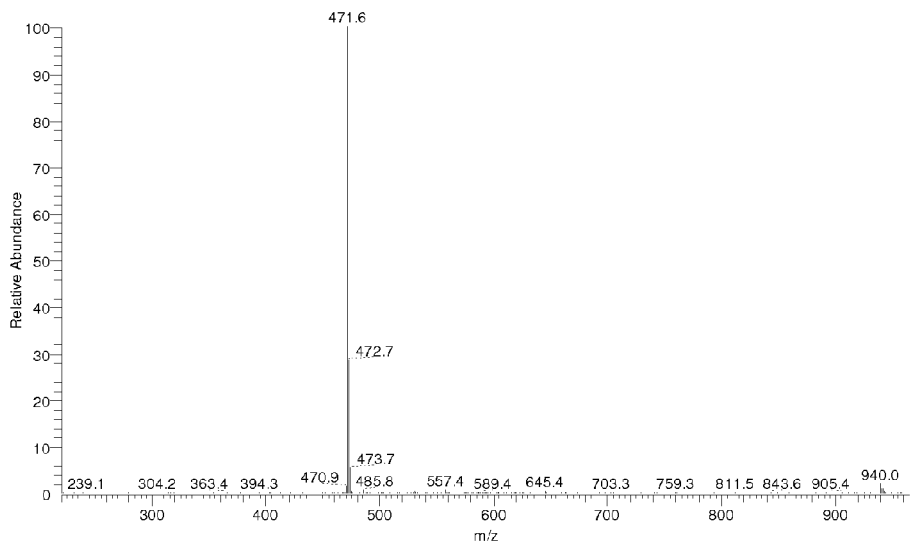
FIG. 7 is a view illustrating a mass spectrum of a compound of Formula 3-1-1-29 according to the exemplary embodiment of the present invention.
Figure 8:
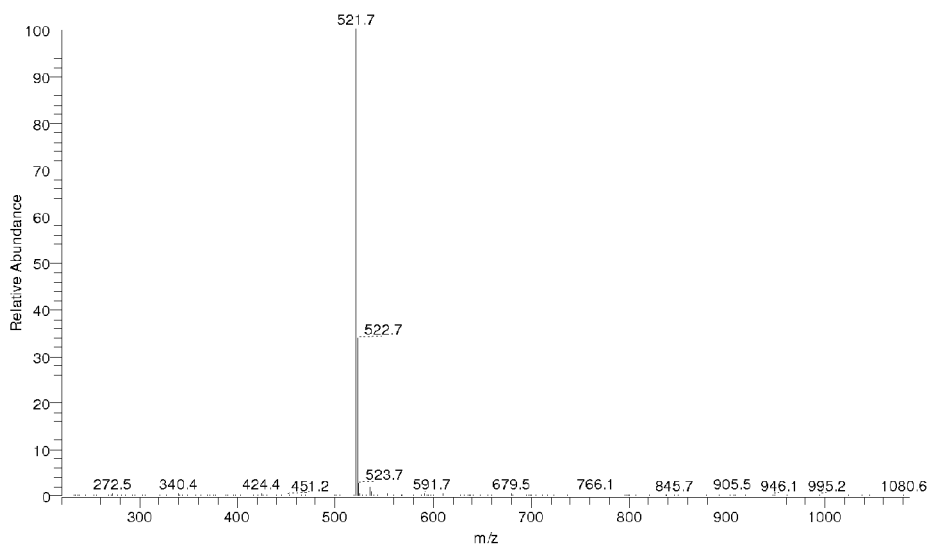
FIG. 8 is a view illustrating a mass spectrum of a compound of Formula 3-1-2-2 according to the exemplary embodiment of the present invention.
Figure 9:
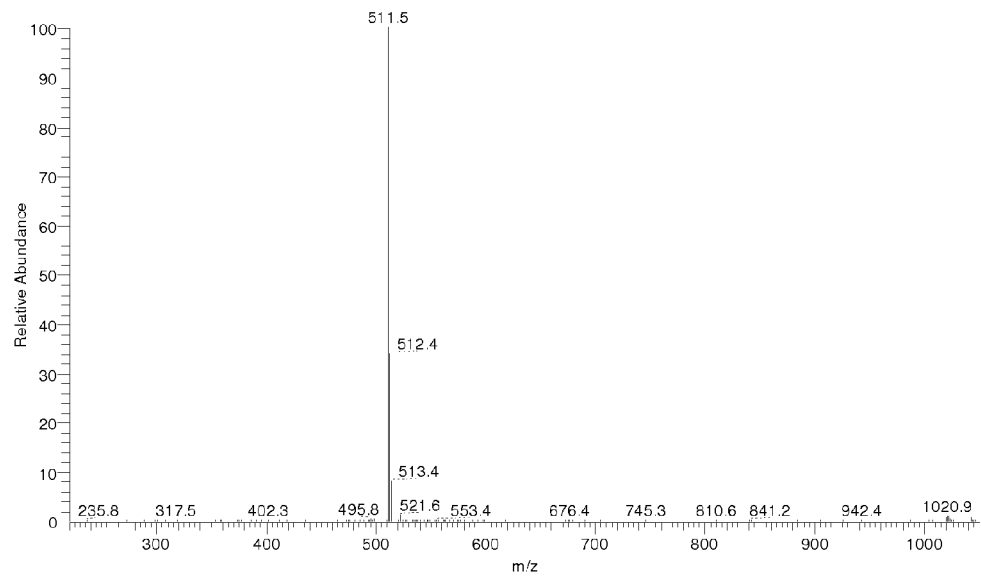
FIG. 9 is a view illustrating a mass spectrum of a compound of Formula 3-2-1-11 according to the exemplary embodiment of the present invention.

FIG. 5 illustrates an organic electronic device having a structure where an anode 2, a light emitting layer 5 and a cathode 7 are sequentially laminated on a substrate 1. In the aforementioned structure, the compound represented by Formula 1 may be comprised in the light emitting layer 5.

For example, the organic electronic device according to the present invention may be manufactured by forming an anode by depositing metal or metal oxides having the conductivity or an alloy thereof on a substrate by using a PVD (physical vapor deposition) method such as sputtering or e-beam evaporation, forming the organic material layer comprising the hole injection layer, the hole transport layer, the light emitting layer and the electron transport layer thereon, and depositing the material that is capable of being used as the cathode thereon.

In addition to this method, the organic electronic device may be manufactured by sequentially depositing a cathode material, an organic material layer and an anode material on a substrate (International Patent Application No. 2003/012890). The organic material layer may have a multilayered structure comprising a hole injection layer, a hole transport layer, a light emitting layer, an electron transport layer and the like, but is not limited thereto and may have a single layer structure. Further, the organic material layer may be manufactured in a smaller number of layer by using various polymer materials and by using not a deposition method but a solvent process, for example, a method such as spin coating, dip coating, doctor blading, screen printing, inkjet printing or a heat transferring method.

In general, it is preferable to use the material having a large work function as the anode material so as to smoothly perform hole injection into the organic material layer. Specific examples of the anode material that can be used in the present invention comprise metal such as vanadium, chrome, copper, zinc and gold or an alloy thereof; metal oxides such as zinc oxides, indium oxides, indium tin oxides (ITO) and indium zinc oxides (IZO); a combination of metal and oxides such as ZnO:Al or $SnO_2$:Sb; and conductive polymers such as poly (3-methylthiophene), poly[3,4-(ethylene-1,2-dioxy) thiophene] (PEDT), polypyrrole and polyaniline, but are not limited thereto.

It is preferable that the cathode material be, in general, a material having a small work function so as to smoothly perform electron injection into the organic material layer. Specific examples of the cathode material include metal such as magnesium, calcium, sodium, potassium, titanium, indium, yttrium, lithium, gadolinium, aluminum, silver, tin and lead or an alloy thereof; a multilayered structure material such as LiF/Al or $LiO_2$/Al and the like, but are not limited thereto.

The hole injection material is a material that is capable of well receiving holes from the anode at a low voltage, and it is preferable that the HOMO (highest occupied molecular orbital) of the hole injection material be a value between the work function of the anode material and the HOMO of the organic material layer around them. Specific examples of the hole injecting material include metal porphyrin, oligothiophene, an arylamine-based organic material, hexanitrile hexaazatriphenylene, a quinacridone-based organic material, a perylene-based organic material, anthraquinone, polyaniline and polythiophene-based conductive polymers and the like, but are not limited thereto.

The hole transport material is a material that is capable of receiving the holes from the anode or the hole injection layer and transferring the holes to the light emitting layer, and it is preferable to use the material having large mobility to the holes. Specific examples thereof include an arylamine-based organic material, a conductive polymer, a block copolymer in which a conjugate portion and a non-conjugate portion are present together and the like, but are not limited thereto.

The light emitting material is a material that receives the holes and the electrons from the hole transport layer and the electron transport layer and combines them to emit light in the range of visible rays, and it is preferable to use the material having excellent photon efficiency to fluorescence or phosphorescence. Specific examples thereof include a 8-hydroxyquinoline aluminum complex ($Alq_3$); a carbazole-based compound; a dimerized styryl compound; BAlq; 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene and the like, but are not limited thereto.

The hole transport material is a material that receives well the electrons from the cathode and transfer the electrons to the light emitting layer, and it is preferable to use the material having large mobility to the electrons. Specific examples thereof include a 8-hydroxyquinoline Al complex; a complex including $Alq_3$; an organic radical compound; a hydroxyflavone metal complex and the like, but are not limited thereto.

The organic light emitting device according to the present invention may be a top emission type, a bottom emission type, or a both-sided emission type according to the used material.

The compound according to the present invention may be applied to an organic electronic device such as an organic solar cell, an organic photoconductor and an organic transistor by the principle that is similar to the principle applied to the organic light emitting device.

Mode for Invention

Hereinafter, preferable Examples will be described in order to help understanding of the present invention. However, the following Examples are set forth to illustrate the present invention, but the scope of the present invention is not limited thereto.

Example

Preparation Example 1

Preparation of the Following Compounds A-1, A-2, A-3 and A-4

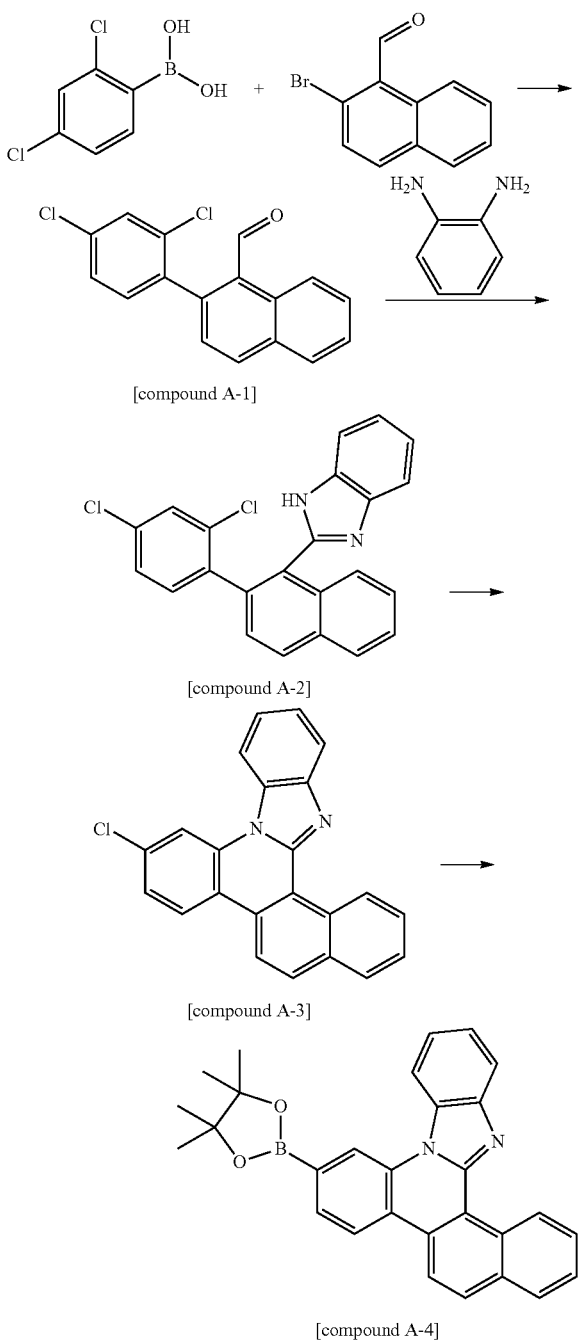

[compound A-1]

[compound A-2]

[compound A-3]

[compound A-4]

Preparation Example 1-1

Preparation of Compound A-1

After 2,4-dichlorophenylboronic acid (18.3 g, 95.8 mmol) and 2-bromo-1-naphthaldehyde (20.5 g, 87.2 mmol) were completely dissolved in tetrahydrofurane (THF) (300 mL), 2M potassium carbonate aqueous solution (180 mL) was added thereto, and tetrakistriphenylphosphino palladium (Pd (PPh$_3$)$_4$) (2.0 g, 2 mol %) was put thereinto, agitated and refluxed for 5 hours. The temperature was lowered to normal temperature, the water layer was removed, and the organic layer was dried by anhydrous magnesium sulfate (MgSO$_4$) and filtered. The filtered solution was concentrated under the reduced pressure, and columned with tetrahydrofurane:hexane=1:10 to prepare compound A-1 (21.0 g, 80%).

MS: [M+H]$^+$=301

Preparation Example 1-2

Preparation of Compound A-2

Compound A-1 (26.2 g, 87.0 mmol) prepared in Preparation Example 1-1 and diaminobenzene (9.4 g, 87.0 mmol) were suspended in dioxane (1,4-dioxane) (200 mL) and acetic acid (AcOH) (20 mL). The obtained mixture was agitated and refluxed for about 6 hours, and cooled to normal temperature. After the mixture was diluted by water (100 mL), the generated solid was filtered, washed by water and ethyl ether to prepare compound A-2 (19.3 g, 57%).

MS: [M+H]$^+$=389

Preparation Example 1-3

Preparation of Compound A-3

Compound A-2 (1.99 g, 5.10 mmol) prepared in Preparation Example 1-2, sodium-tertiary-butoxide (NaOt-Bu) (0.58 g, 6.01 mmol) and Pd[P(t-Bu)$_3$]$_2$ (51 mg, 2 mol %) were suspended in toluene (50 mL). The obtained mixture was agitated and refluxed for about 6 hours, and cooled to normal temperature. Distilled water was put into the reaction solution to terminate the reaction, and the organic layer was extracted, dried by anhydrous magnesium sulfate and filtered. The filtered solution was concentrated under the reduced pressure, and columned with tetrahydrofurane:hexane=1:5 to prepare compound A-3 (0.756 g, 42%).

MS: [M+H]$^+$=353

Preparation Example 1-4

Preparation of Compound A-4

Compound A-3 (14.4 g, 40.8 mmol) prepared in Preparation Example 1-3, bis(pinacolato)diboron (11.4 g, 4.49 mmol) and potassium acetate (KOAc) (12.0 g, 122 mmol) were suspended in dioxane (250 mL). Pd(dba)$_2$ (0.70 g, 3 mol %) and PCy$_3$ (0.69 g, 6 mol %) were added to the suspension solution. The mixture was agitated and refluxed for about 8 hours, and cooled to normal temperature. The mixture was diluted by water (250 mL), and extracted by dichloromethane (3×150 mL). The organic extract material was dried over magnesium sulfate and then filtered. The filtered solution was concentrated under the reduced pressure, recrystallized by ethyl ether and hexane to prepare compound A-4 (14.5 g, 80%).

MS: [M+H]$^+$=445

Preparation Example 2

Preparation of the Following Compounds A-5, A-6, A-7 and A-8

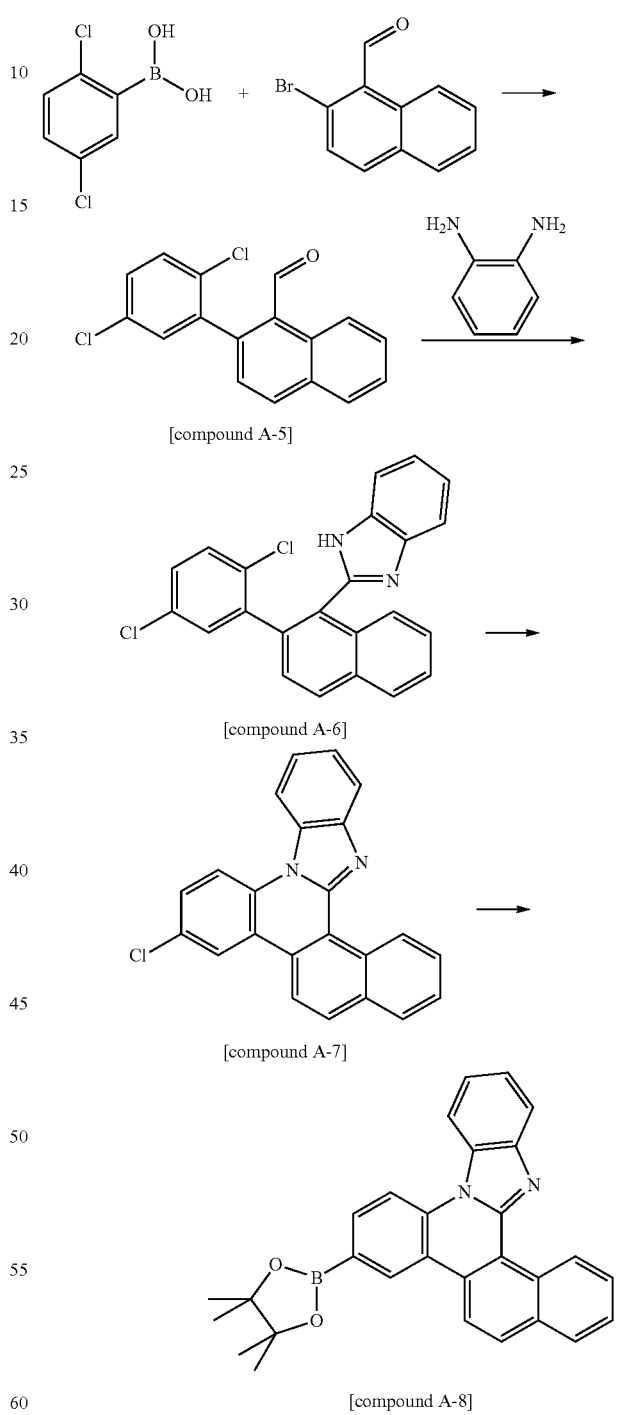

[compound A-5]

[compound A-6]

[compound A-7]

[compound A-8]

Compound A-8 was prepared by using the same method as Preparation Example 1, except that 2,5-dichlorophenylboronic acid was used instead of 2,4-dichlorophenyl-boronic acid in Preparation Example 1.

MS: [M+H]$^+$=445

Preparation Example 3

Preparation of the Following Compounds A-9, A-10, A-11 and A-12

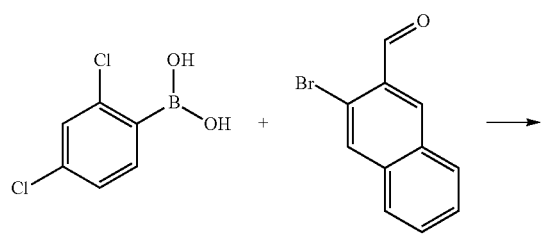

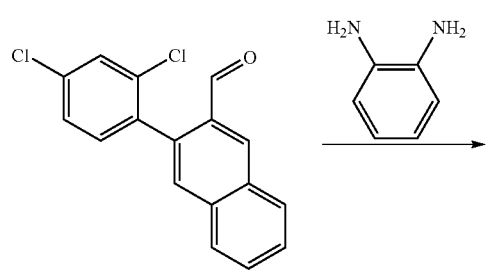

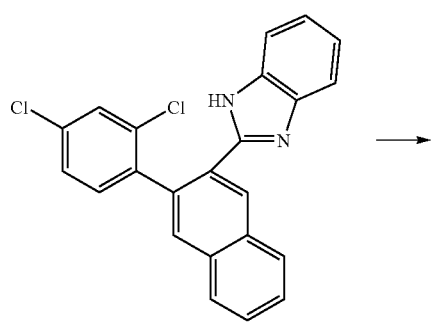

[compound A-9]

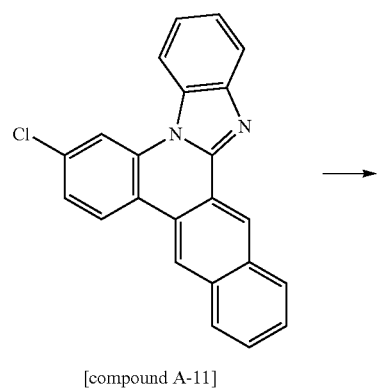

[compound A-10]

[compound A-11]

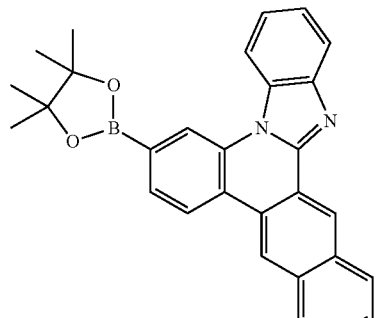

[compound A-12]

Compound A-12 was prepared by using the same method as Preparation Example 1, except that 3-bromo-2-naphthaldehyde was used instead of 2-bromo-1-naphthaldehyde in Preparation Example 1.

MS: $[M+H]^+=445$

Preparation Example 4

Preparation of the Following Compounds A-13, A-14, A-15 and A-16

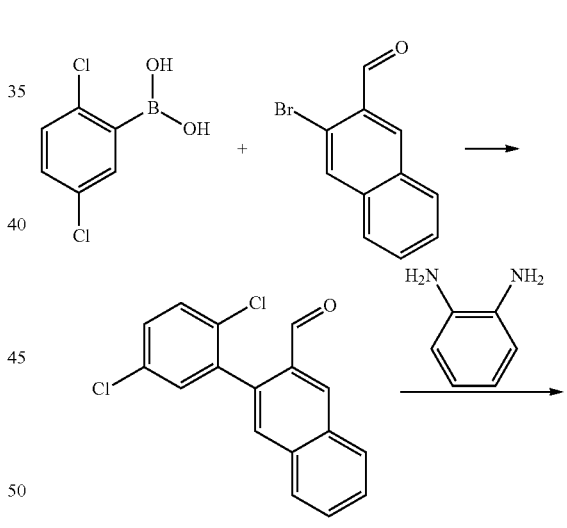

[compound A-13]

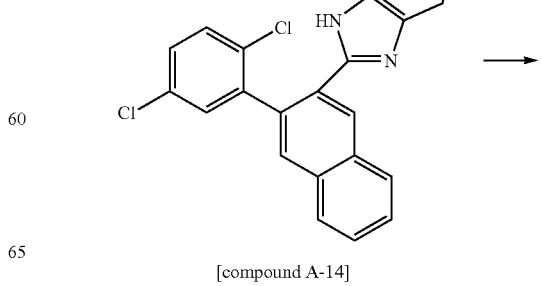

[compound A-14]

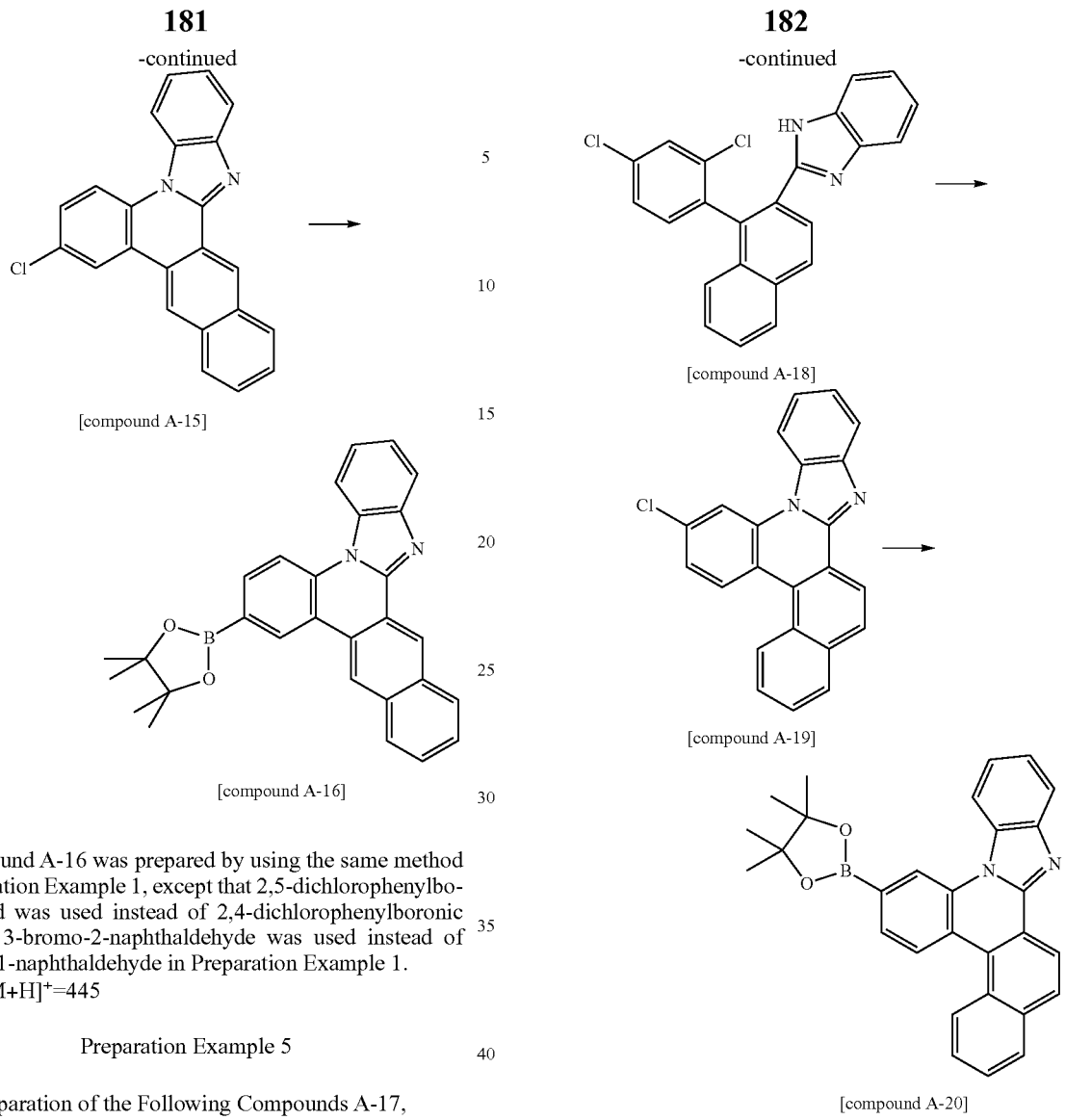

[compound A-15]

[compound A-16]

[compound A-18]

[compound A-19]

[compound A-20]

Compound A-16 was prepared by using the same method as Preparation Example 1, except that 2,5-dichlorophenylboronic acid was used instead of 2,4-dichlorophenylboronic acid and 3-bromo-2-naphthaldehyde was used instead of 2-bromo-1-naphthaldehyde in Preparation Example 1.

MS: [M+H]$^+$=445

Preparation Example 5

Preparation of the Following Compounds A-17, A-18, A-19 and A-20

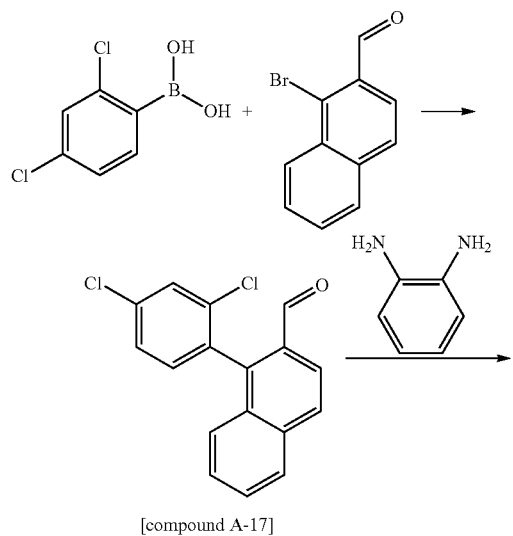

[compound A-17]

Compound A-20 was prepared by using the same method as Preparation Example 1, except that 1-bromo-2-naphthaldehyde was used instead of 2-bromo-1-naphthaldehyde in Preparation Example 1.

MS: [M+H]$^+$=445

Preparation Example 6

Preparation of the Following Compounds A-21, A-22, A-23 and A-24

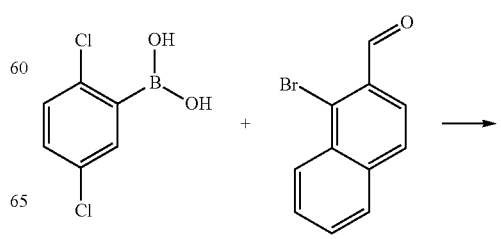

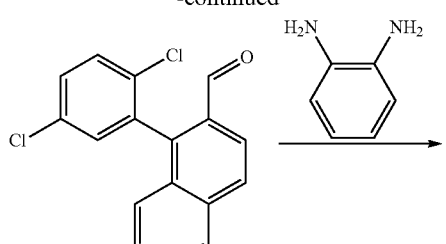

[compound A-21]

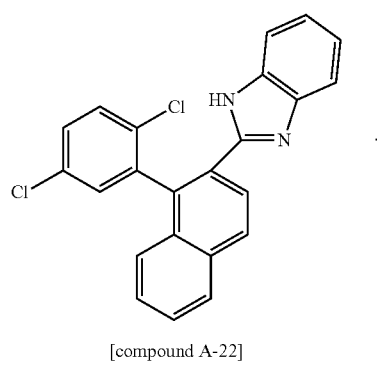

[compound A-22]

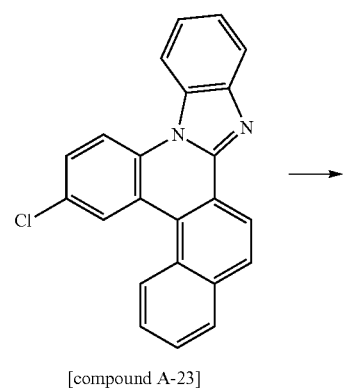

[compound A-23]

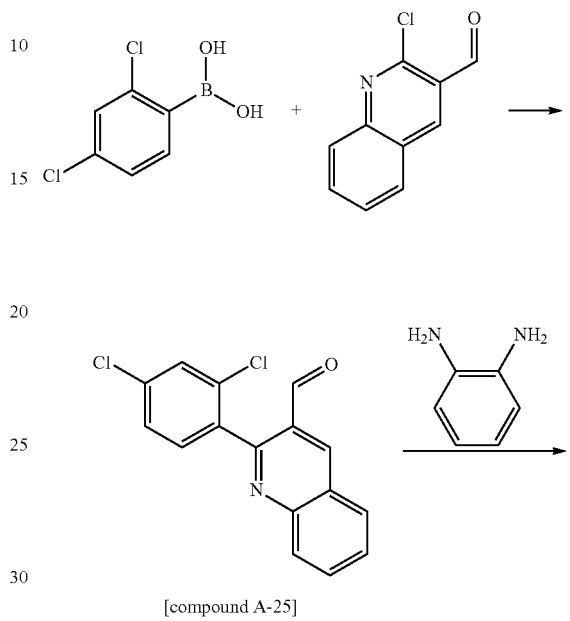

[compound A-24]

Compound A-24 was prepared by using the same method as Preparation Example 1, except that 2,5-dichlorophenylboronic acid was used instead of 2,4-dichlorophenylboronic acid and 1-bromo-2-naphthaldehyde was used instead of 2-bromo-1-naphthaldehyde in Preparation Example 1.

MS: $[M+H]^+=445$

Preparation Example 7

Preparation of the Following Compounds A-25, A-26, A-27 and A-28

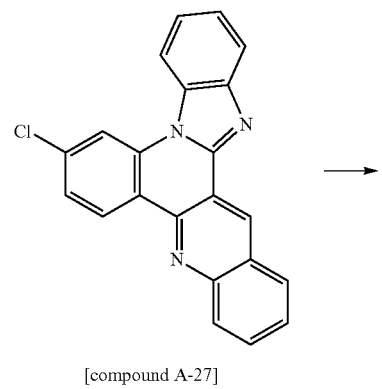

[compound A-25]

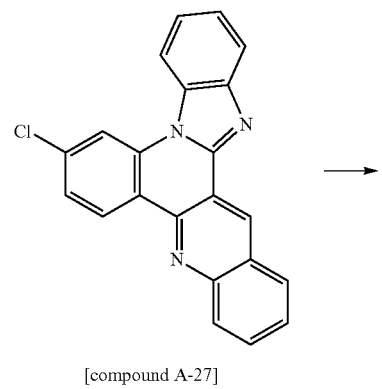

[compound A-26]

[compound A-27]

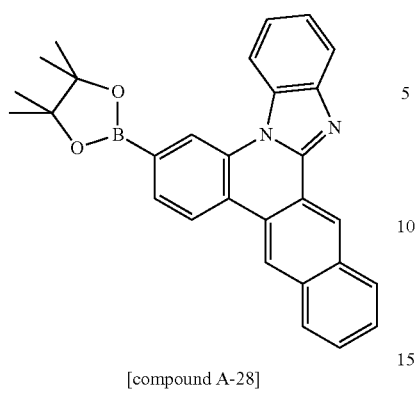

[compound A-28]

Compound A-28 was prepared by using the same method as Preparation Example 1, except that 2-chloro-3-quinolinecarboxaldehyde was used instead of 2-bromo-1-naphthaldehyde in Preparation Example 1.

MS: [M+H]$^+$=446

Preparation Example 8

Preparation of the Following Compounds A-29, A-30, A-31 and A-32

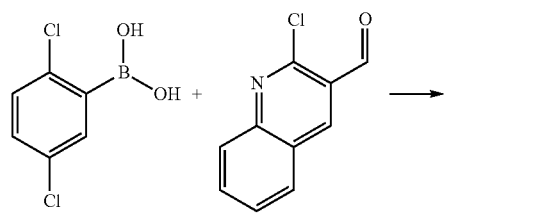

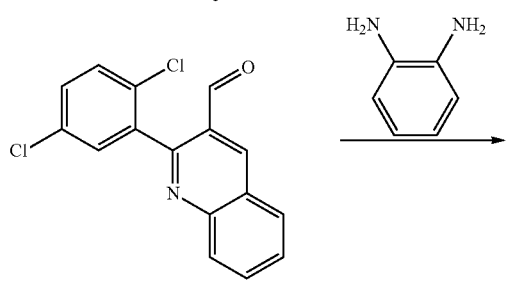

[compound A-29]

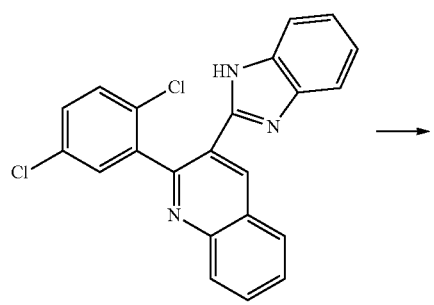

[compound A-30]

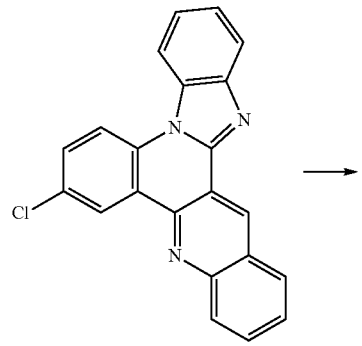

[compound A-31]

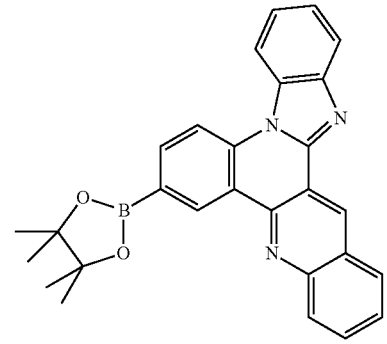

[compound A-32]

Compound A-32 was prepared by using the same method as Preparation Example 1, except that 2,5-dichlorophenylboronic acid was used instead of 2,4-dichlorophenylboronic acid and 2-chloro-3-quinolinecarboxaldehyde was used instead of 2-bromo-1-naphthaldehyde in Preparation Example 1.

MS: [M+H]$^+$=446

Preparation Example 9

Preparation of the Following Compounds A-33, A-34 and A-35

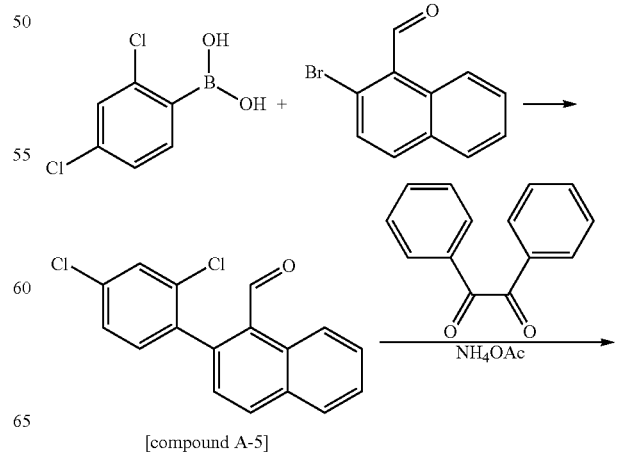

[compound A-5]

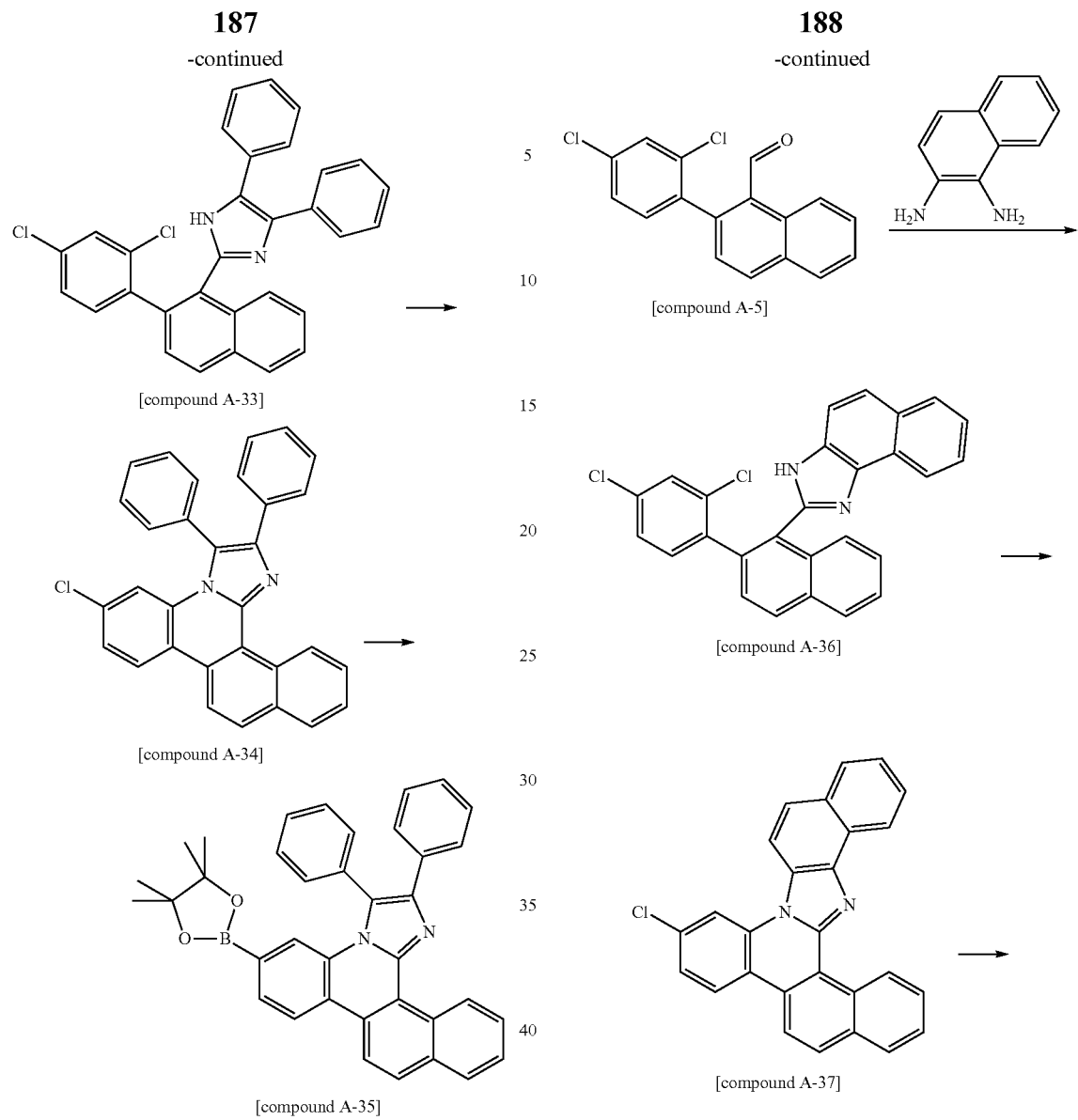

Compound A-35 was prepared by using the same method as Preparation Example 1, except that ammonium acetate and benzil were used instead of diaminobenzene in Preparation Example 1.

MS: [M+H]$^+$=547

Preparation Example 10

Preparation of the Following Compounds A-36, A-37 and A-38

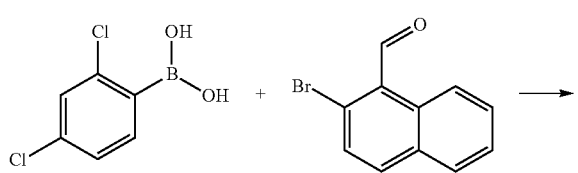

Compound A-38 was prepared by using the same method as Preparation Example 1, except that diaminonaphthalene was used instead of diaminobenzene in Preparation Example 1.

MS: [M+H]$^+$=495

Preparation Example 11

Preparation of the Following Compounds A-39, A-40, A-41 and A-42

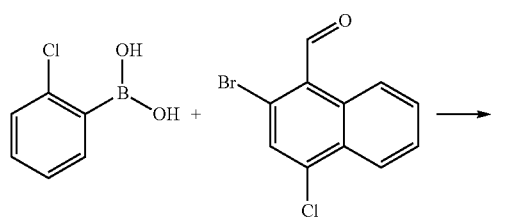

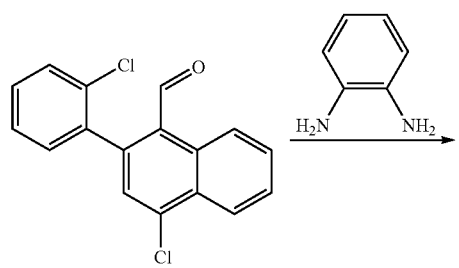

[compound A-39]

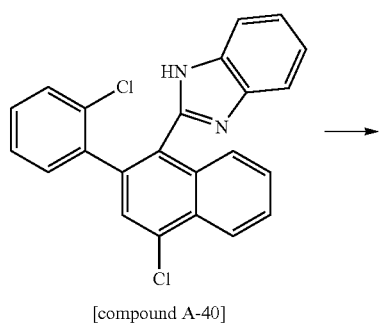

[compound A-40]

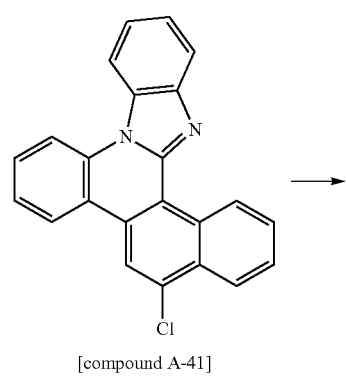

[compound A-41]

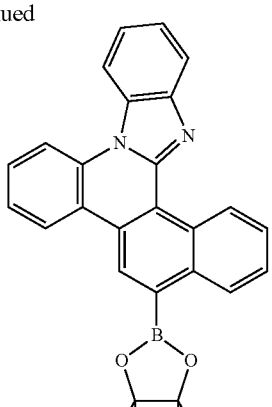

[compound A-42]

Preparation Example 11-1

Preparation of Compound A-39

After 2-chlorophenylboronic acid (17.2 g, 110 mmol) and 2-bromo-4-chloro-1-naphthaldehyde (26.9 g, 100 mmol) were completely dissolved in tetrahydrofurane (THF) (300 mL), 2M potassium carbonate aqueous solution (180 mL) was added thereto, and tetrakistriphenylphosphino palladium (Pd(PPh$_3$)$_4$) (2.3 g, 2 mol %) was put thereinto, agitated and refluxed for 5 hours. The temperature was lowered to normal temperature, the water layer was removed, and the organic layer was dried by anhydrous magnesium sulfate (MgSO$_4$) and filtered. The filtered solution was concentrated under the reduced pressure, and columned with tetrahydrofurane:hexane=1:10 to prepare compound A-39 (22.8 g, 76%).

MS: [M+H]$^+$=301

Preparation Example 11-2

Preparation of Compound A-40

Compound A-40 was prepared by using the same method as Preparation Example 1-2, except that compound A-39 was used instead of compound A-1 in Preparation Example 1-2.

MS: [M+H]$^+$=389

Preparation Example 11-3

Preparation of Compound A-41

Compound A-41 was prepared by using the same method as Preparation Example 1-3, except that compound A-40 was used instead of compound A-2 in Preparation Example 1-3.

MS: [M+H]$^+$=353

Preparation Example 11-4

Preparation of Compound A-42

Compound A-42 was prepared by using the same method as Preparation Example 1-3, except that compound A-41 was used instead of compound A-3 in Preparation Example 1-4.

MS: [M+H]$^+$=445

Preparation Example 12

Preparation of the Following Compounds A-43, A-44, A-45 and A-46

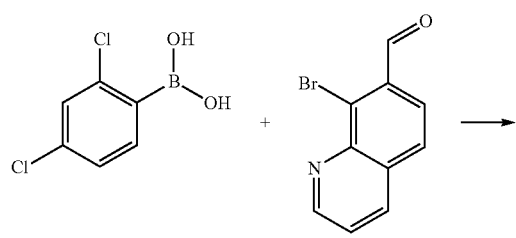

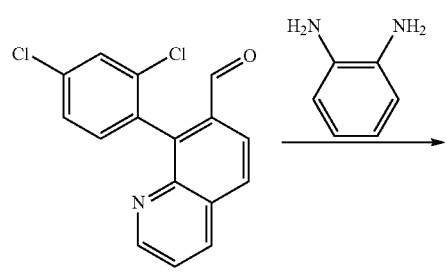

[compound A-43]

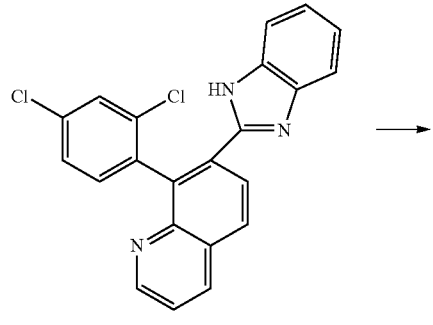

[compound A-44]

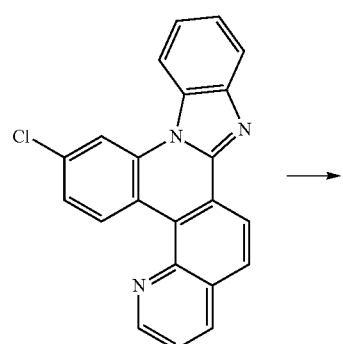

[compound A-45]

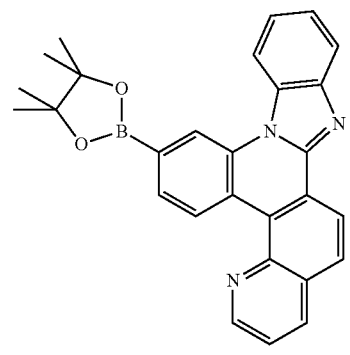

[compound A-46]

Compound A-46 was prepared by using the same method as Preparation Example 1, except that 8-bromo-7-quinolinecarboxaldehyde was used instead of 2-bromo-1-naphthaldehyde in Preparation Example 1.

MS: $[M+H]^+=446$

Preparation Example 13

Preparation of the Following Compounds A-47, A-48, A-49 and A-50

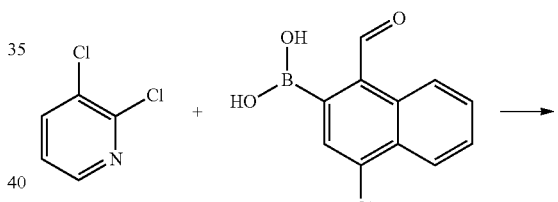

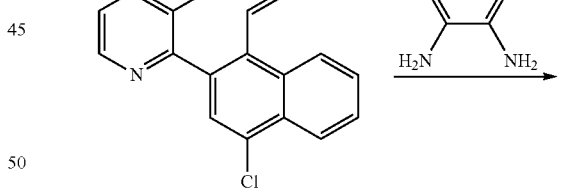

[compound A-47]

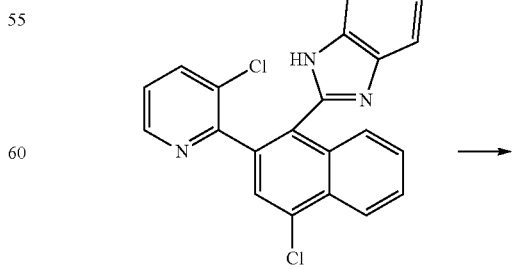

[compound A-48]

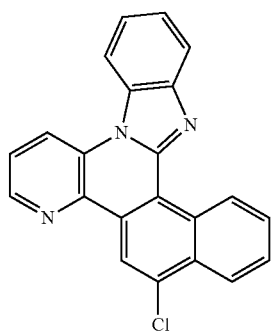

[compound A-49]

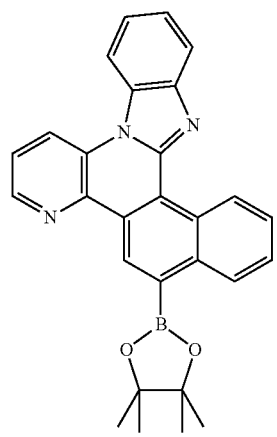

[compound A-50]

Compound A-50 was prepared by using the same method as Preparation Example 11, except that 2,3-dichloropyridine was used instead of 2-chlorophenyl-boronic acid and 4-chloro-1-formyl-2-naphthalene-2-boronic acid was used instead of 2-bromo-4-chloro-1-naphthaldehyde in Preparation Example 11.

MS: [M+H]$^+$=446

Example 1

Preparation of Formula 3-1-1-2

[Formula 3-1-1-2]

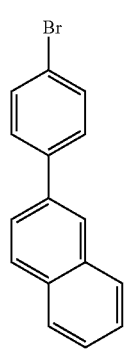

+

After 2-(4-bromophenyl)naphthalene (2.83 g, 10.0 mmol) and compound A-4 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-1-1-2 (3.54 g, 68%).

MS: [M+H]$^+$=521

Example 2

Preparation of the Compound of Formula 3-1-1-6

[compound B-1]

[Formula 3-1-1-6]

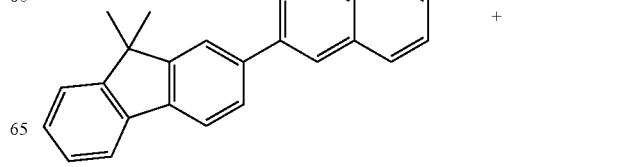

+

-continued

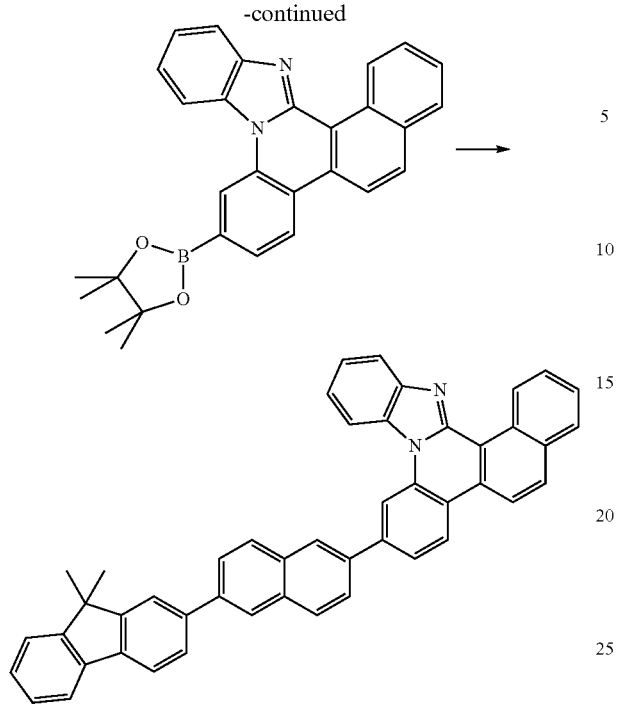

Formula 3-1-1-6 was prepared by using the same method as Example 1, except that compound B-1 was used instead of 2-(4-bromophenyl)naphthalene in Example 1.

MS: [M+H]$^+$=637

Example 3

Preparation of the Compound of Formula 3-1-1-7

[compound B-2]

[Formula 3-1-1-7]

-continued

Formula 3-1-1-7 was prepared by using the same method as Example 1, except that compound B-2 was used instead of 2-(4-bromophenyl)naphthalene in Example 1.

MS: [M+H]$^+$=621

Example 4

Preparation of the Compound of Formula 3-1-1-12

[compound B-3]

[Formula 3-1-1-12]

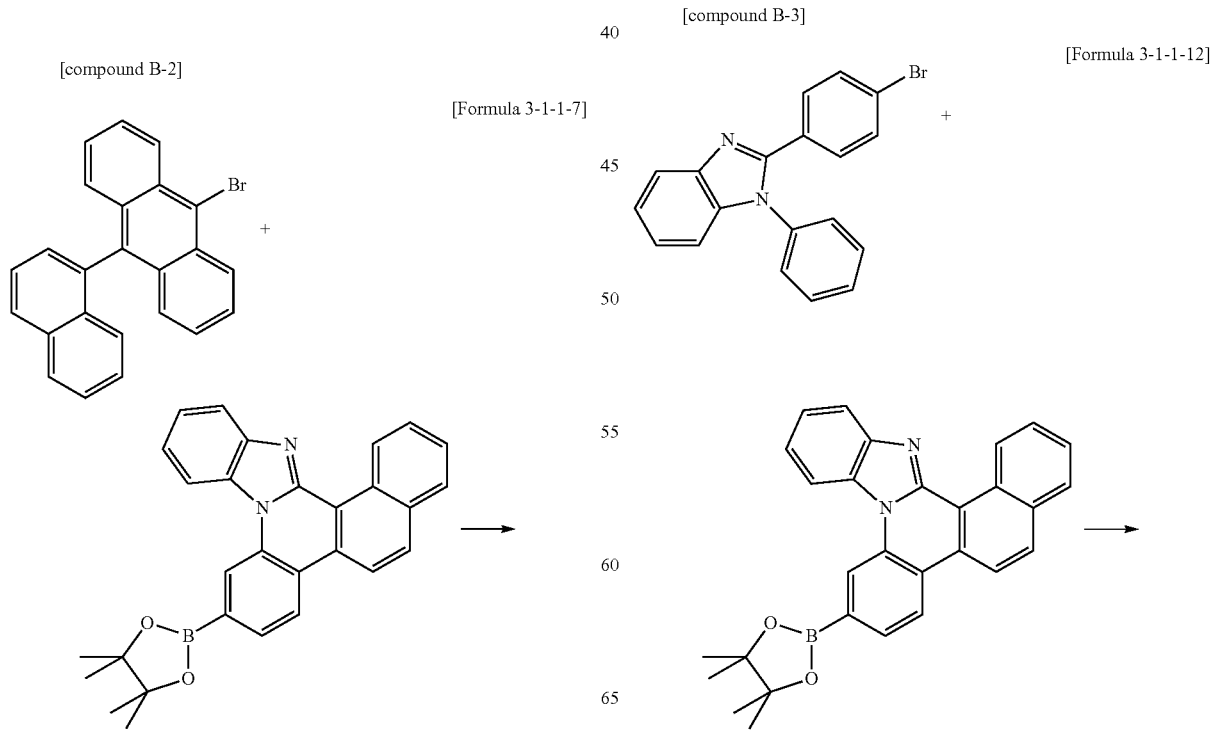

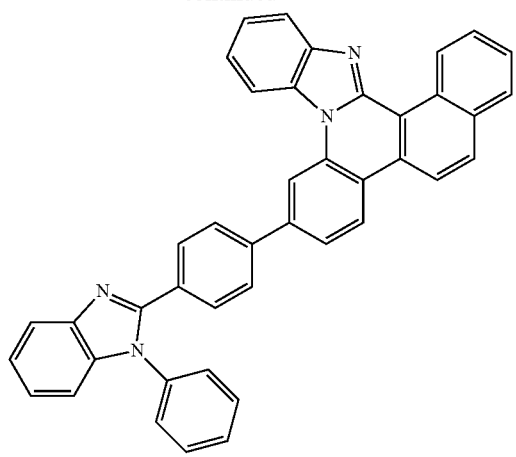

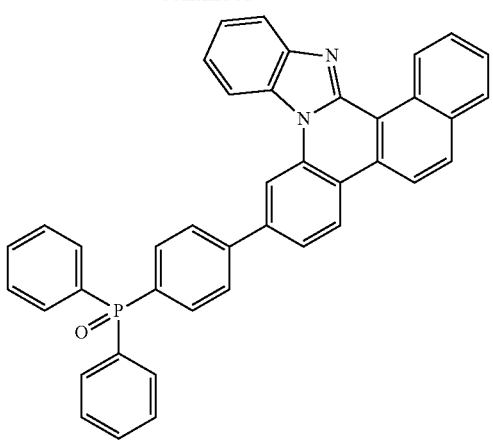

Formula 3-1-1-12 was prepared by using the same method as Example 1, except that compound B-3 was used instead of 2-(4-bromophenyl)naphthalene in Example 1.

MS: [M+H]$^+$=587

Formula 3-1-1-24 was prepared by using the same method as Example 1, except that compound B-4 was used instead of 2-(4-bromophenyl)naphthalene in Example 1.

MS: [M+H]$^+$=595

Example 5

Preparation of the Compound of Formula 3-1-1-24

[compound B-4]

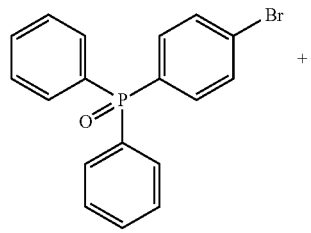

+

Example 6

Preparation of the Compound of Formula 3-1-2-2

[Formula 3-1-1-24]

[Formula 3-1-2-2]

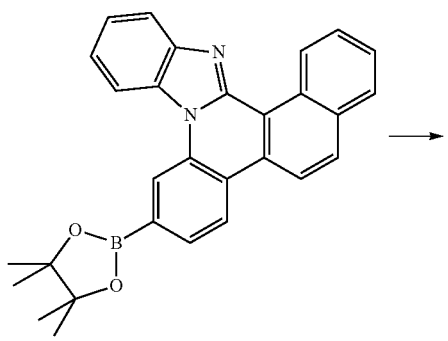

→

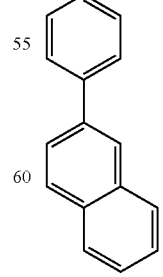

+

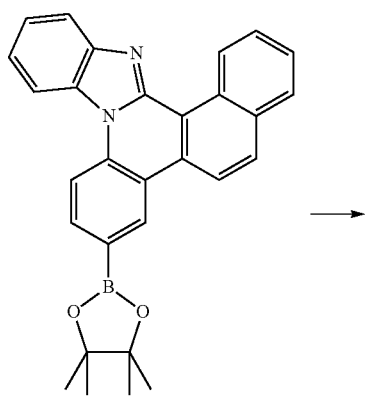

→

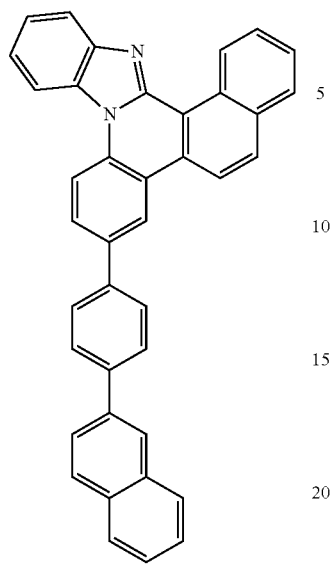

After 2-(4-bromophenyl)naphthalene (2.83 g, 10.0 mmol) and compound A-8 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-1-2-2 (3.75 g, 72%).

MS: [M+H]$^+$=521

Example 7

Preparation of the Compound of Formula 3-1-2-15

[compound C-1]

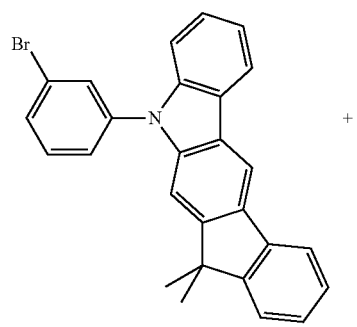

[Formula 3-1-2-15]

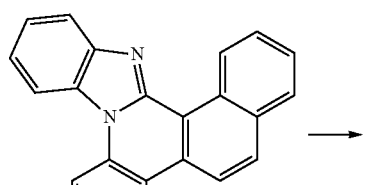

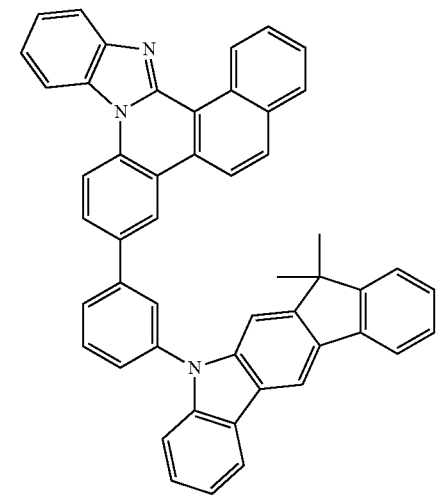

Formula 3-1-2-15 was prepared by using the same method as Example 6, except that compound C-1 was used instead of 2-(4-bromophenyl)naphthalene in Example 6.

MS: [M+H]$^+$=676

Example 8

Preparation of the Compound of Formula 3-1-2-21

[compound C-2]

[Formula 3-1-2-21]

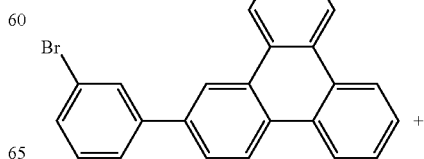

+

-continued

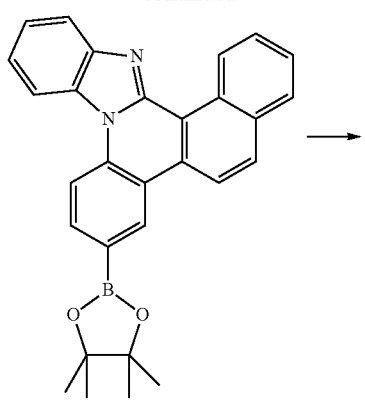

Formula 3-1-2-21 was prepared by using the same method as Example 6, except that compound C-2 was used instead of 2-(4-bromophenyl)naphthalene in Example 6.

MS: [M+H]$^+$=621

Example 9

Preparation of the Compound of Formula 3-2-1-2

[Formula 3-2-1-2]

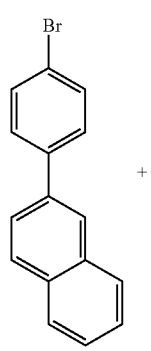

+

-continued

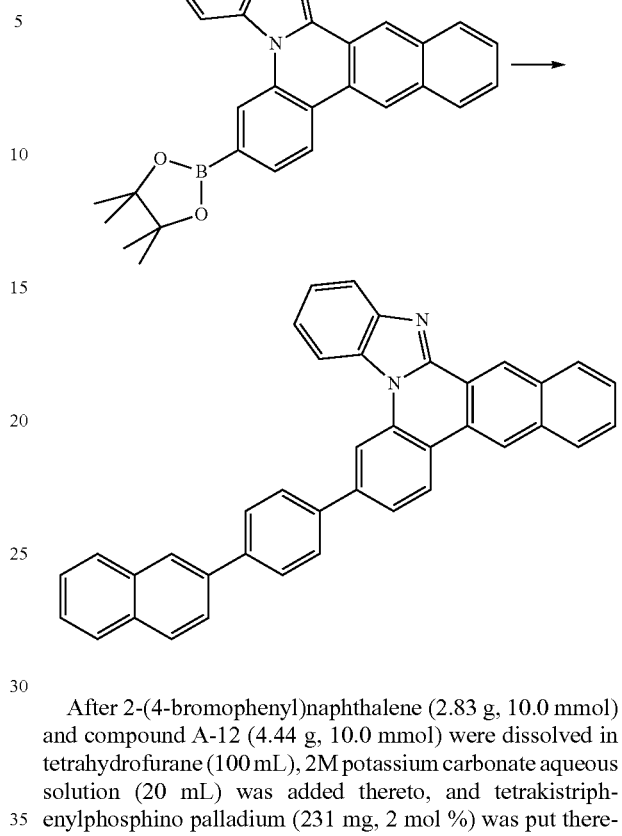

After 2-(4-bromophenyl)naphthalene (2.83 g, 10.0 mmol) and compound A-12 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-2-1-2 (2.76 g, 53%).

MS: [M+H]$^+$=521

Example 10

Preparation of the Compound of Formula 3-2-1-11

[compound D-1]

[Formula 3-2-1-11]

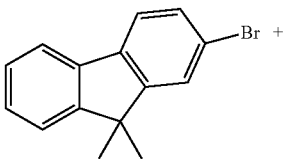

+

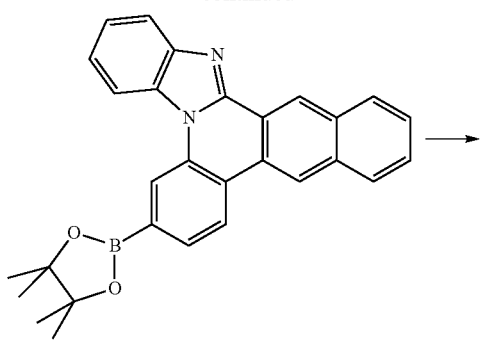

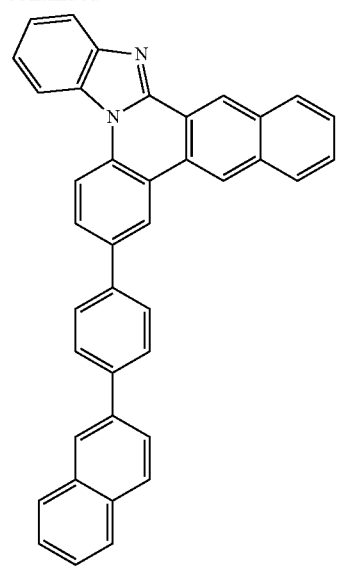

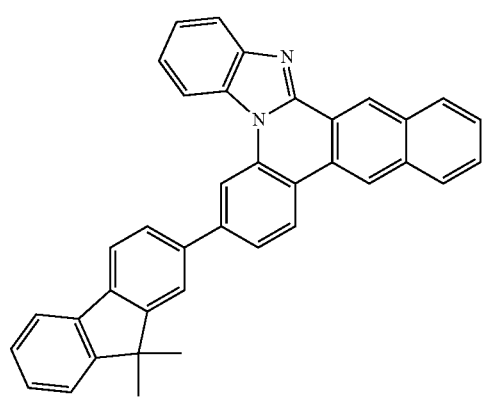

Formula 3-2-1-11 was prepared by using the same method as Example 9, except that compound D-1 was used instead of 2-(4-bromophenyl)naphthalene in Example 9.

MS: $[M+H]^+=511$

After 2-(4-bromophenyl)naphthalene (2.83 g, 10.0 mmol) and compound A-16 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-2-2-2 (3.13 g, 60%).

MS: $[M+H]^+=521$

Example 11

Preparation of the Compound of Formula 3-2-2-2

[Formula 3-2-2-2]

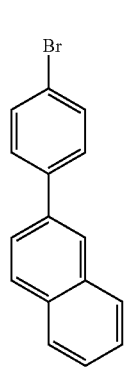
+
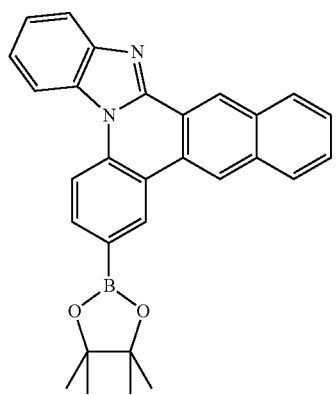
→

Example 12

Preparation of the Compound of Formula 3-2-2-14

[compound E-1]

[Formula 3-2-2-14]

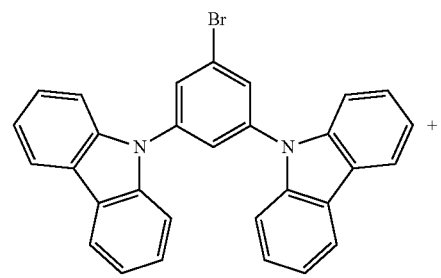
+

205
-continued

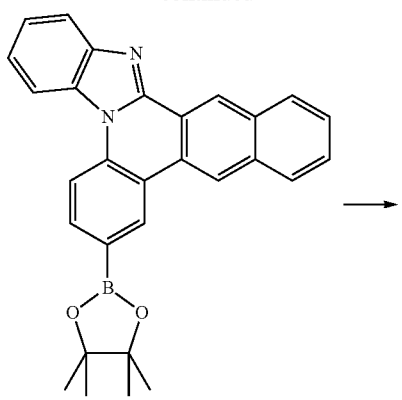

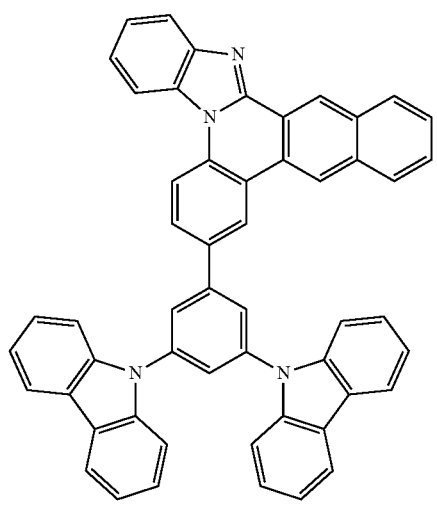

Formula 3-2-2-14 was prepared by using the same method as Example 11, except that compound E-1 was used instead of 2-(4-bromophenyl)naphthalene in Example 11.

MS: [M+H]⁺=725

Example 13

Preparation of the Compound of Formula 3-3-1-2

[Formula 3-3-1-2]

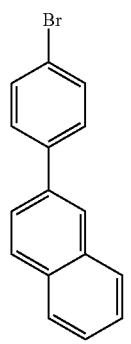

+

206
-continued

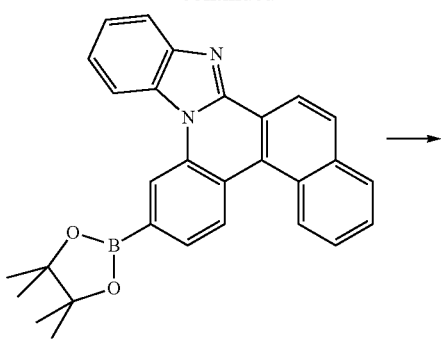

After 2-(4-bromophenyl)naphthalene (2.83 g, 10.0 mmol) and compound A-20 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-3-1-2 (3.80 g, 73%).

MS: [M+H]⁺=521

Example 14

Preparation of the Compound of Formula 3-3-1-18

[compound F-1]

[Formula 3-3-1-18]

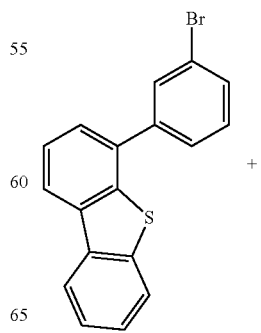

+

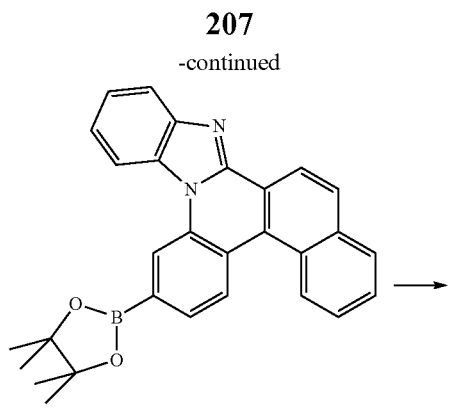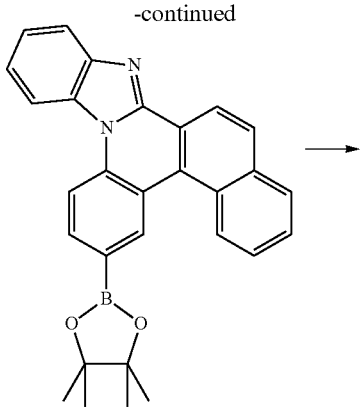

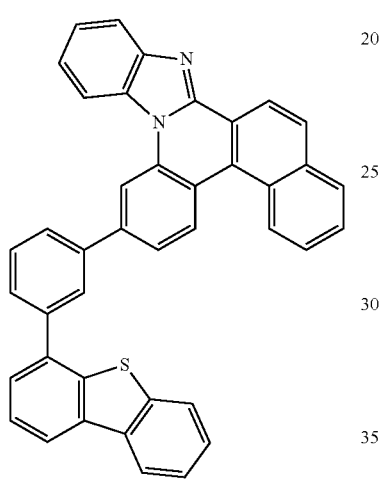

Formula 3-3-1-18 was prepared by using the same method as Example 13, except that compound F-1 was used instead of 2-(4-bromophenyl)naphthalene in Example 13.

MS: [M+H]⁺=577

Example 15

Preparation of the Compound of Formula 3-3-2-2

[Formula 3-3-2-2]

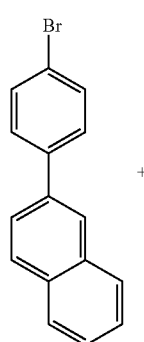 +

After 2-(4-bromophenyl)naphthalene (2.83 g, 10.0 mmol) and compound A-24 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-3-2-2 (3.39 g, 65%).

MS: [M+H]⁺=521

Example 16

Preparation of the Compound of Formula 3-8-1-2

[Formula 3-8-1-2]

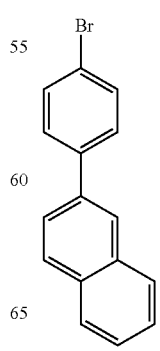 +

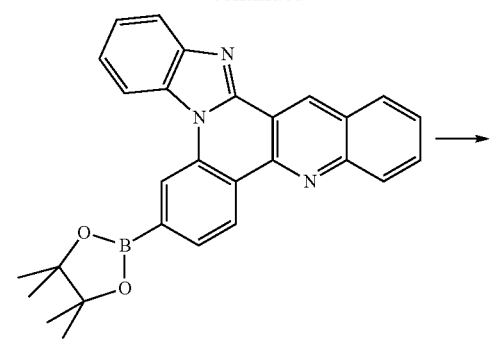

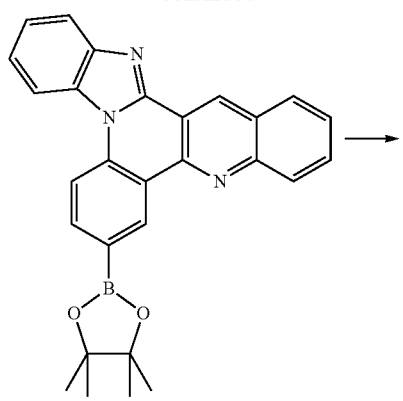

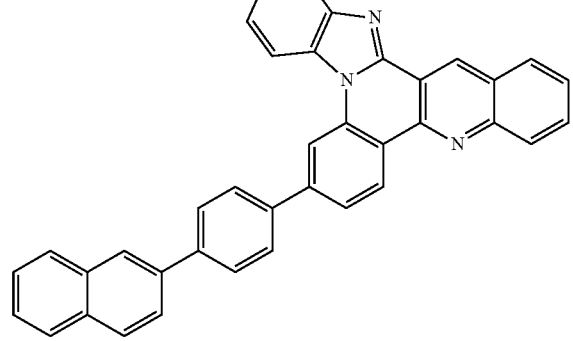

Formula 3-8-1-2 was prepared by using the same method as Example 1, except that compound A-28 was used instead of compound A-4 in Example 1.

MS: [M+H]$^+$=522

Formula 3-8-2-2 was prepared by using the same method as Example 1, except that compound A-32 was used instead of compound A-4 in Example 1.

MS: [M+H]$^+$=522

Example 17

Preparation of the Compound of Formula 3-8-2-2

Example 18

Preparation of the Compound of Formula 3-1-1-29

[Formula 3-8-2-2]

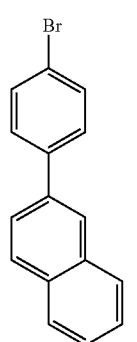 +

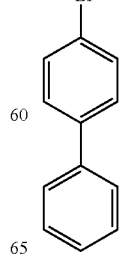 + 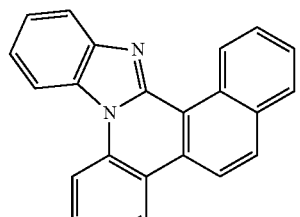 →

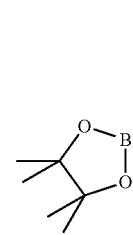

-continued

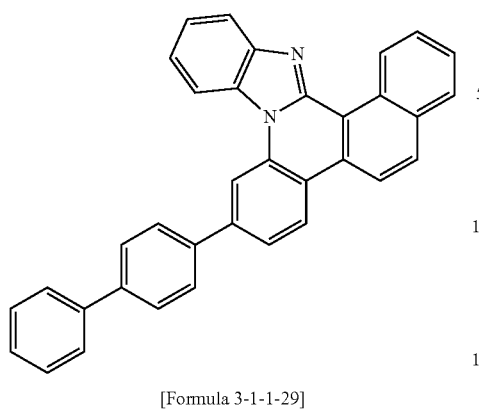

[Formula 3-1-1-29]

Formula 3-1-1-29 was prepared by using the same method as Example 1, except that 4-bromobiphenyl was used instead of 2-(4-bromophenyl)naphthalene in Example 1.

MS: $[M+H]^+ = 471$

Example 19

Preparation of the Compound of Formula 3-1-1-30

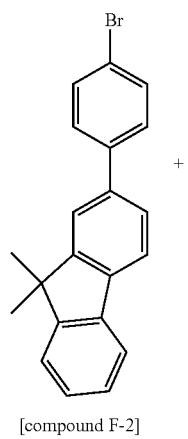

[compound F-2]

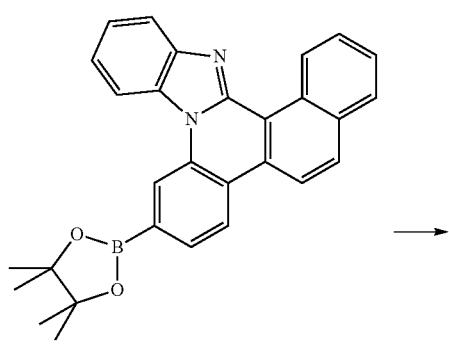

-continued

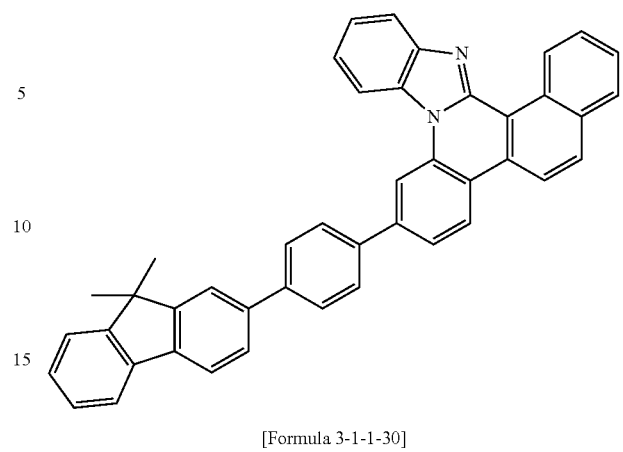

[Formula 3-1-1-30]

Formula 3-1-1-30 was prepared by using the same method as Example 1, except that compound F-2 was used instead of 2-(4-bromophenyl)naphthalene in Example 1.

MS: $[M+H]^+ = 587$

Example 20

Preparation of the Compound of Formula 3-1-1-33

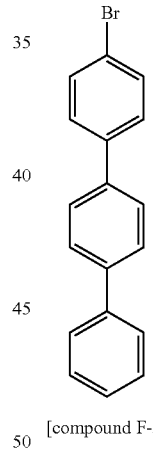

[compound F-3]

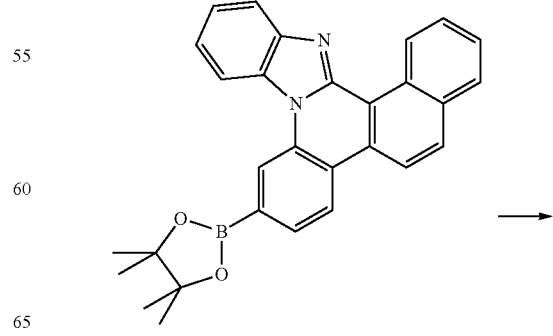

-continued

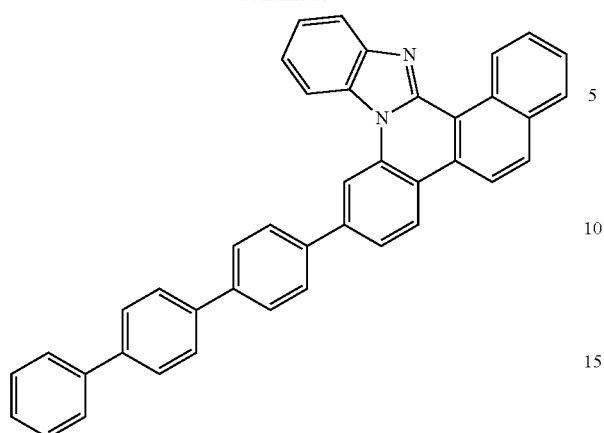

[Formula 3-1-1-33]

Formula 3-1-1-33 was prepared by using the same method as Example 1, except that compound F-3 was used instead of 2-(4-bromophenyl)naphthalene in Example 1.

MS: [M+H]$^+$=547

Example 21

Preparation of the Compound of Formula 3-1-2-14

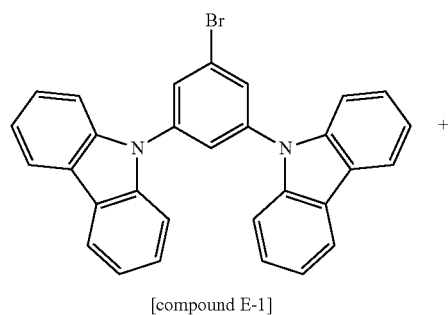

[compound E-1]

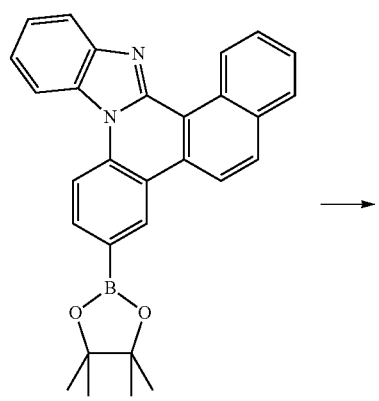

-continued

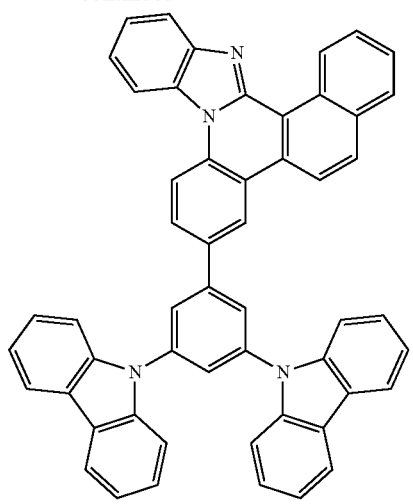

[Formula 3-1-2-14]

Formula 3-1-2-14 was prepared by using the same method as Example 6, except that compound E-1 was used instead of 2-(4-bromophenyl)naphthalene in Example 6.

MS: [M+H]$^+$=725

Example 22

Preparation of the Compound of Formula 3-1-2-29

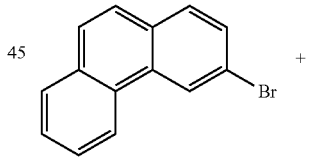

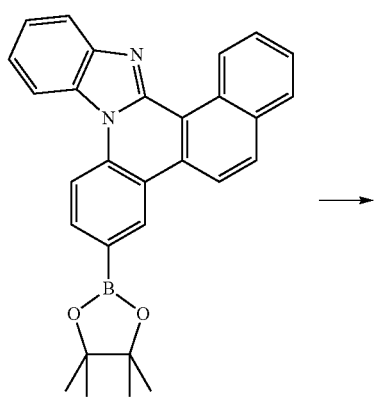

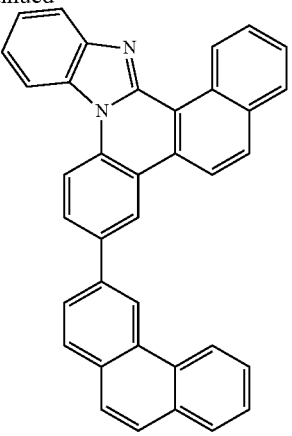

[Formula 3-1-2-29]

Formula 3-1-2-29 was prepared by using the same method as Example 6, except that 3-bromophenanthrene was used instead of 2-(4-bromophenyl)naphthalene in Example 6.

MS: [M+H]$^+$=495

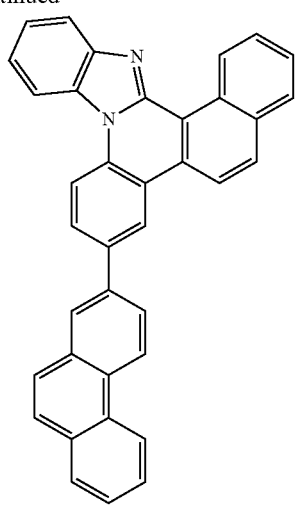

Formula 3-1-2-30 was prepared by using the same method as Example 6, except that 2-bromophenanthrene was used instead of 2-(4-bromophenyl)naphthalene in Example 6.

MS: [M+H]$^+$=495

Example 23

Preparation of the Compound of Formula 3-1-2-30

Example 24

Preparation of the Compound of Formula 3-1-2-33

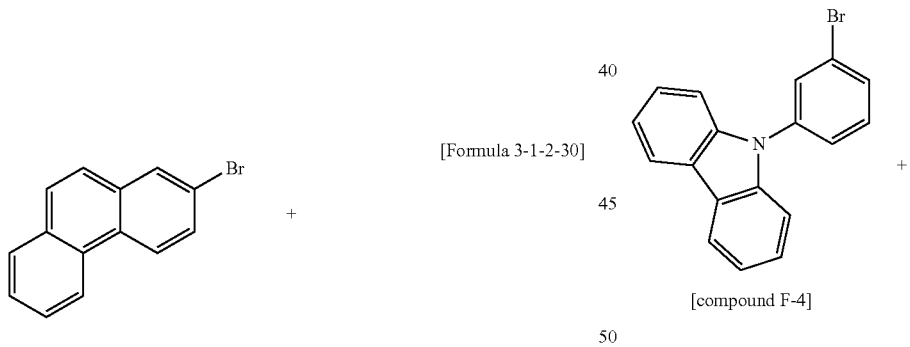

[Formula 3-1-2-30]

[compound F-4]

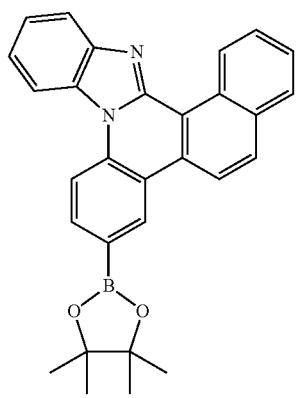

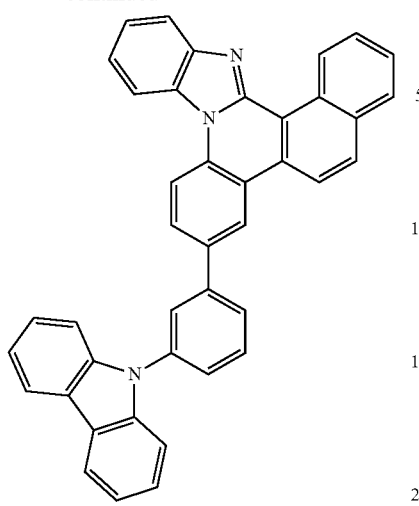

[Formula 3-1-2-33]

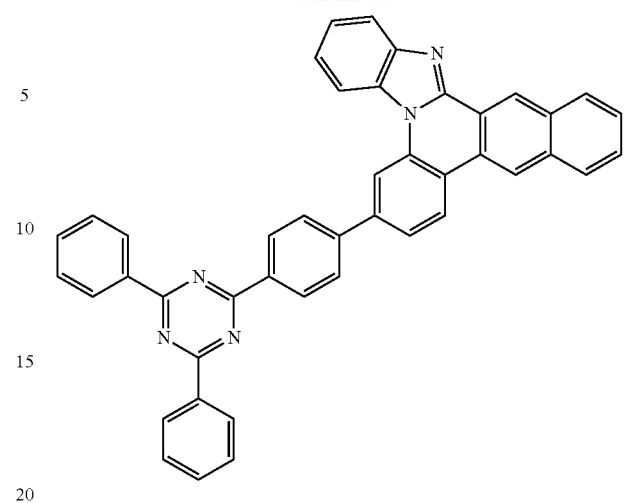

[Formula 3-2-1-23]

Formula 3-1-2-33 was prepared by using the same method as Example 6, except that compound F-4 was used instead of 2-(4-bromophenyl)naphthalene in Example 6.

MS: $[M+H]^+=560$

Example 25

Preparation of the Compound of Formula 3-2-1-23

Formula 3-2-1-23 was prepared by using the same method as Example 9, except that compound F-5 was used instead of 2-(4-bromophenyl)naphthalene in Example 9.

MS: $[M+H]^+=626$

Example 26

Preparation of the Compound of Formula 3-3-2-28

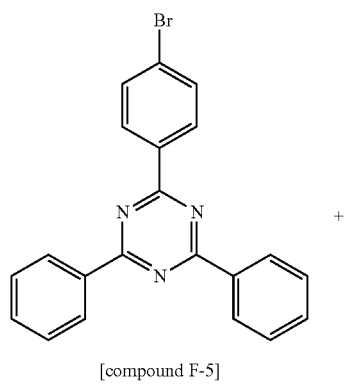

[compound F-5]

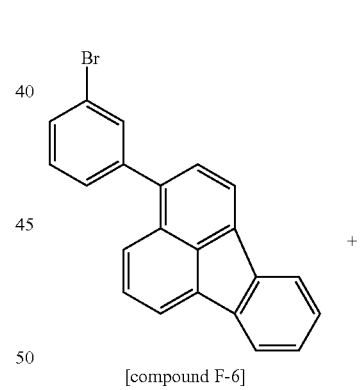

[compound F-6]

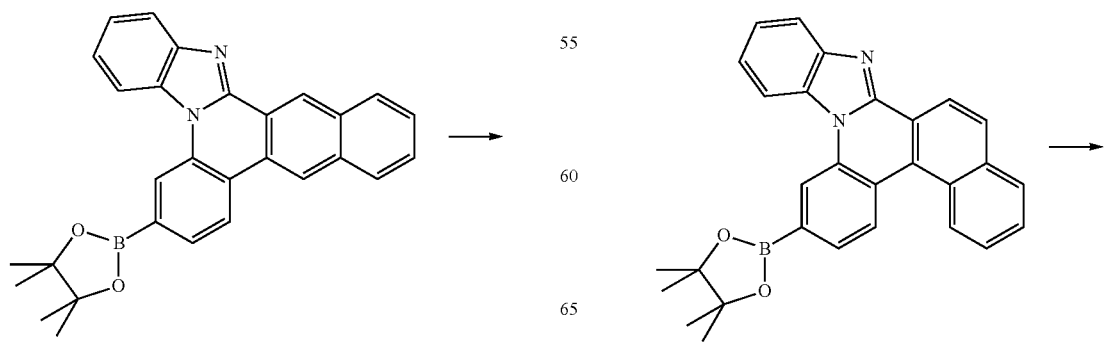

-continued

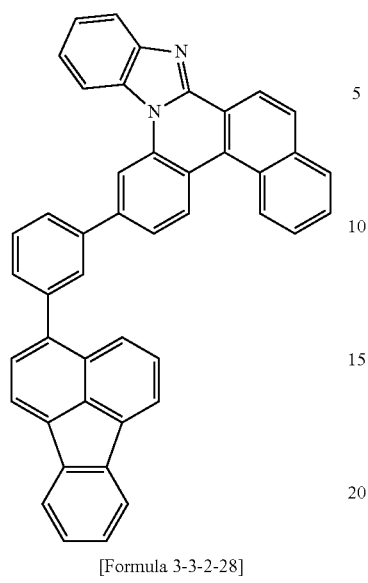

[Formula 3-3-2-28]

Formula 3-3-2-28 was prepared by using the same method as Example 15, except that compound F-6 was used instead of 2-(4-bromophenyl)naphthalene in Example 15.

MS: [M+H]$^+$=595

Example 27

Preparation of the Compound of Formula 3-4-1-4

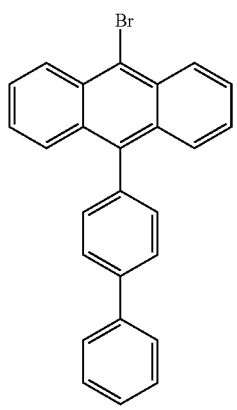

[compound F-7]

-continued

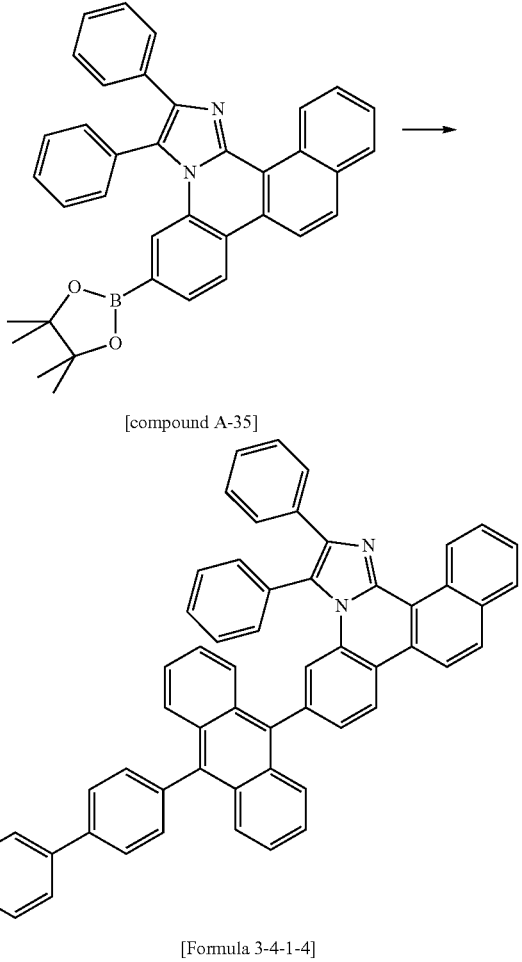

[compound A-35]

[Formula 3-4-1-4]

After compound F-7 (4.09 g, 10.0 mmol) and compound A-35 (5.46 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-4-1-4 (5.31 g, 71%).

MS: [M+H]$^+$=749

Example 28

Preparation of the Compound of Formula 3-4-1-6

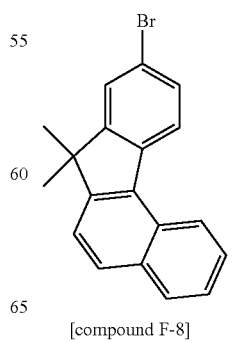

[compound F-8]

-continued

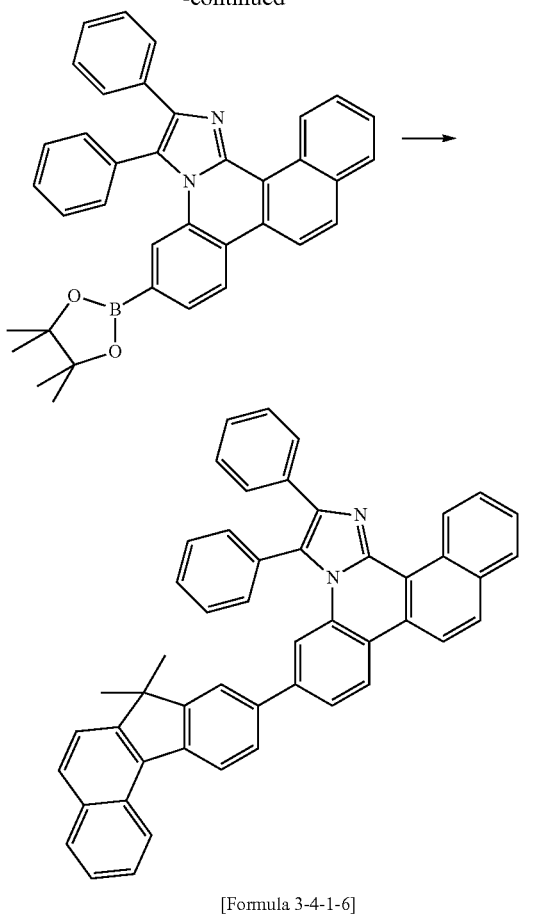

[Formula 3-4-1-6]

Formula 3-4-1-6 was prepared by using the same method as Example 27, except that compound F-8 was used instead of compound F-7 in Example 27.

MS: [M+H]$^+$=663

Example 29

Preparation of the Compound of Formula 3-5-1-1

-continued

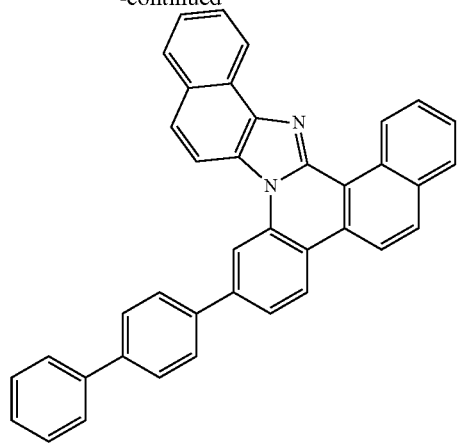

[Formula 3-5-1-1]

After 4-bromobiphenyl (2.33 g, 10.0 mmol) and compound A-38 (4.94 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-5-1-1 (3.85 g, 74%).

MS: [M+H]$^+$=521

Example 30

Preparation of the Compound of Formula 3-5-1-7

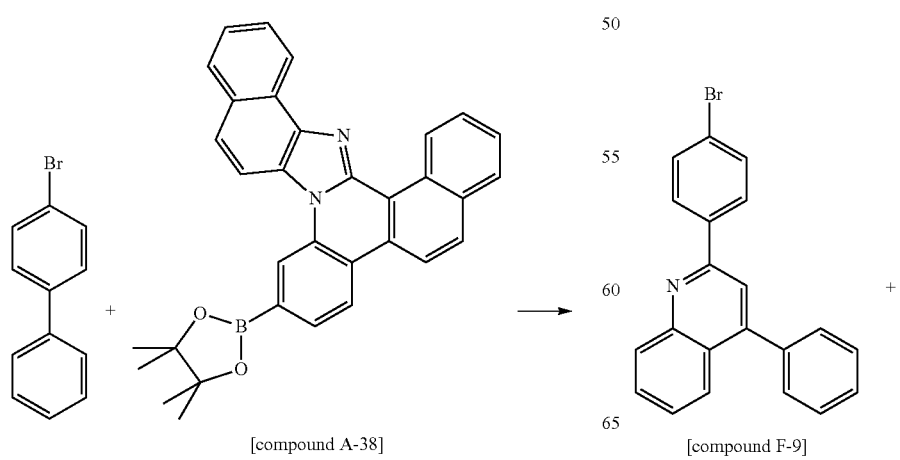

[compound A-38]   [compound F-9]

-continued

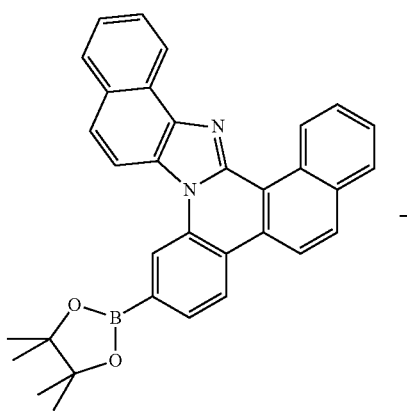

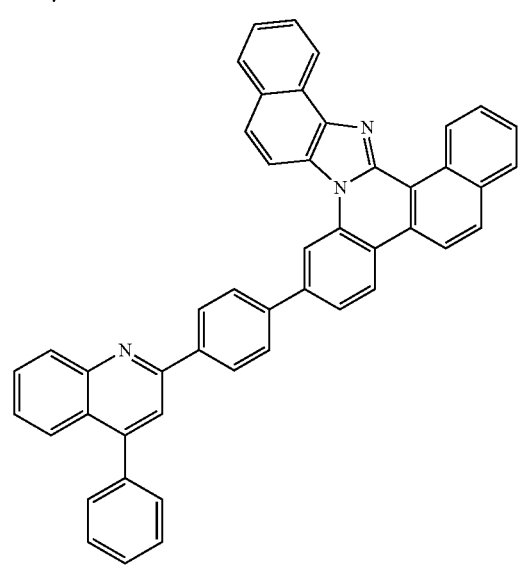

[Formula 3-5-1-7]

Formula 3-5-1-7 was prepared by using the same method as Example 29, except that compound F-9 was used instead of 4-bromobiphenyl in Example 29.

MS: [M+H]$^+$=548

Example 31

Preparation of the Compound of Formula 3-6-1-1

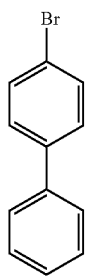

+

-continued

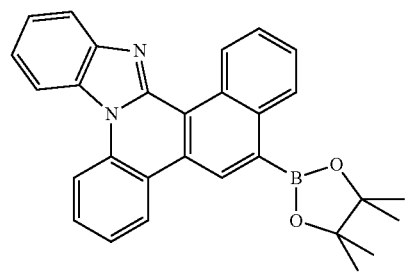

[compound A-42]

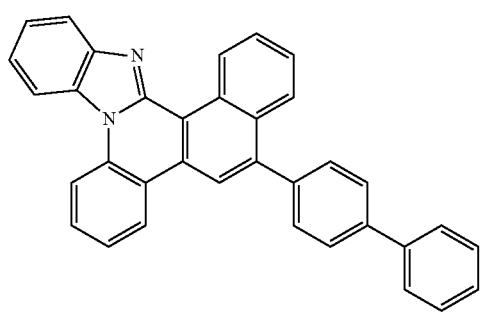

[Formula 3-6-1-1]

After 4-bromobiphenyl (2.33 g, 10.0 mmol) and compound A-42 (4.44 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-6-1-1 (3.05 g, 65%).

MS: [M+H]$^+$=471

Example 32

Preparation of the Compound of Formula 3-6-1-4

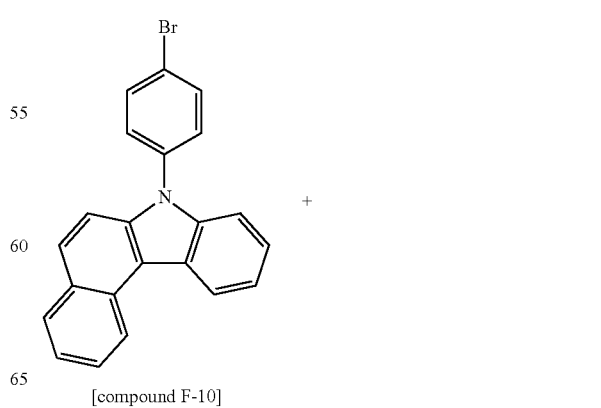

[compound F-10]

+

-continued

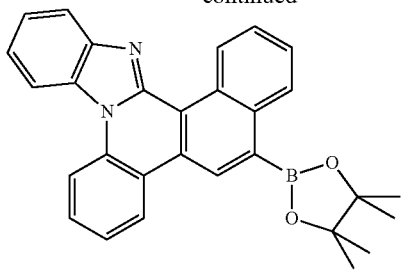

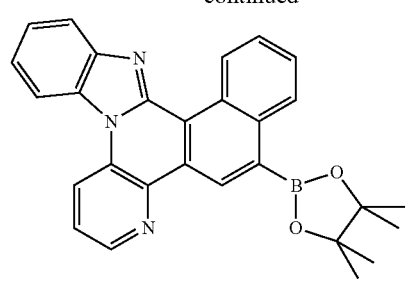

[compound A-50]

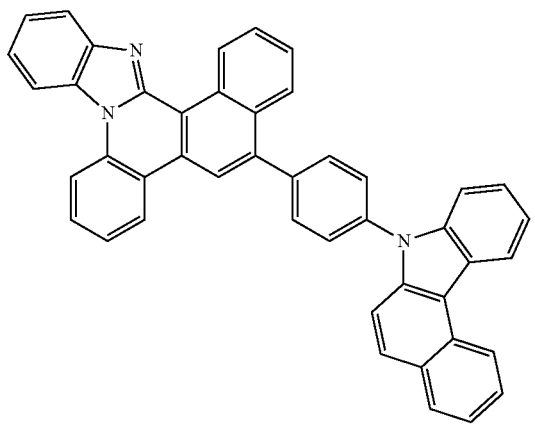

[Formula 3-6-1-4]

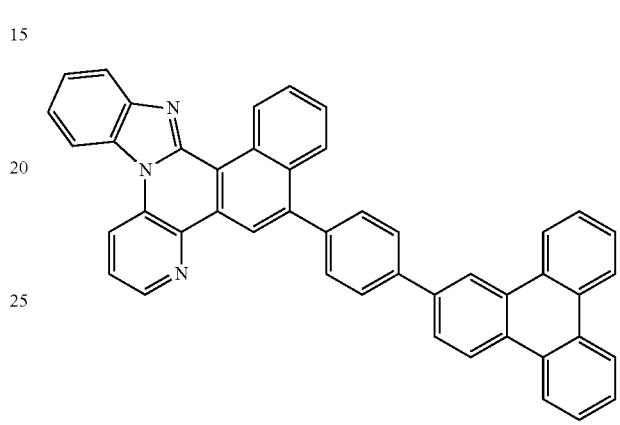

[Formula 3-6-2-7]

Formula 3-6-1-4 was prepared by using the same method as Example 31, except that compound F-10 was used instead of 4-bromobiphenyl in Example 31.
MS: [M+H]$^+$=610

After compound F-11 (3.83 g, 10.0 mmol) and compound A-50 (4.45 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-6-2-7 (4.04 g, 65%).
MS: [M+H]$^+$=622

Example 33

Preparation of the Compound of Formula 3-6-2-7

Example 34

Preparation of the Compound of Formula 3-6-2-9

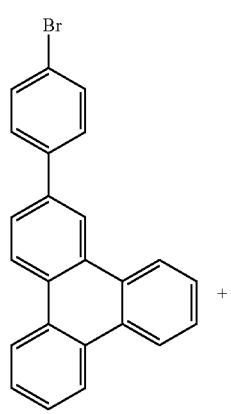

+

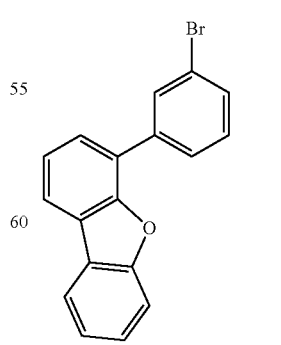

+

[compound F-11]

[compound F-12]

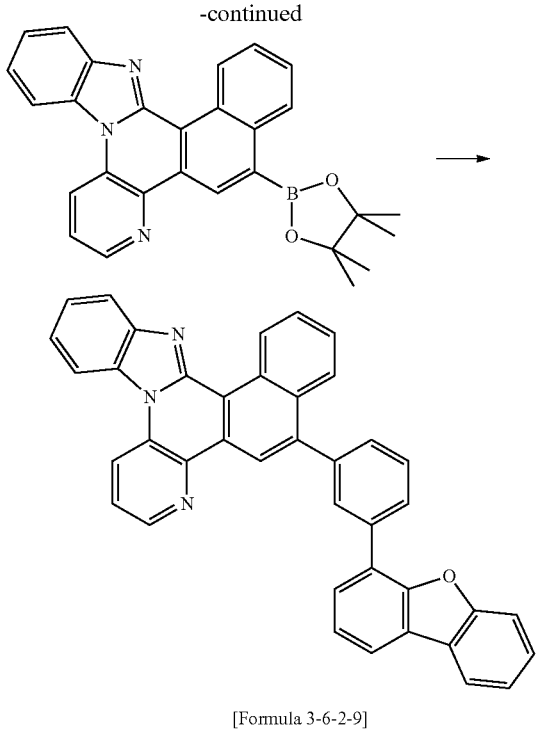

[Formula 3-6-2-9]

Formula 3-6-2-9 was prepared by using the same method as Example 33, except that compound F-12 was used instead of compound F-11 in Example 33.
MS: [M+H]$^+$=562

Example 35

Preparation of the Compound of Formula 3-8-2-16

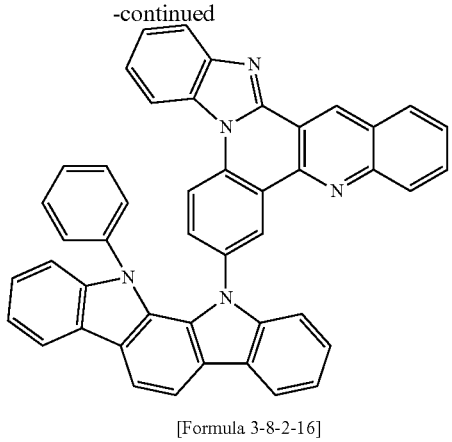

[Formula 3-8-2-16]

Compound F-13 (6.71 g, 20.2 mmol) and compound A-31 (7.13 g, 20.2 mmol) were dispersed in xylene (150 mL), and NaOt-Bu (2.9 g, 30.3 mmol) and Pd[P(t-Bu)$_3$]$_2$ (0.1 g, 0.20 mmol) were added thereto, agitated and refluxed for 5 hours. The temperature was lowered to normal temperature, and the generated solid was filtered. The filtered solid was recrystallized by chloroform and ethanol, filtered, and dried to prepare the compound of Formula 3-8-2-16 (6.69 g, 51%).
MS: [M+H]$^+$=650

Example 36

Preparation of the Compound of Formula 3-9-1-11

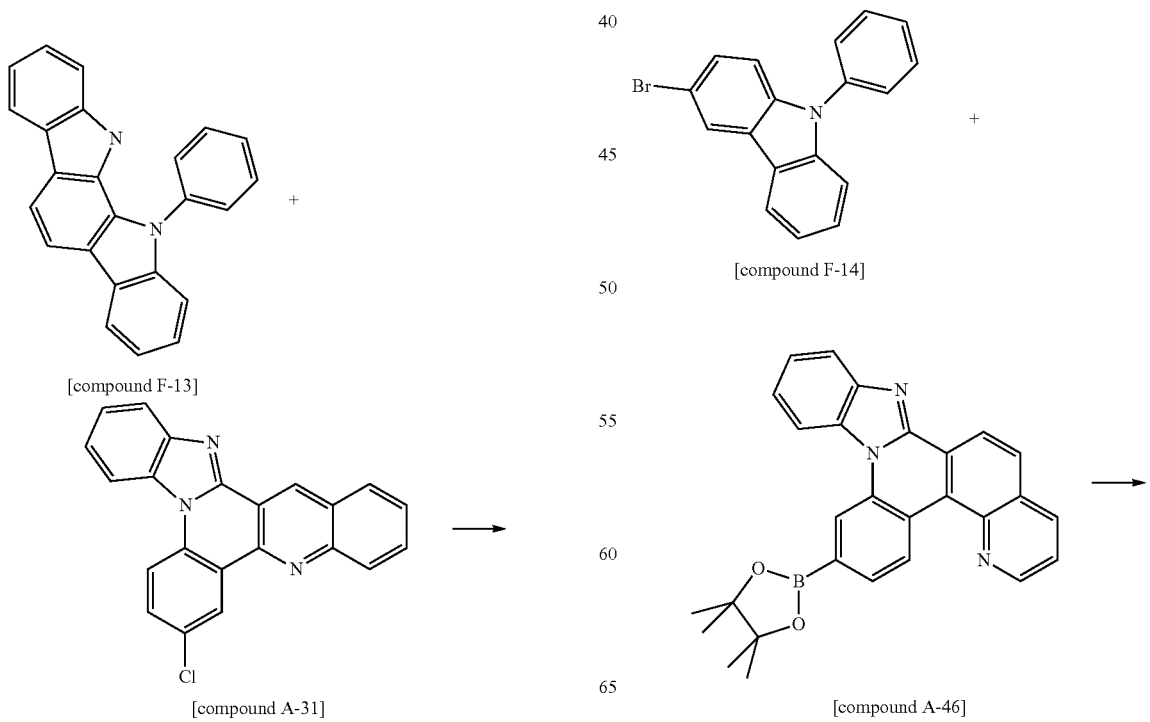

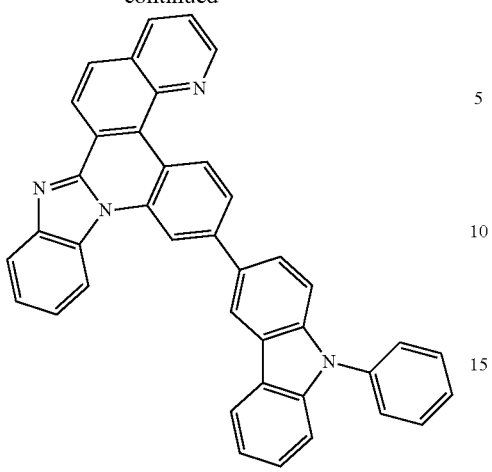

[Formula 3-9-1-11]

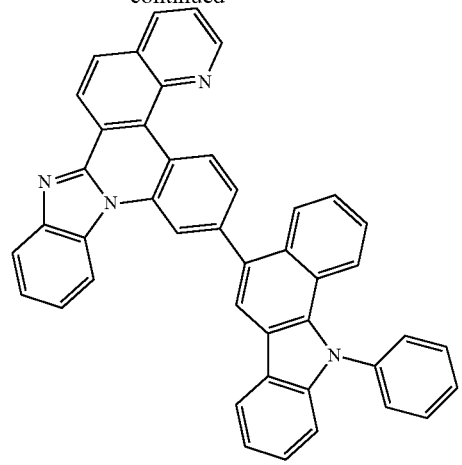

[Formula 3-9-1-13]

After compound F-14 (3.22 g, 10.0 mmol) and compound A-46 (4.45 g, 10.0 mmol) were dissolved in tetrahydrofurane (100 mL), 2M potassium carbonate aqueous solution (20 mL) was added thereto, and tetrakistriphenylphosphino palladium (231 mg, 2 mol %) was put thereinto, agitated and refluxed for 5 hours. The temperature was lowered to normal temperature, and the generated solid was filtered. The filtered solid was recrystallized by chloroform and ethanol, filtered, and dried to prepare the compound of Formula 3-9-1-11 (3.47 g, 62%).

MS: [M+H]$^+$=561

Example 37

Preparation of the Compound of Formula 3-9-1-13

Formula 3-9-1-13 was prepared by using the same method as Example 36, except that compound F-15 was used instead of compound F-14 in Example 36.

MS: [M+H]$^+$=611

Example 38

Preparation of the Compound of Formula 3-1-1-34

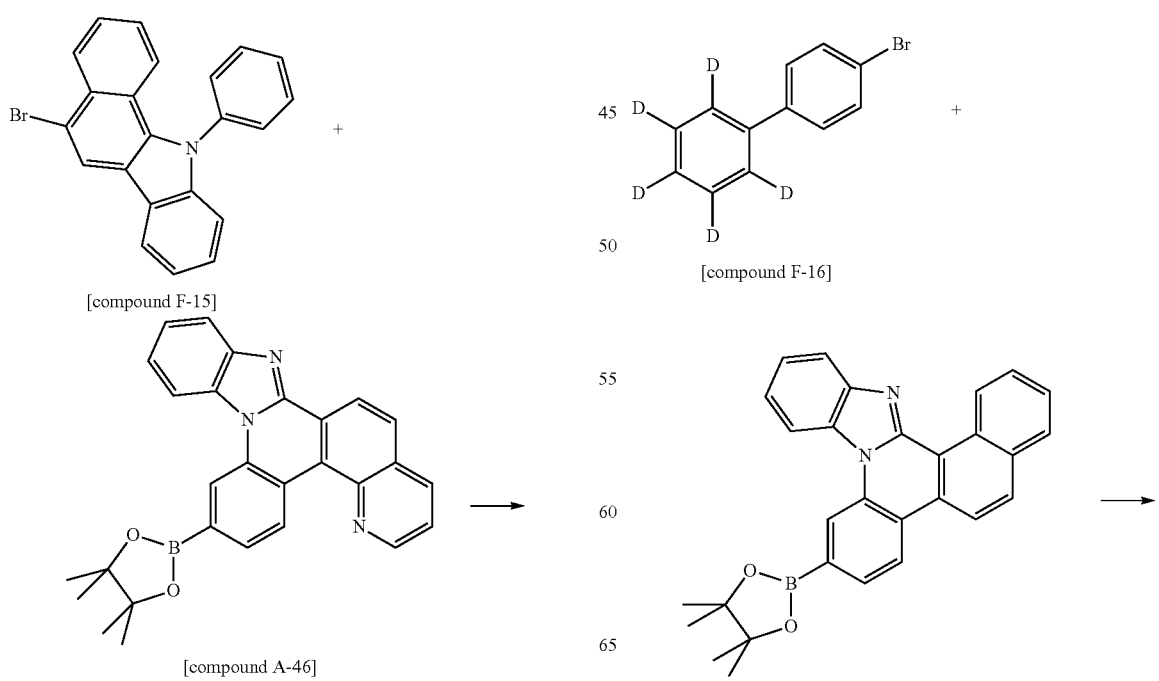

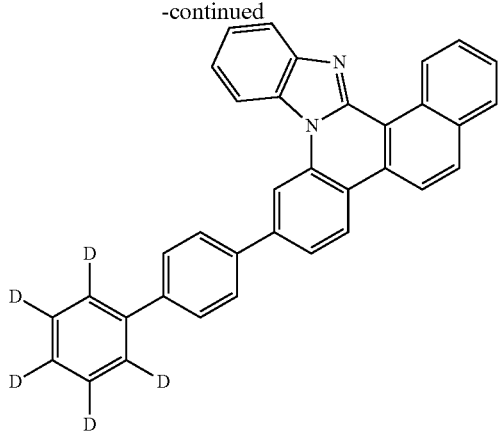

[Formula 3-1-1-34]

Formula 3-1-1-34 was prepared by using the same method as Example 1, except that compound F-16 was used instead of 2-(4-bromophenyl)naphthalene in Example 1.

MS: $[M+H]^+=476$

Experimental Example

Experimental Example 1-1-1

A glass substrate on which a thin film of indium tin oxide (ITO) was applied to a thickness of 500 Å was immersed in distilled water having a detergent dissolved therein and washed by the ultrasonic wave. In this case, the used detergent was a product commercially available from Fisher Co. and the distilled water was one which had been twice filtered by using a filter commercially available from Millipore Co. ITO was washed for 30 minutes, and then washing with ultrasonic waves was repeated twice for 10 minutes by distilled water. After washing with distilled water was finished, washing with ultrasonic waves was performed by using solvents such as isopropyl alcohol, acetone and methanol, and the resultant product was dried and transported to the plasma washing machine. In addition, the substrate was washed by using the oxygen plasma for 5 minutes, and then transported to the vacuum deposition machine.

Hexanitrile hexaazatriphenylene (HAT) of the following Formula was applied to thicknesses of 500 Å by thermal vacuum deposition on the ITO transparent electrode thus prepared to form a hole injecting layer.

[HAT]

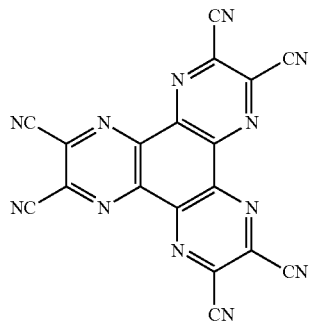

[NPB]

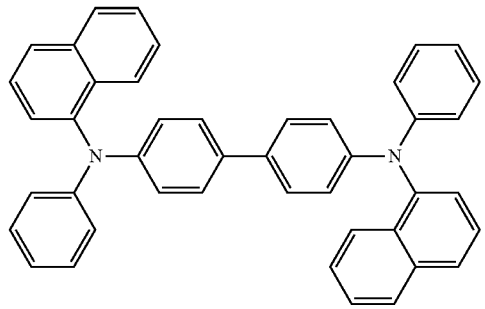

4,4'-bis[N-(1-naphthyl)-N-phenylamino]biphenyl (NPB) (250 Å), hexanitrile hexaazatriphenylene (HAT) (50 Å) and 4,4'-bis[N-(1-naphthyl)-N-phenylamino]biphenyl (NPB) (400 Å) of the aforementioned Formulas were sequentially vacuum deposited on the hole injection layer to form the hole transport layer.

Subsequently, GH and GD shown below were vacuum deposited at a weight ratio of 20:1 on the hole transport layer to form the light emitting layer in a film thickness of 300 Å.

[GH]

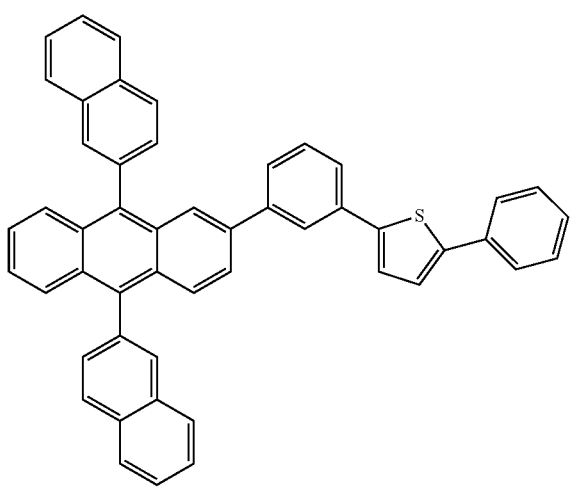

[GD]

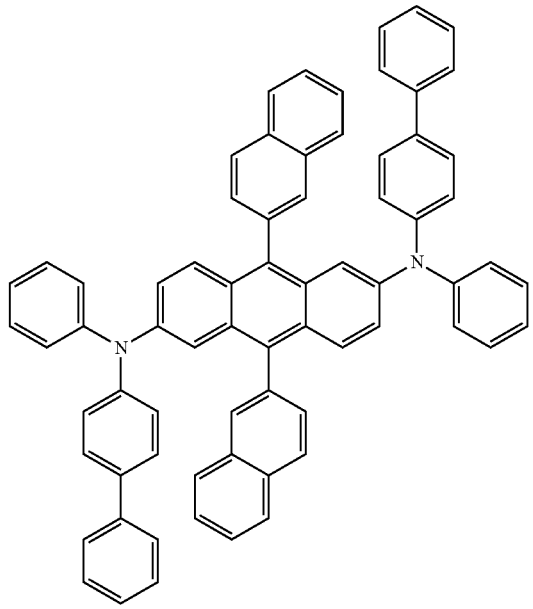

The compound of Formula 3-1-1-2 prepared in Example 1 and the following Formula LiQ (lithium quinalate) were vacuum deposited at a weight ratio of 1:1 on the light emitting layer to form the electronic injection and transport layer in a thickness of 200 Å.

[LiQ]

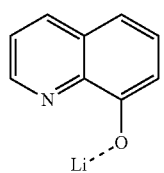

Lithium fluoride (LiF) in a thickness of 15 Å and aluminum in a thickness of 1,000 Å were subsequently deposited on the electron injection and transport layer to form the cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at $2 \times 10^{-7}$ to $5 \times 10^{-8}$ torr to manufacture the organic light emitting device.

Comparative Example 1

The organic light emitting device was manufactured by using the same method as Experimental Example 1-1-1, except that the following compound of Formula ET-A was used instead of the compound of Formula 3-1-1-2 in Experimental Example 1-1-1.

[ET-A]

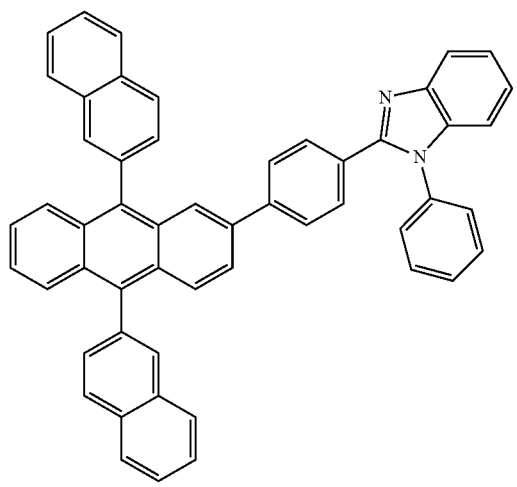

Comparative Example 2

The organic light emitting device was manufactured by using the same method as Experimental Example 1-1-1, except that the following compound of Formula ET-B was used instead of the compound of Formula 3-1-1-2 in Experimental Example 1-1-1.

[ET-B]

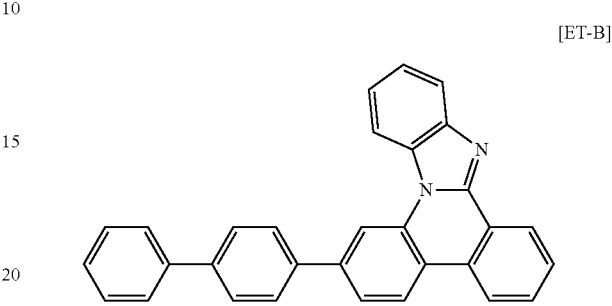

Experimental Examples 1-1-2 to 1-1-21

The organic light emitting device was manufactured by using the same method as Experimental Example 1-1-1, except that each compound shown in Table 1 was used instead of the compound of Formula 3-1-1-2 in Experimental Example 1-1-1.

When the current (10 mA/cm$^2$) was applied to the organic light emitting devices manufactured in Experimental Examples 1-1-1 to 1-1-21 and Comparative Examples 1 and 2, the results of Table 1 were obtained.

TABLE 1

| | Compound | Voltage (V) | Efficiency (cd/A) | Color coordinate (x, y) |
|---|---|---|---|---|
| Experimental Example 1-1-1 | 3-1-1-2 | 4.14 | 31.24 | (0.314, 0.650) |
| Experimental Example 1-1-2 | 3-1-1-6 | 4.01 | 32.01 | (0.314, 0.649) |
| Experimental Example 1-1-3 | 3-1-1-7 | 3.71 | 33.53 | (0.314, 0.650) |
| Experimental Example 1-1-4 | 3-1-1-12 | 4.05 | 30.10 | (0.313, 0.650) |
| Experimental Example 1-1-5 | 3-1-1-24 | 4.40 | 29.95 | (0.315, 0.650) |
| Experimental Example 1-1-6 | 3-1-1-29 | 4.09 | 32.57 | (0.314, 0.650) |
| Experimental Example 1-1-7 | 3-1-1-30 | 4.05 | 32.87 | (0.315, 0.649) |
| Experimental Example 1-1-8 | 3-1-1-33 | 3.85 | 32.23 | (0.314, 0.650) |
| Experimental Example 1-1-9 | 3-1-1-34 | 4.07 | 32.47 | (0.314, 0.650) |
| Experimental Example 1-1-10 | 3-1-2-2 | 4.53 | 30.95 | (0.314, 0.649) |
| Experimental Example 1-1-11 | 3-2-1-2 | 3.92 | 32.88 | (0.313, 0.649) |
| Experimental Example 1-1-12 | 3-2-1-11 | 4.30 | 29.15 | (0.314, 0.651) |
| Experimental Example 1-1-13 | 3-2-1-23 | 4.02 | 31.57 | (0.315, 0.648) |
| Experimental Example 1-1-14 | 3-2-2-14 | 4.28 | 28.31 | (0.315, 0.650) |
| Experimental Example 1-1-15 | 3-3-1-2 | 3.83 | 32.50 | (0.314, 0.650) |

TABLE 1-continued

| Compound | Voltage (V) | Efficiency (cd/A) | Color coordinate (x, y) |
|---|---|---|---|
| Experimental Example 1-1-16 | 3-3-1-18 | 4.45 | 29.87 | (0.315, 0.651) |
| Experimental Example 1-1-17 | 3-4-1-4 | 3.92 | 32.20 | (0.314, 0.650) |
| Experimental Example 1-1-18 | 3-5-1-1 | 4.01 | 32.06 | (0.315, 0.649) |
| Experimental Example 1-1-19 | 3-6-1-1 | 3.95 | 31.84 | (0.314, 0.651) |
| Experimental Example 1-1-20 | 3-8-1-2 | 4.51 | 27.95 | (0.314, 0.651) |
| Experimental Example 1-1-21 | 3-8-2-2 | 4.25 | 29.33 | (0.315, 0.649) |
| Comparative Example 1 | ET-A | 4.36 | 28.66 | (0.315, 0.650) |
| Comparative Example 2 | ET-B | 4.29 | 27.98 | (0.314, 0.650) |

From the results of Table 1, it can be seen that the new compound according to the present invention may be used as a material of an organic material layer of an organic electronic device comprising an organic light emitting device, and the organic electronic device comprising the organic light emitting device using the same exhibits excellent properties in views of efficiency, driving voltage, stability and the like. In particular, the new compound according to the present invention has excellent thermal stability, a deep HOMO level, a high triplet state and hole stability, thus exhibiting excellent properties. The compound may be used alone in the organic electronic device comprising the organic light emitting device, or may be used while being mixed with the n-type dopant such as LiQ. The new compound according to the present invention may improve efficiency and stability of the device by thermal stability of the compound.

Experimental Example 2-1-1

Hexanitrile hexaazatriphenylene (HAT) of the aforementioned Formula was applied to thicknesses of 100 Å by thermal vacuum deposition on the ITO transparent electrode prepared in Experimental Example 1-1-1 to form a hole injecting layer.

4,4'-bis[N-(1-naphthyl)-N-phenylamino]biphenyl (NPB) (700 Å), hexanitrile hexaazatriphenylene (HAT) (50 Å) and 4,4'-bis[N-(1-naphthyl)-N-phenylamino]biphenyl (NPB) (700 Å) of the aforementioned Formulas were sequentially applied by vacuum deposition on the hole injection layer to form a hole transport layer.

Subsequently, BH and BD shown below were applied by vacuum deposition at a weight ratio of 25:1 on the hole transport layer to form a light emitting layer in a film thickness of 200 Å.

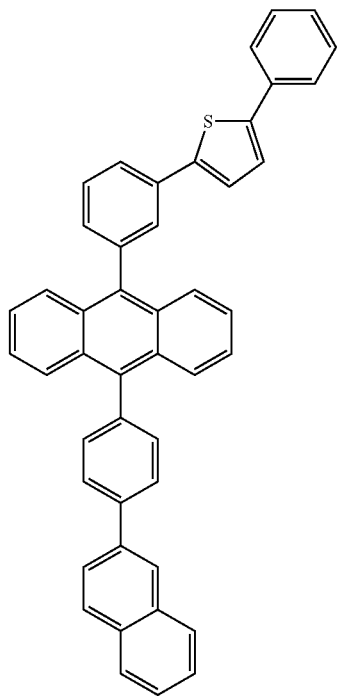

[BH]

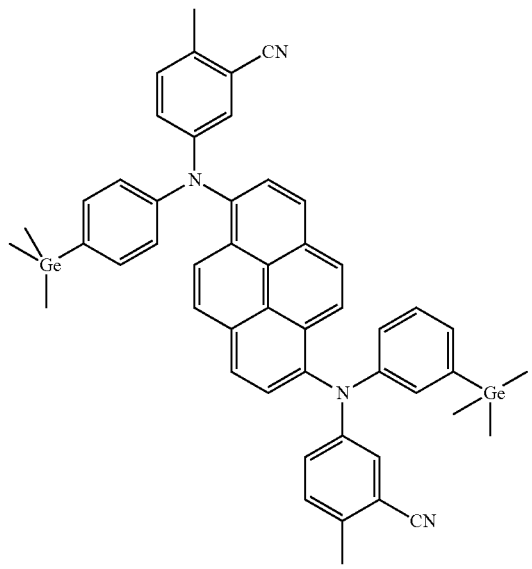

[BD]

The compound of Formula 3-1-2-2 (200 Å) prepared in Example 11 and the compound of ET-A (100 Å) were sequentially applied by vacuum deposition on the light emitting layer to form an electronic injection and transport layer.

Lithium fluoride (LiF) in a thickness of 15 Å and aluminum in a thickness of 1,000 Å were subsequently deposited on the electron injection and transport layer to form a cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at $2 \times 10^{-7}$ to $5 \times 10^{-8}$ torr to manufacture the organic light emitting device.

Comparative Example 3

The organic light emitting device was manufactured by using the same method as Experimental Example 2-1-1, except that the following compound of Formula ET-C was used instead of the compound of Formula 3-1-2-2 in Experimental Example 2-1-1.

[ET-C]

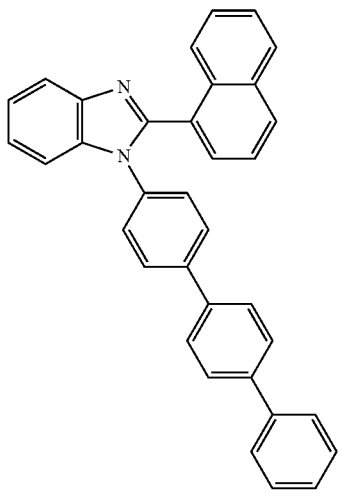

Experimental Examples 2-1-2 to 2-1-12

The organic light emitting device was manufactured by using the same method as Experimental Example 2-1-1, except that each compound shown in Table 2 was used instead of the compound of Formula 3-1-2-2 in Experimental Example 2-1-1.

When the current (10 mA/cm$^2$) was applied to the organic light emitting devices manufactured in Experimental Examples 2-1-1 to 2-1-12 and Comparative Example 3, the results of Table 2 were obtained.

TABLE 2

| | Compound | Voltage (V) | Efficiency (cd/A) | Color coordinate (x, y) |
|---|---|---|---|---|
| Experimental Example 2-1-1 | 3-1-2-2 | 4.17 | 5.79 | (0.134, 0.159) |
| Experimental Example 2-1-2 | 3-1-2-21 | 4.23 | 5.89 | (0.134, 0.160) |
| Experimental Example 2-1-3 | 3-1-2-29 | 4.30 | 5.62 | (0.134, 0.158) |
| Experimental Example 2-1-4 | 3-1-2-30 | 4.02 | 5.95 | (0.135, 0.161) |
| Experimental Example 2-1-5 | 3-1-2-33 | 4.15 | 6.02 | (0.134, 0.160) |
| Experimental Example 2-1-6 | 3-2-2-2 | 4.25 | 5.91 | (0.136, 0.162) |
| Experimental Example 2-1-7 | 3-3-2-2 | 4.17 | 5.72 | (0.134, 0.159) |
| Experimental Example 2-1-8 | 3-3-2-28 | 4.21 | 5.95 | (0.135, 0.160) |
| Experimental Example 2-1-9 | 3-4-1-6 | 4.09 | 5.86 | (0.134, 0.159) |
| Experimental Example 2-1-10 | 3-5-1-7 | 4.41 | 5.74 | (0.135, 0.160) |
| Experimental Example 2-1-11 | 3-6-2-9 | 4.42 | 6.15 | (0.135, 0.161) |
| Experimental Example 2-1-12 | 3-9-1-11 | 4.19 | 5.78 | (0.134, 0.160) |
| Comparative Example 3 | ET-C | 4.82 | 3.26 | (0.135, 0.162) |

From the results of Table 2, it can be seen that the new compound according to the present invention may be used as a material of an organic material layer of an organic electronic device comprising an organic light emitting device, and the organic electronic device comprising the organic light emitting device using the same exhibits excellent properties in views of efficiency, driving voltage, stability and the like. Particularly, the new compound according to the present invention had excellent hole blocking and electron transporting abilities, thus exhibiting high efficiency properties.

Experimental Example 3-1-1

Hexanitrile hexaazatriphenylene (HAT) of the aforementioned Formula was applied to thicknesses of 100 Å by thermal vacuum deposition on the ITO transparent electrode prepared in Experimental Example 1-1-1 to form a hole injecting layer.

4,4'-bis[N-(1-naphthyl)-N-phenylamino]biphenyl (NPB) (800 Å) of the aforementioned Formula was applied by vacuum deposition on the hole injection layer to form a hole transport layer.

Subsequently, the compound of Formula 3-1-2-14 prepared in Example 21 and the dopant compound RD shown below were applied by vacuum deposition at a weight ratio of 10:1 on the hole transport layer to form a light emitting layer in a film thickness of 300 Å.

[RD]

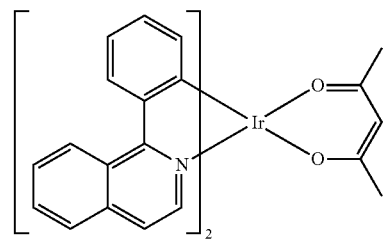

The compound of Formula ET-A and the aforementioned Formula LiQ (lithium quinalate) were applied at a weight ratio of 1:1 by vacuum deposition on the light emitting layer to form an electronic injection and transport layer in a thickness of 300 Å.

Lithium fluoride (LiF) in a thickness of 15 Å and aluminum in a thickness of 1,000 Å were subsequently deposited on the electron injection and transport layer to form a cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at $2 \times 10^{-7}$ to $5 \times 10^{-8}$ torr to manufacture an organic light emitting device.

Comparative Example 4

The organic light emitting device was manufactured by using the same method as Experimental Example 3-1-1, except that the following compound of Formula RH-A was used instead of the compound of Formula 3-1-2-14 in Experimental Example 3-1-1.

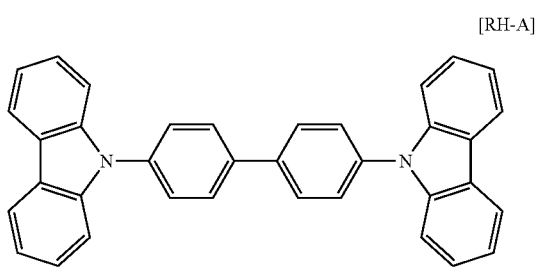 [SMILES: c1ccc2c(c1)c1ccccc1n2-c1ccc(-c2ccc(-n3c4ccccc4c4ccccc43)cc2)cc1]

Experimental Examples 3-1-2 to 3-1-8

The organic light emitting device was manufactured by using the same method as Experimental Example 3-1-1, except that each compound shown in Table 3 was used instead of the compound of Formula 3-1-2-14 in Experimental Example 3-1-1.

When the current (10 mA/cm$^2$) was applied to the organic light emitting devices manufactured in Experimental Examples 3-1-1 to 3-1-8 and Comparative Example 4, the results of Table 3 were obtained.

TABLE 3

| | Compound | Voltage (V) | Efficiency (cd/A) | Color coordinate (x, y) |
|---|---|---|---|---|
| Experimental Example 3-1-1 | 3-1-2-14 | 4.73 | 17.52 | (0.671, 0.329) |
| Experimental Example 3-1-2 | 3-1-2-15 | 4.82 | 16.32 | (0.670, 0.330) |
| Experimental Example 3-1-3 | 3-2-2-14 | 4.65 | 18.96 | (0.671, 0.331) |
| Experimental Example 3-1-4 | 3-4-1-6 | 4.89 | 15.32 | (0.672, 0.330) |
| Experimental Example 3-1-5 | 3-6-1-4 | 4.82 | 18.23 | (0.671, 0.332) |
| Experimental Example 3-1-6 | 3-6-2-7 | 4.98 | 19.32 | (0.670, 0.331) |
| Experimental Example 3-1-7 | 3-8-2-16 | 4.75 | 16.21 | (0.669, 0.330) |
| Experimental Example 3-1-8 | 3-9-1-13 | 4.86 | 19.21 | (0.671, 0.331) |
| Comparative Example 3 | RH-A | 6.12 | 12.26 | (0.672, 0.329) |

From the results of Table 3, it can be seen that the new compound according to the present invention may be used as a material of a light emitting layer of an organic electronic device comprising an organic light emitting device, and the organic electronic device comprising the organic light emitting device using the same exhibits excellent properties in views of efficiency, driving voltage, stability and the like. Particularly, the compound may reduce driving voltage and introduce an increase in efficiency to improve power consumption.

The invention claimed is:
1. A compound represented by the following Formula 1:

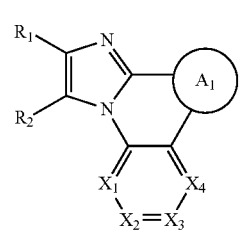

[Formula 1]

wherein,
$X_1$ is N or $CR_3$, $X_2$ is N or $CR_4$, $X_3$ is N or $CR_5$, $X_4$ is N or $CR_6$, and all of $X_1$ to $X_4$ are not simultaneously N,
$R_3$ to $R_6$ are each independently -($L_1$)p-($Y_1$)q where p is an integer of 0 to 10, q is an integer of 1 to 10, two or more adjacent groups of $R_3$ to $R_6$ may form a monocycle or a polycycle,
$L_1$ is oxygen; sulfur; substituted or unsubstituted nitrogen; substituted or unsubstituted phosphorus; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms,
$Y_1$ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms,
$R_1$ and $R_2$ may be connected to each other to form or not to form a substituted or unsubstituted aliphatic, aromatic or heteroaromatic monocycle or polycycle, and in the case where $R_1$ and $R_2$ do not form a cycle, $R_1$ and $R_2$ are the same as or different from each other, and each independently hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms, the aromatic or heteroaromatic monocycle and polycycle formed by connecting $R_1$, $R_2$, and $R_1$ and $R_2$ to each other may be each independently substituted by $-(L_1)p-(Y_1)q$, in the case where two or more $L_1$ and two or more $Y_1$ are present in Formula 1, $L_1$ and $Y_1$ are each independently the same as or different from each other, a $A_1$ cycle is represented by Formula 2,

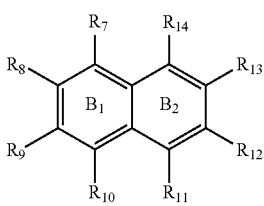

[Formula 2]

wherein, $R_7$ and $R_8$, $R_8$ and $R_9$, or $R_9$ and $R_{10}$ are groups connected to Formula 1, the group that is not used in connection to Formula 1 among $R_7$ to $R_{10}$, $R_{11}$, $R_{12}$, $R_{13}$ and $R_{14}$ are each independently $-(L_2)r-(Y_2)s$ where r is an integer of 0 to 10, s is an integer of 1 to 10, and two or more adjacent groups of the group that is not used in connection to Formula 1 among $R_7$ to $R_{10}$, $R_{11}$, $R_{12}$, $R_{13}$ and $R_{14}$ may form a monocycle or a polycycle, $L_2$ is oxygen; sulfur; substituted or unsubstituted nitrogen; substituted or unsubstituted P; a substituted or unsubstituted arylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, $Y_2$ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heterocyclic group comprising one or more of N, O and S atoms, aromatic or hetero aromatic monocycle and polycycle formed by connecting two or more adjacent groups of the group that is not used in connection to Formula 1 among $R_7$ to $R_{10}$, $R_{11}$, $R_{12}$, $R_{13}$ and $R_{14}$ to each other may be each independently substituted by $-(L_2)r-(Y_2)s$, in the case where two or more $L_2$ and two or more $Y_2$ are present in Formula 2, $L_2$ and $Y_2$ are each independently the same as or different from each other, $B_1$ is an aryl group where one or more carbons constituting a cycle may be further replaced by nitrogen, and $B_2$ is an aryl group where one or more carbons constituting a cycle may be replaced by nitrogen, in the case where R1 and R2 form a cycle, Formula 1 is represented by any one of the following Formulas 1-1 to 1-4:

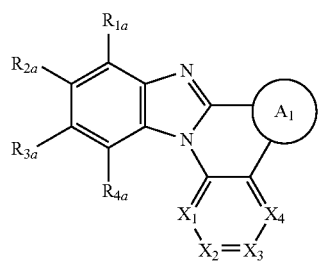

[Formula 1-1]

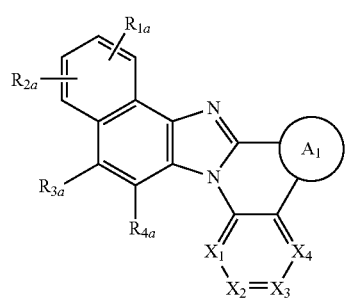

[Formula 1-2]

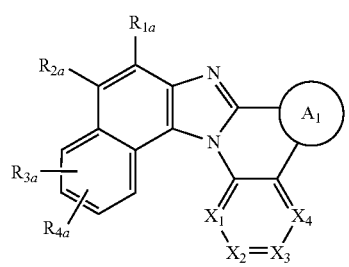

[Formula 1-3]

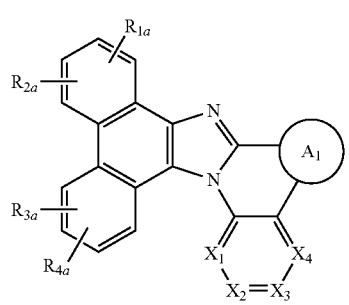

[Formula 1-4]

in the Formulas 1-2 to 1-4, $R_{1a}$ to $R_{4a}$ are the same as definitions of $R_1$ to $R_2$ of Formula 1, and $A_1$, and $X_1$ to $X_4$ are the same as definitions of Formula 1, Formula 1-1 is represented by any one of the following Formulas 3-1 to 3-4, 3-6- to 3-18:

[Formula 3-1]
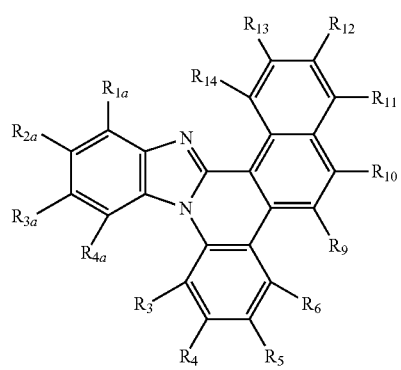
[Formula 3-2]
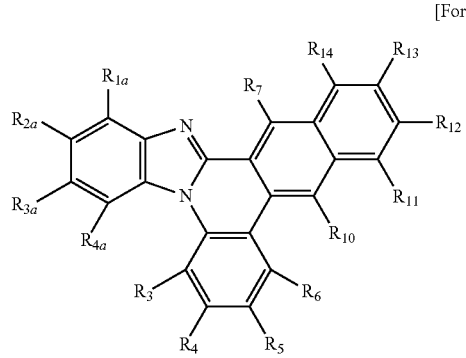
[Formula 3-3]
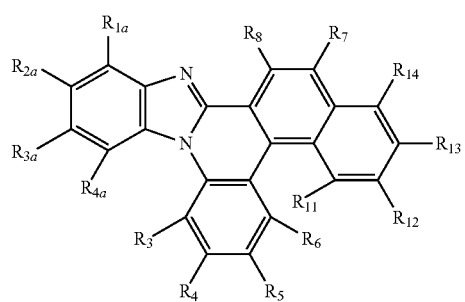
[Formula 3-4]
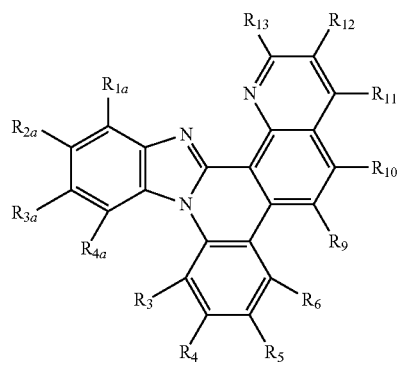
[Formula 3-7]
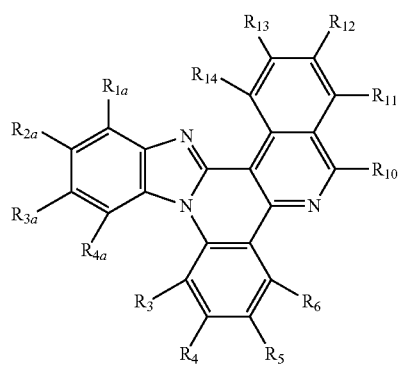
[Formula 3-8]
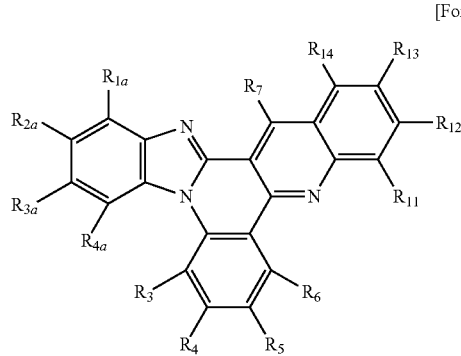
[Formula 3-9]
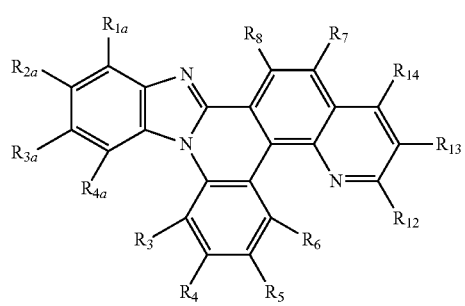
[Formula 3-10]
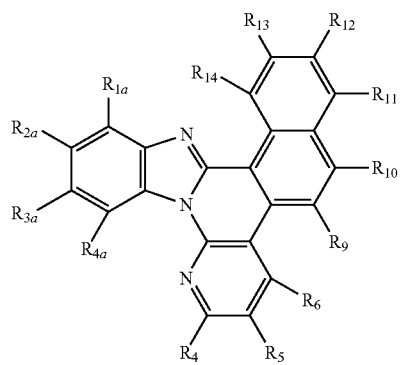

[Formula 3-11]
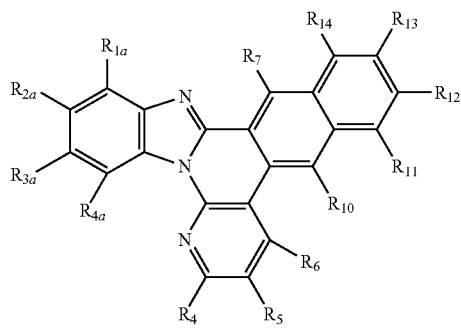
[Formula 3-12]
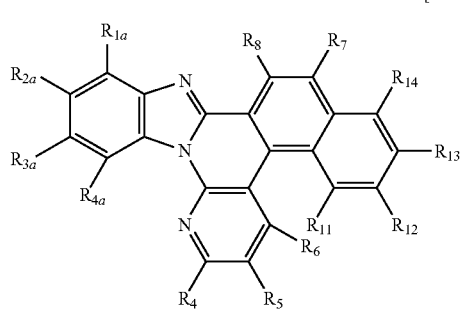
[Formula 3-13]
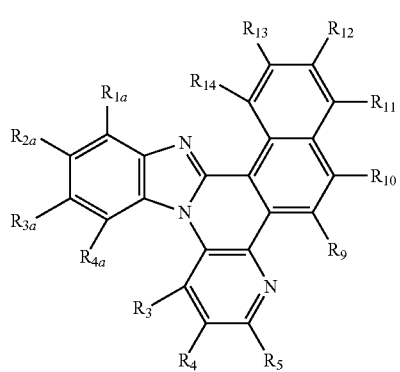
[Formula 3-14]
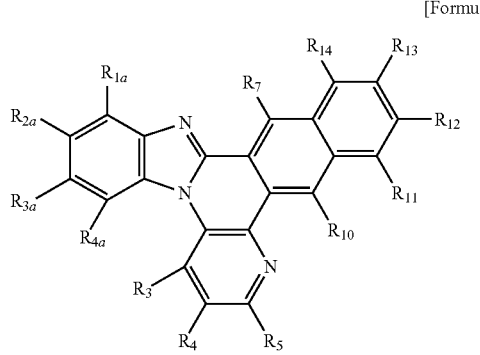
[Formula 3-15]
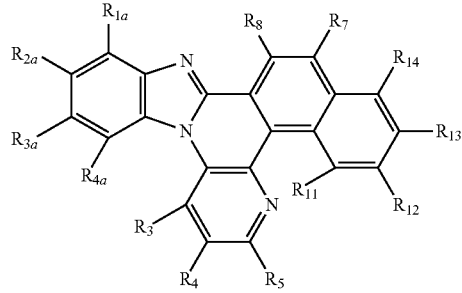
[Formula 3-16]
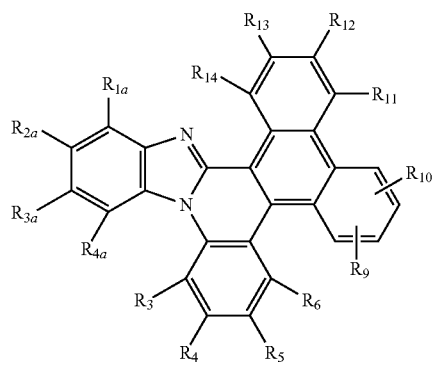
[Formula 3-17]
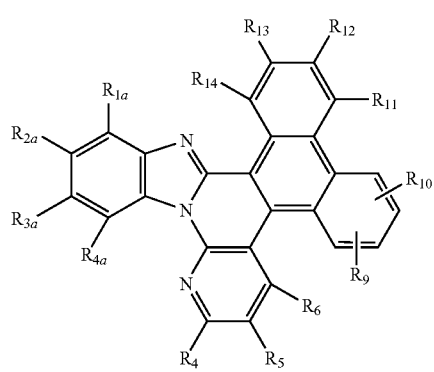
[Formula 3-18]
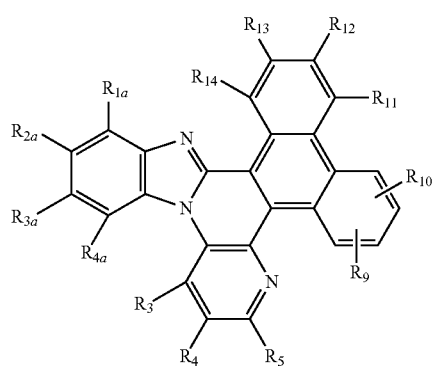
in the Formulas 3-1 to 3-4 and 3-6 to 3-18,
$R_7$ to $R_{14}$ are the same as definitions of Formula 2, and $R_{1a}$ to $R_{4a}$ and $R_3$ to $R_6$ are each independently -$(L_1)p$-$(Y_1)q$ where p is an integer of 0 to 10, q is an integer of 1 to 10, two or more adjacent groups of $R_3$ to $R_6$ may form a monocycle or a polycycle, L₁ is oxygen; sulfur; substituted or unsubstituted nitrogen; substituted or unsubstituted phosphorus; a substituted or unsubstituted phenylene group; a substituted or unsubstituted biphenylene group; a substituted or unsubstituted terphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, Y₁ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted pyrenyl group; a substituted or unsubstituted phenanthrenyl group; a substituted or unsubstituted perylenyl group; a substituted or unsubstituted tetracenyl group; a substituted or unsubstituted triphenylene group; a substituted or unsubstituted fluoranthenyl group; a substituted or unsubstituted fluorenyl group; a substituted or unsubstituted carbazole group; or a substituted or unsubstituted heterocyclic group comprising one or more of N, O and S atoms.

2. The compound of claim 1, wherein Formula 1 is represented by any one of the following Formulas 3-1 to 3-3 and 3-16:

[Formula 3-1]

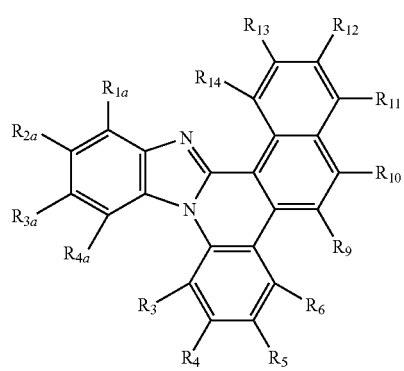

[Formula 3-2]

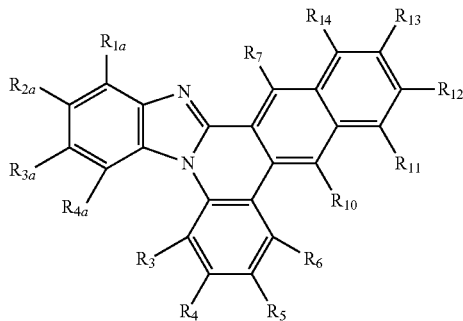

[Formula 3-3]

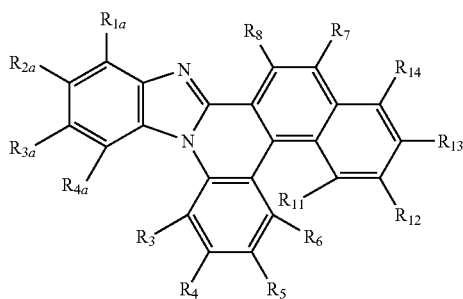

[Formula 3-16]

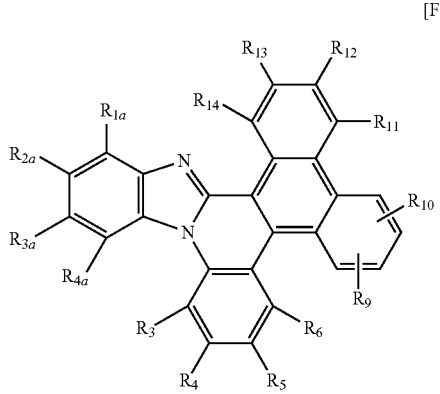

wherein,
$R_{1a}$ to $R_{4a}$, $R_3$, $R_6$ and $R_7$ to $R_{14}$ are hydrogen,
$R_4$ and $R_5$ are each independently $-(L_2)r-(Y_2)s$ where r is an integer of 0 to 10 and s is an integer of 1 to 10,
L₂ is oxygen; sulfur; substituted or unsubstituted nitrogen; substituted or unsubstituted P; a substituted or unsubstituted phenylene group; a substituted or unsubstituted biphenylene group; a substituted or unsubstituted terphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, Y$_2$ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted pyrenyl group; a substituted or unsubstituted phenanthrenyl group; a substituted or unsubstituted perylenyl group; a substituted or unsubstituted tetracenyl group; a substituted or unsubstituted triphenylene group; a substituted or unsubstituted fluoranthenyl group; a substituted or unsubstituted fluorenyl group; a substituted or unsubstituted carbazole group; or a substituted or unsubstituted heterocyclic group comprising one or more of N, O and S atoms.

3. The compound of claim 2, wherein

L$_2$ is oxygen; sulfur; substituted or unsubstituted nitrogen; substituted or unsubstituted phosphorus; a phenylene group; a naphthylene group; a substituted or unsubstituted alkenylene group; a substituted or unsubstituted fluorenylene group; a substituted or unsubstituted carbazolylene group; or a substituted or unsubstituted heteroarylene group comprising one or more of N, O and S atoms, and Y$_2$ is hydrogen; heavy hydrogen; a halogen group; a nitrile group; a nitro group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a phenyl group, a naphthyl group, a phenanthrenyl group, a fluorene group, a dimethylfluorene group, a triphenylene group, a benzocrycene group or a fluoranthrene group; a substituted or unsubstituted carbazole group; or a substituted or unsubstituted heterocyclic group comprising one or more of N, O and S atoms.

4. The compound of claim 1, wherein Formula 1 is represented by any one of the following Formulas 4-1 to 4-4:

[Formula 4-1]

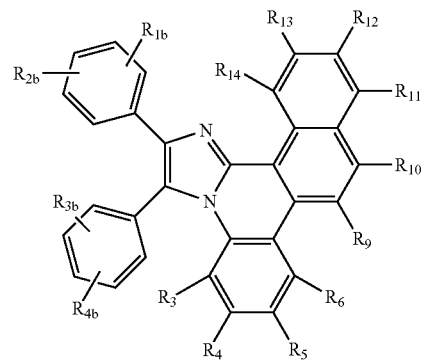

[Formula 4-2]

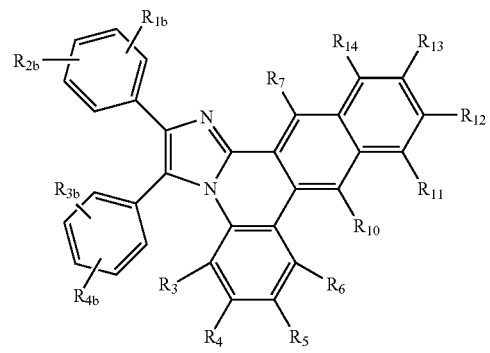

[Formula 4-3]

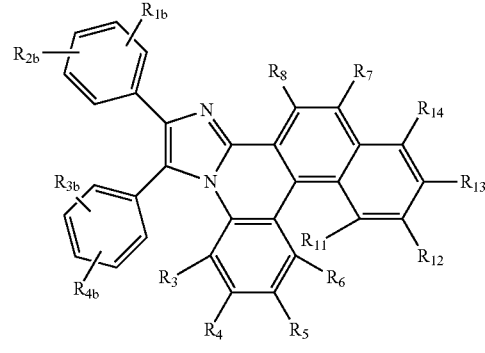

[Formula 4-4]

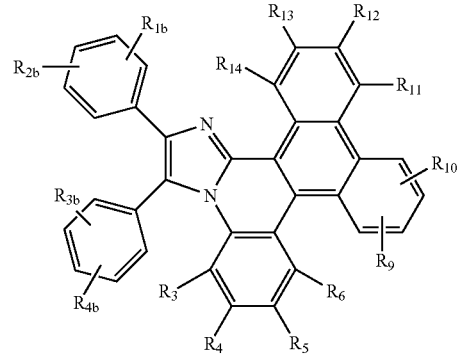

wherein,

R$_{1b}$ to R$_{4b}$ are the same as definitions of R$_1$ to R$_2$ of Formula 1, R$_3$ to R$_6$ are the same as definitions of Formula 1 and, R$_7$ to R$_{14}$ are the same as definitions of Formula 2.

5. The compound of claim 1, wherein Formula 1 is represented by any one of the following Formulas 5-1 to 5-25:
[Formula 5-1]
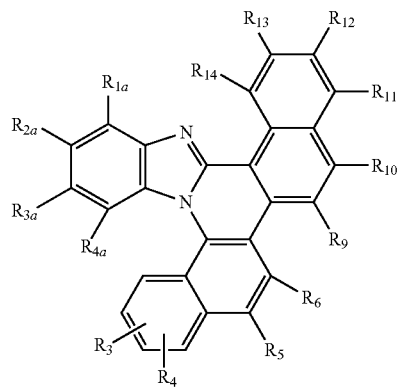
[Formula 5-2]
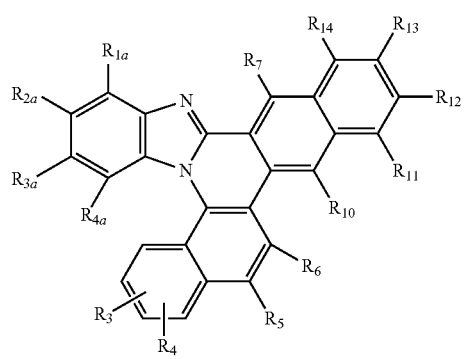
[Formula 5-3]
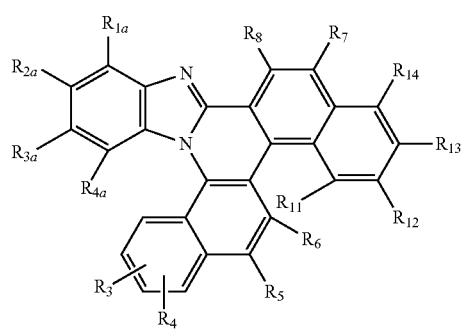
[Formula 5-4]
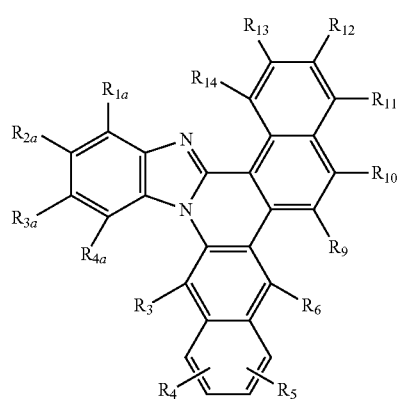
-continued
[Formula 5-5]
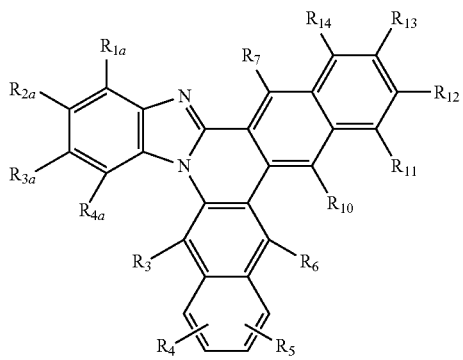
[Formula 5-6]
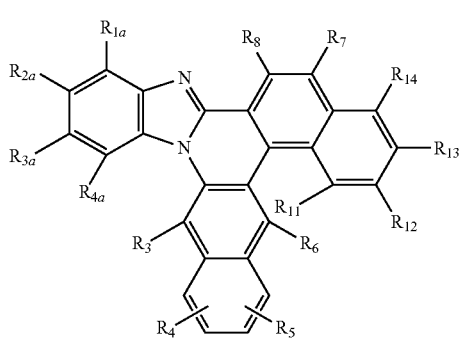
[Formula 5-7]
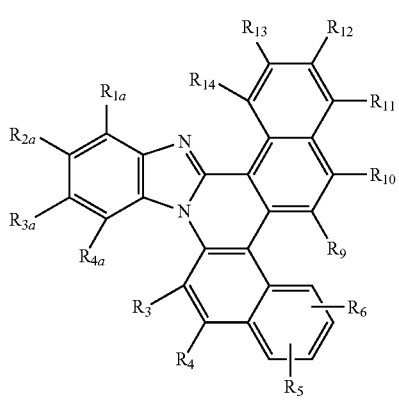
[Formula 5-8]
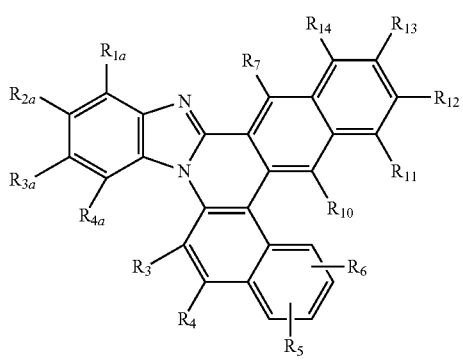

-continued
[Formula 5-9]
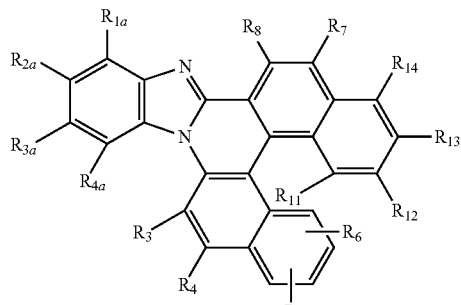
[Formula 5-10]
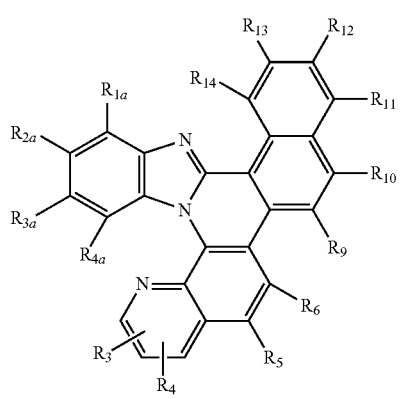
[Formula 5-11]
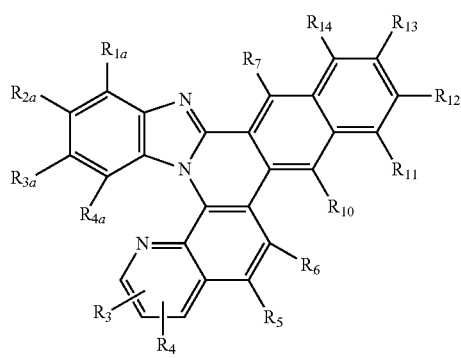
[Formula 5-12]
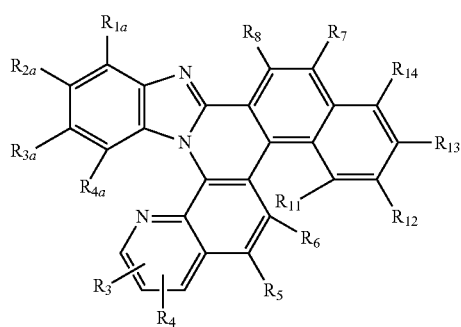
-continued
[Formula 5-13]
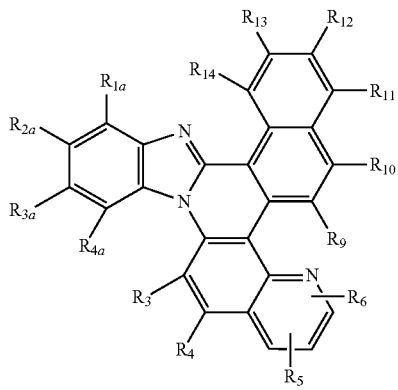
[Formula 5-14]
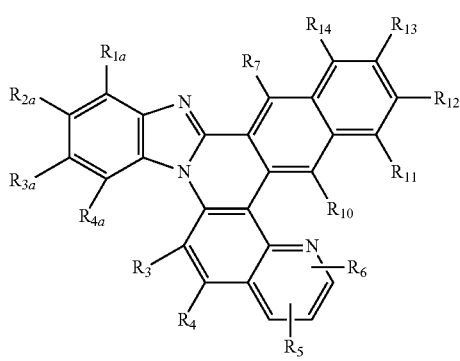
[Formula 5-15]
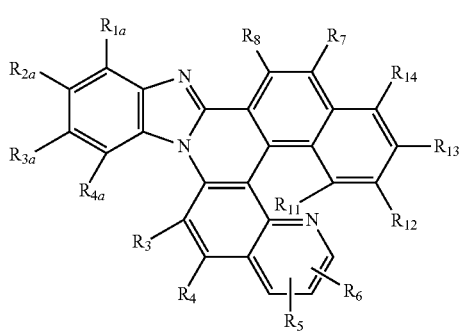
[Formula 5-16]
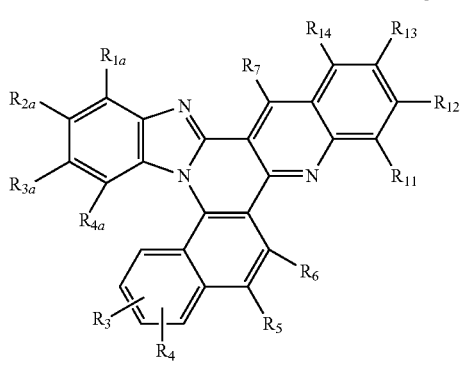

[Formula 5-17]
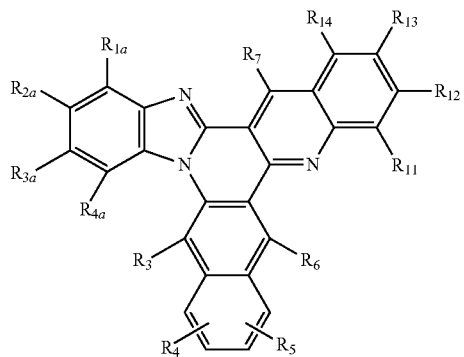
[Formula 5-18]
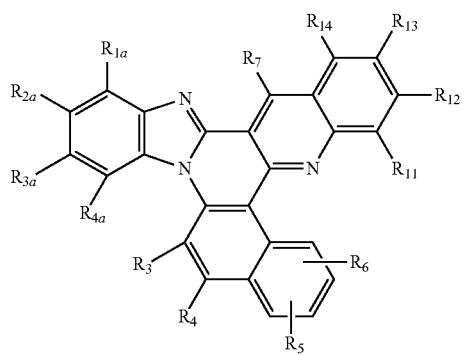
[Formula 5-19]
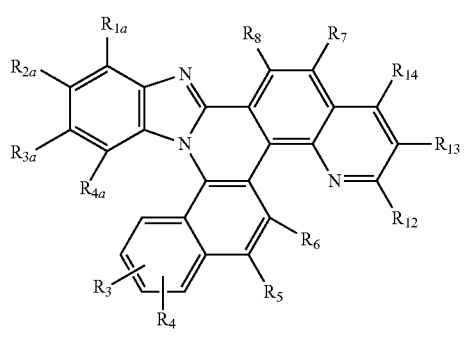
[Formula 5-20]
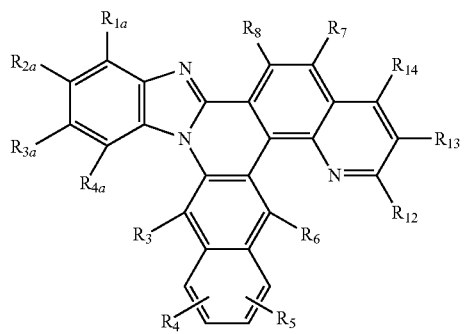
[Formula 5-21]
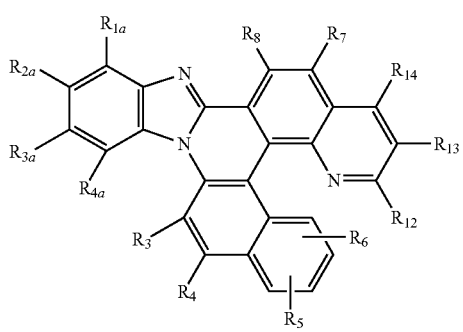
[Formula 5-22]
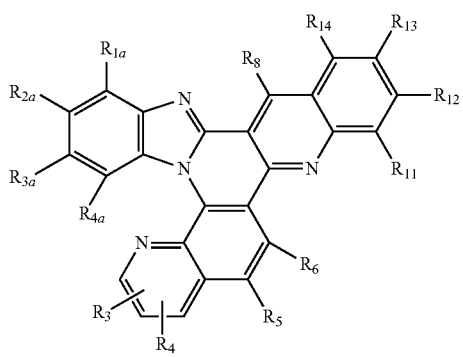
[Formula 5-23]
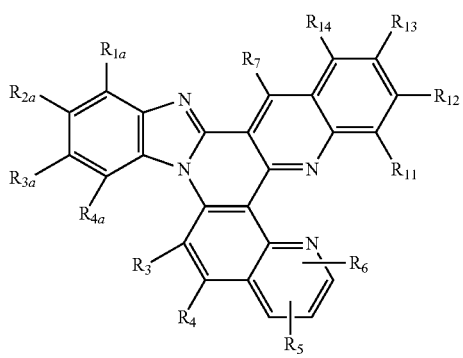
[Formula 5-24]
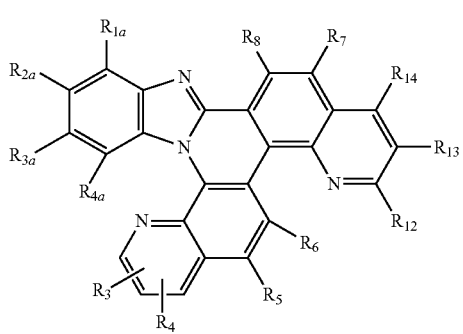

[Formula 5-25]
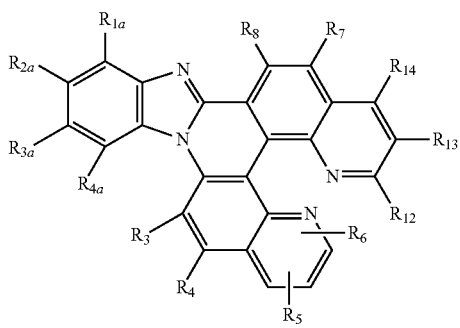
wherein,
R$_{1a}$ to R$_{4a}$ are the same as definitions of R$_1$ to R$_2$ of Formula 1, R$_3$ to R$_6$ are the same as definitions of Formula 1, and R$_7$ to R$_{14}$ are the same as definitions of Formula 2.
6. The compound of claim 1, wherein Formula 1 is represented by any one of the following Formulas 6-1 to 6-8:
[Formula 6-1]
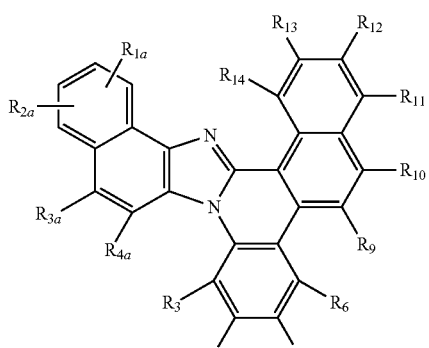
[Formula 6-2]
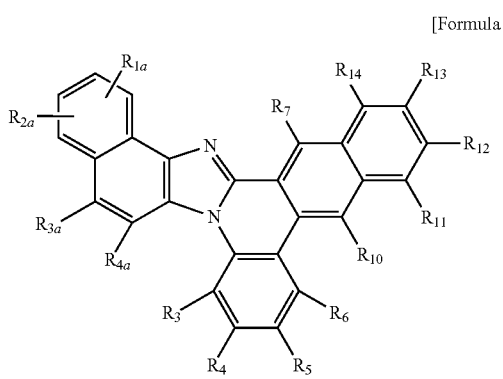
[Formula 6-3]
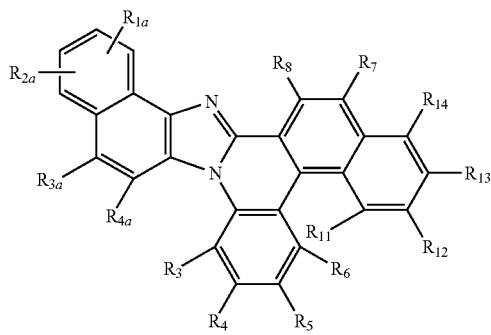
[Formula 6-4]
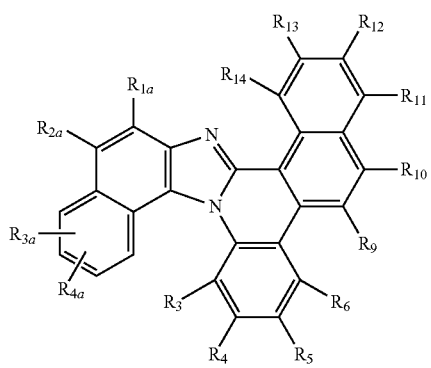
[Formula 6-5]
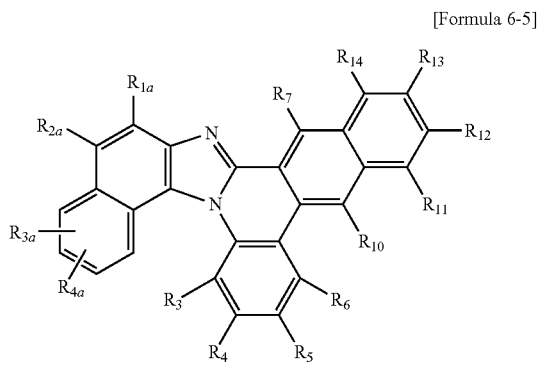
[Formula 6-6]
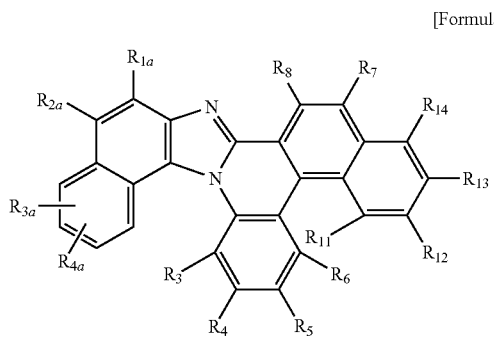

-continued

[Formula 6-7]

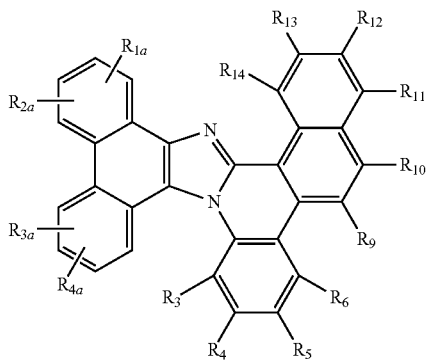

[Formula 6-8]

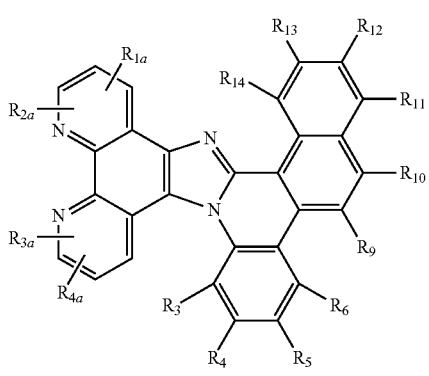

wherein,

R$_{1a}$ to R$_{4a}$ are the same as definitions of R$_1$ to R$_2$ of Formula 1, R$_3$ to R$_6$ are the same as definitions of Formula 1, and R$_7$ to R$_{14}$ are the same as definitions of Formula 2.

7. The compound of claim 1, wherein p is 0, and Y$_1$ is heavy hydrogen, a nitrile group, a halogen group, a substituted or unsubstituted boron group, a substituted or unsubstituted phenyl group, a substituted or unsubstituted biphenyl group, a substituted or unsubstituted terphenyl group, a substituted or unsubstituted naphthyl group, a substituted or unsubstituted fluorenyl group, a substituted or unsubstituted pyrenyl group, a substituted or unsubstituted phenanthrenyl group, a substituted or unsubstituted perylenyl group, a substituted or unsubstituted tetracenyl group, a substituted or unsubstituted triphenylene group, a substituted or unsubstituted fluoranthenyl group, or a substituted or unsubstituted heterocyclic group.

8. The compound of claim 1, wherein L$_1$ is a substituted or unsubstituted phenylene group; a substituted or unsubstituted biphenylene group; a substituted or unsubstituted terphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; or a substituted or unsubstituted heteroarylene group, and Y$_1$ is a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted pyrenyl group; a substituted or unsubstituted phenanthrenyl group; a substituted or unsubstituted perylenyl group; a substituted or unsubstituted tetracenyl group; a substituted or unsubstituted triphenylene group; a substituted or unsubstituted fluoranthenyl group; a substituted or unsubstituted fluorenyl group; a substituted or unsubstituted carbazole group; or a substituted or unsubstituted heterocyclic group comprising one or more of N, O and S atoms.

9. The compound of claim 1, wherein the compound is any one selected from the group consisting of the following Structural Formulas:

[Formula 3-1-1-1]

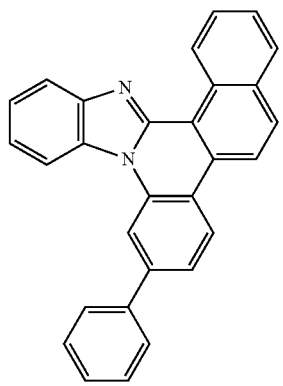

[Formula 3-1-1-2]

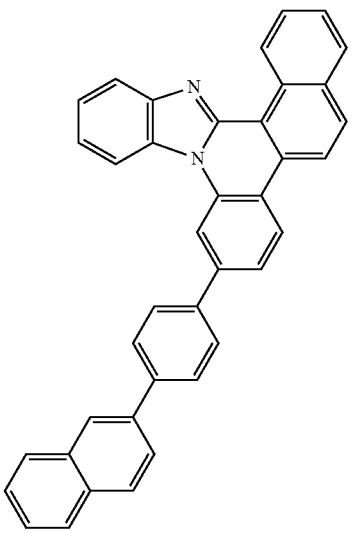

[Formula 3-1-1-3]
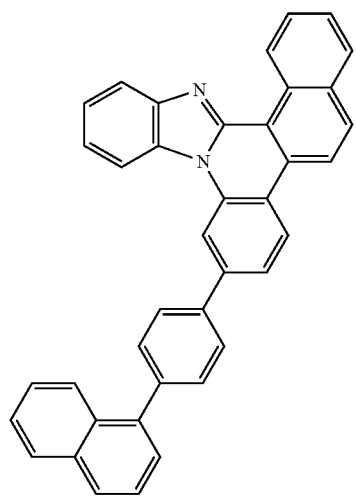
[Formula 3-1-1-6]
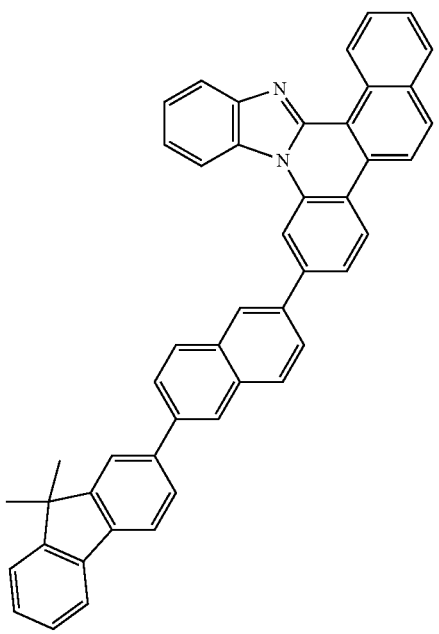
[Formula 3-1-1-4]
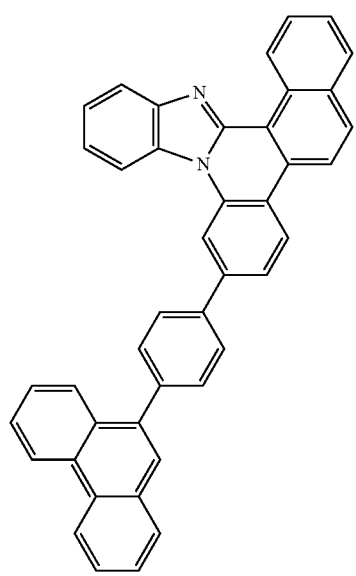
[Formula 3-1-1-9]
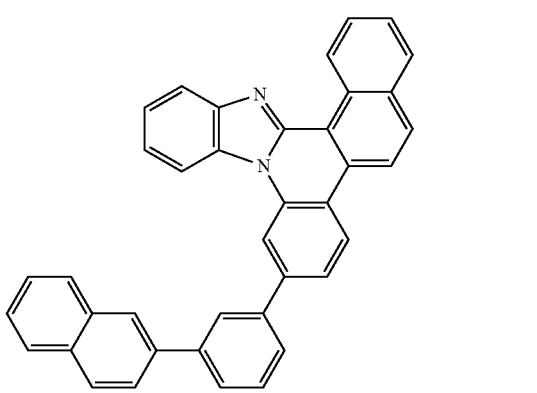
[Formula 3-1-1-5]
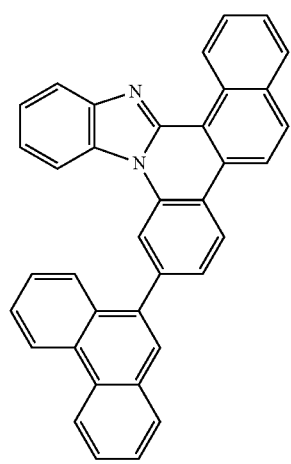
[Formula 3-1-1-10]
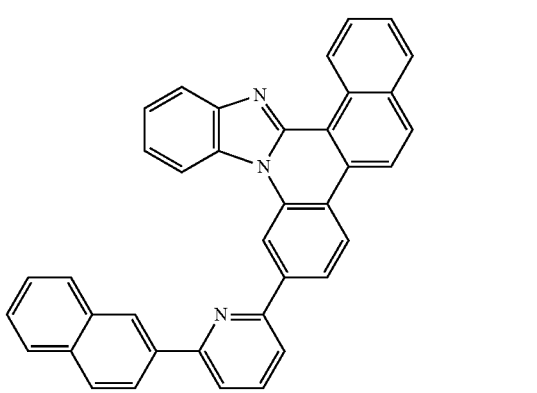

[Formula 3-1-1-11]
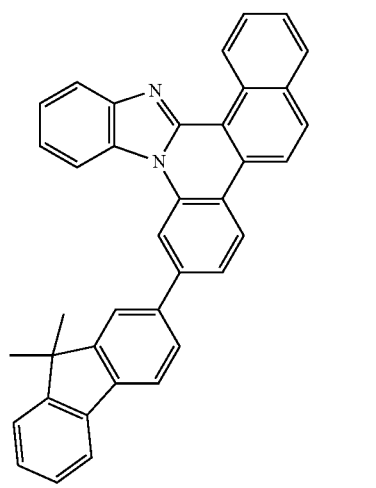
[Formula 3-1-1-12]
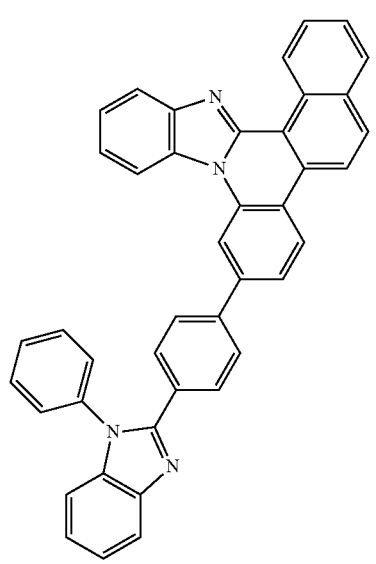
[Formula 3-1-1-13]
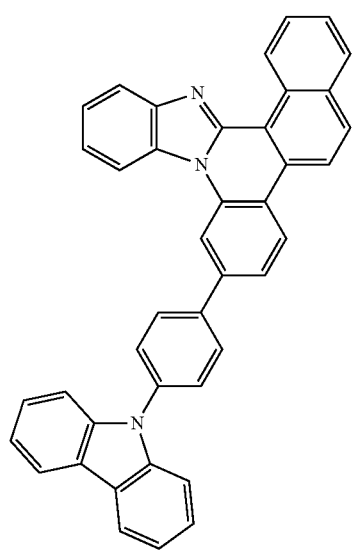
[Formula 3-1-1-14]
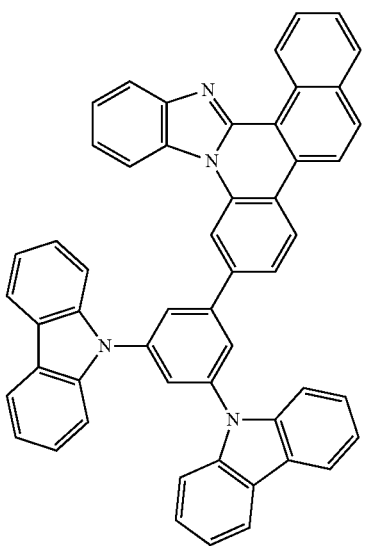
[Formula 3-1-1-15]
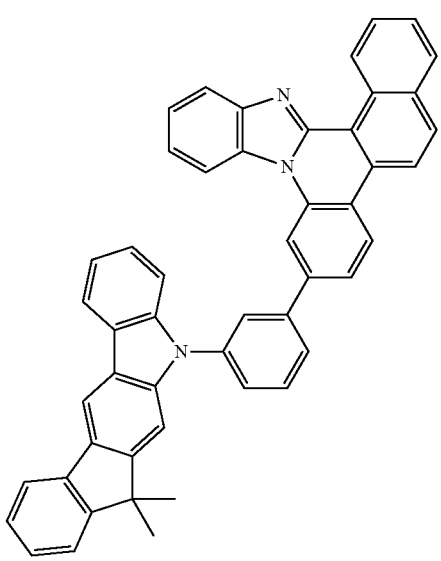
[Formula 3-1-1-16]
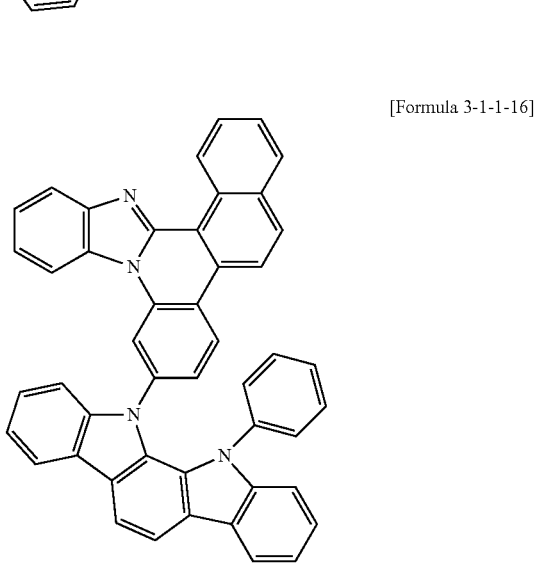

[Formula 3-1-1-17]
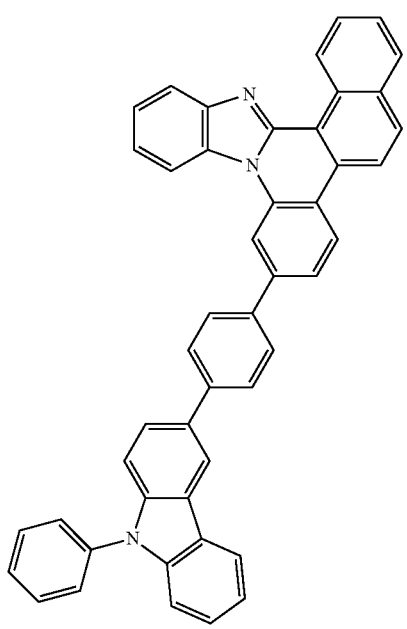
[Formula 3-1-1-18]
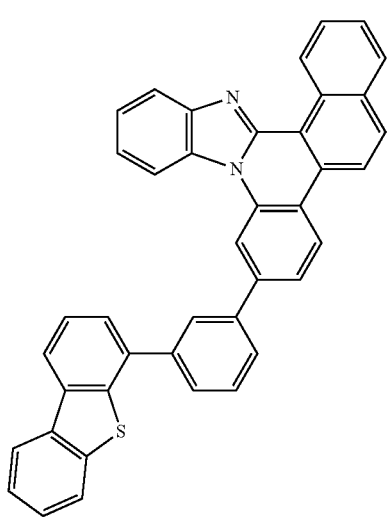
[Formula 3-1-1-19]
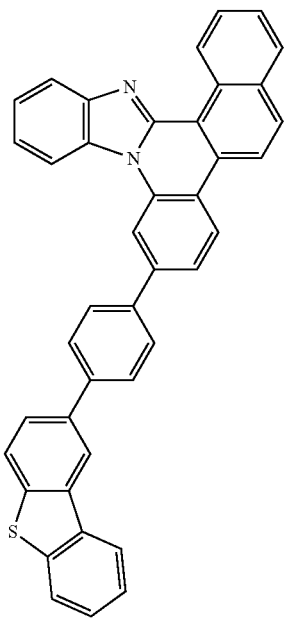
[Formula 3-1-1-20]
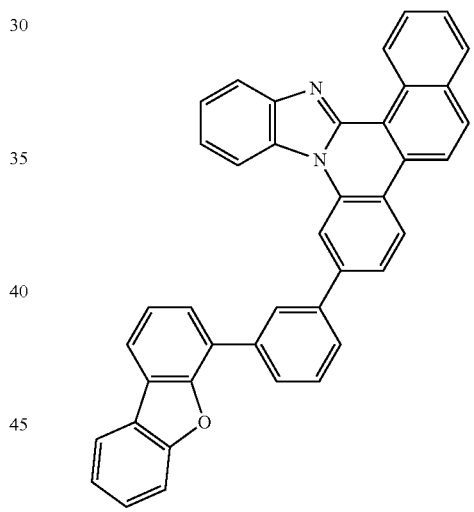
[Formula 3-1-1-21]
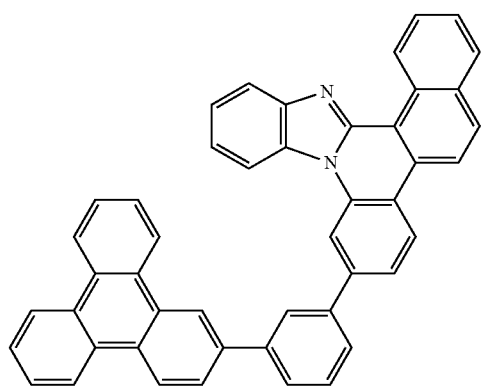

[Formula 3-1-1-22]
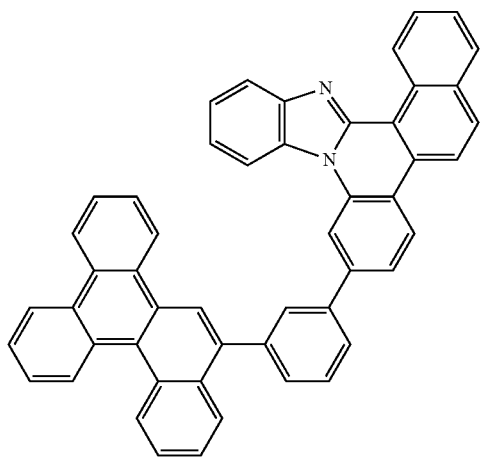
[Formula 3-1-1-23]
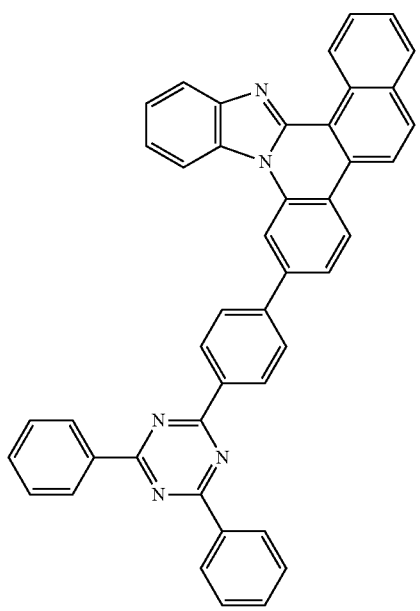
[Formula 3-1-1-24]
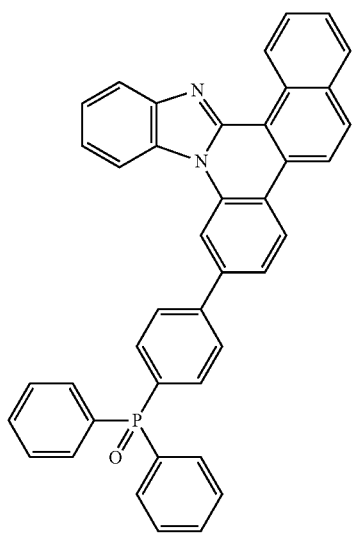
[Formula 3-1-1-25]
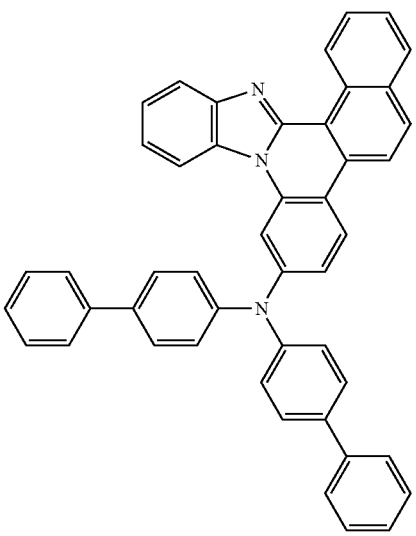
[Formula 3-1-1-26]
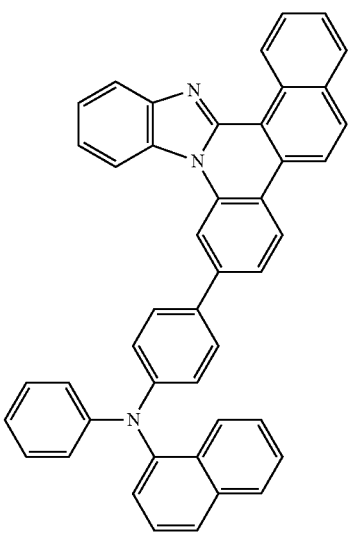
[Formula 3-1-1-27]
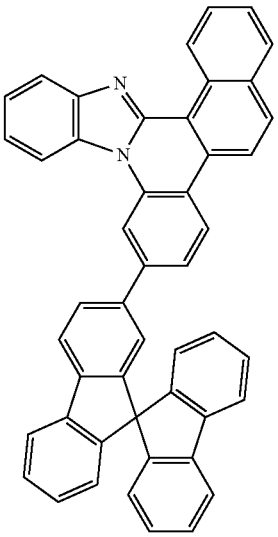

[Formula 3-1-1-28]
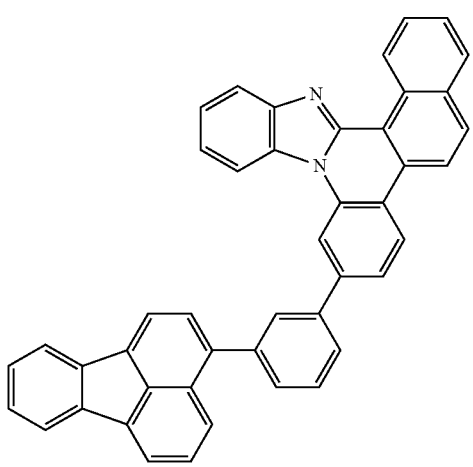
[Formula 3-1-1-29]
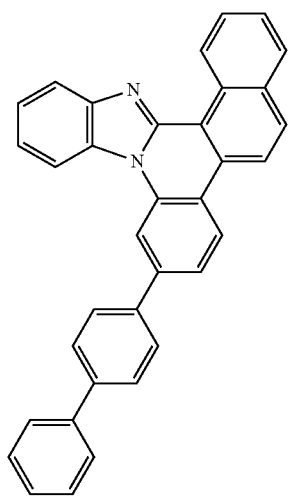
[Formula 3-1-1-30]
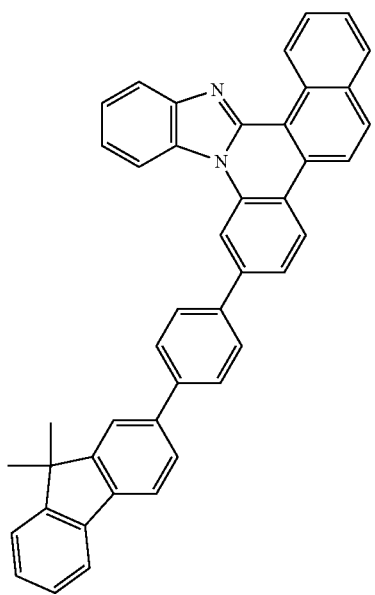
[Formula 3-1-1-31]
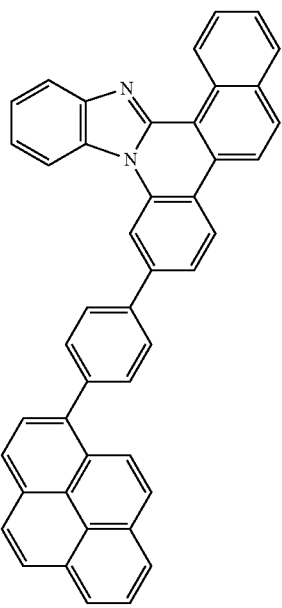
[Formula 3-1-1-32]
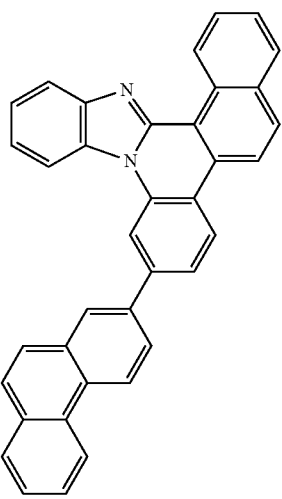

[Formula 3-1-1-33]
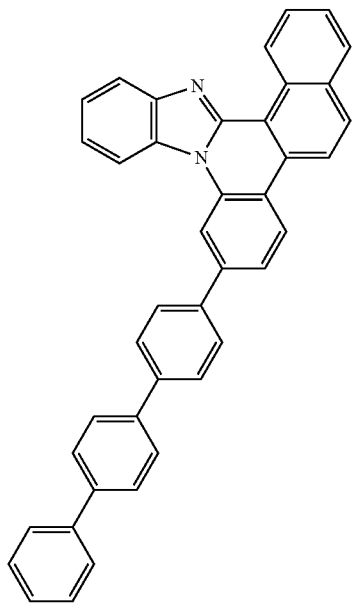
[Formula 3-1-1-34]
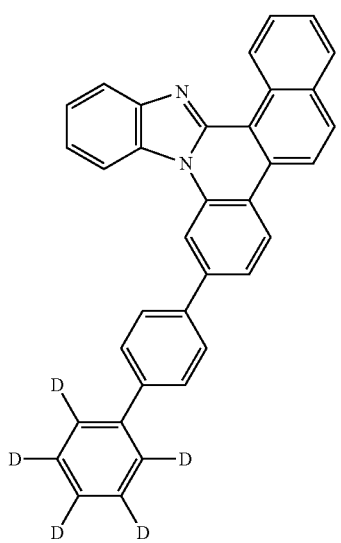
[Formula 3-1-1-35]
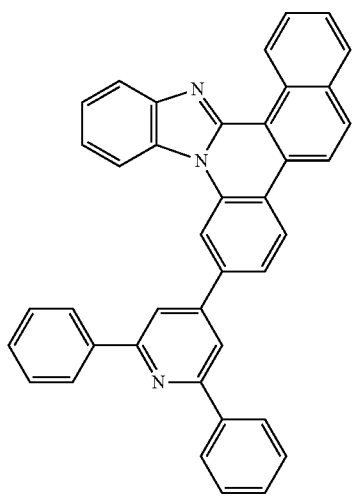
[Formula 3-1-1-36]
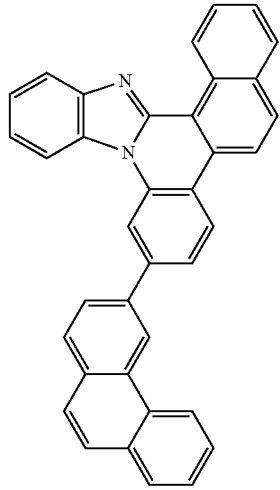
[Formula 3-1-2-1]
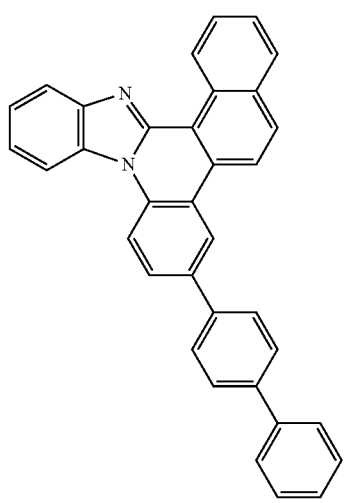
[Formula 3-1-2-2]
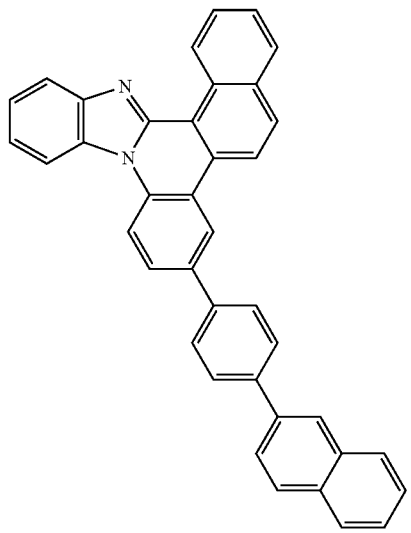

[Formula 3-1-2-3]
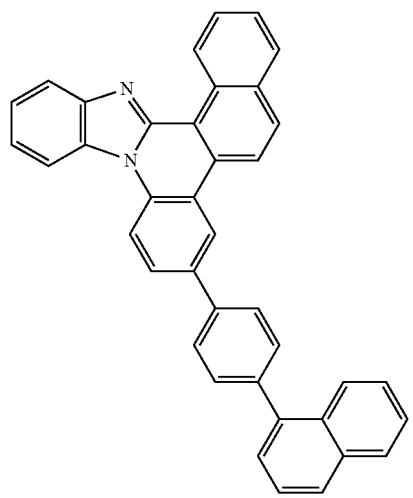
[Formula 3-1-2-4]
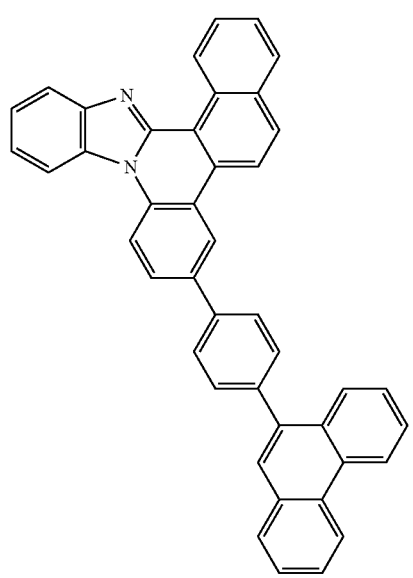
[Formula 3-1-2-5]
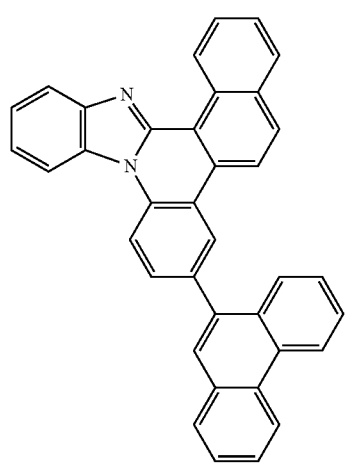
[Formula 3-1-2-6]
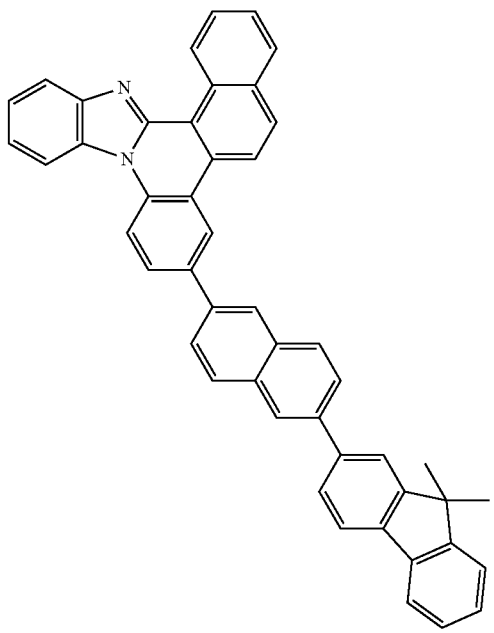
[Formula 3-1-2-9]
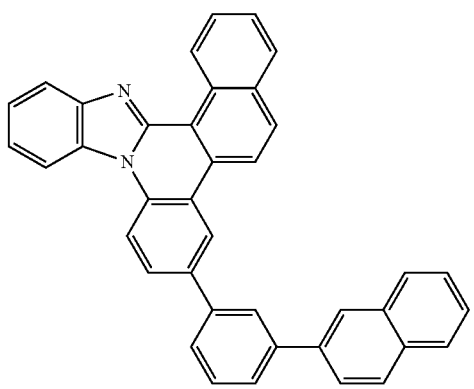
[Formula 3-1-2-10]
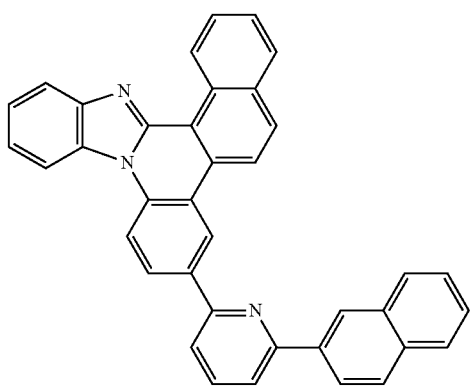

[Formula 3-1-2-11]
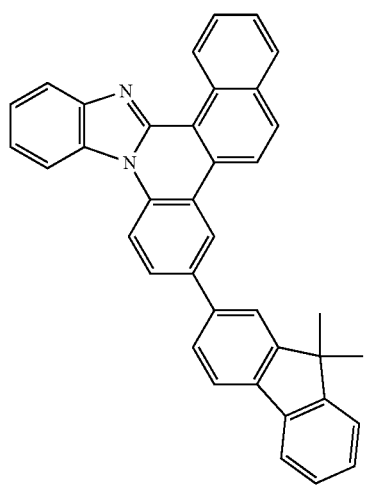
[Formula 3-1-2-12]
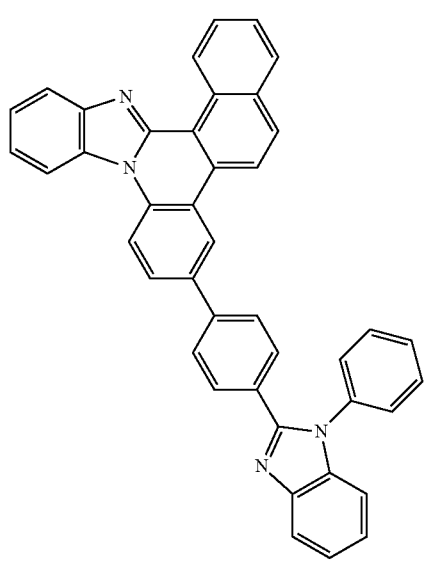
[Formula 3-1-2-13]
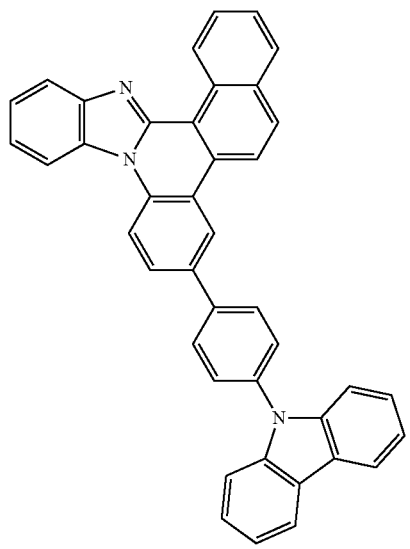
[Formula 3-1-2-14]
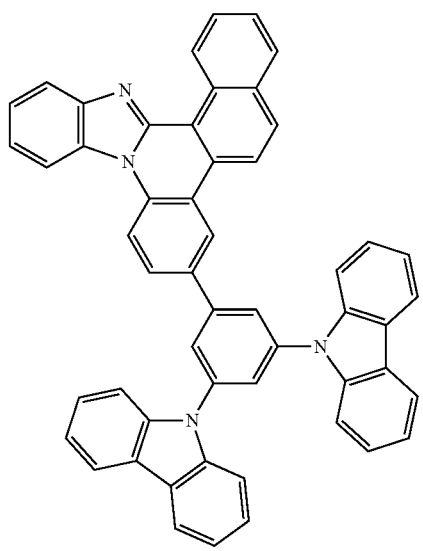
[Formula 3-1-2-15]
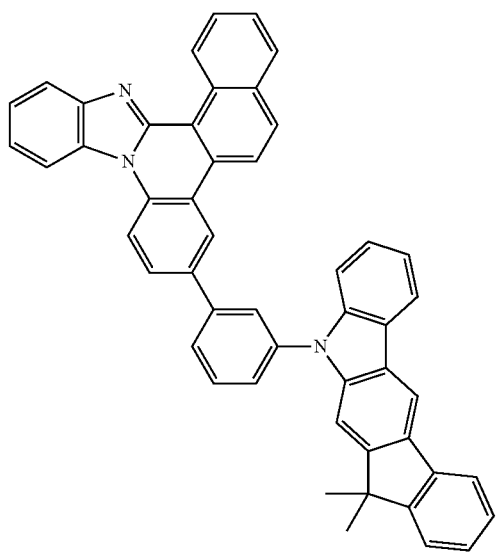
[Formula 3-1-2-16]
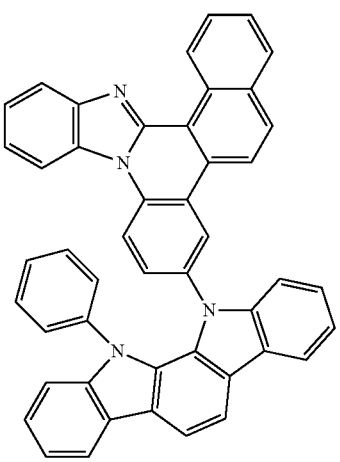

[Formula 3-1-2-17]
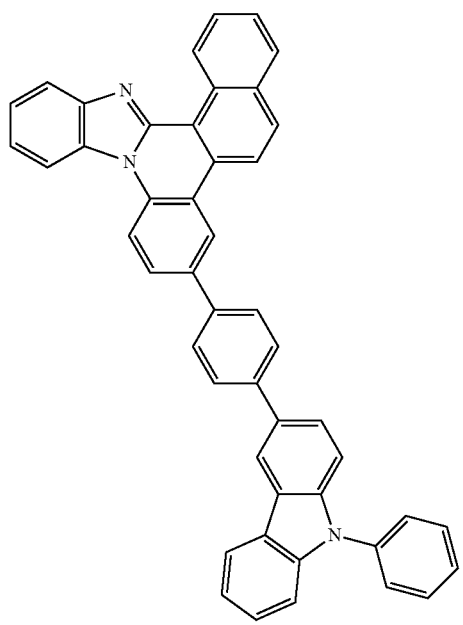
[Formula 3-1-2-18]
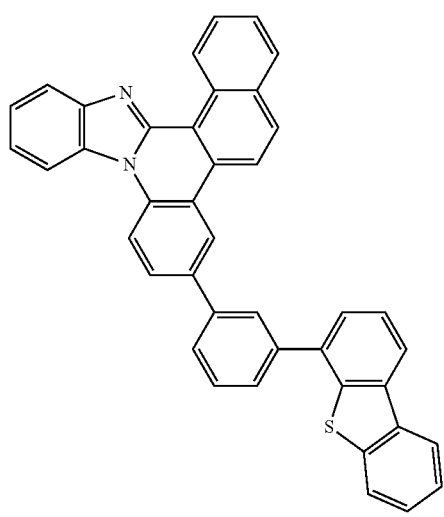
[Formula 3-1-2-19]
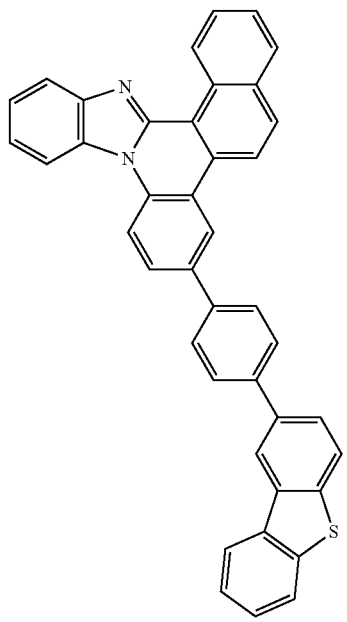
[Formula 3-1-2-20]
[Formula 3-1-2-21]
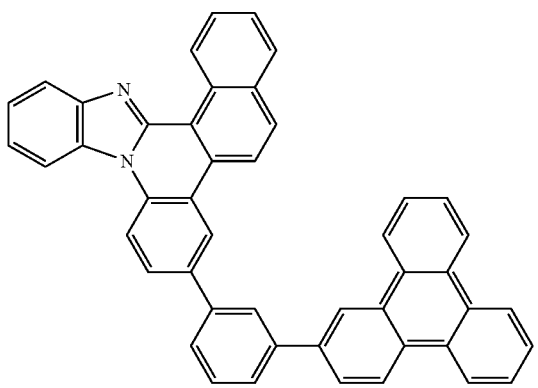

[Formula 3-1-2-22]
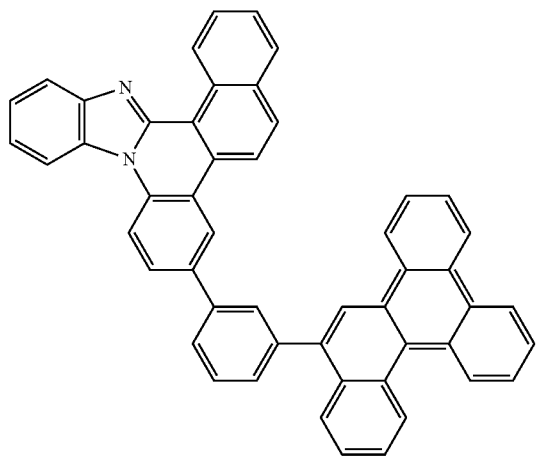
[Formula 3-1-2-23]
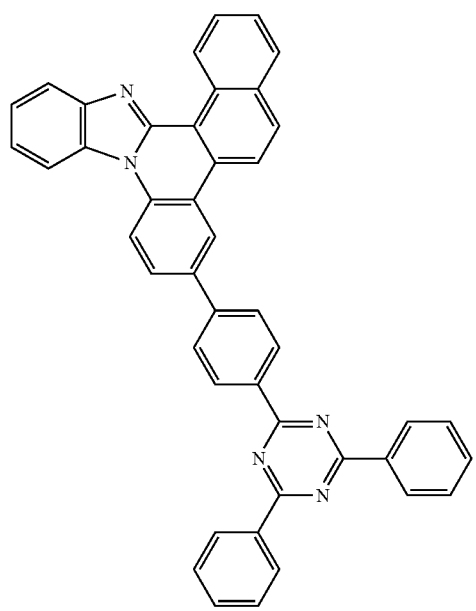
[Formula 3-1-2-24]
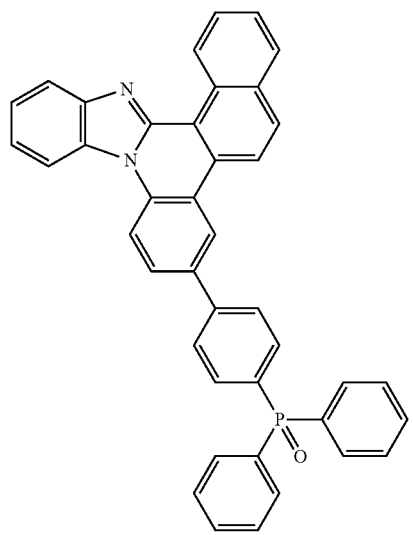
[Formula 3-1-2-25]
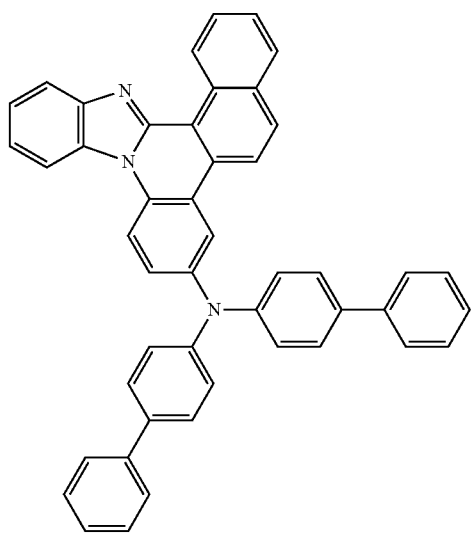
[Formula 3-1-2-26]
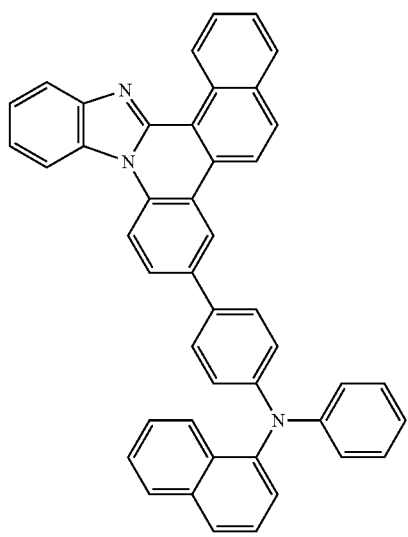
[Formula 3-1-2-27]
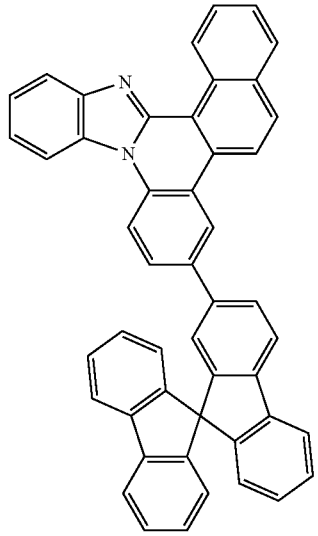

-continued
[Formula 3-1-2-28]
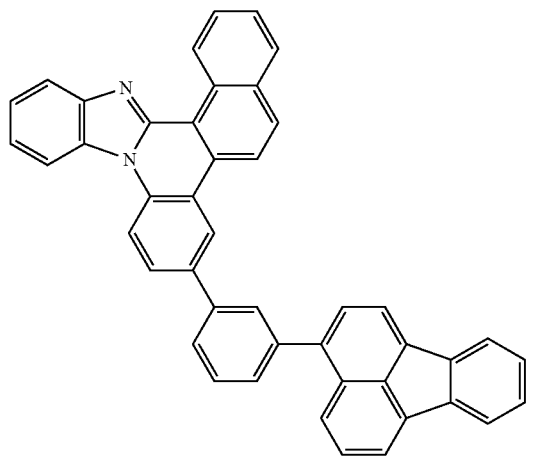
[Formula 3-1-2-29]
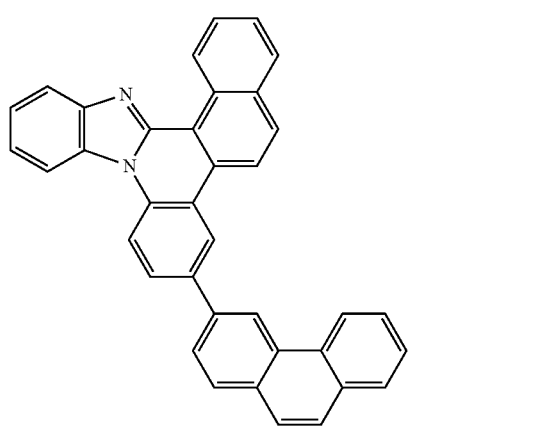
[Formula 3-1-2-30]
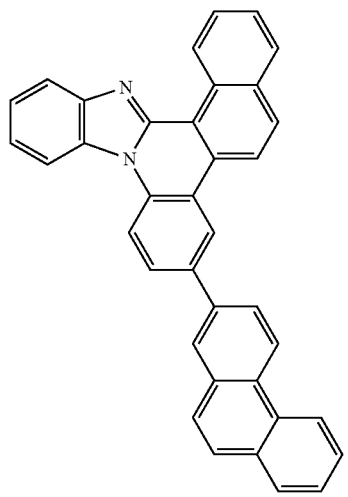
-continued
[Formula 3-1-2-31]
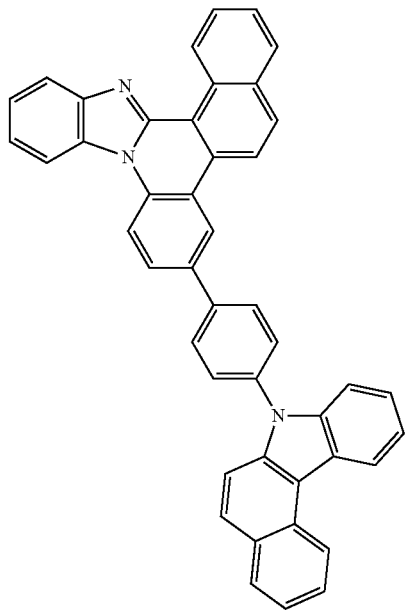
[Formula 3-1-2-32]
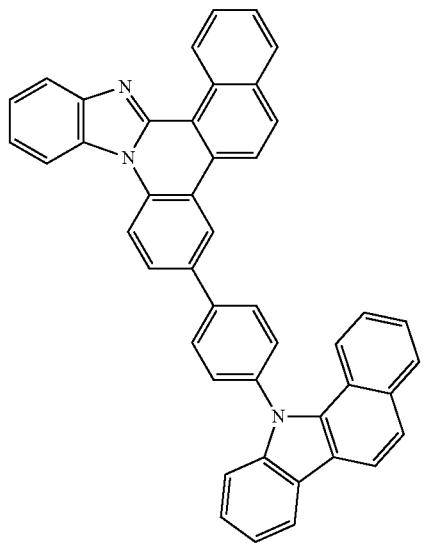

[Formula 3-1-2-33]
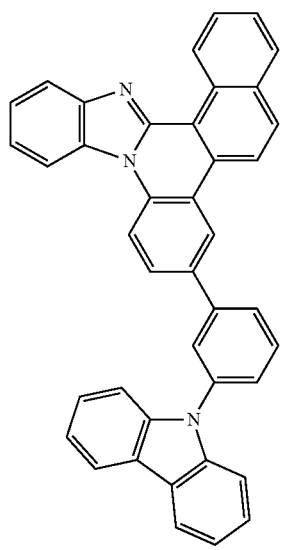
[Formula 3-1-2-34]
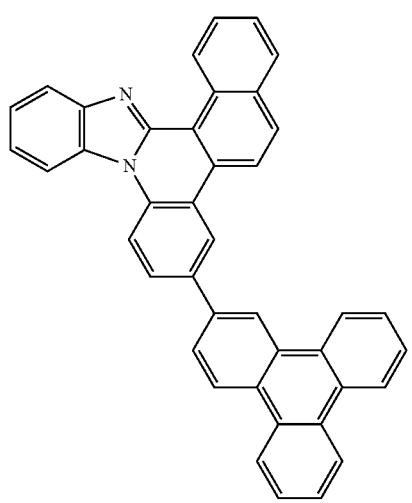
[Formula 3-1-2--35]
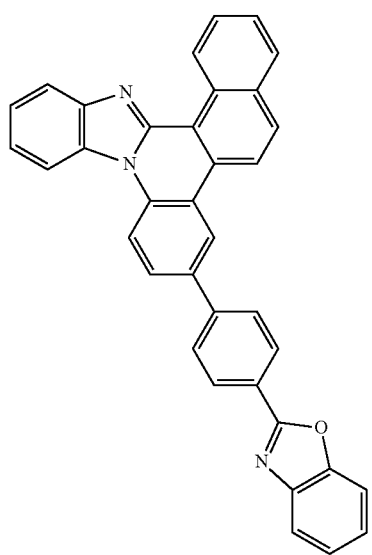
[Formula 3-1-2-36]
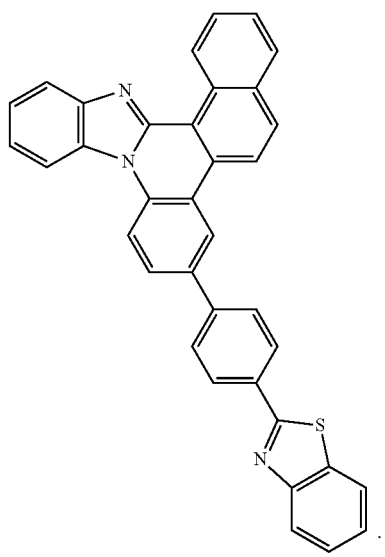
10. The compound of claim 1, wherein the compound is any one selected from the group consisting of the following Structural Formulas:
[Formula 3-2-1-1]
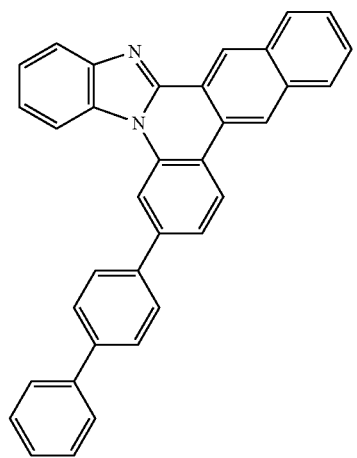

285
-continued
[Formula 3-2-1-2]
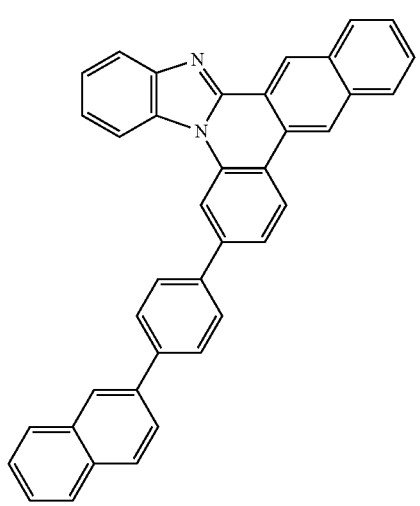
[Formula 3-2-1-3]
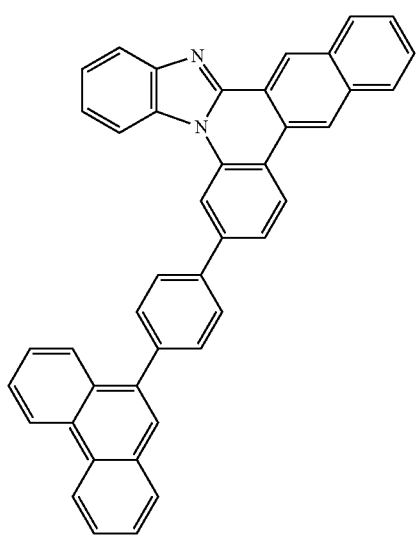
[Formula 3-2-1-4]
286
-continued
[Formula 3-2-1-5]
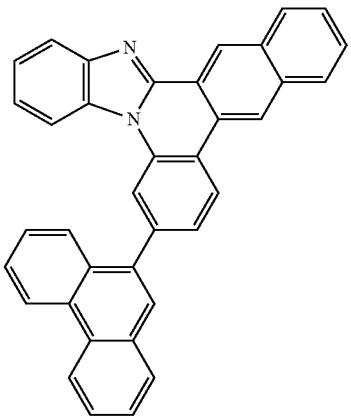
[Formula 3-2-1-6]
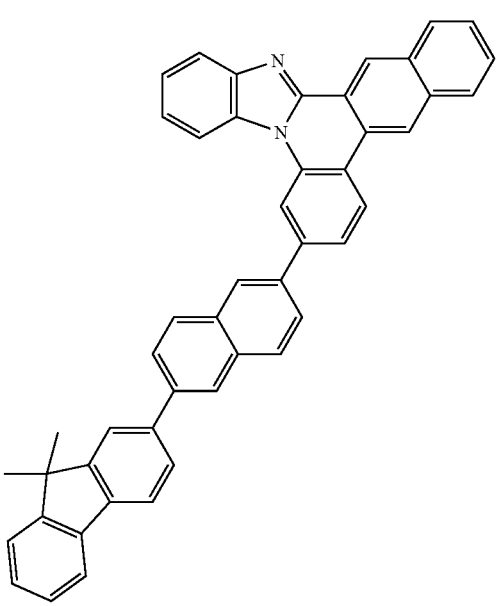
[Formula 3-2-1-9]

[Formula 3-2-1-10]
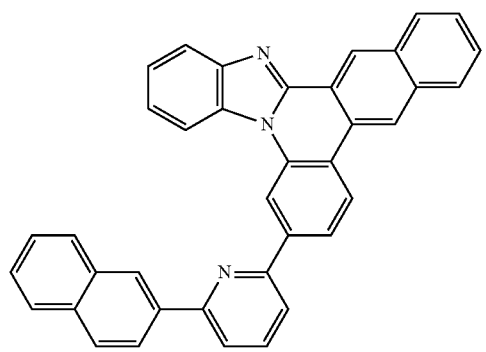
[Formula 3-2-1-11]
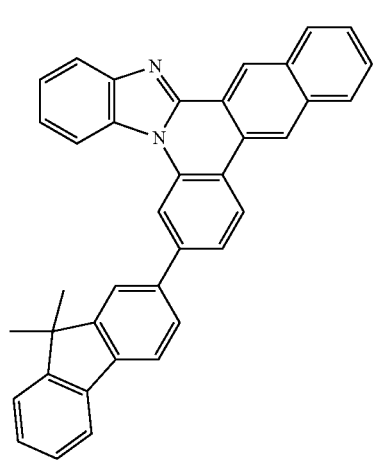
[Formula 3-2-1-12]
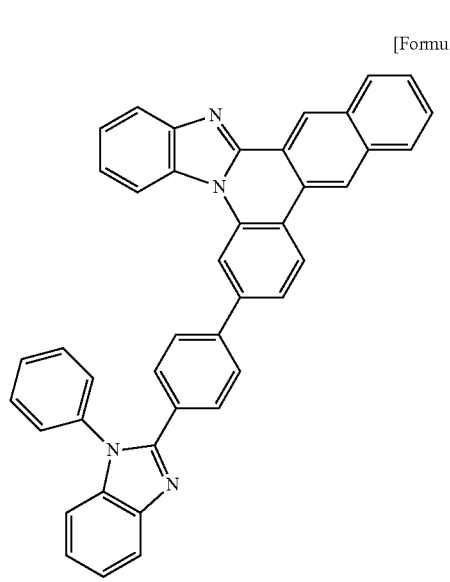
[Formula 3-2-1-13]
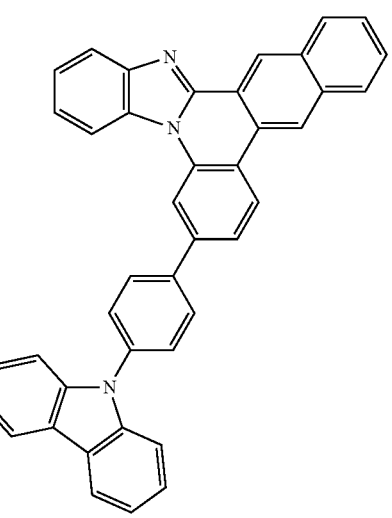
[Formula 3-2-1-14]
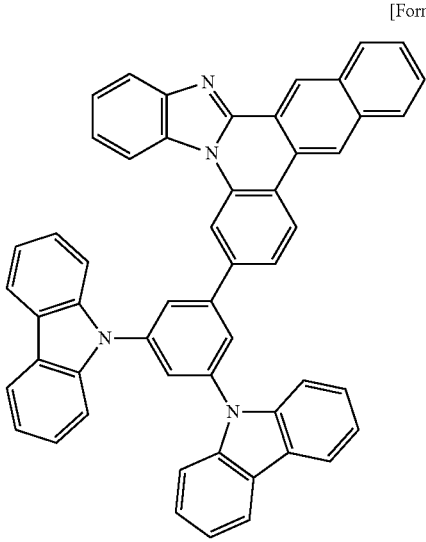
[Formula 3-2-1-15]
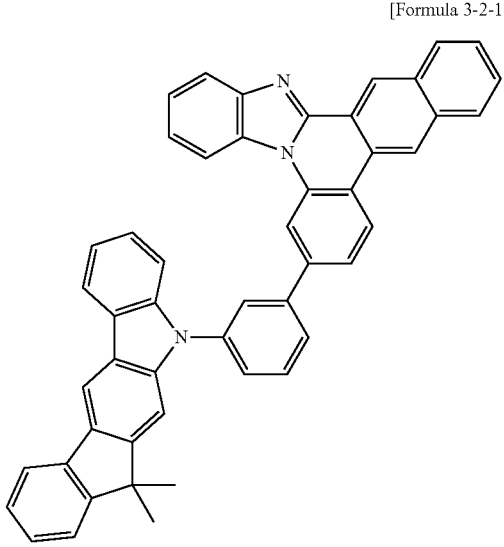

[Formula 3-2-1-16]
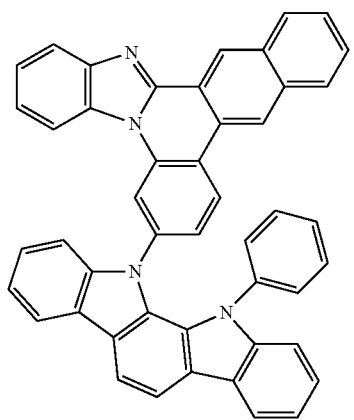
[Formula 3-2-1-17]
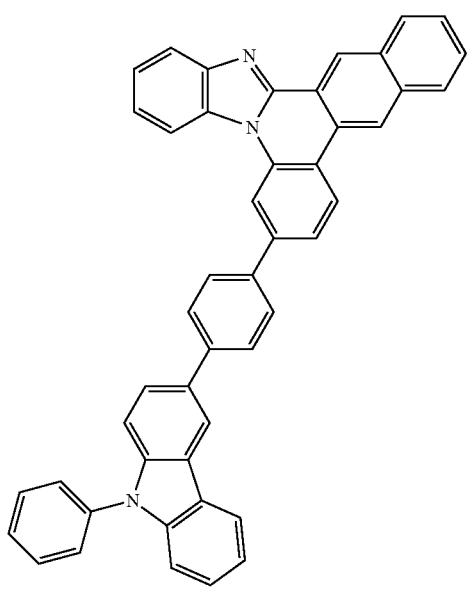
[Formula 3-2-1-18]
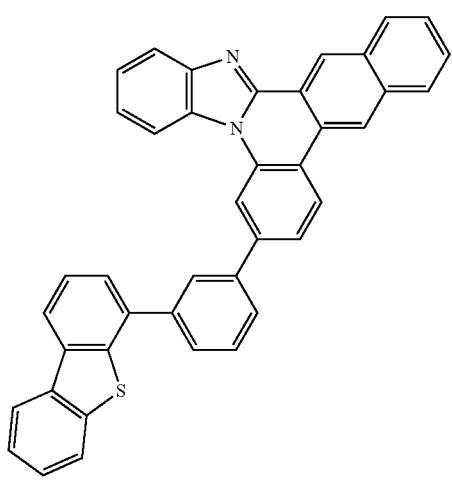
[Formula 3-2-1-19]
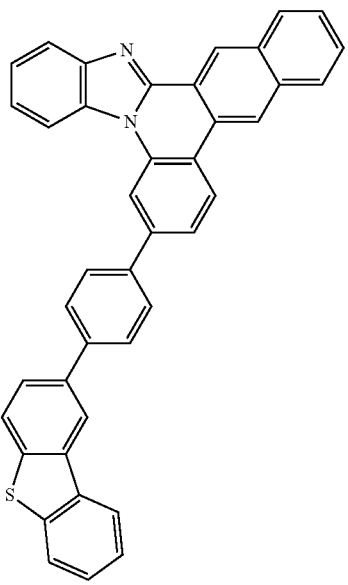
[Formula 3-2-1-20]
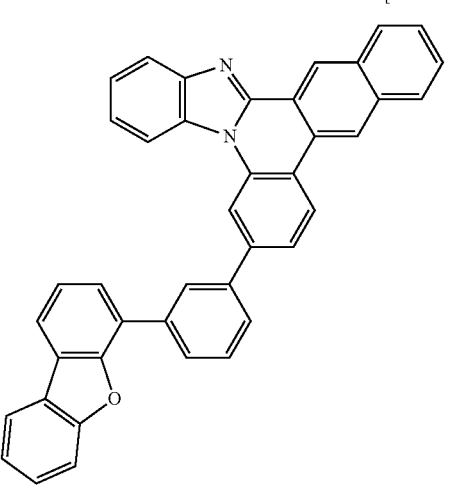
[Formula 3-2-1-21]
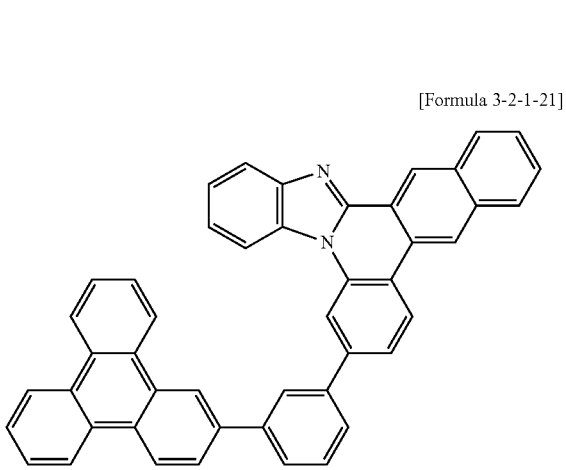

[Formula 3-2-1-22]
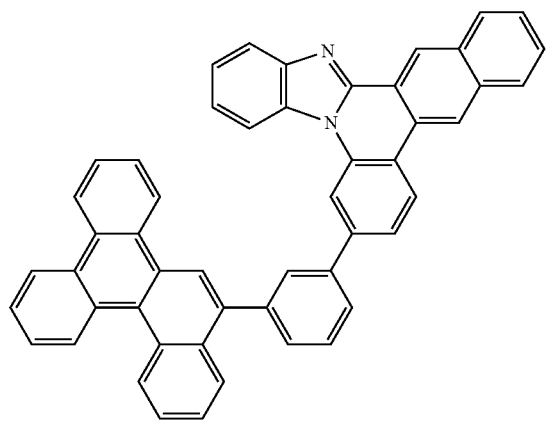
[Formula 3-2-1-23]
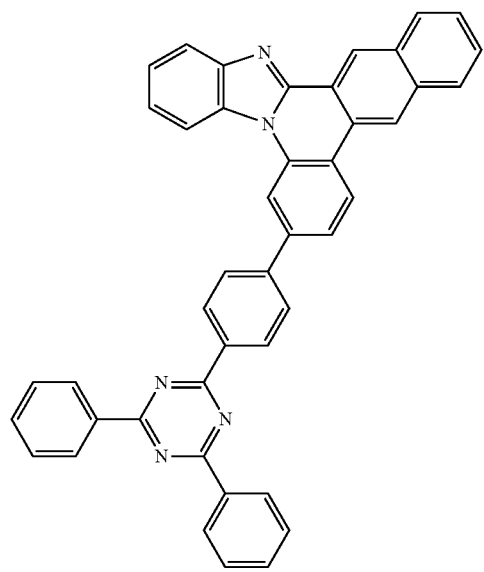
[Formula 3-2-1-24]
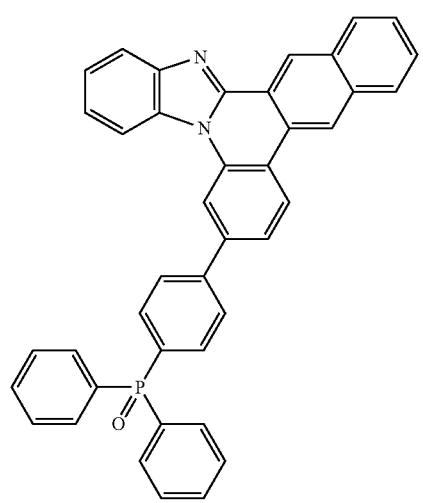
[Formula 3-2-1-25]
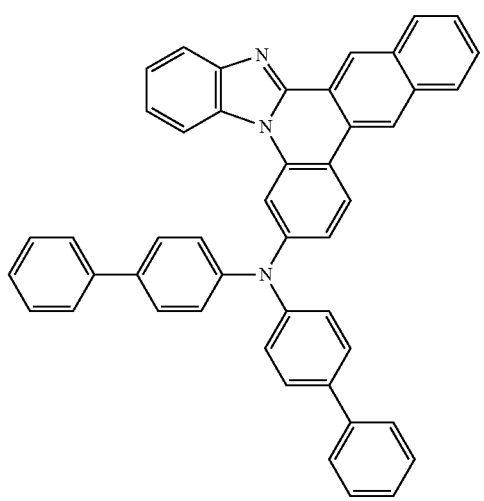
[Formula 3-2-1-26]
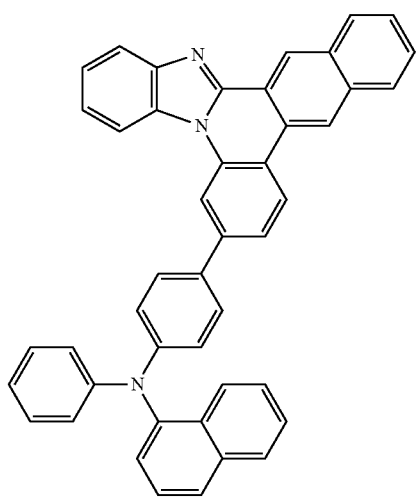
[Formula 3-2-1-27]
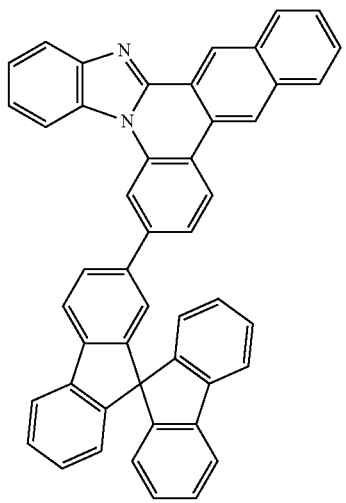

[Formula 3-2-1-28]
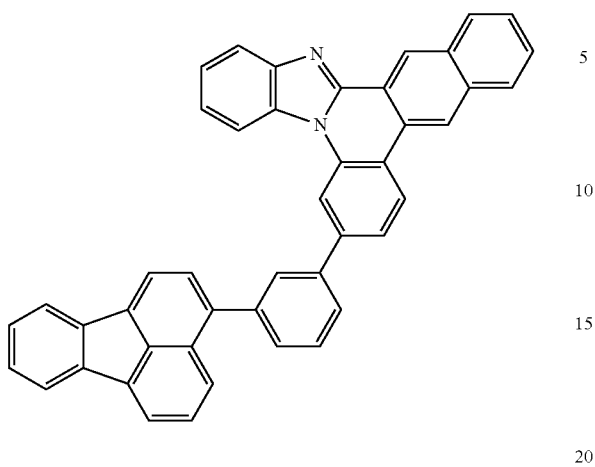
[Formula 3-2-2-1]
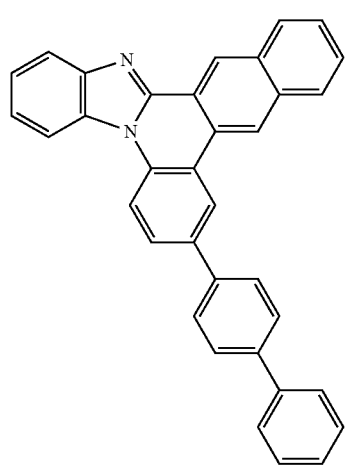
[Formula 3-2-2-2]
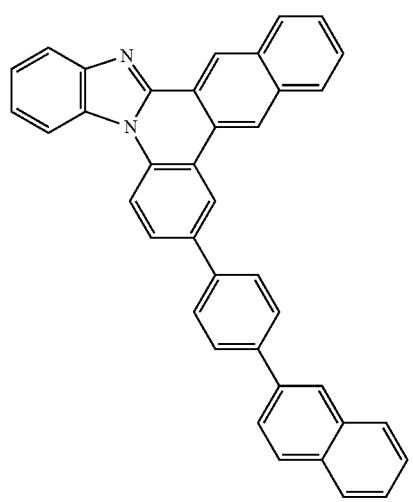
[Formula 3-2-2-3]
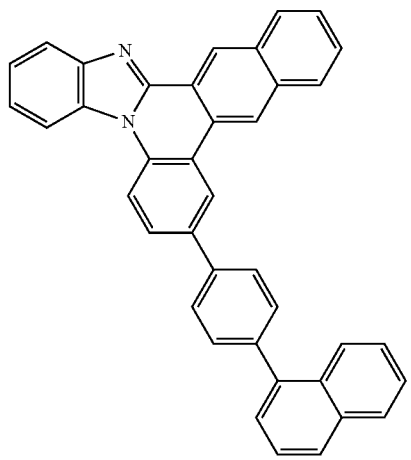
[Formula 3-2-2-4]
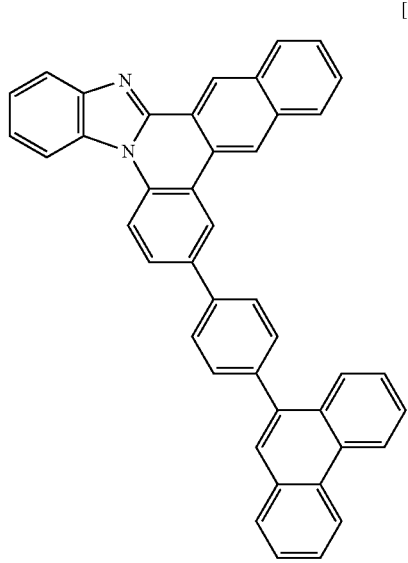
[Formula 3-2-2-5]
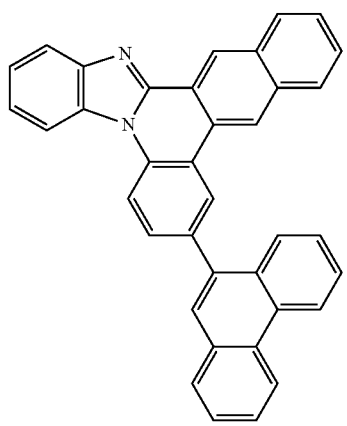

[Formula 3-2-2-6]
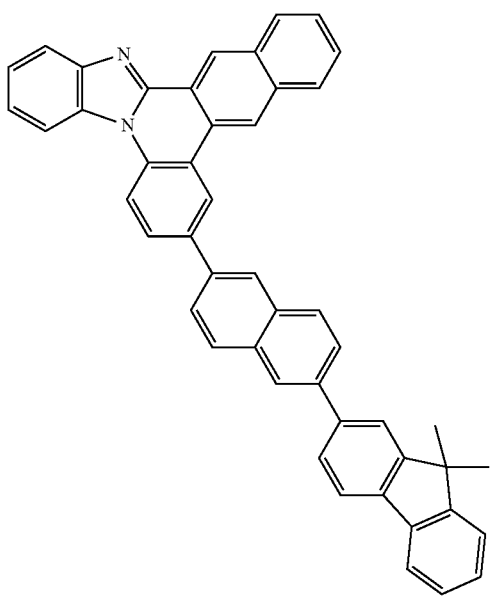
[Formula 3-2-2-9]
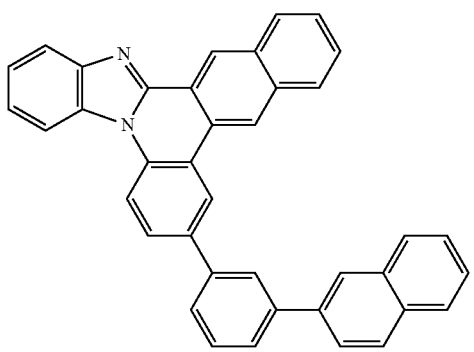
[Formula 3-2-2-10]
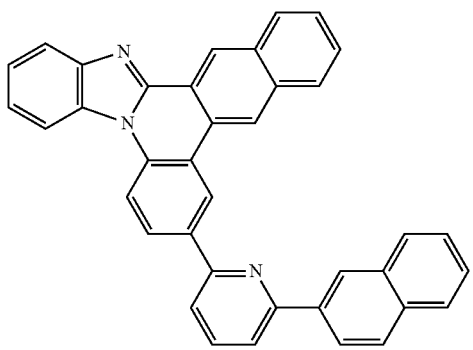
[Formula 3-2-2-11]
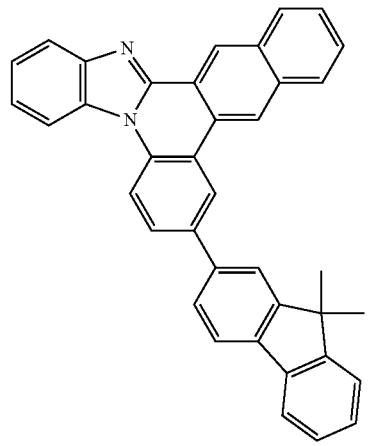
[Formula 3-2-2-12]
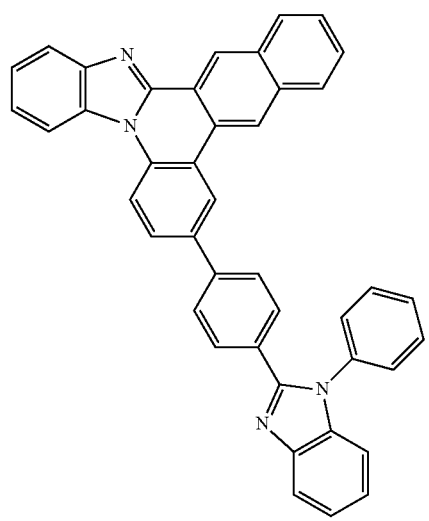
[Formula 3-2-2-13]
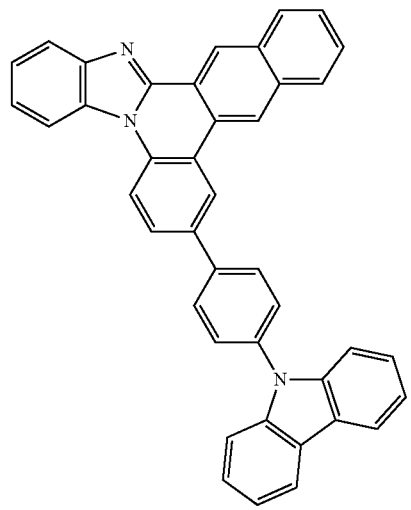

[Formula 3-2-2-14]
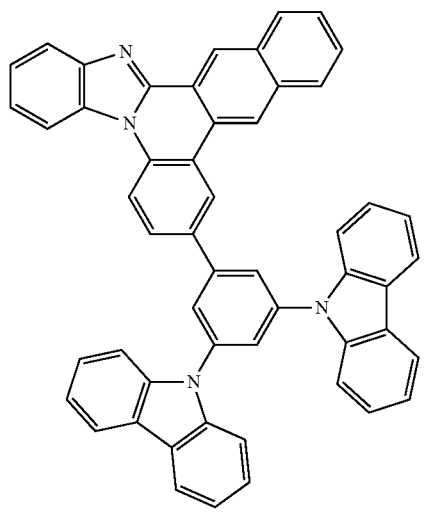
[Formula 3-2-2-15]
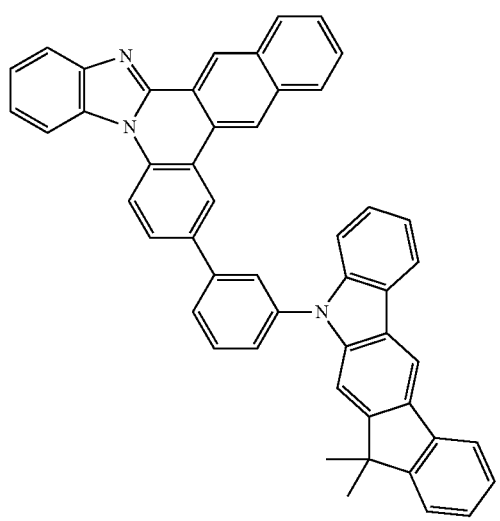
[Formula 3-2-2-16]
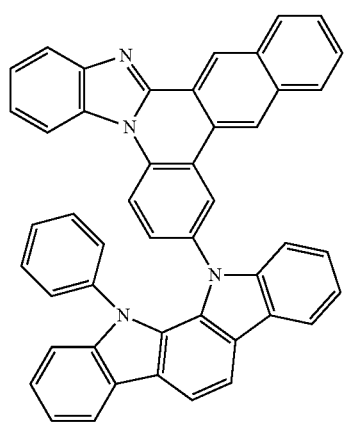
[Formula 3-2-2-17]
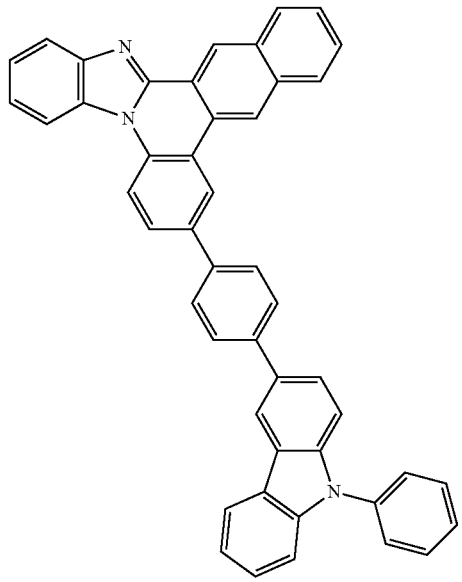
[Formula 3-2-2-18]
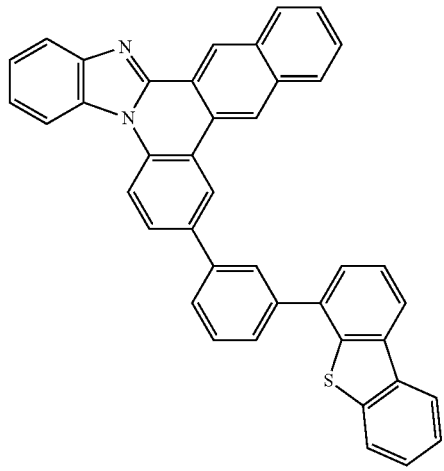
[Formula 3-2-2-19]
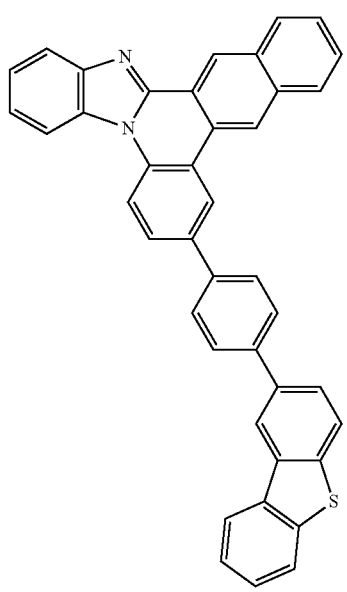

[Formula 3-2-2-20]
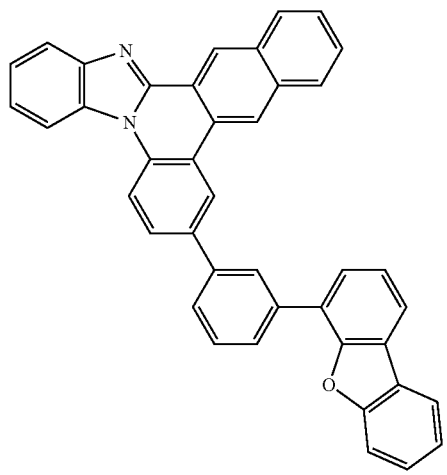
[Formula 3-2-2-21]
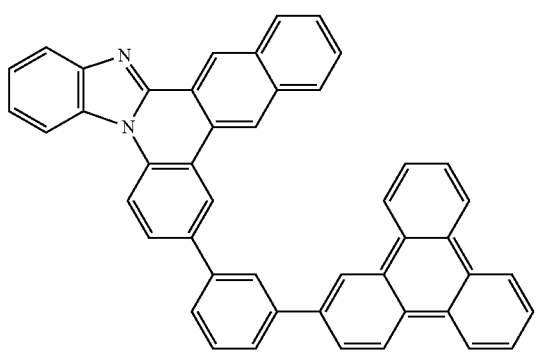
[Formula 3-2-2-22]
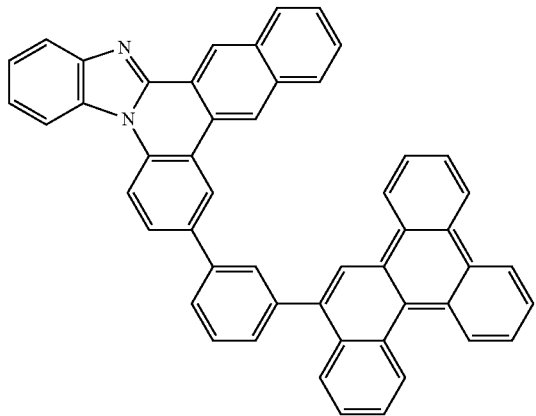
[Formula 3-2-2-23]
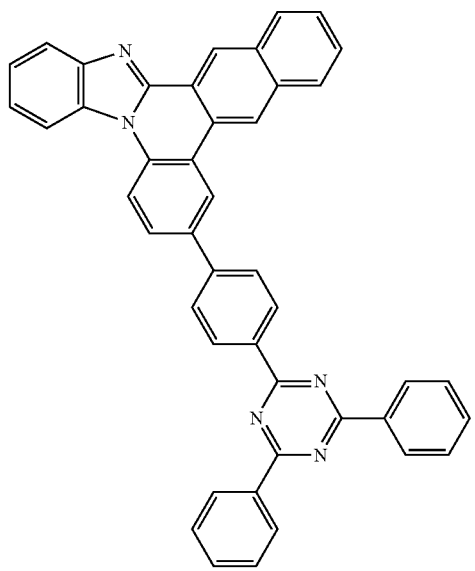
[Formula 3-2-2-24]
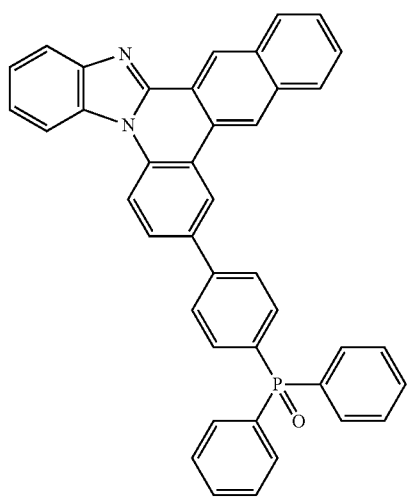
[Formula 3-2-2-25]
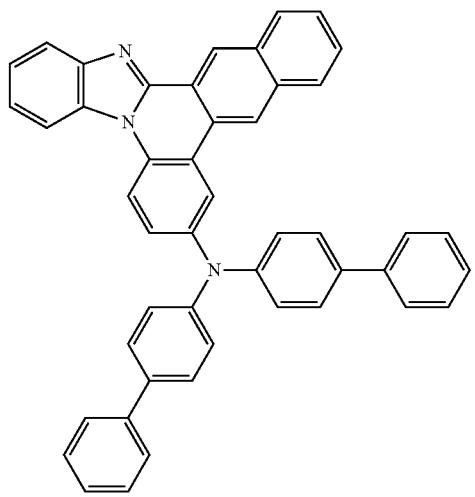

[Formula 3-2-2-26]
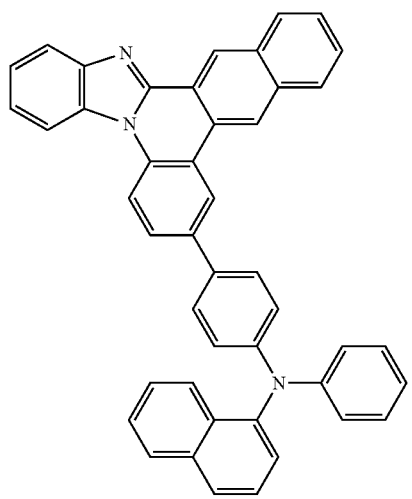
[Formula 3-2-2-27]
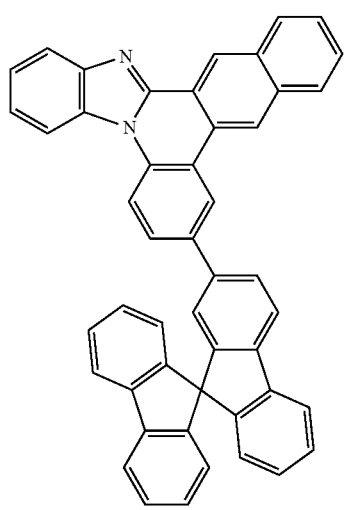
[Formula 3-2-2-28]
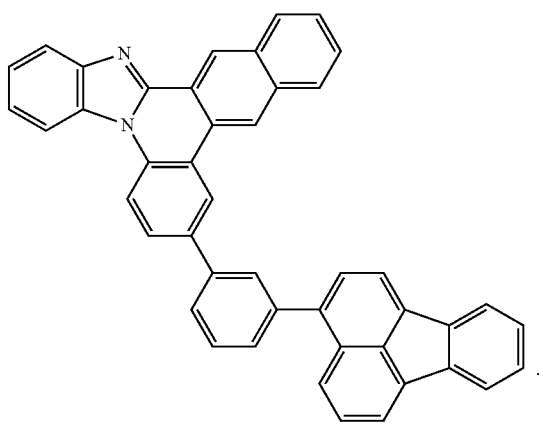
11. The compound of claim 1, wherein the compound is any one selected from the group consisting of the following Structural Formulas:
[Formula 3-3-1-1]
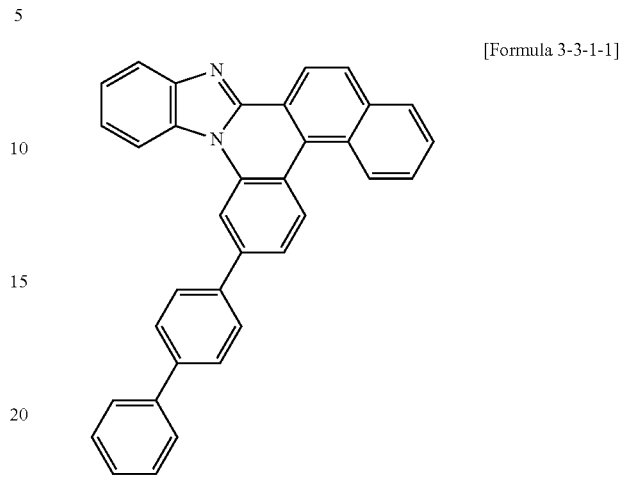
[Formula 3-3-1-2]
[Formula 3-3-1-3]
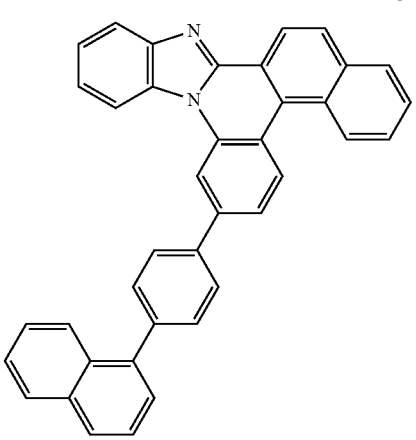

[Formula 3-3-1-4]
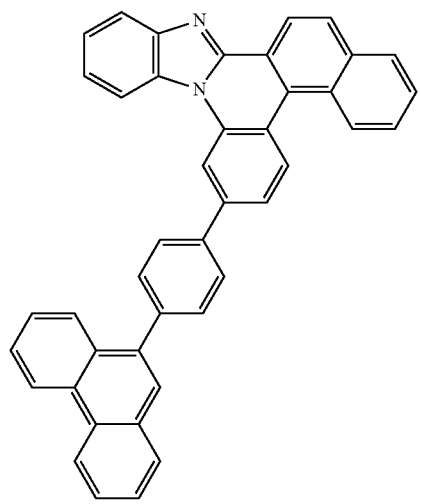
[Formula 3-3-1-5]
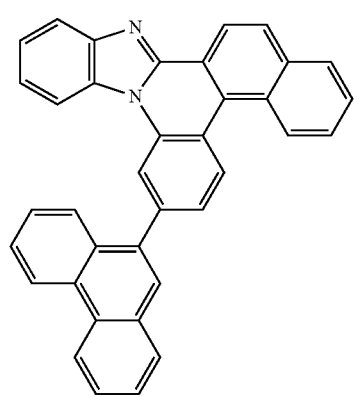
[Formula 3-3-1-6]
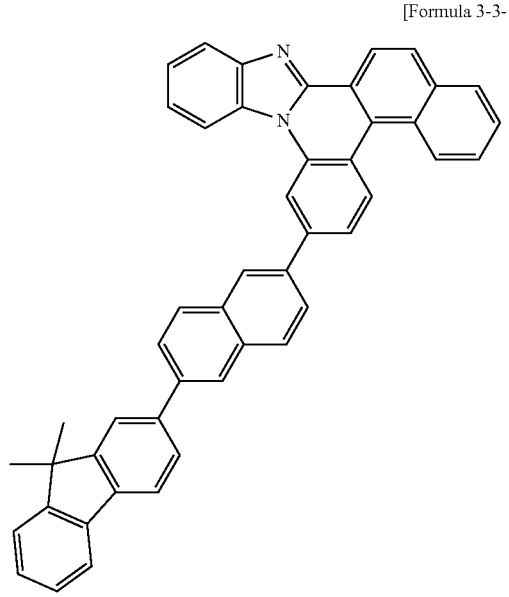
[Formula 3-3-1-9]
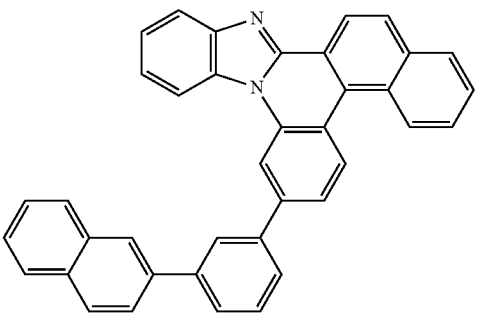
[Formula 3-3-1-10]
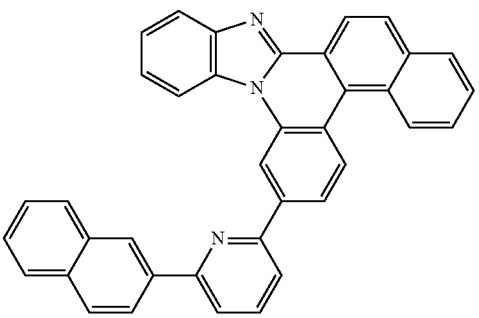
[Formula 3-3-1-11]
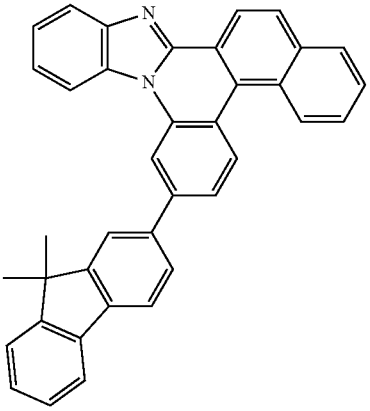
[Formula 3-3-1-12]
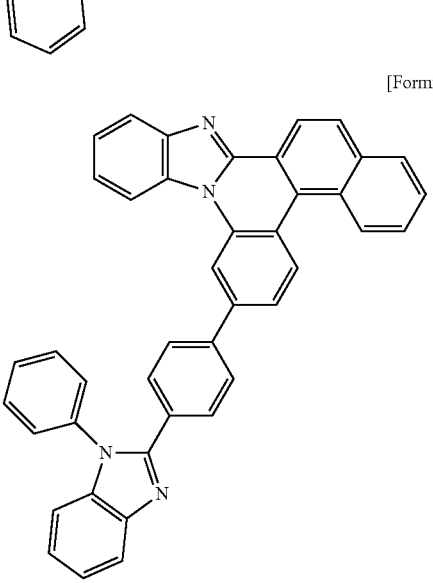

[Formula 3-3-1-13]
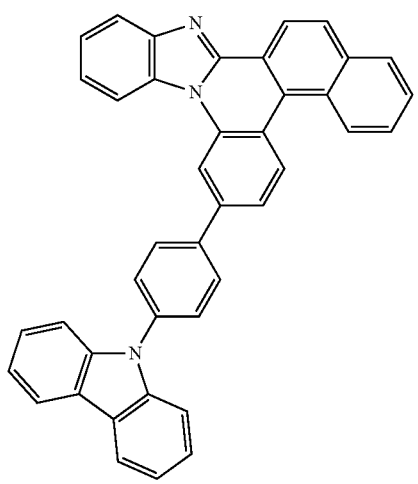
[Formula 3-3-1-14]
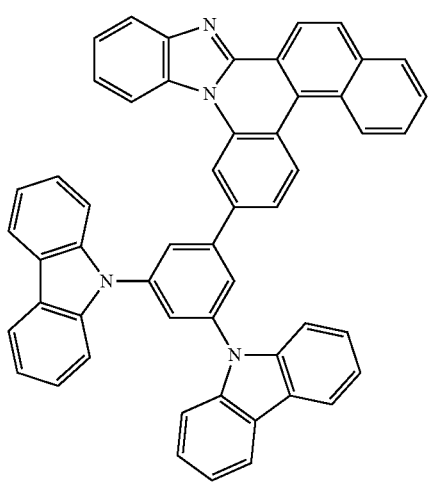
[Formula 3-3-1-15]
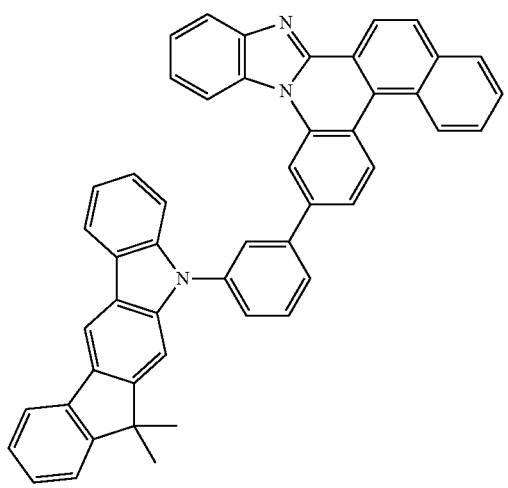
[Formula 3-3-1-16]
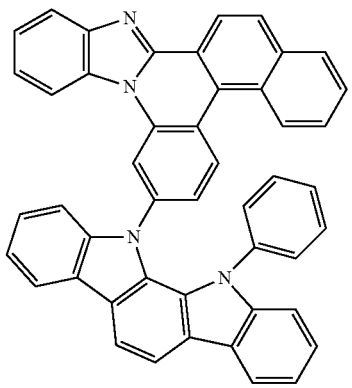
[Formula 3-3-1-17]
[Formula 3-3-1-18]
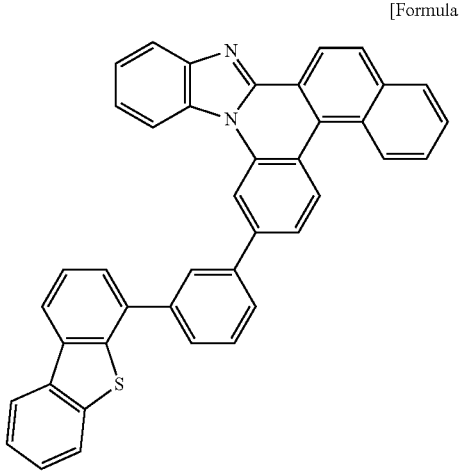

[Formula 3-3-1-19]
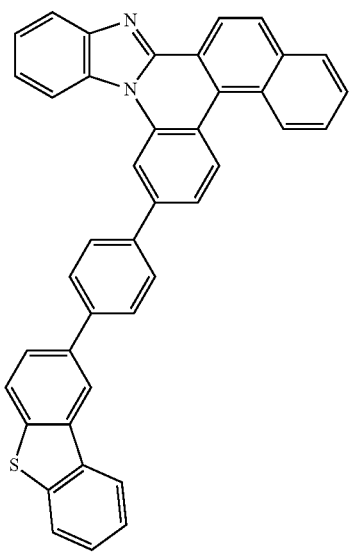
[Formula 3-3-1-22]
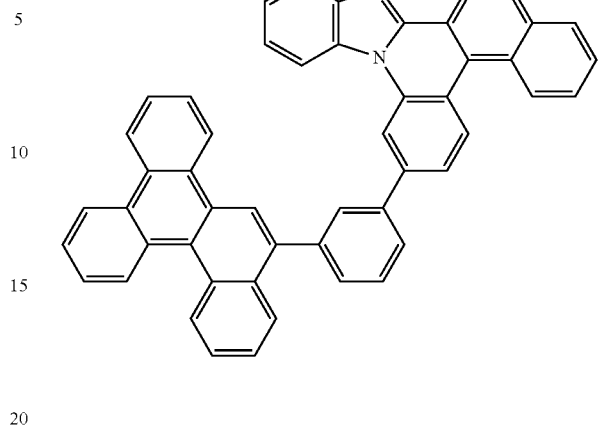
[Formula 3-3-1-20]
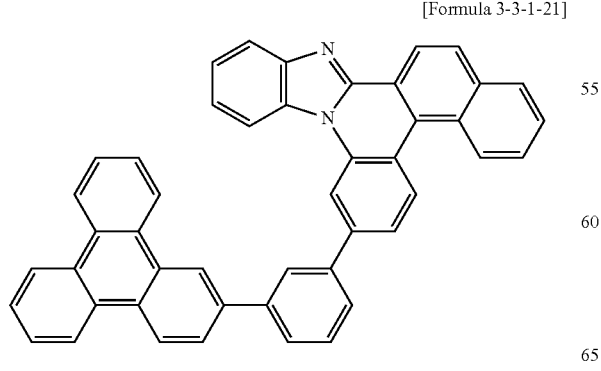
[Formula 3-3-1-23]
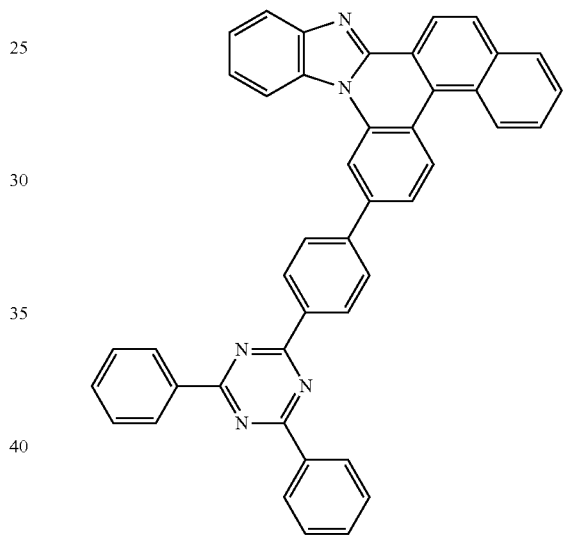
[Formula 3-3-1-21]
[Formula 3-3-1-24]
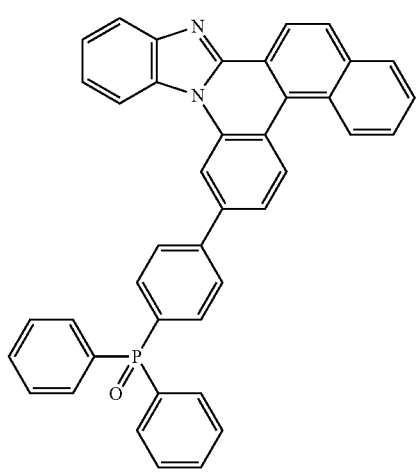

[Formula 3-3-1-25]
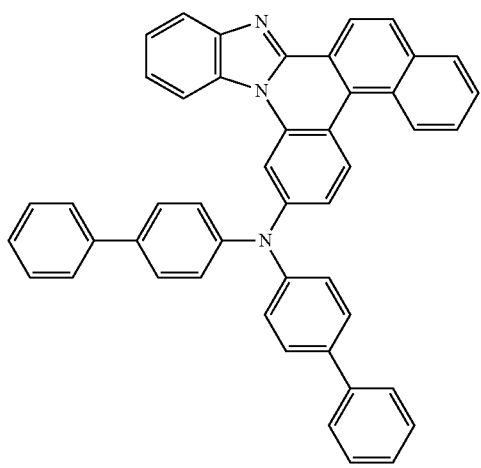
[Formula 3-3-1-26]
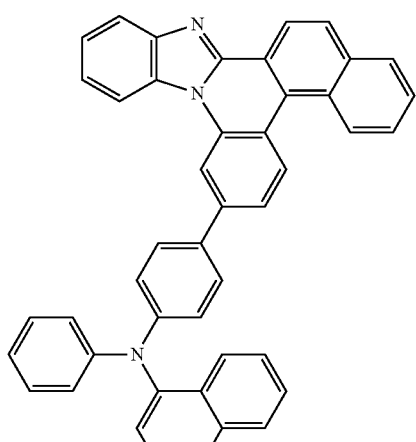
[Formula 3-3-1-27]
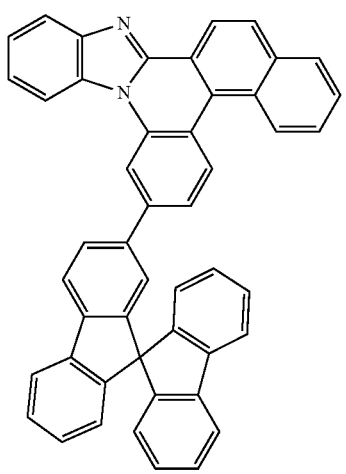
[Formula 3-3-1-28]
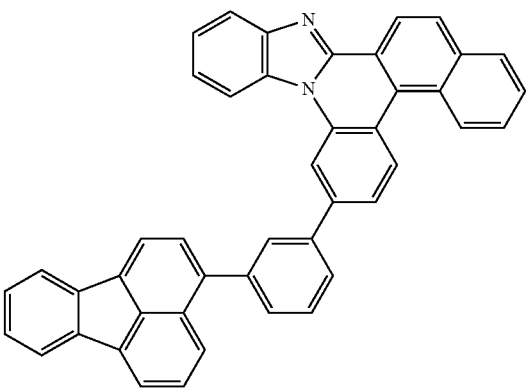
[Formula 3-3-2-1]
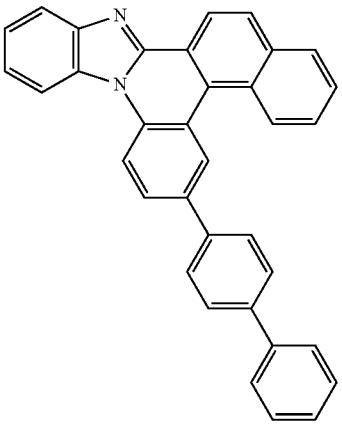
[Formula 3-3-2-2]
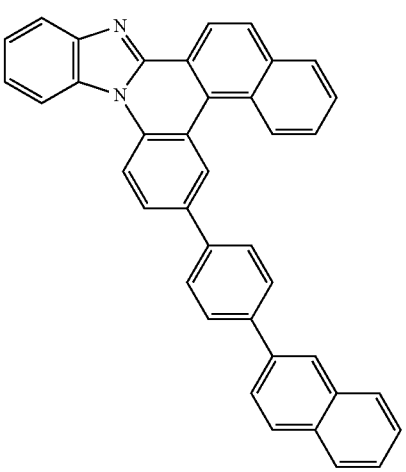

[Formula 3-3-2-3]
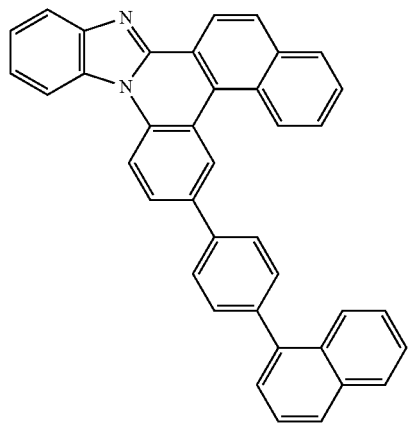
[Formula 3-3-2-6]
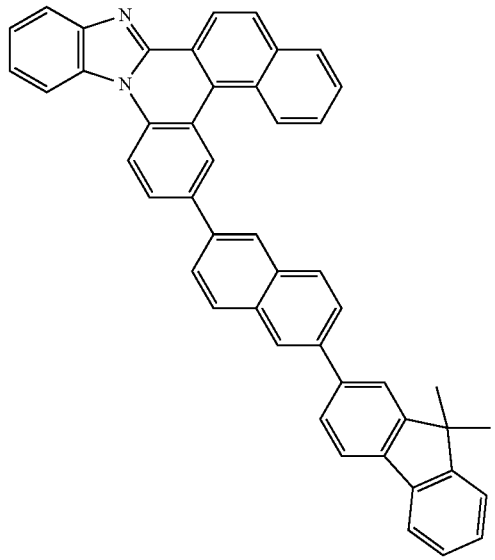
[Formula 3-3-2-4]
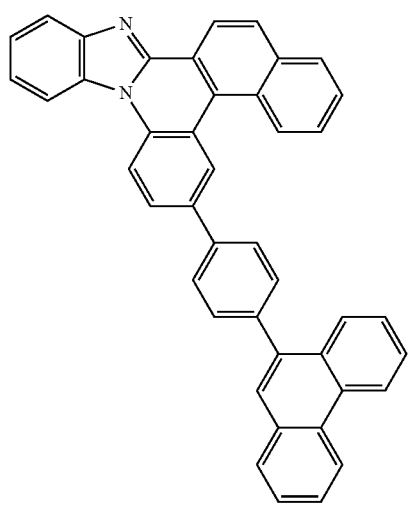
[Formula 3-3-2-7]
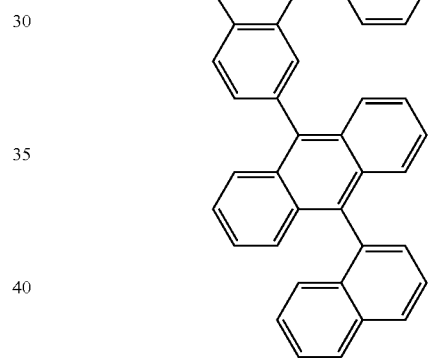
[Formula 3-3-2-5]
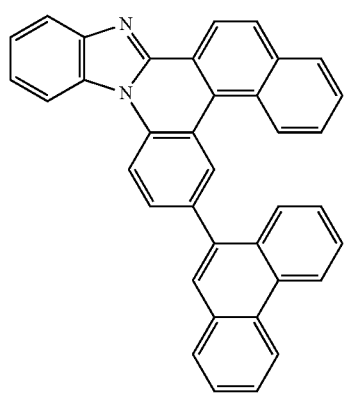
[Formula 3-3-2-8]
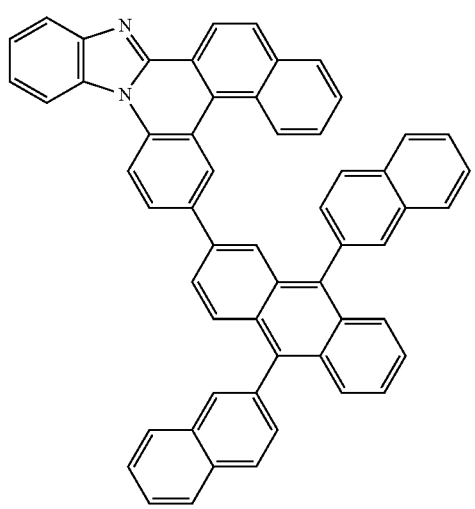

[Formula 3-3-2-9]
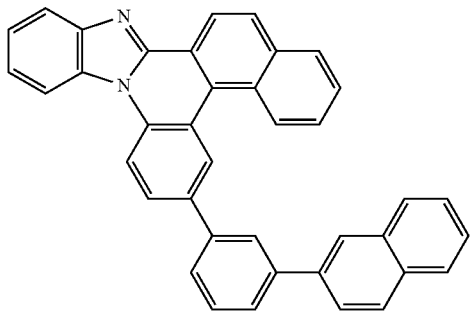
[Formula 3-3-2-10]
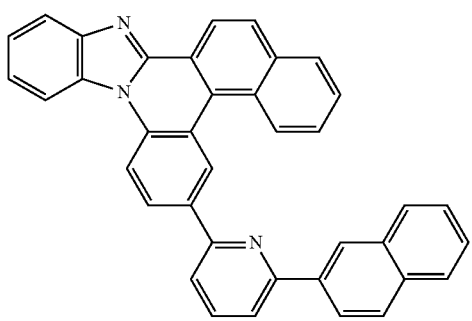
[Formula 3-3-2-11]
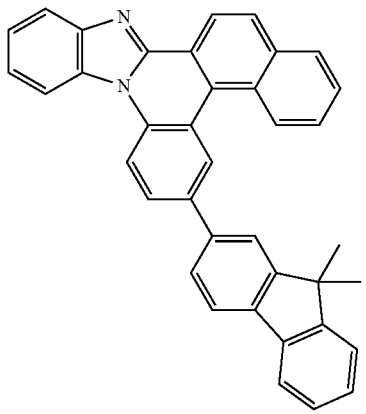
[Formula 3-3-2-12]
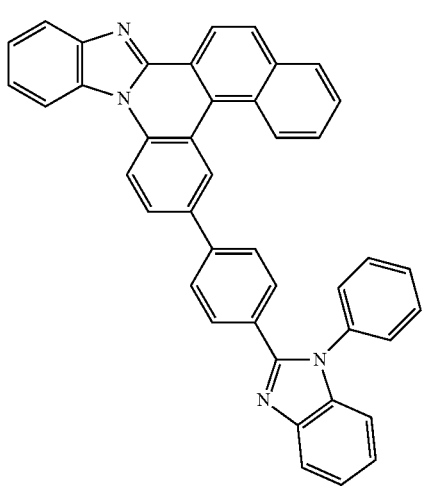
[Formula 3-3-2-13]
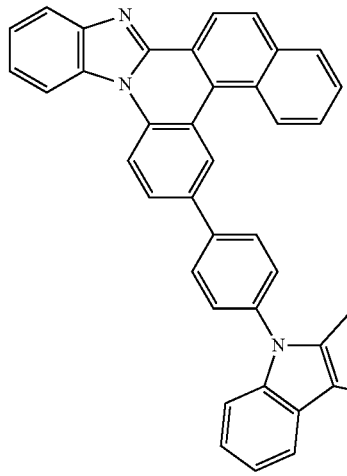
[Formula 3-3-2-14]
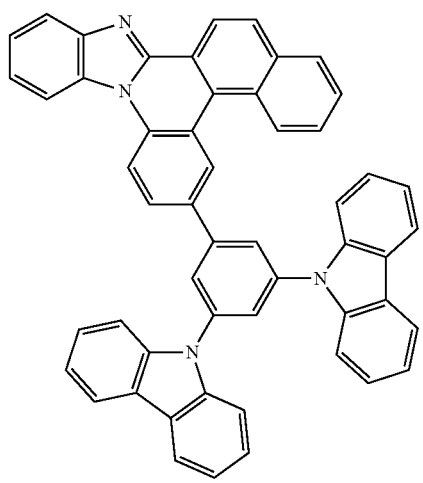
[Formula 3-3-2-15]
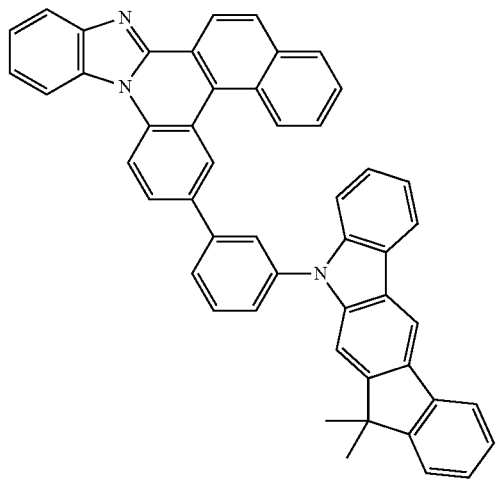

[Formula 3-3-2-16]
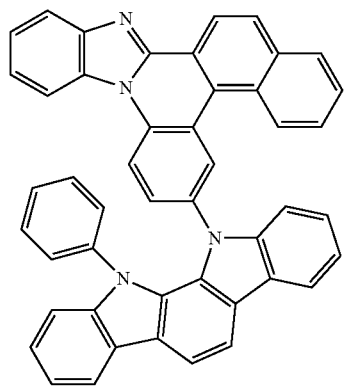
[Formula 3-3-2-17]
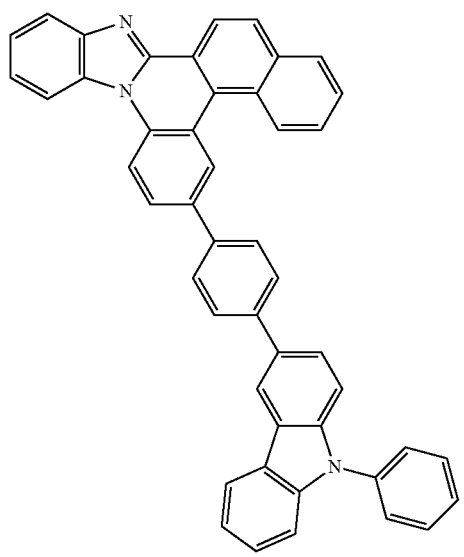
[Formula 3-3-2-18]
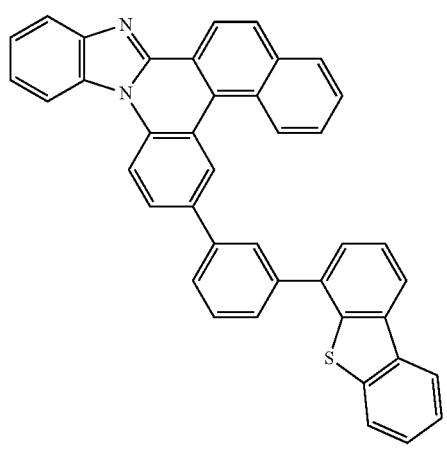
[Formula 3-3-2-19]
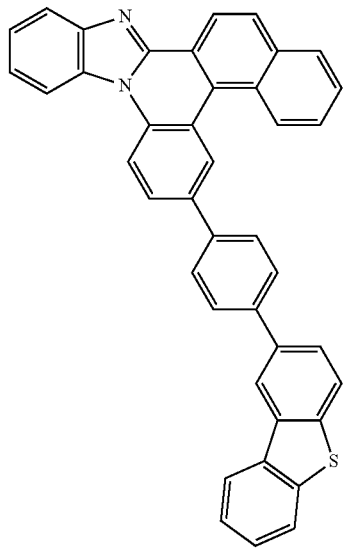
[Formula 3-3-2-20]
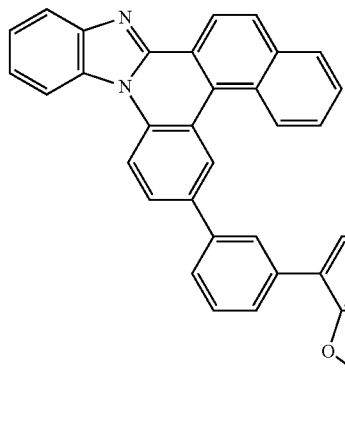
[Formula 3-3-2-21]
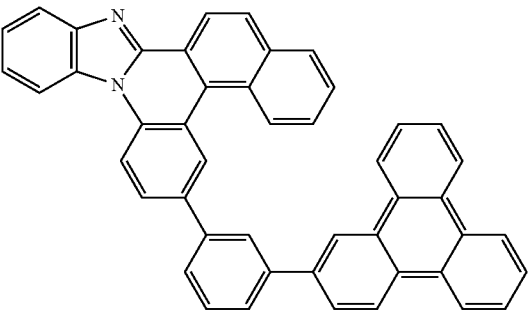

-continued
[Formula 3-3-2-22]
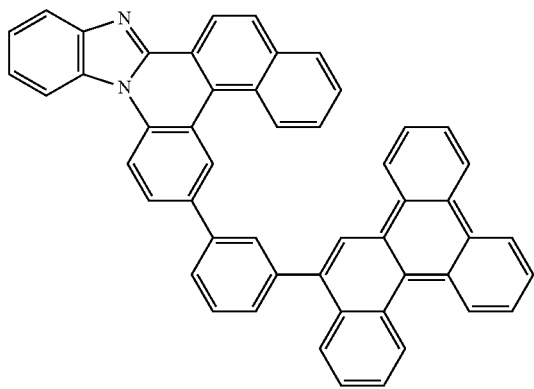
[Formula 3-3-2-23]
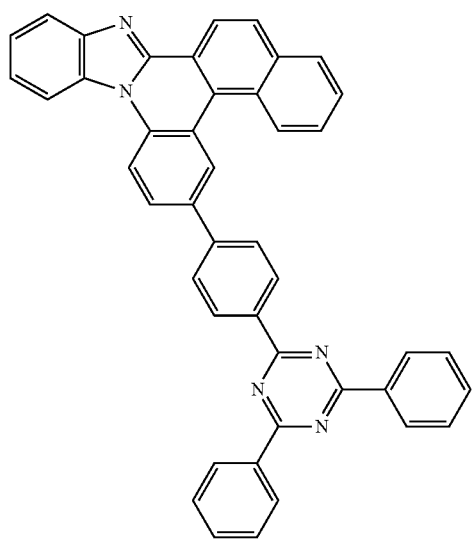
[Formula 3-3-2-24]
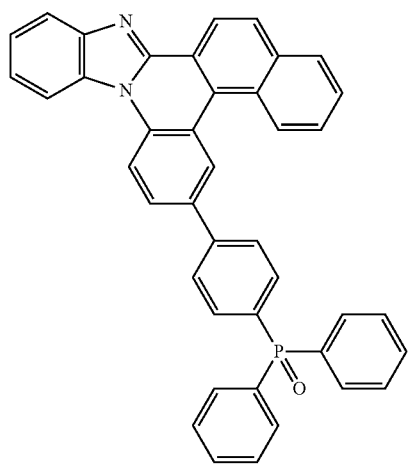
-continued
[Formula 3-3-2-25]
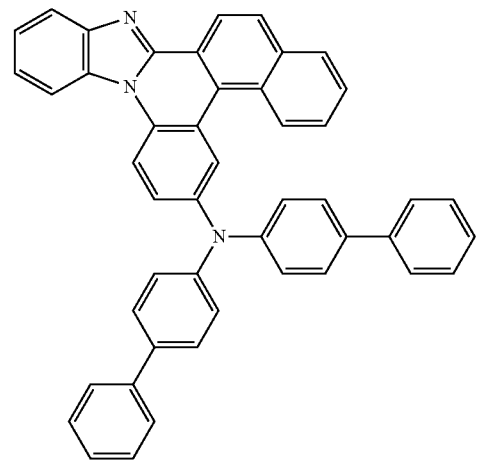
[Formula 3-3-2-26]
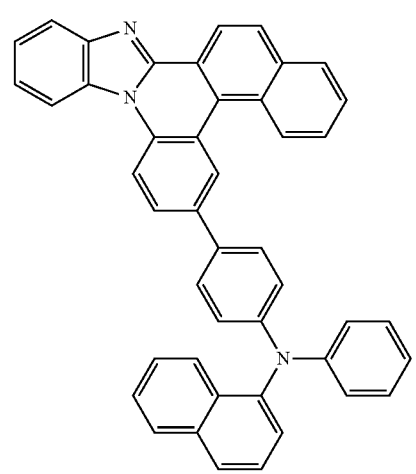
[Formula 3-3-2-27]
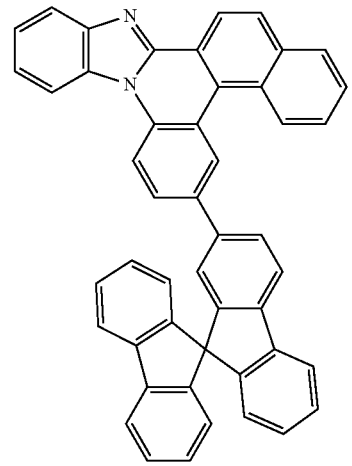

[Formula 3-3-2-28]
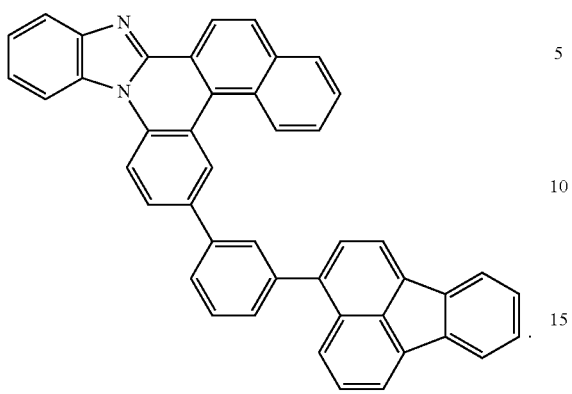
[Formula 3-4-1-3]
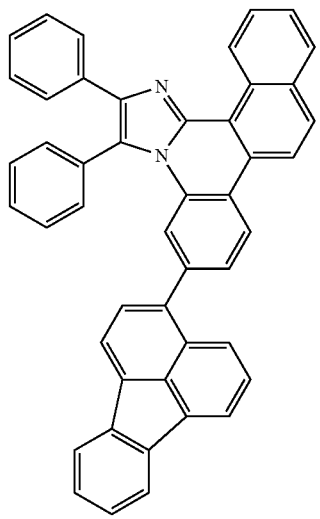
12. The compound of claim 1, wherein the compound is any one selected from the group consisting of the following Structural Formulas:
[Formula 3-4-1-1]
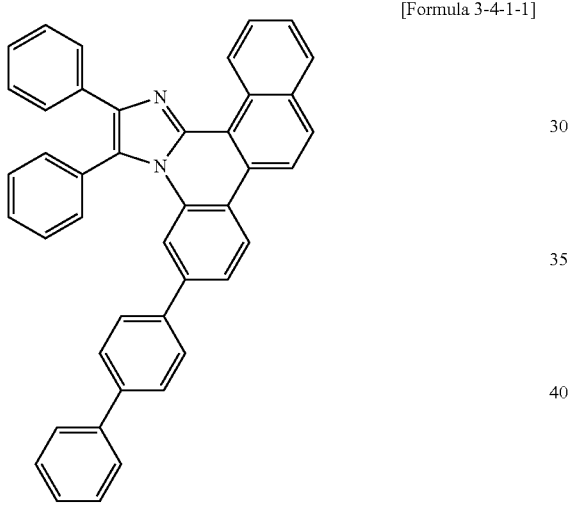
[Formula 3-4-1-2]
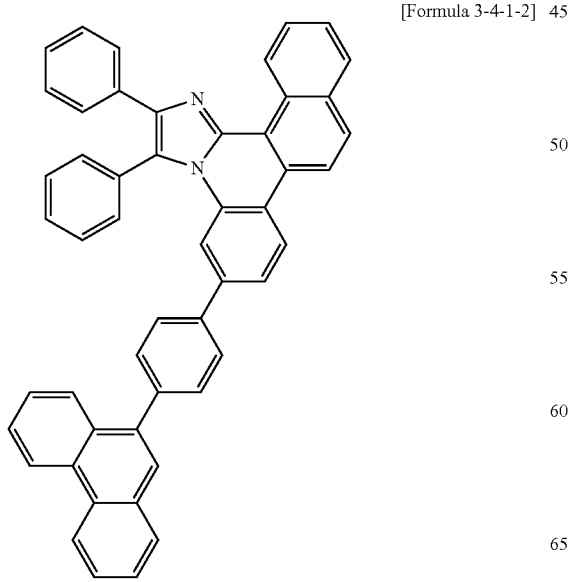
[Formula 3-4-1-4]
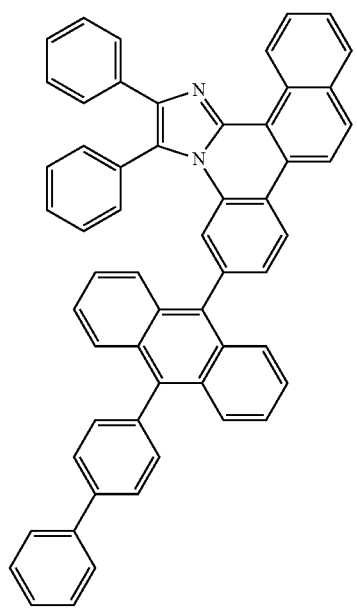

321
-continued
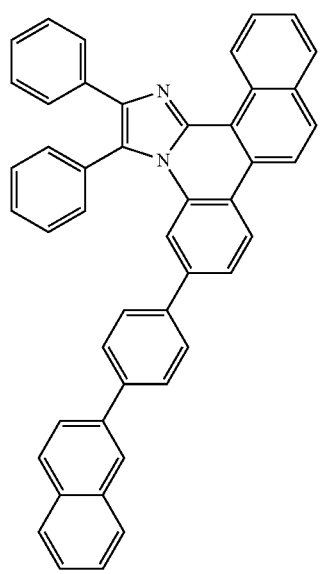
[Formula 3-4-1-5]
322
-continued
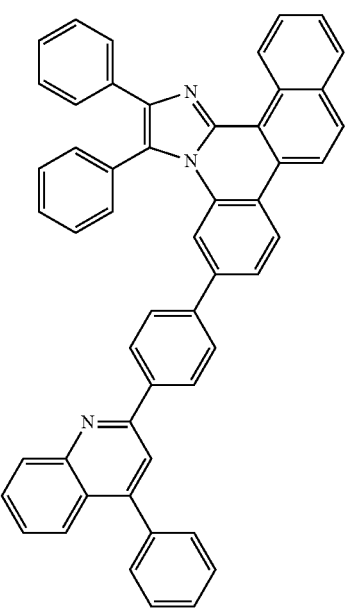
[Formula 3-4-1-7]
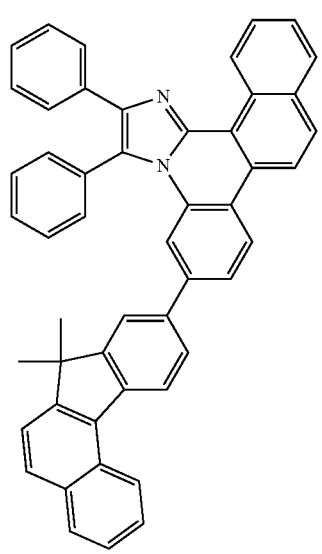
[Formula 3-4-1-6]
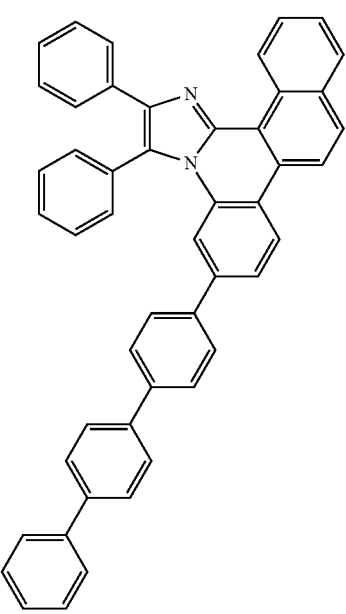
[Formula 3-4-1-8]

-continued
[Formula 3-4-1-9]
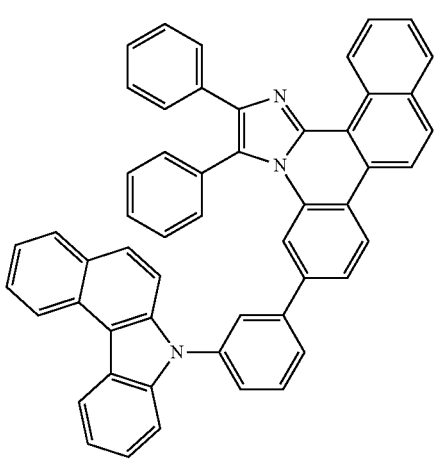
[Formula 3-4-1-10]
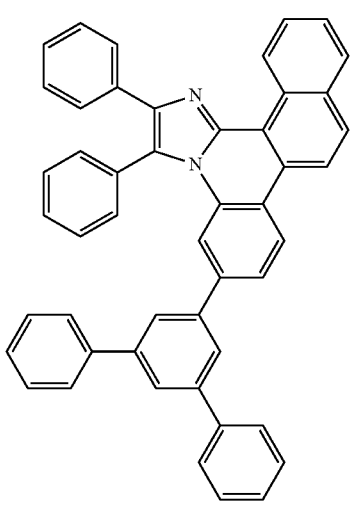
[Formula 3-4-1-11]
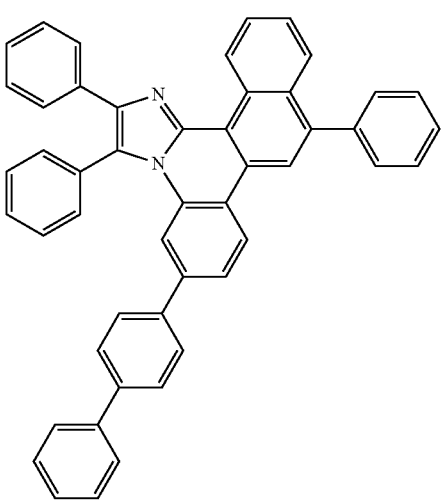
-continued
[Formula 3-4-1-12]
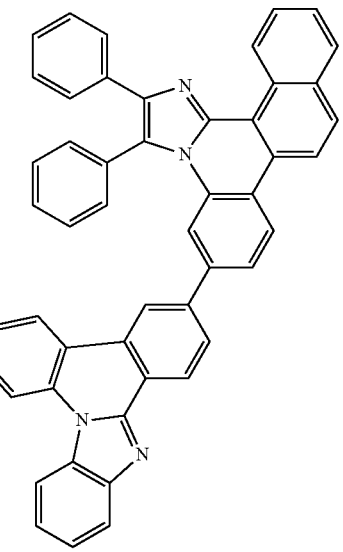
[Formula 3-5-1-1]
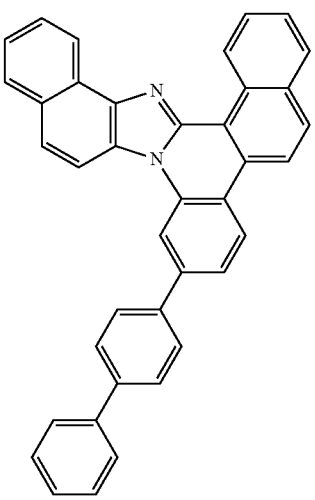
[Formula 3-5-1-2]
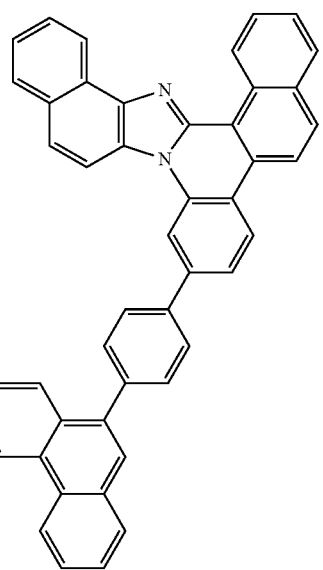

325
-continued
[Formula 3-5-1-3]
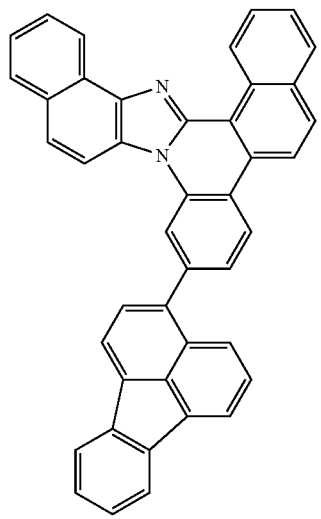
[Formula 3-5-1-4]
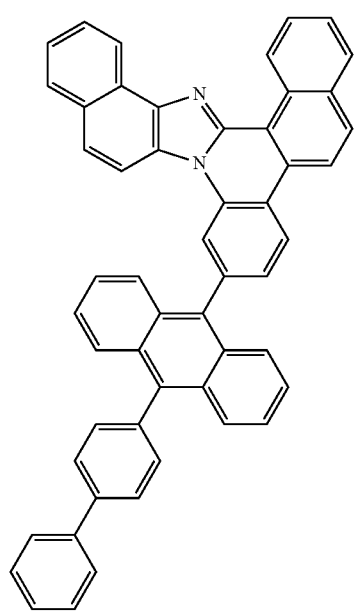
326
-continued
[Formula 3-5-1-5]
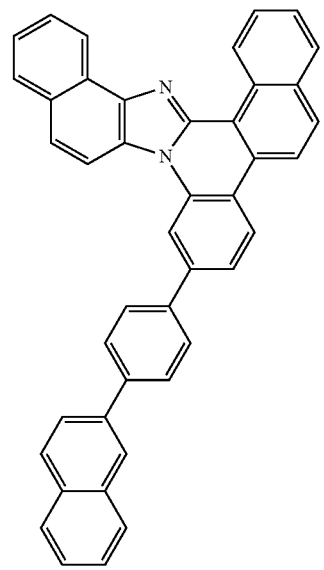
[Formula 3-5-1-6]
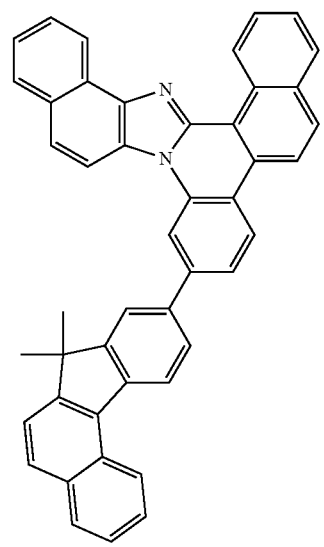

-continued
[Formula 3-5-1-7]
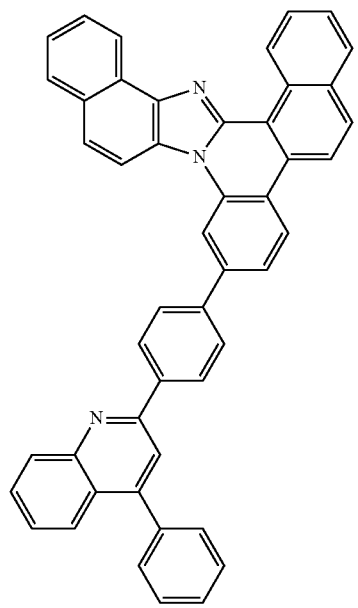
[Formula 3-5-1-8]
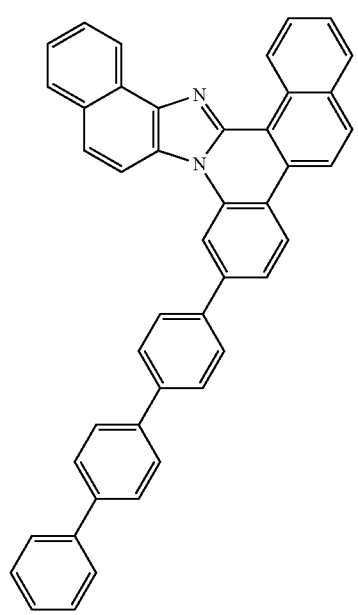
-continued
[Formula 3-5-1-9]
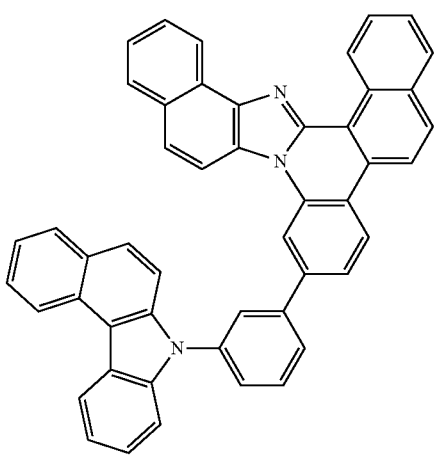
[Formula 3-5-1-10]
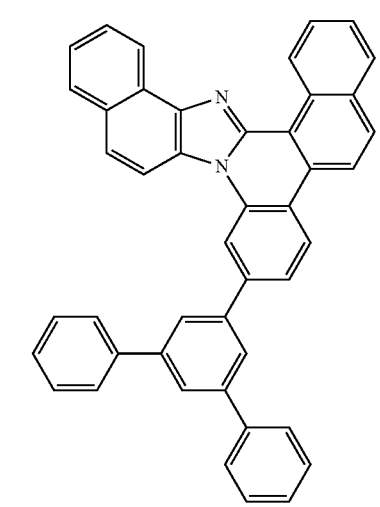
[Formula 3-5-1-11]
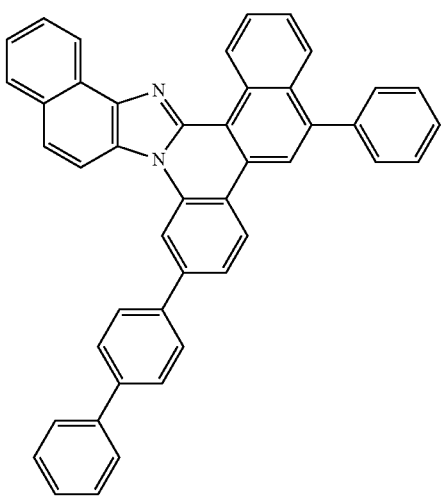

329
-continued
[Formula 3-5-1-12]
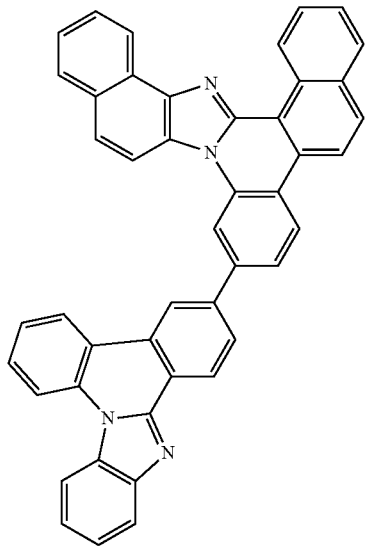
[Formula 3-6-1-1]
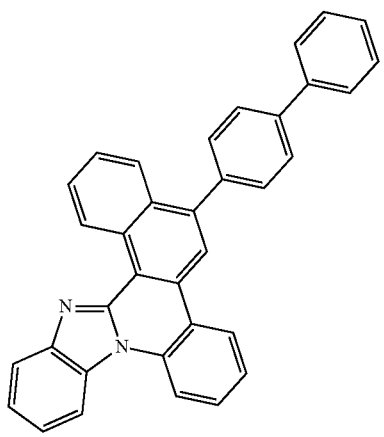
[Formula 3-6-1-2]
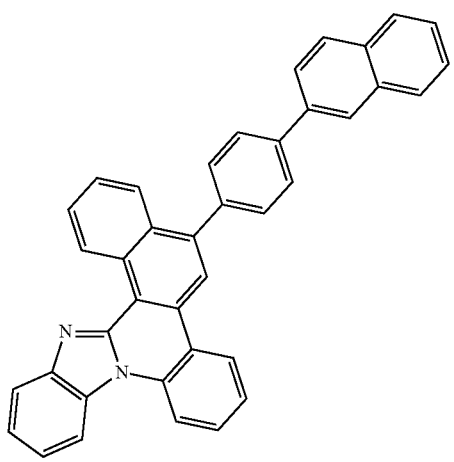
330
-continued
[Formula 3-6-1-3]
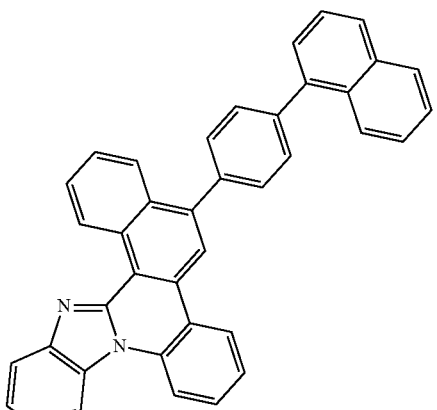
[Formula 3-6-1-4]
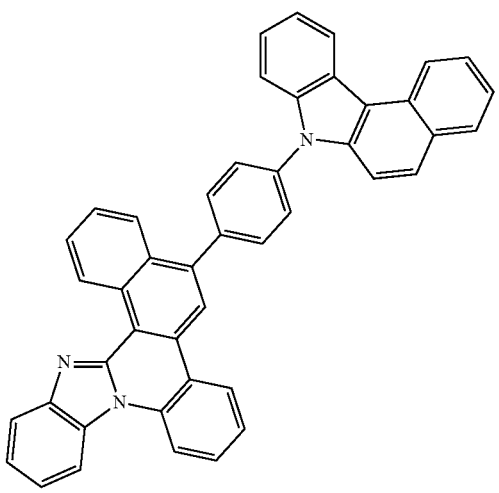
[Formula 3-6-1-5]
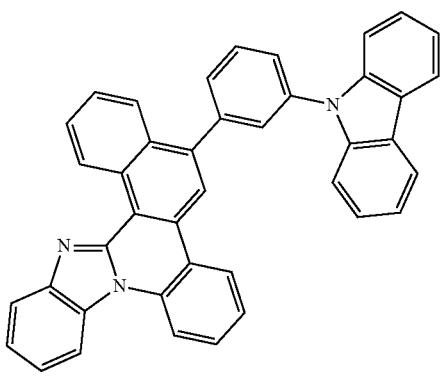

[Formula 3-6-1-6]
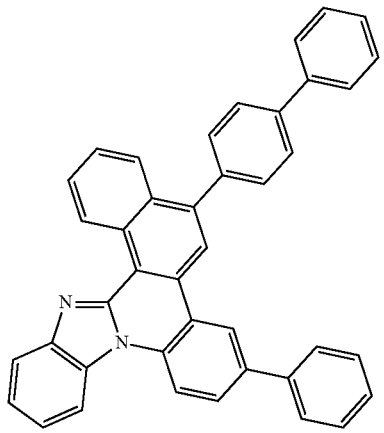
[Formula 3-6-1-7]
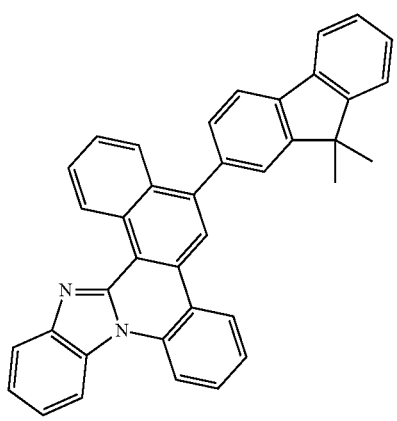
[Formula 3-6-1-8]
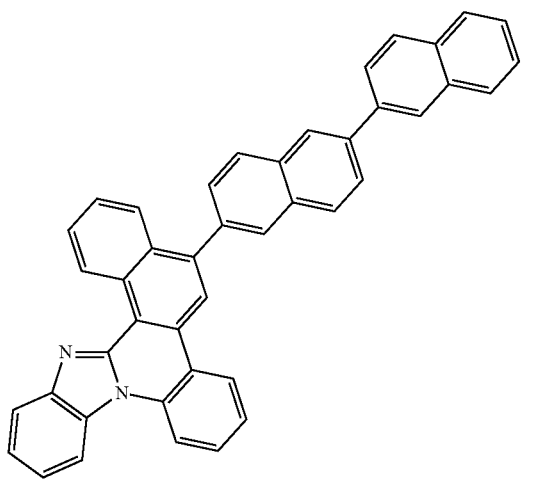
[Formula 3-6-1-9]
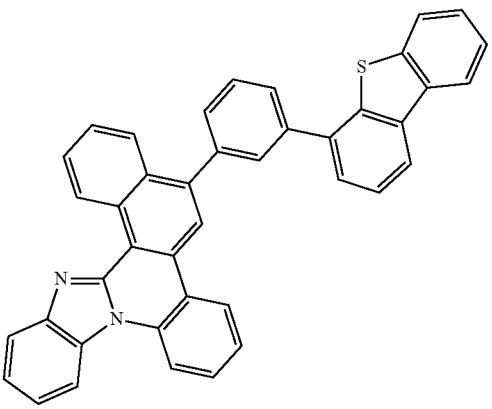
[Formula 3-6-1-10]
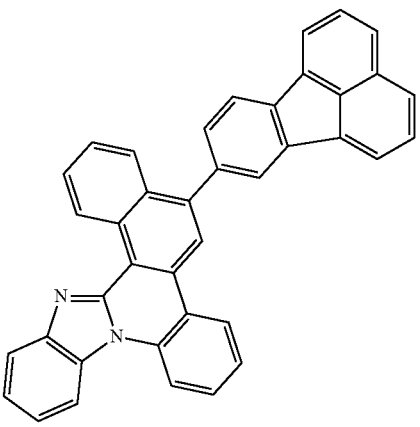
[Formula 3-6-1-11]
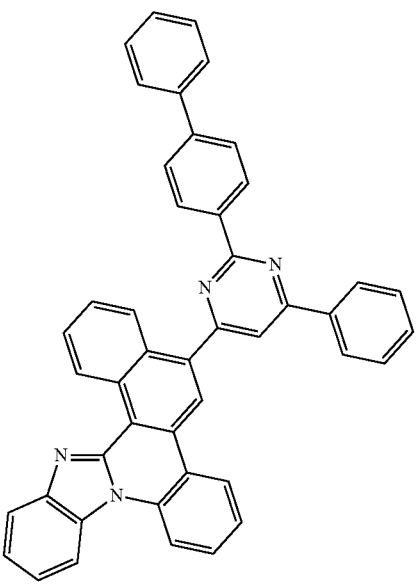

[Formula 3-6-1-12]
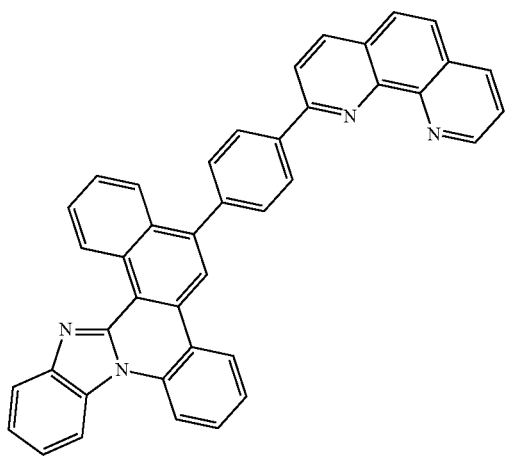
[Formula 3-6-2-1]
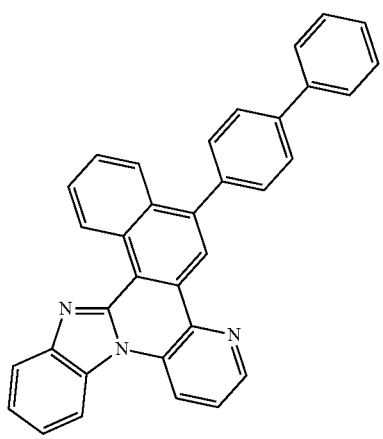
[Formula 3-6-2-2]
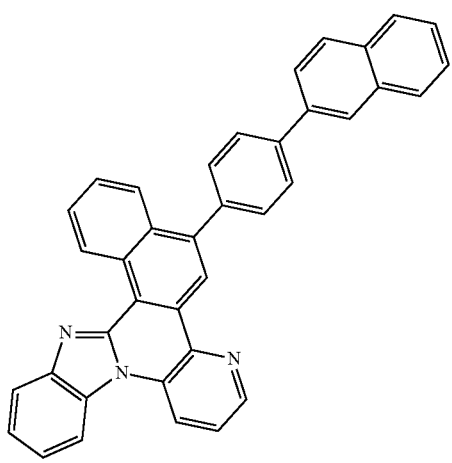
[Formula 3-6-2-3]
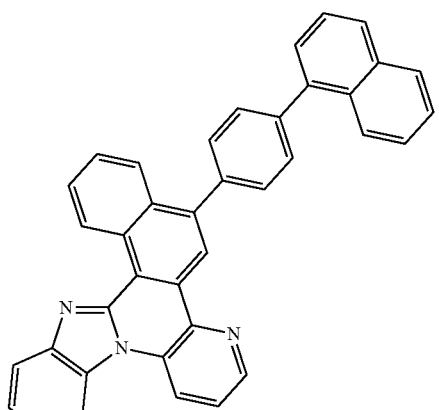
[Formula 3-6-2-4]
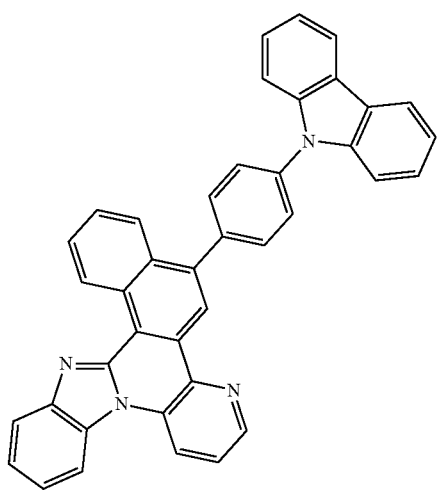
[Formula 3-6-2-5]
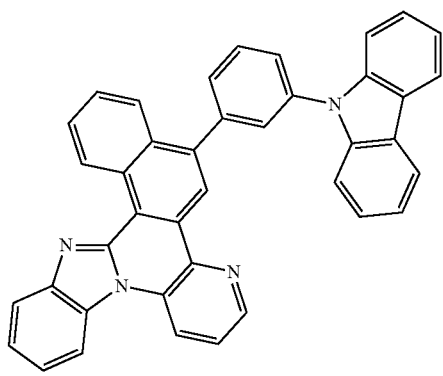

[Formula 3-6-2-6]
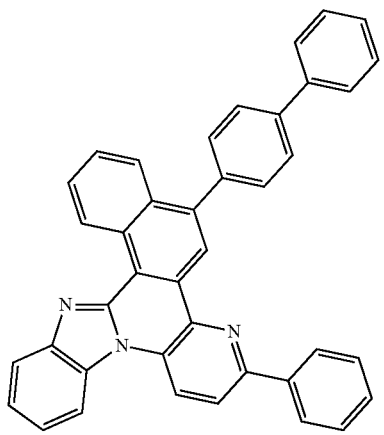
[Formula 3-6-2-9]
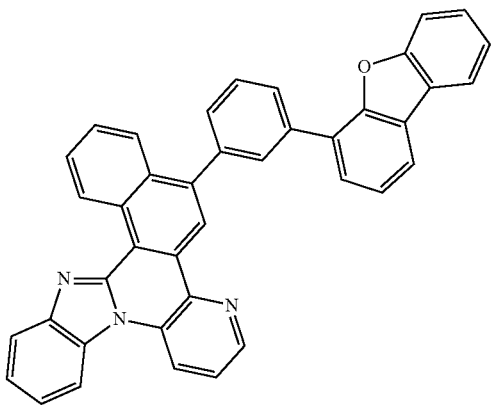
[Formula 3-6-2-7]
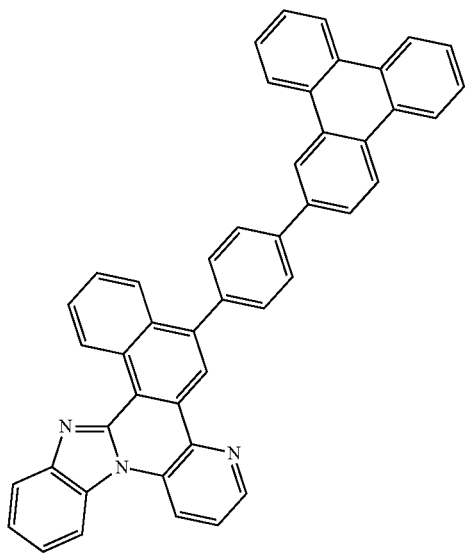
[Formula 3-6-2-10]
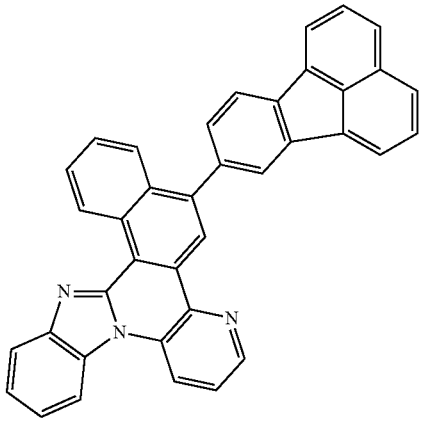
[Formula 3-6-2-8]
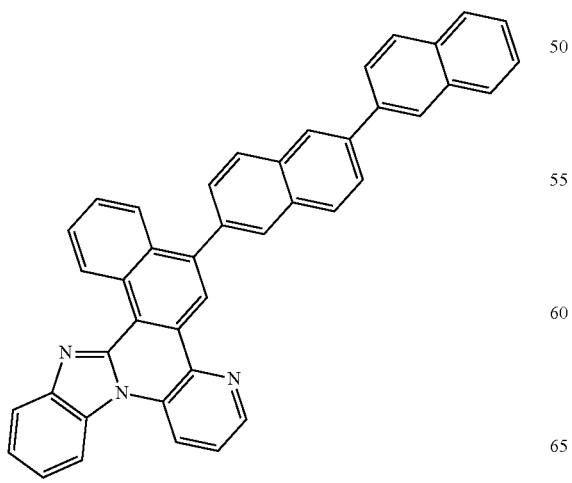
[Formula 3-6-2-11]
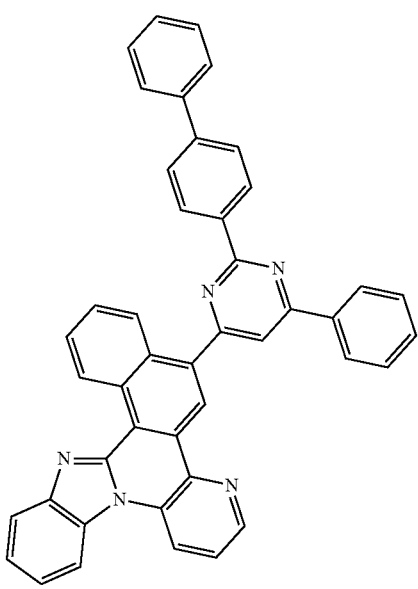

[Formula 3-6-2-12]
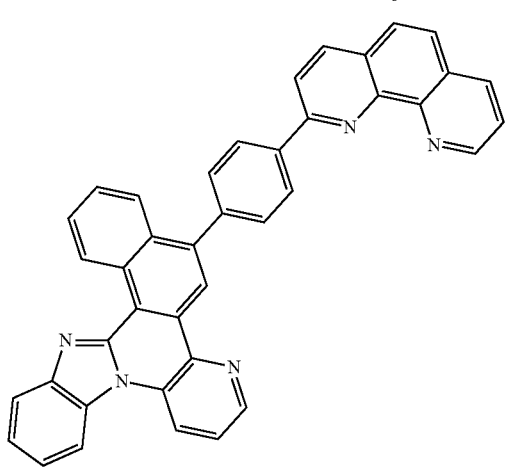
13. The compound of claim 1, wherein the compound is any one selected from the group consisting of the following Structural Formulas:
[Formula 3-7-1-1]
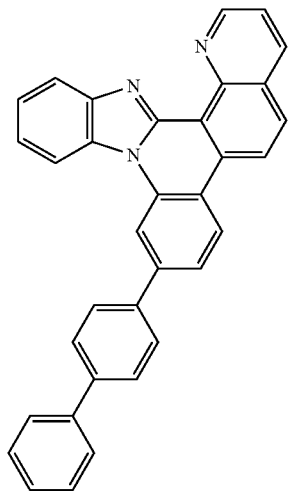
[Formula 3-7-1-2]
[Formula 3-7-1-3]
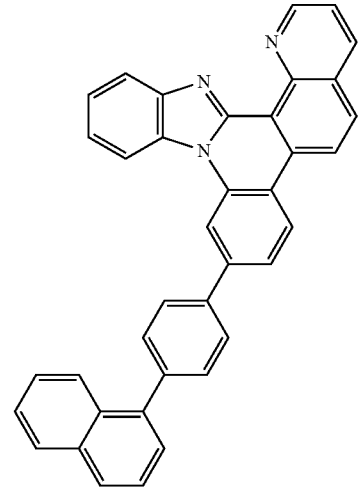
[Formula 3-7-1-4]
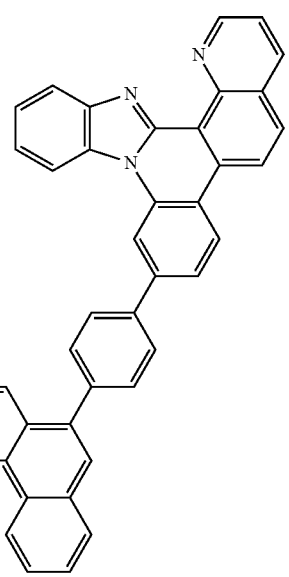
[Formula 3-7-1-5]
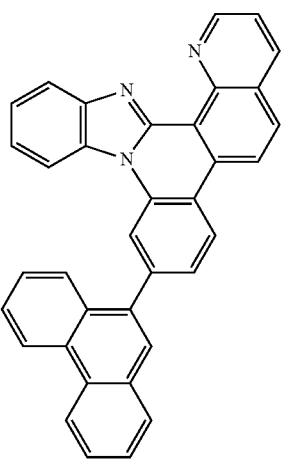

[Formula 3-7-1-6]
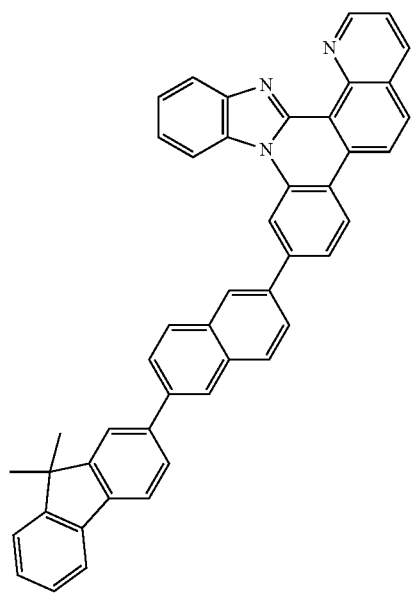
[Formula 3-7-1-9]
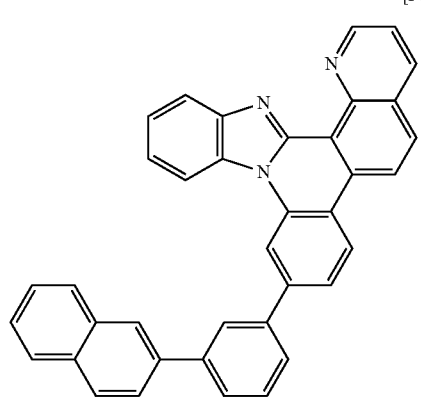
[Formula 3-7-1-10]
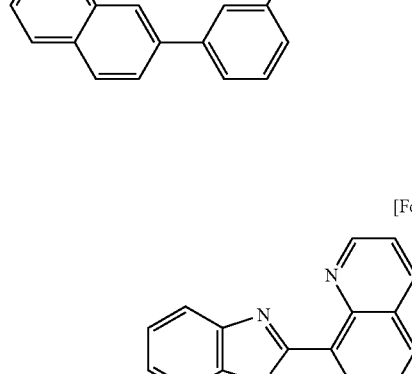
[Formula 3-7-1-11]
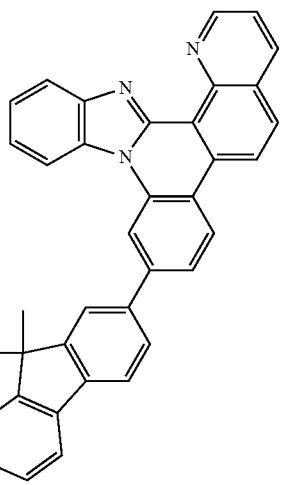
[Formula 3-7-1-12]
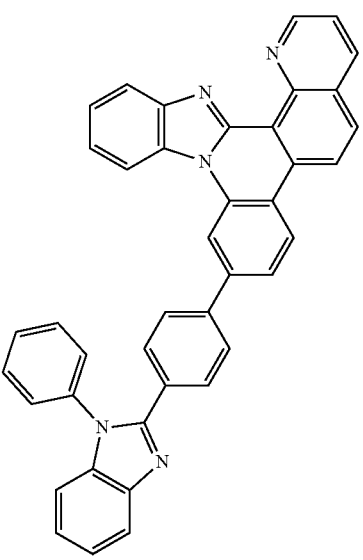
[Formula 3-7-1-13]
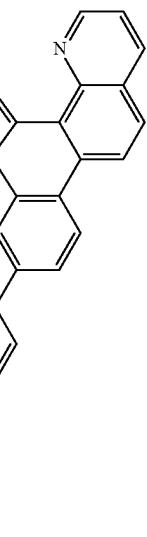

[Formula 3-7-1-14]
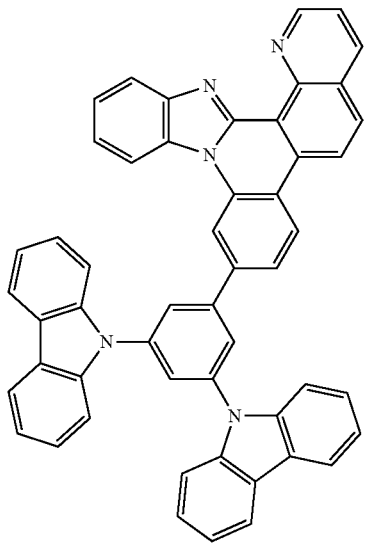
[Formula 3-7-1-15]
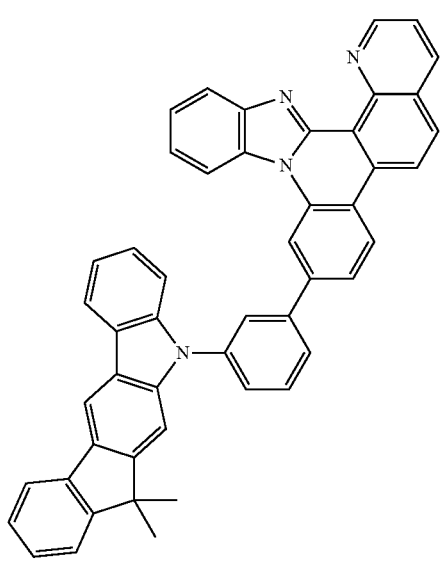
[Formula 3-7-1-16]
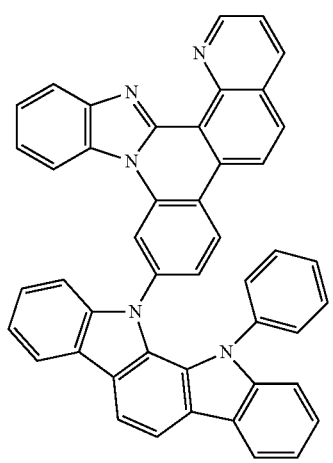
[Formula 3-7-1-17]
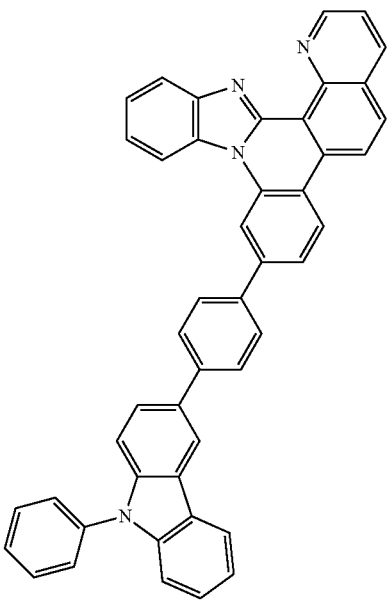
[Formula 3-7-1-18]
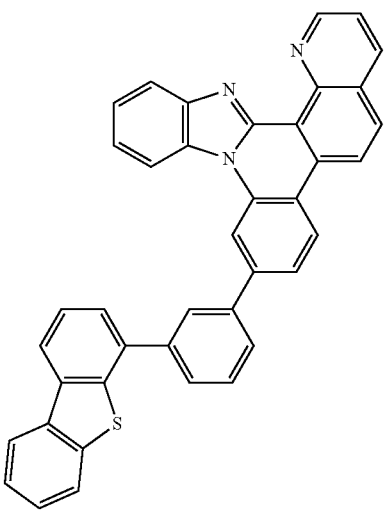

[Formula 3-7-1-19]
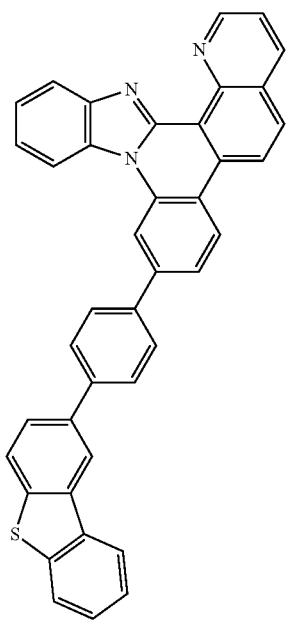
[Formula 3-7-1-20]
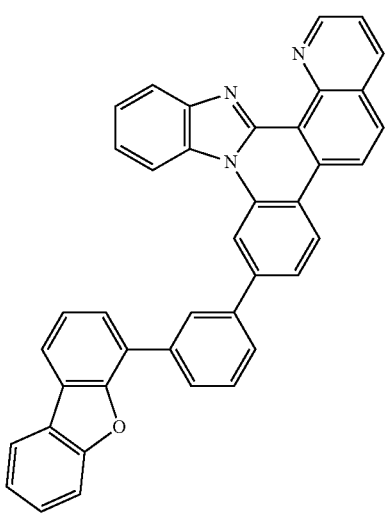
[Formula 3-7-1-21]
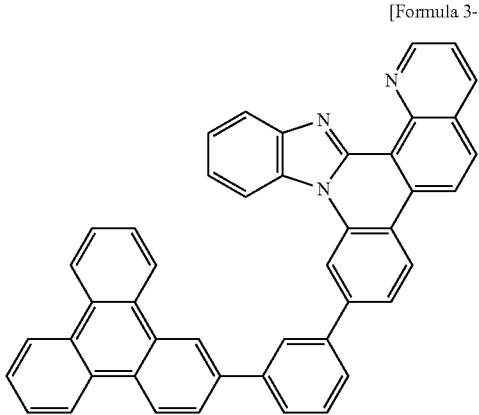
[Formula 3-7-1-22]
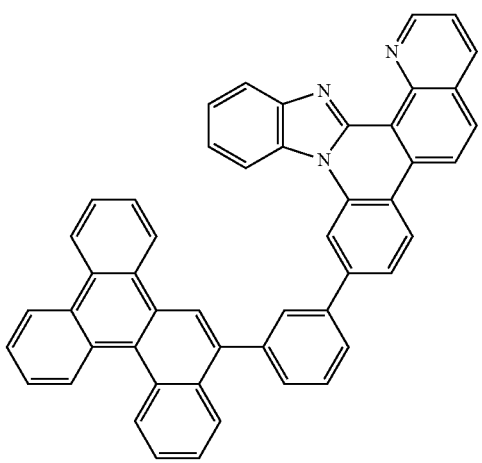
[Formula 3-7-1-23]
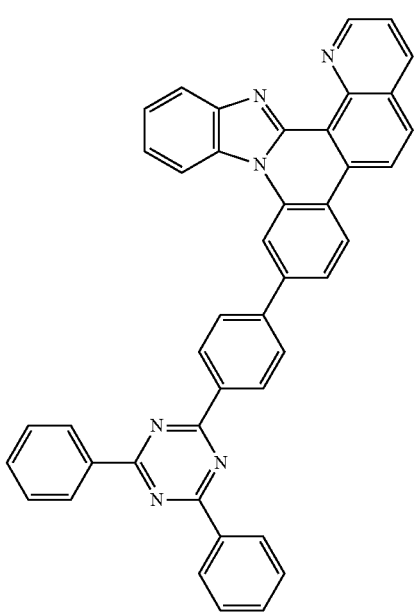
[Formula 3-7-1-24]
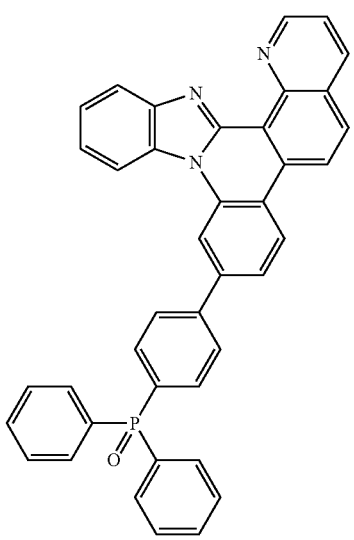

[Formula 3-7-1-25]
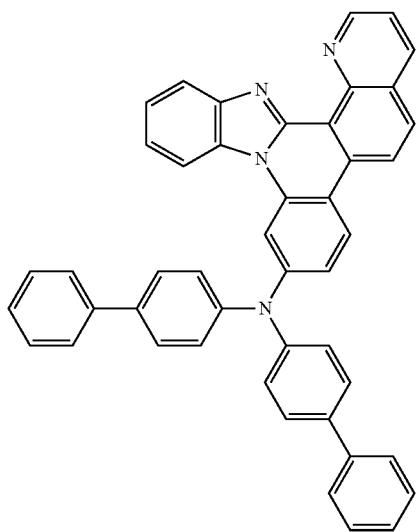
[Formula 3-7-1-26]
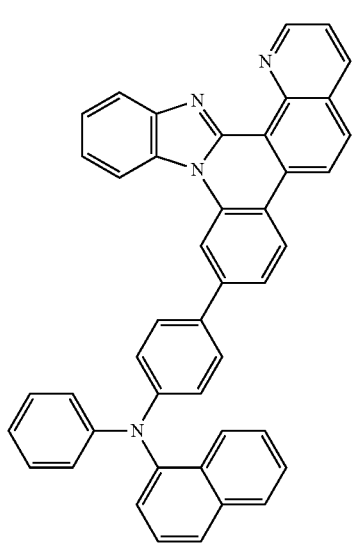
[Formula 3-7-1-27]
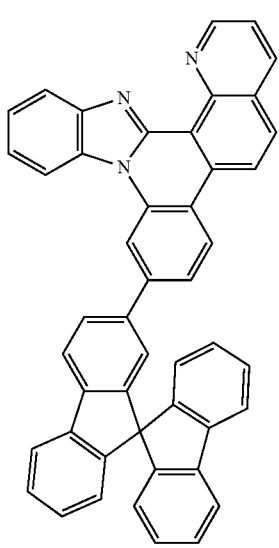
[Formula 3-7-1-28]
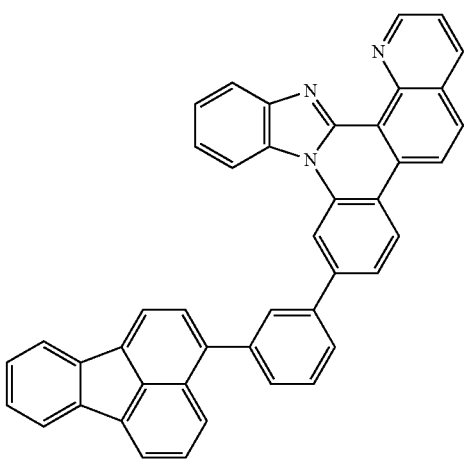
[Formula 3-7-2-1]
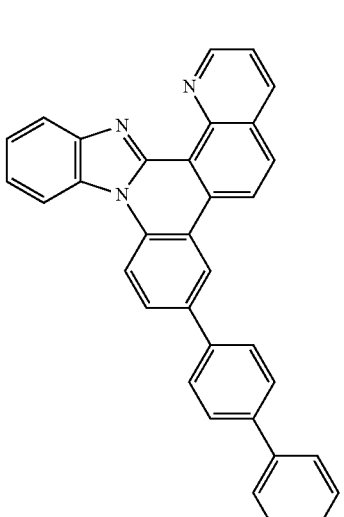
[Formula 3-7-2-2]
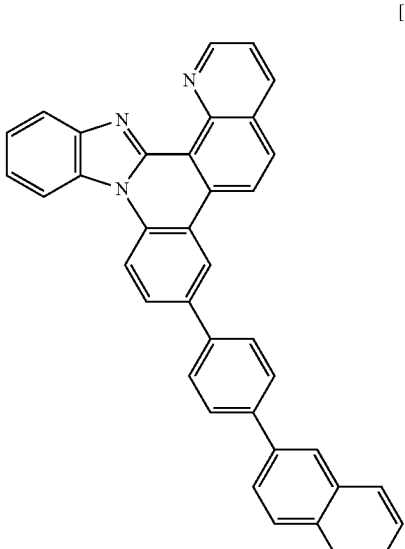

[Formula 3-7-2-3]
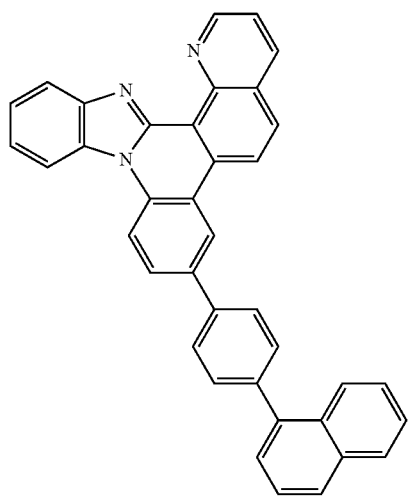
[Formula 3-7-2-4]
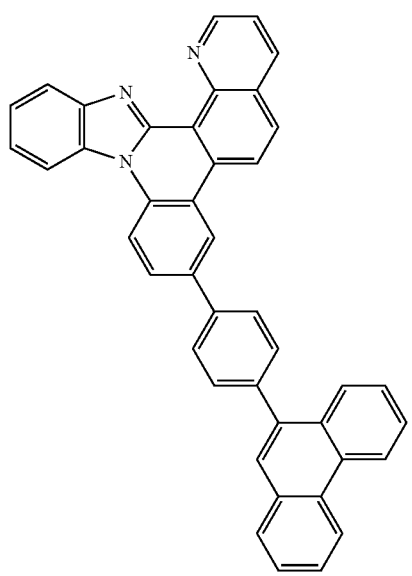
[Formula 3-7-2-5]
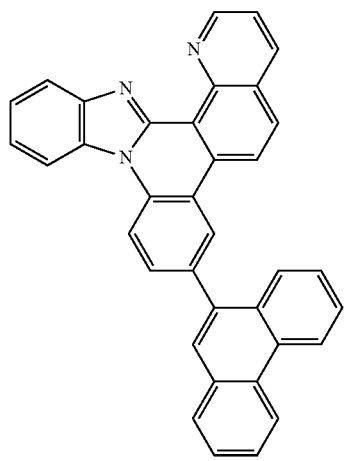
[Formula 3-7-2-6]
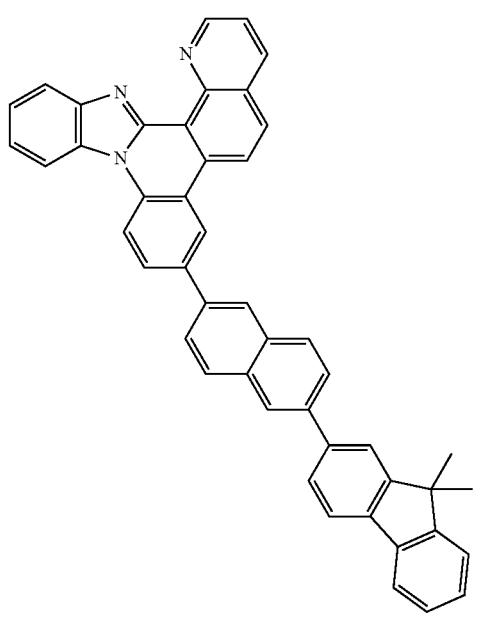
[Formula 3-7-2-9]
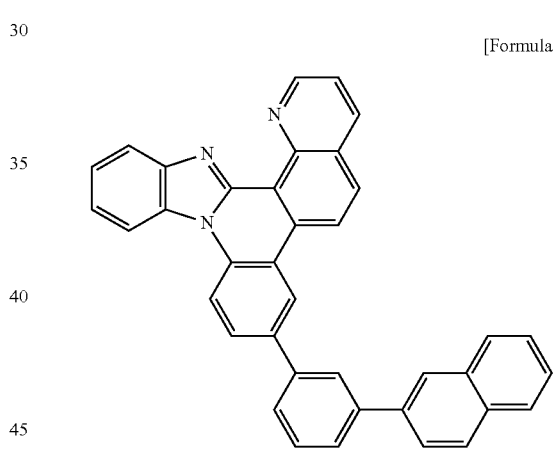
[Formula 3-7-2-10]
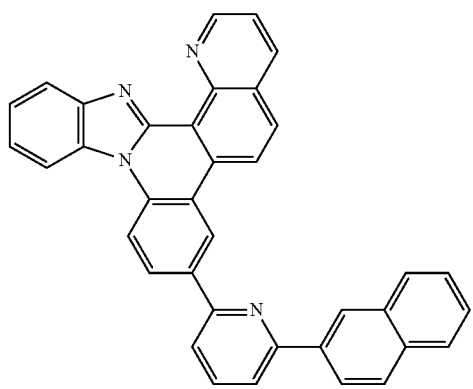

[Formula 3-7-2-11]
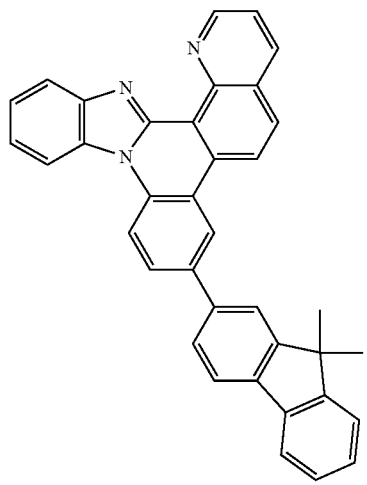
[Formula 3-7-2-12]
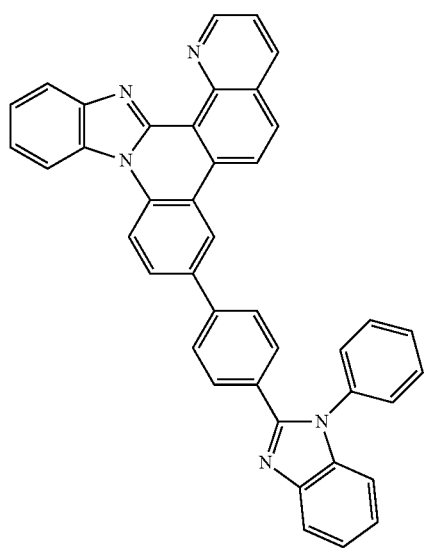
[Formula 3-7-2-13]
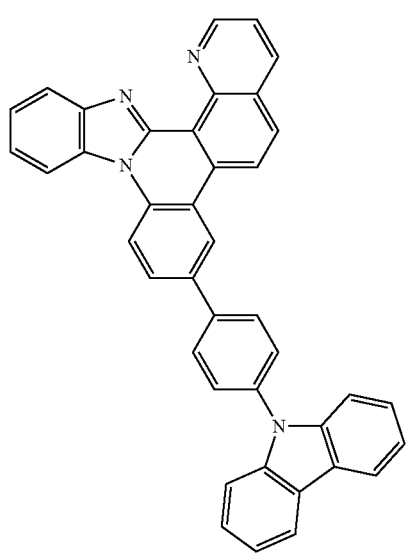
[Formula 3-7-2-14]
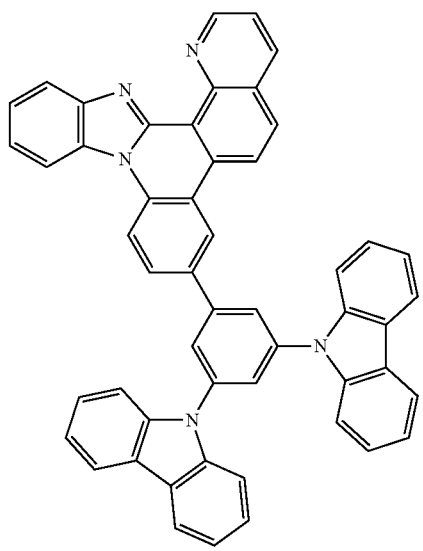
[Formula 3-7-2-15]
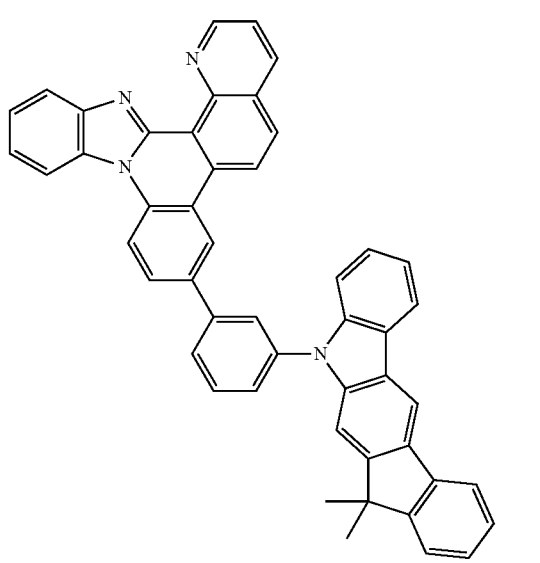
[Formula 3-7-2-16]
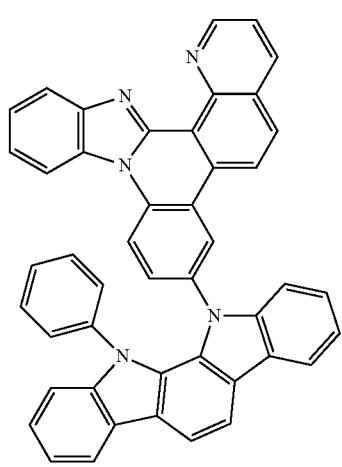

[Formula 3-7-2-17]
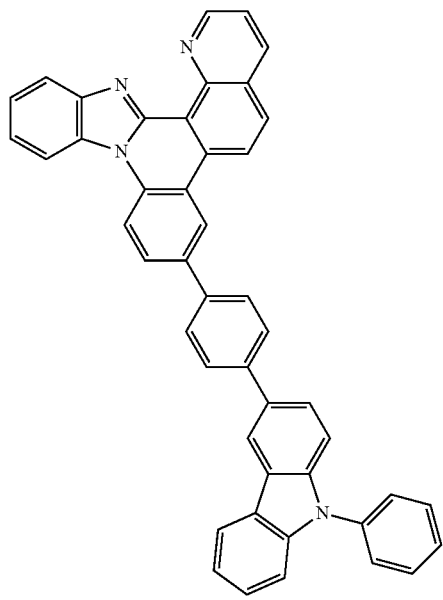
[Formula 3-7-2-18]
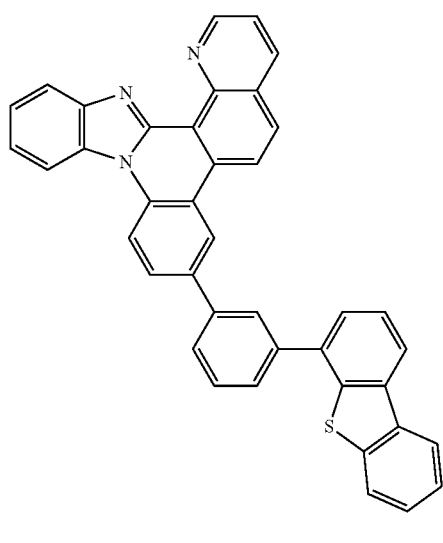
[Formula 3-7-2-19]
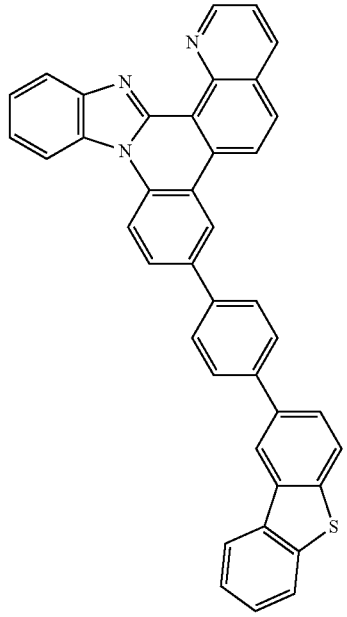
[Formula 3-7-2-20]
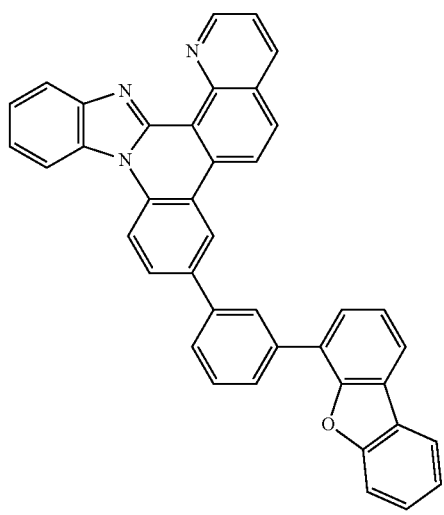
[Formula 3-7-2-21]
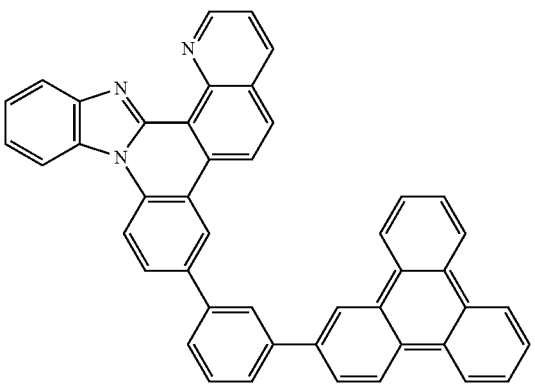

[Formula 3-7-2-22]
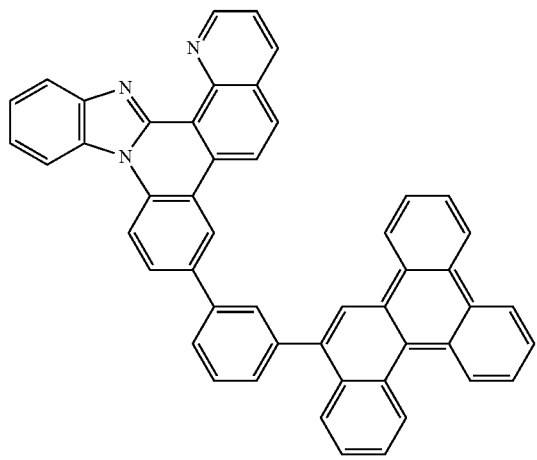
[Formula 3-7-2-23]
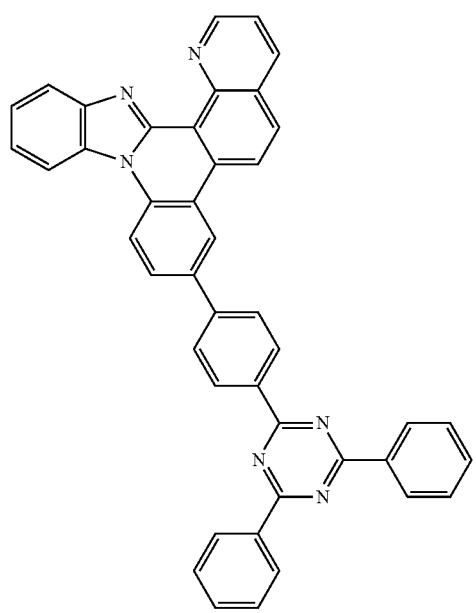
[Formula 3-7-2-24]
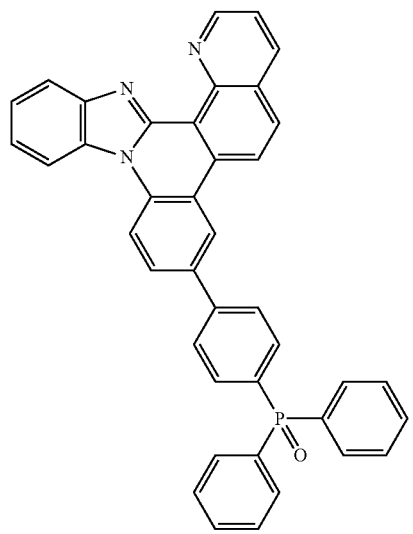
[Formula 3-7-2-25]
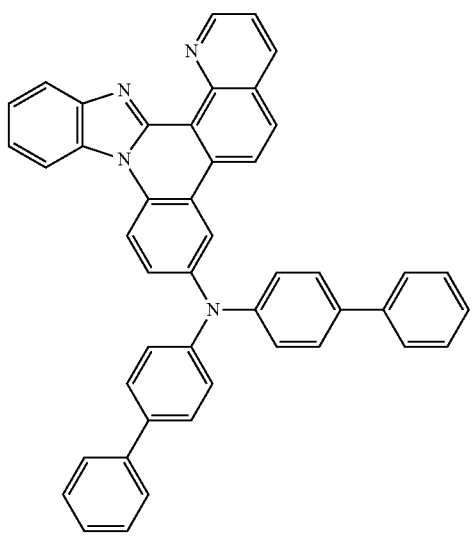
[Formula 3-7-2-26]
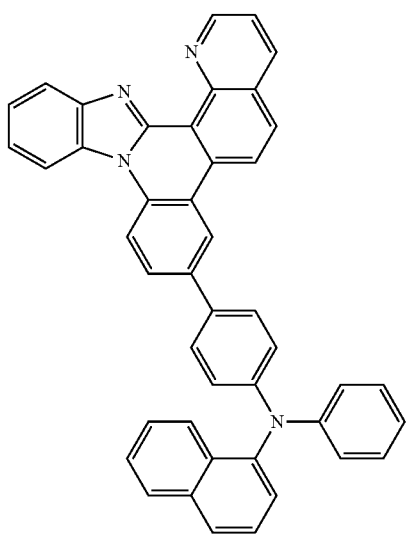
[Formula 3-7-2-27]
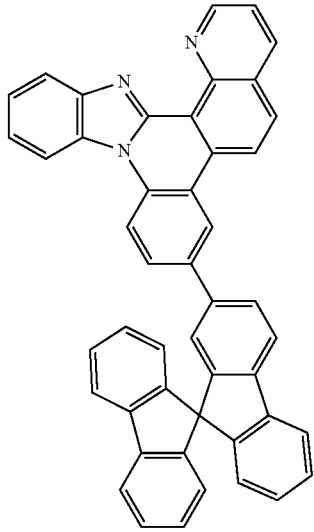

[Formula 3-7-2-28]
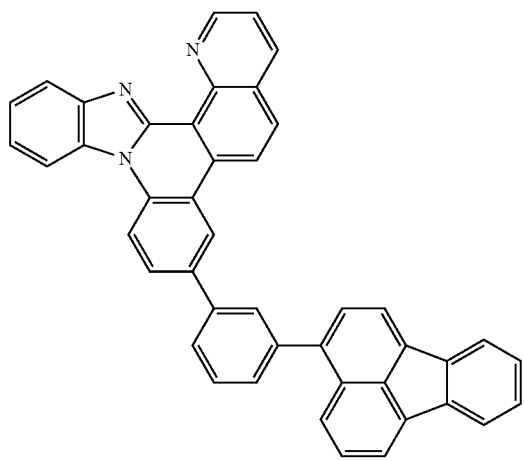
[Formula 3-8-1-3]
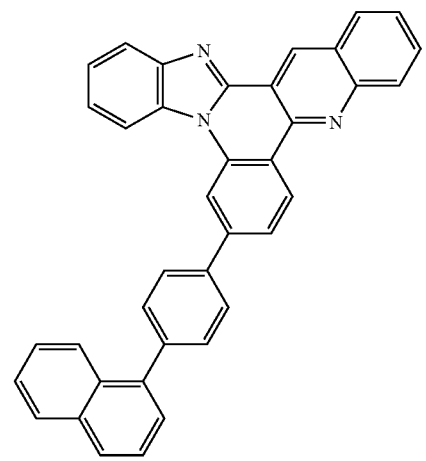
14. The compound of claim 1, wherein the compound is any one selected from the group consisting of the following Structural Formulas:
[Formula 3-8-1-1]
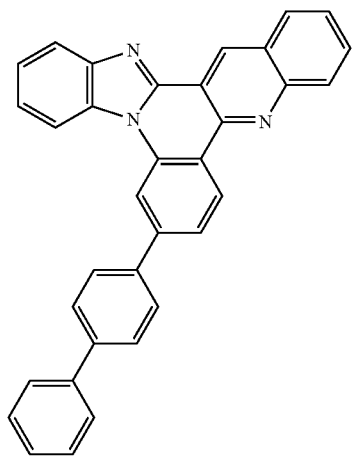
[Formula 3-8-1-4]
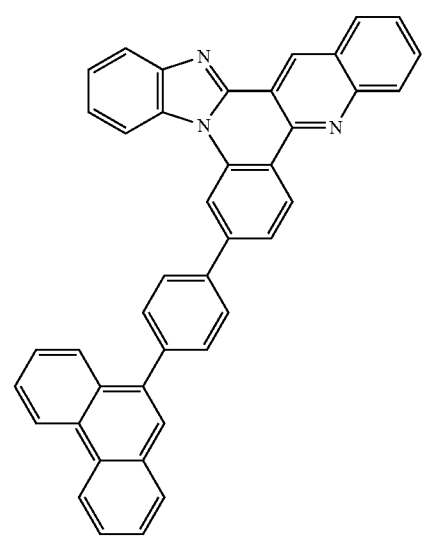
[Formula 3-8-1-2]
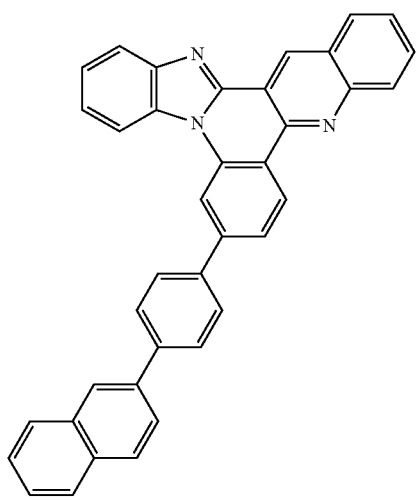
[Formula 3-8-1-5]
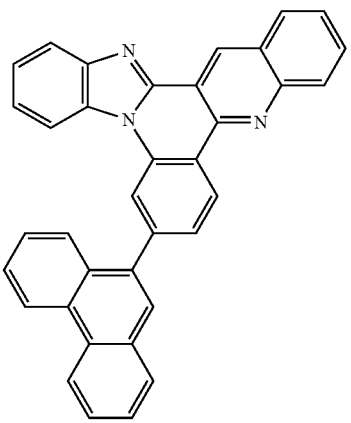

[Formula 3-8-1-6]
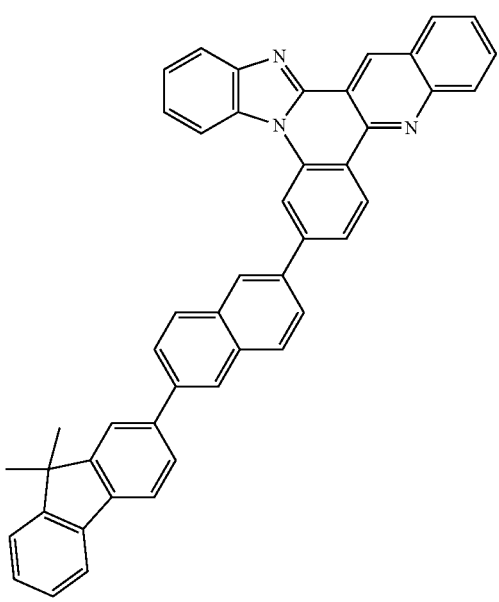
[Formula 3-8-1-9]
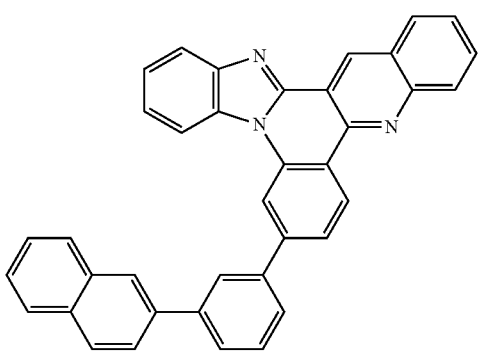
[Formula 3-8-1-10]
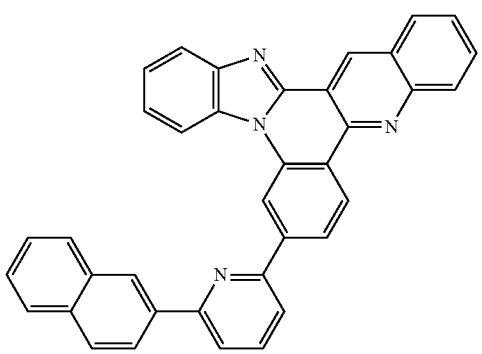
[Formula 3-8-1-11]
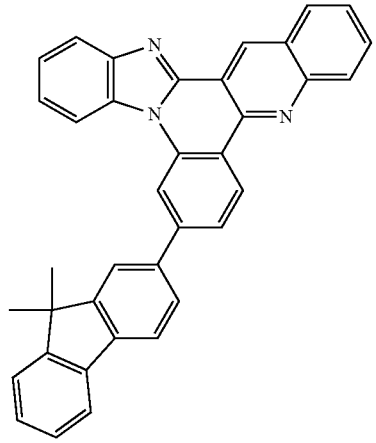
[Formula 3-8-1-12]
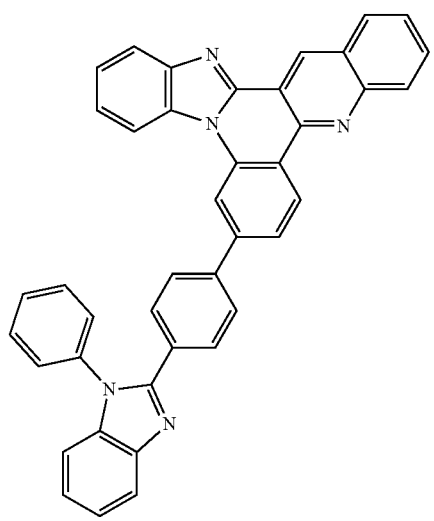
[Formula 3-8-1-13]
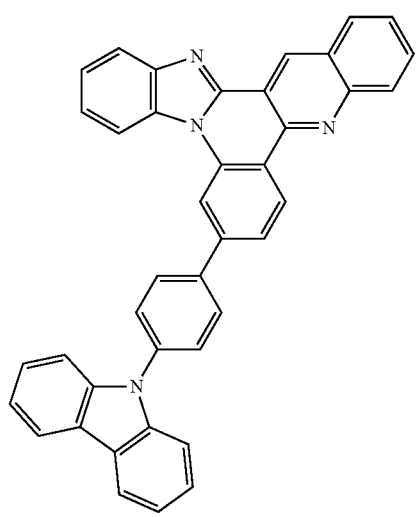

[Formula 3-8-1-14]
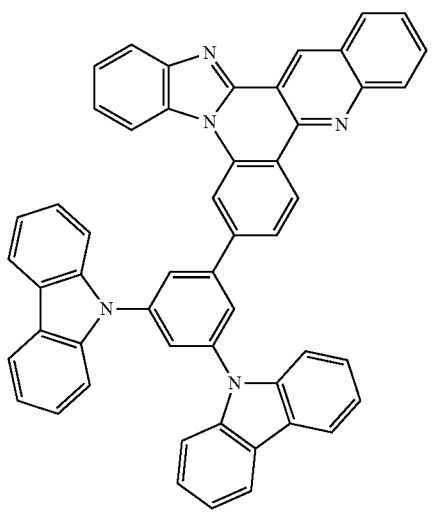
[Formula 3-8-1-17]
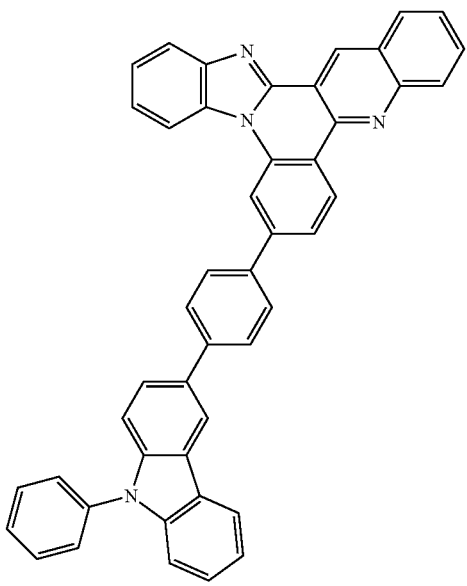
[Formula 3-8-1-15]
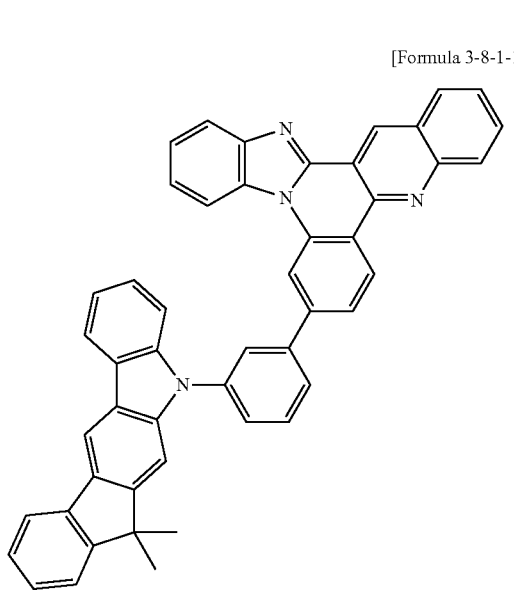
[Formula 3-8-1-18]
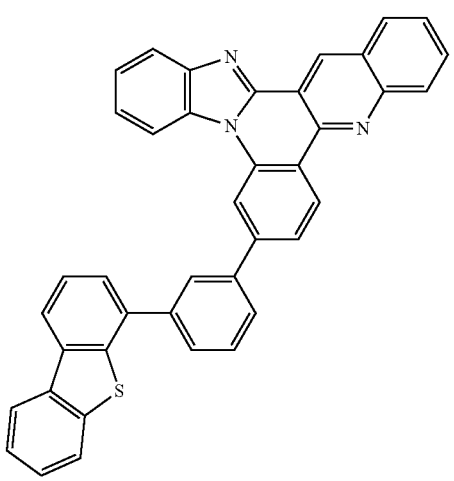
[Formula 3-8-1-16]
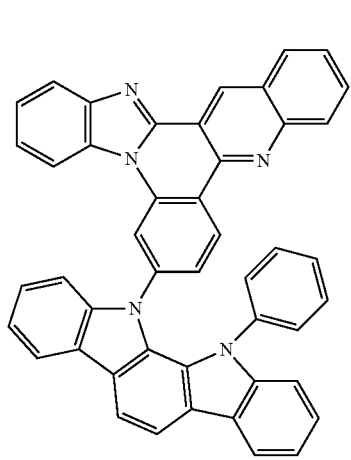
[Formula 3-8-1-19]
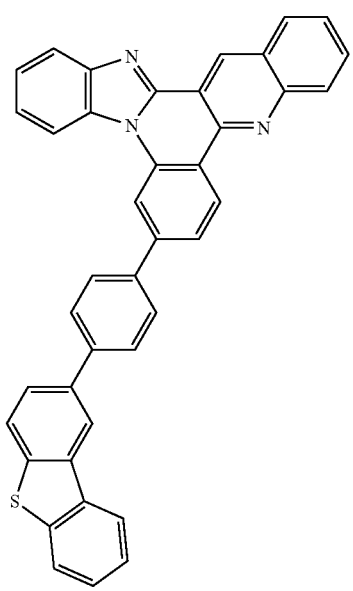

[Formula 3-8-1-20]
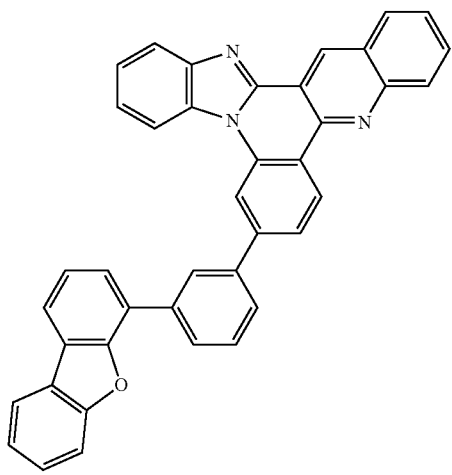
[Formula 3-8-1-21]
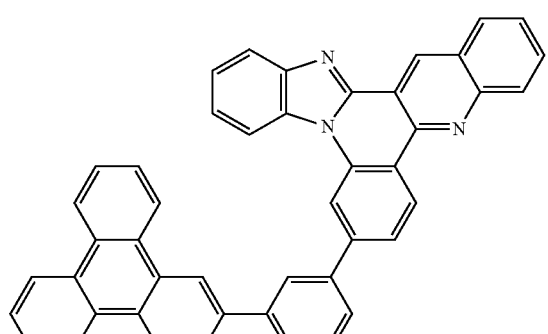
[Formula 3-8-1-22]
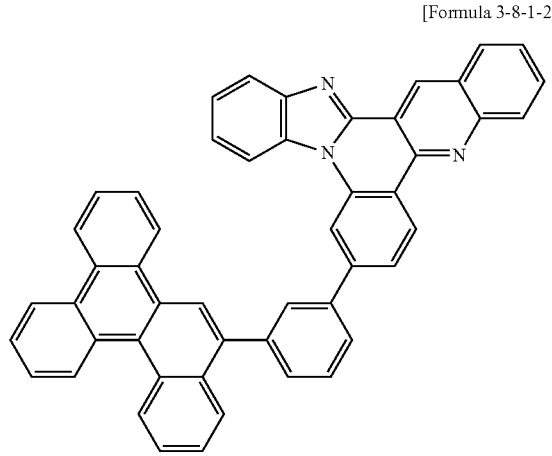
[Formula 3-8-1-23]
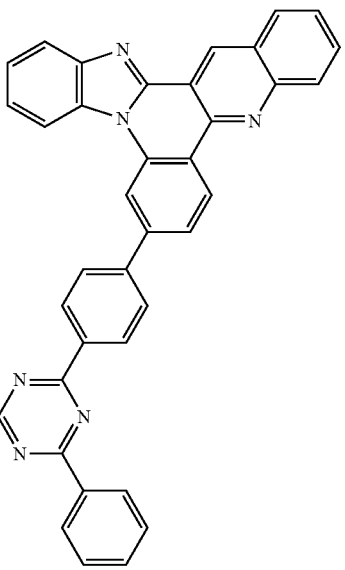
[Formula 3-8-1-24]
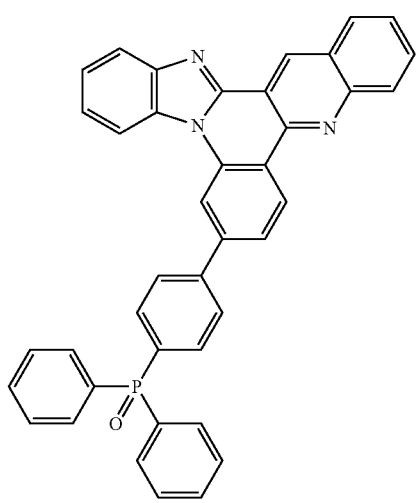
[Formula 3-8-1-25]
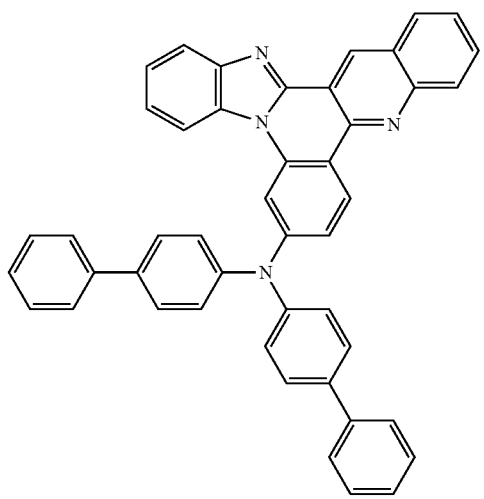

[Formula 3-8-1-26]
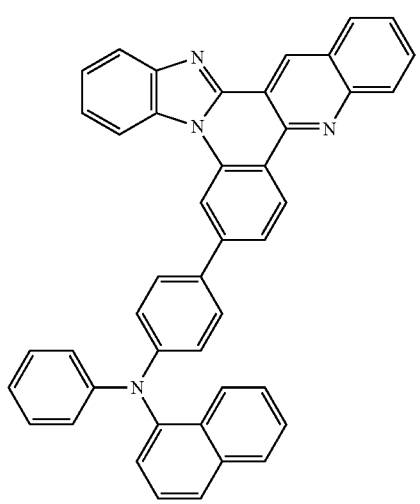
[Formula 3-8-1-27]
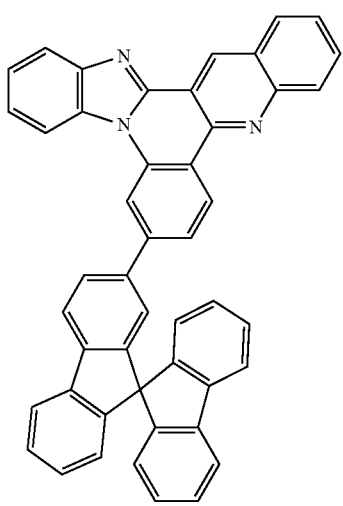
[Formula 3-8-1-28]
[Formula 3-8-2-1]
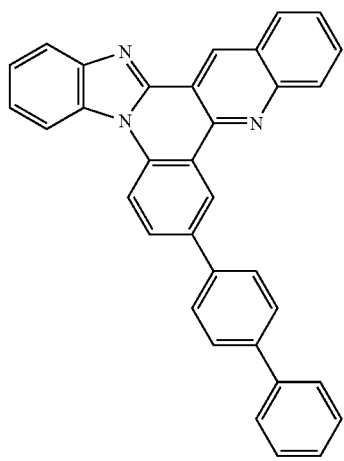
[Formula 3-8-2-2]
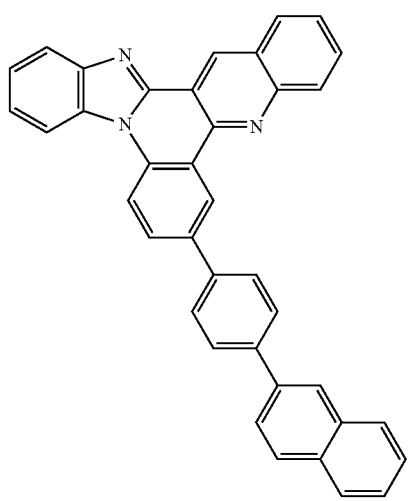
[Formula 3-8-2-3]
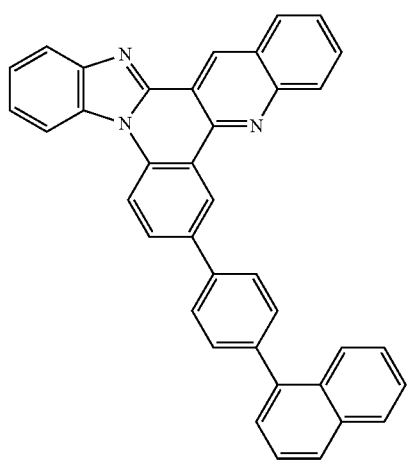

[Formula 3-8-2-4]
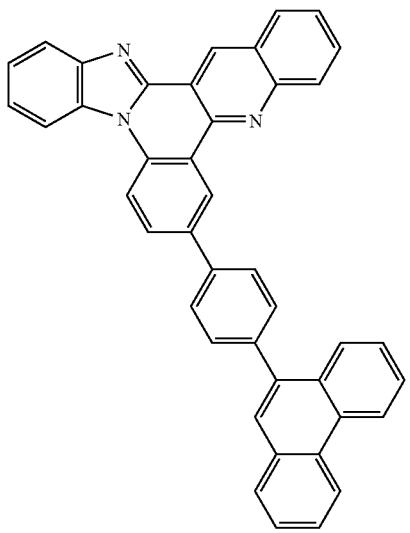
[Formula 3-8-2-5]
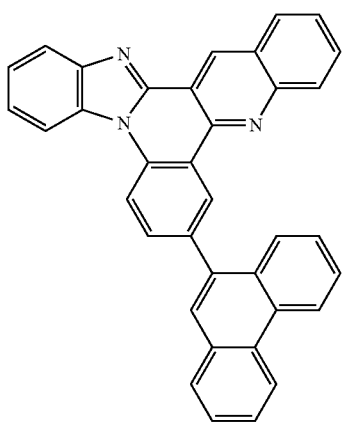
[Formula 3-8-2-6]
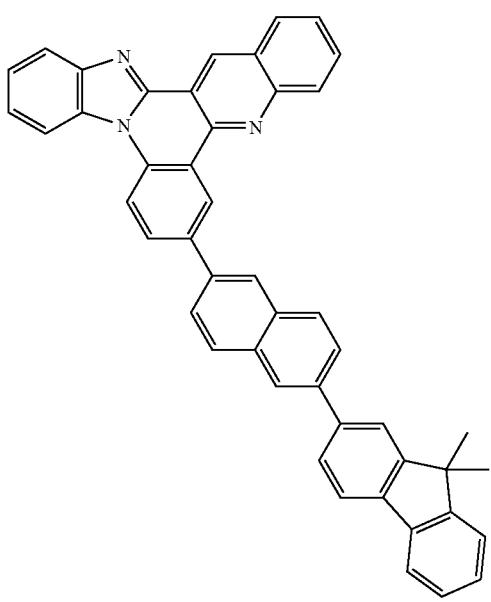
[Formula 3-8-2-9]
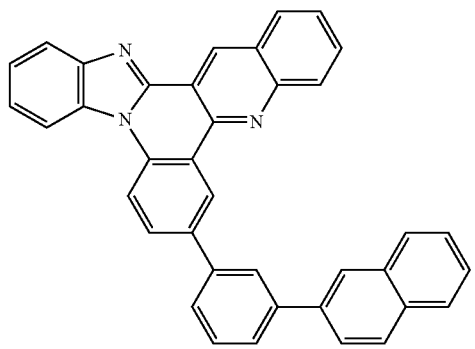
[Formula 3-8-2-10]
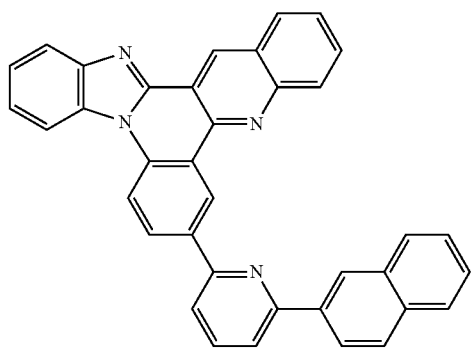
[Formula 3-8-2-11]
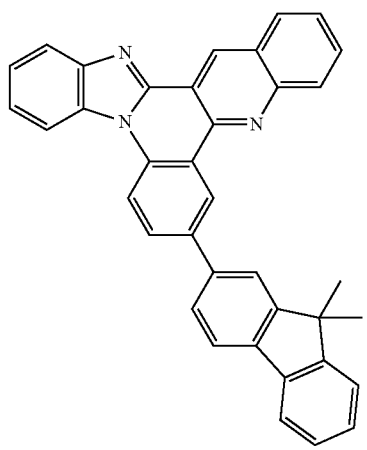

[Formula 3-8-2-12]
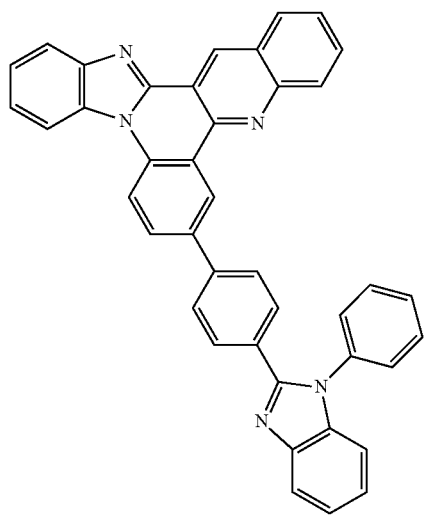
[Formula 3-8-2-13]
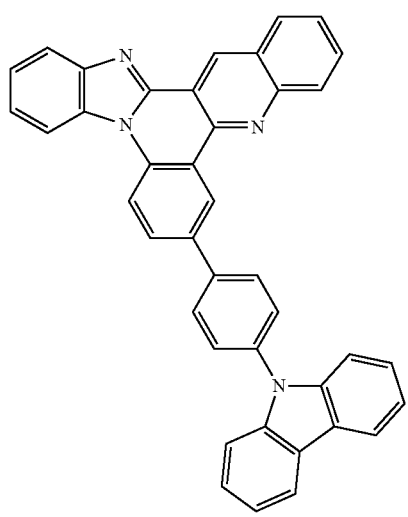
[Formula 3-8-2-14]
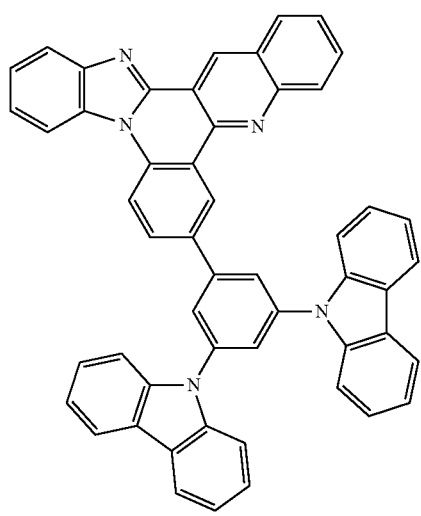
[Formula 3-8-2-15]
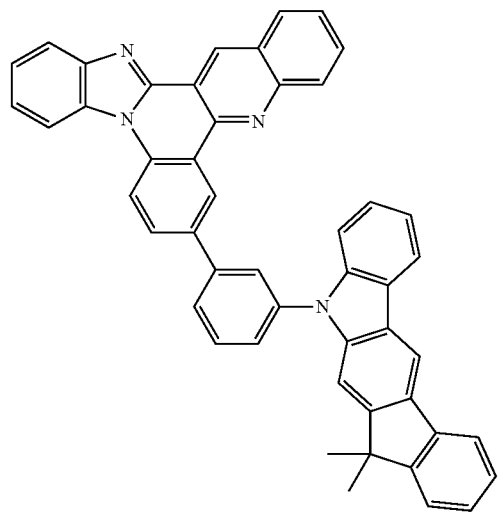
[Formula 3-8-2-16]
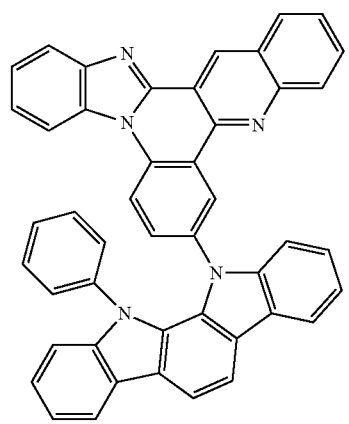
[Formula 3-8-2-17]
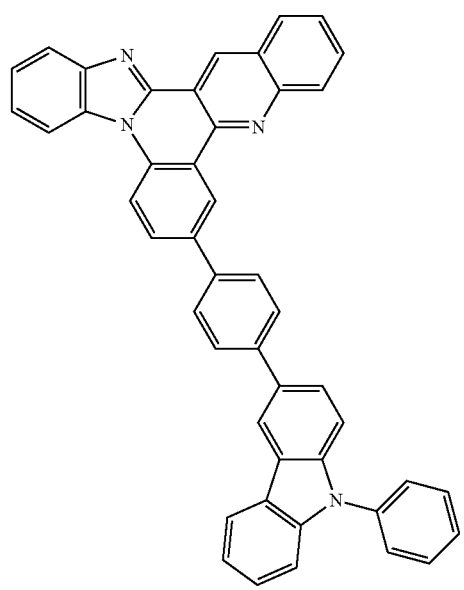

[Formula 3-8-2-18]
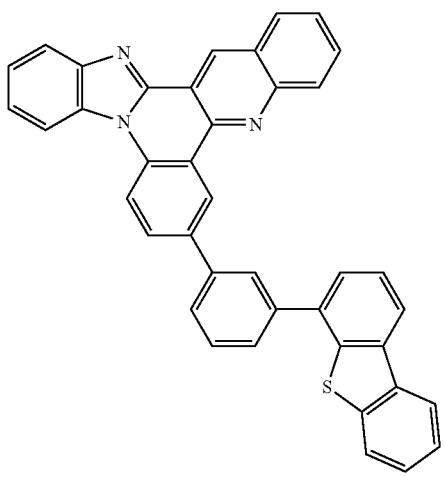
[Formula 3-8-2-19]
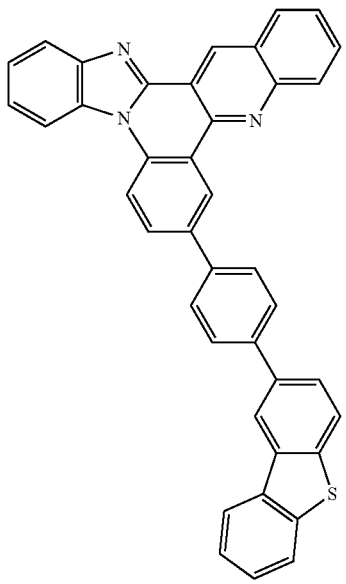
[Formula 3-8-2-20]
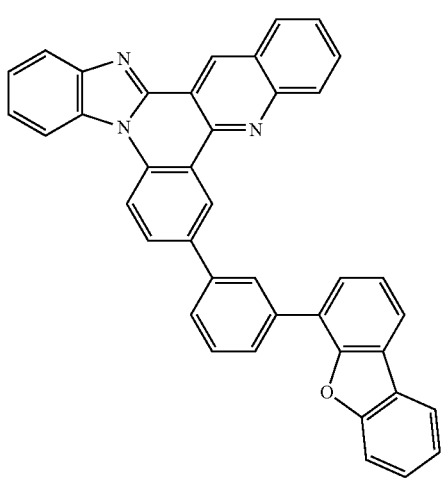
[Formula 3-8-2-21]
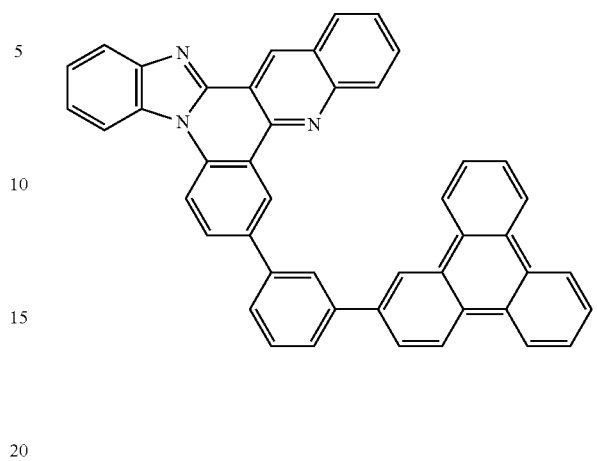
[Formula 3-8-2-22]
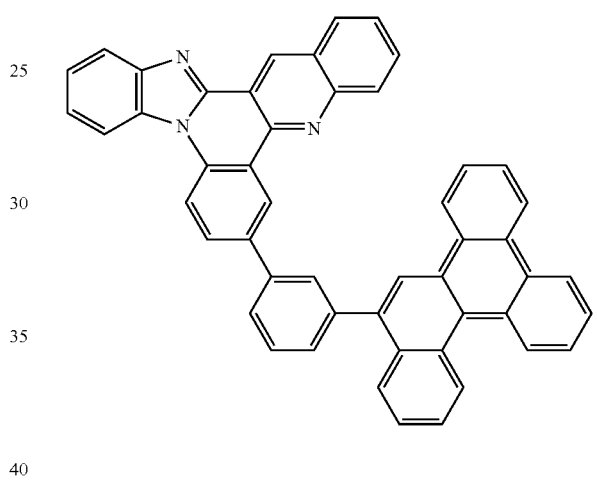
[Formula 3-8-2-23]
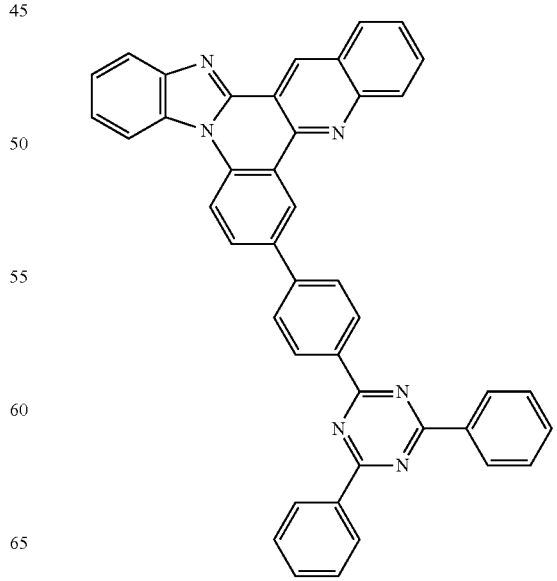

[Formula 3-8-2-24]
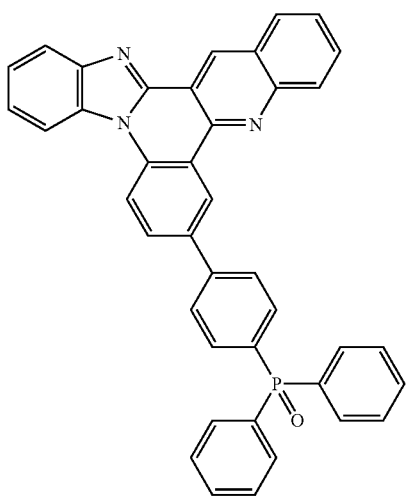
[Formula 3-8-2-27]
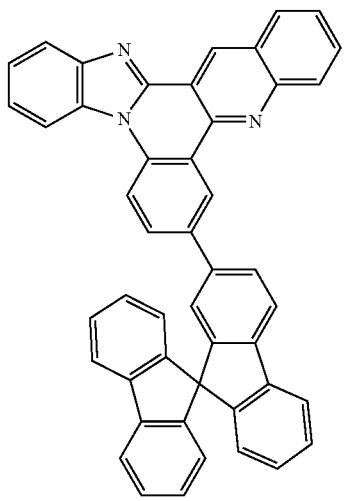
[Formula 3-8-2-25]
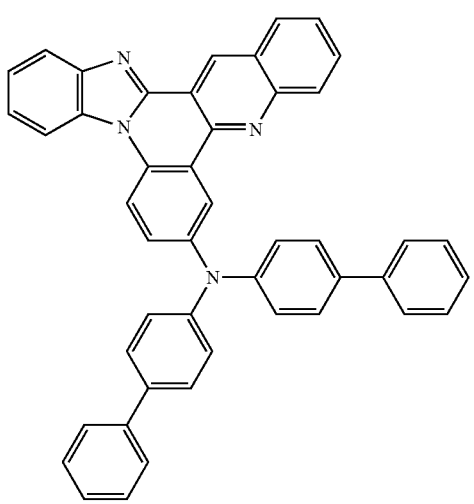
[Formula 3-8-2-28]
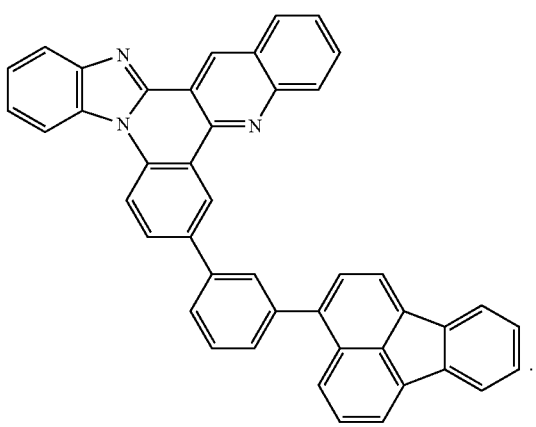
[Formula 3-8-2-26]
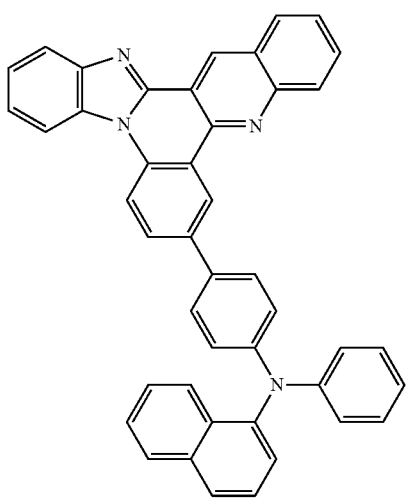
15. The compound of claim 1, wherein the compound is any one selected from the group consisting of the following Structural Formulas:
[Formula 3-9-1-1]
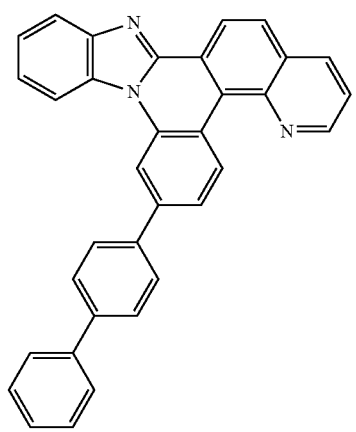

[Formula 3-9-1-2]
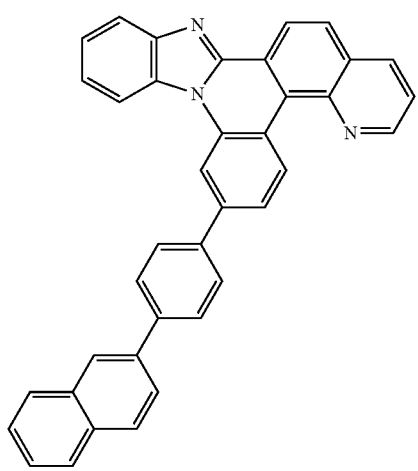
[Formula 3-9-1-3]
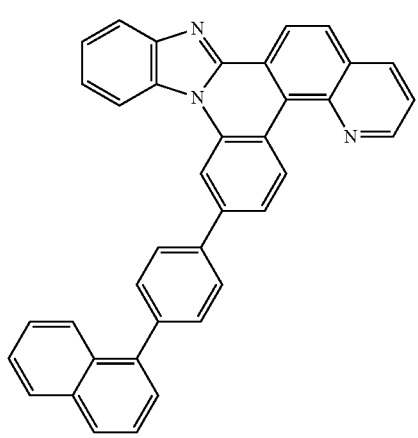
[Formula 3-9-1-4]
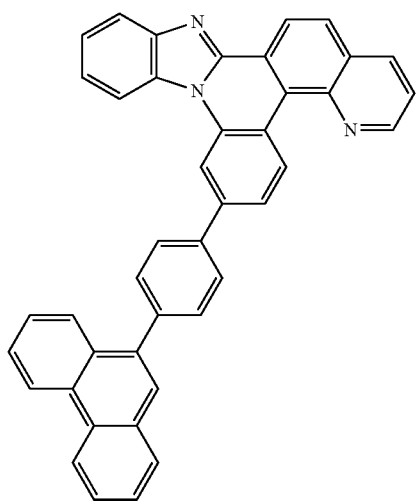
[Formula 3-9-1-5]
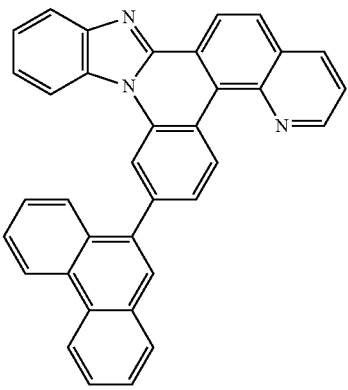
[Formula 3-9-1-6]
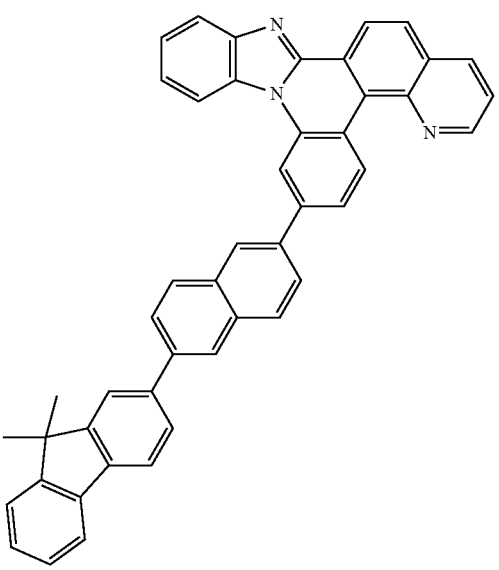
[Formula 3-9-1-9]
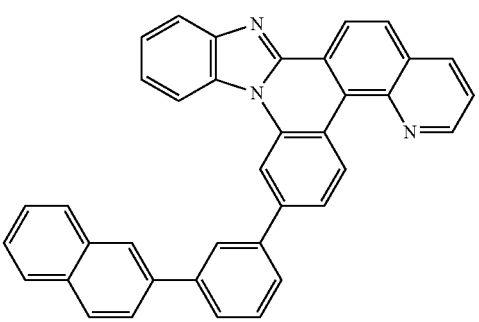
[Formula 3-9-1-10]
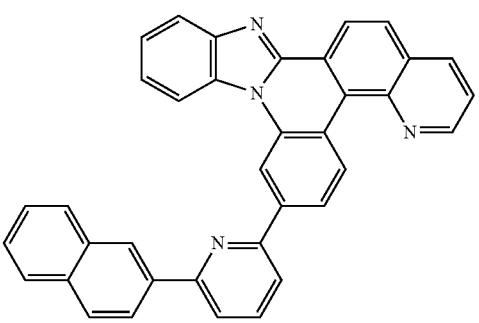

[Formula 3-9-1-11]
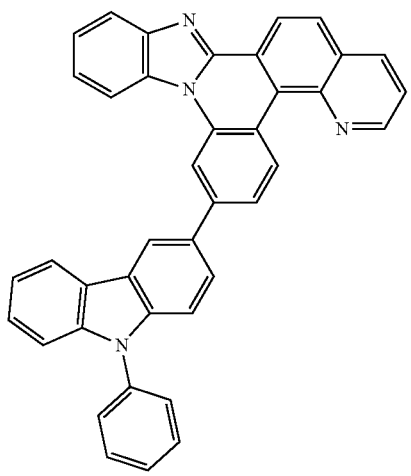
[Formula 3-9-1-12]
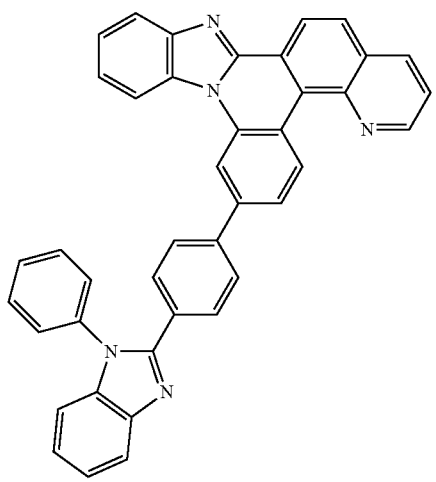
[Formula 3-9-1-13]
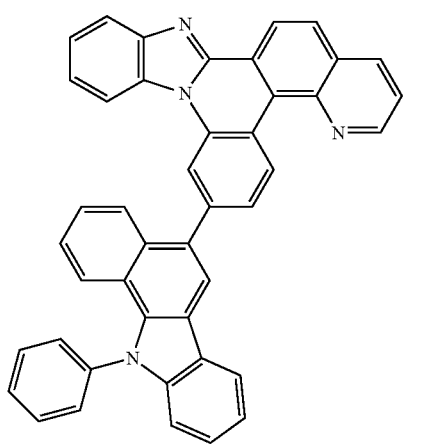
[Formula 3-9-1-14]
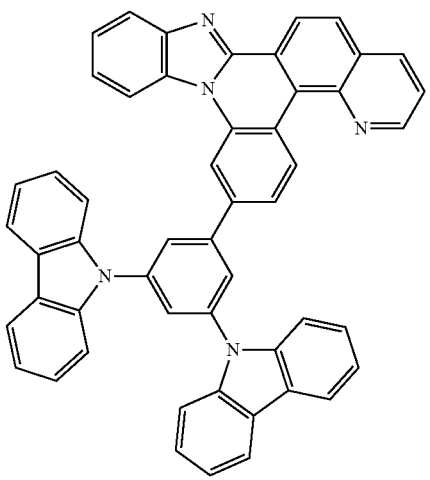
[Formula 3-9-1-15]
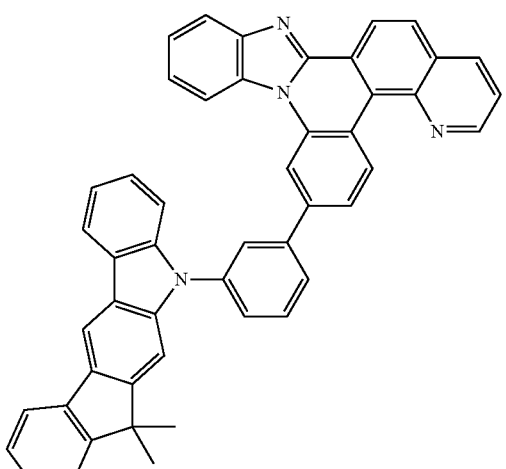
[Formula 3-9-1-16]
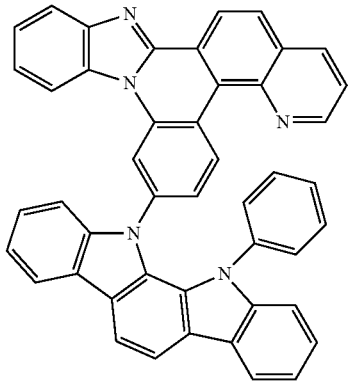

[Formula 3-9-1-17]
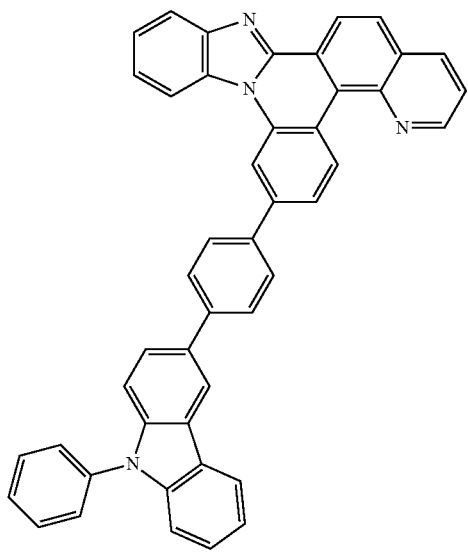
[Formula 3-9-1-18]
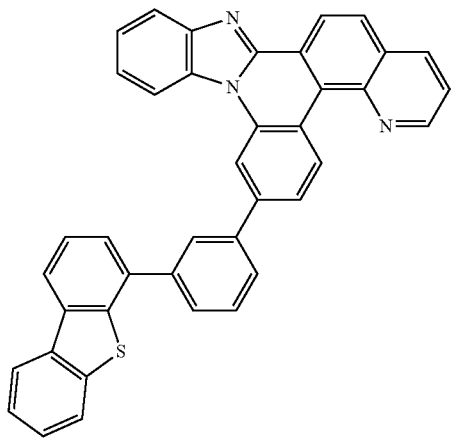
[Formula 3-9-1-19]
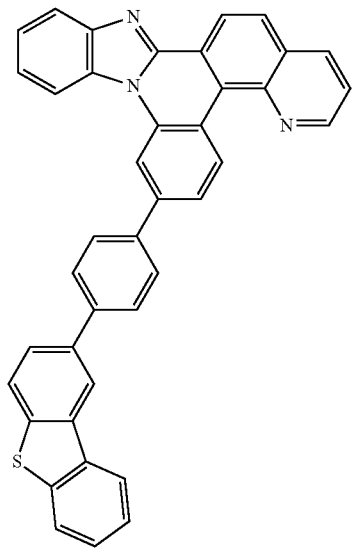
[Formula 3-9-1-20]
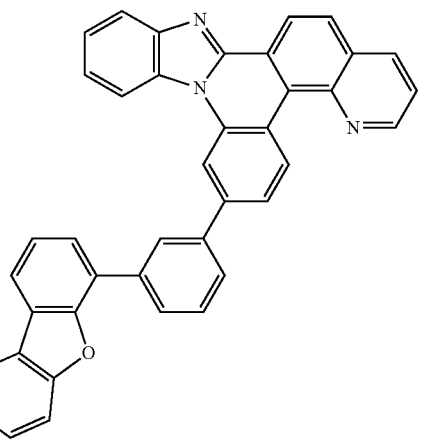
[Formula 3-9-1-21]
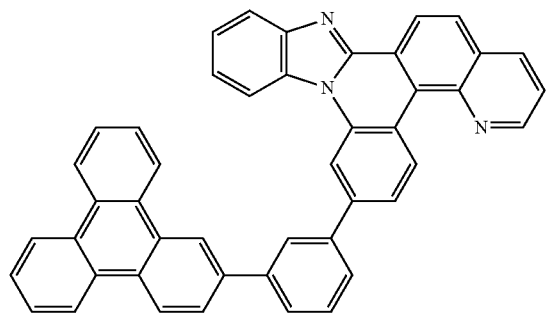
[Formula 3-9-1-22]
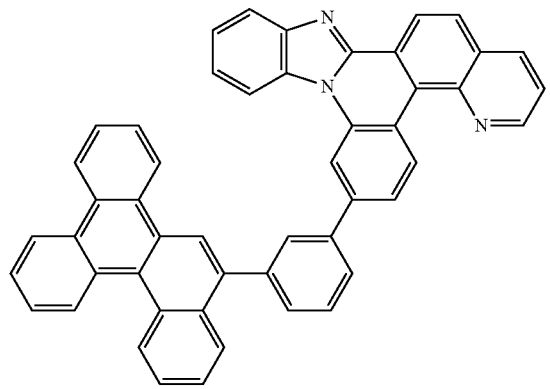

[Formula 3-9-1-23]
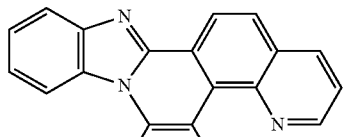
[Formula 3-9-1-26]
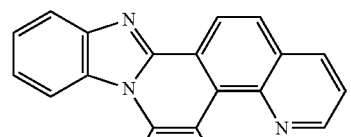
[Formula 3-9-1-24]
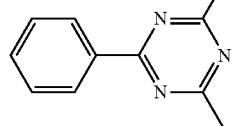
[Formula 3-9-1-27]
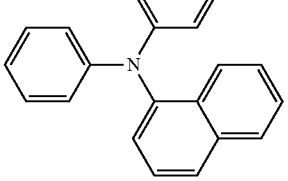
[Formula 3-9-1-25]
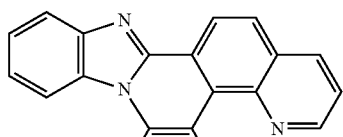
[Formula 3-9-1-28]
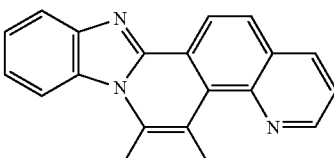

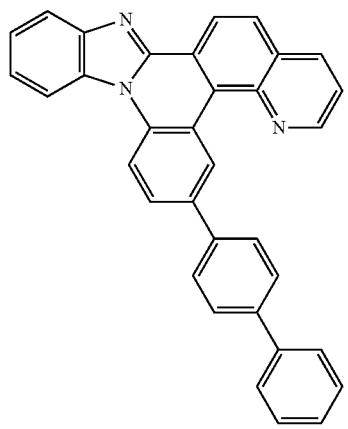
[Formula 3-9-2-1]
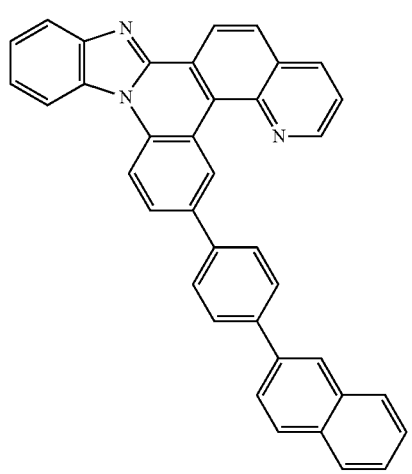
[Formula 3-9-2-2]
[Formula 3-9-2-3]
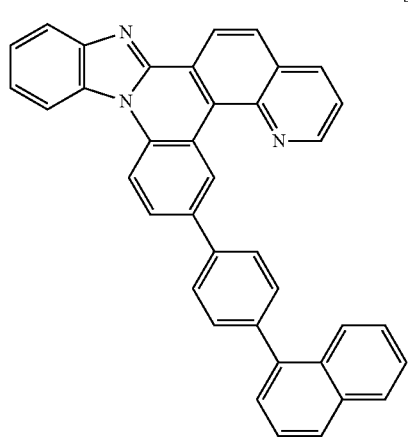
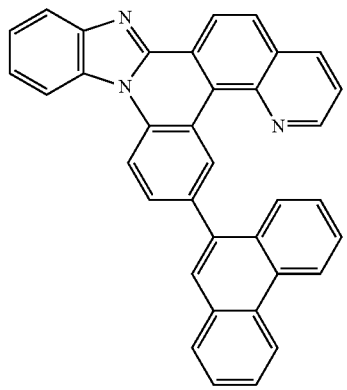
[Formula 3-9-2-4]
[Formula 3-9-2-5]
[Formula 3-9-2-6]
[Formula 3-9-2-9]

[Formula 3-9-2-10]
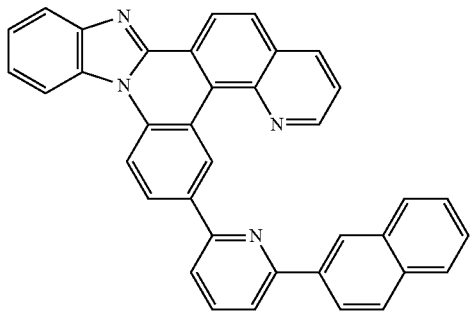
[Formula 3-9-2-11]
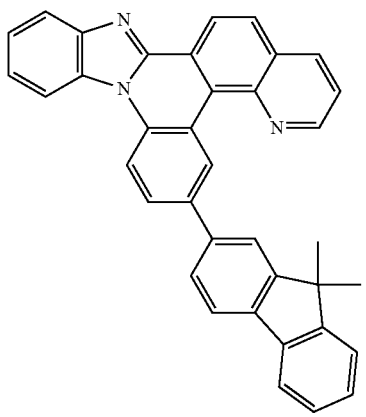
[Formula 3-9-2-12]
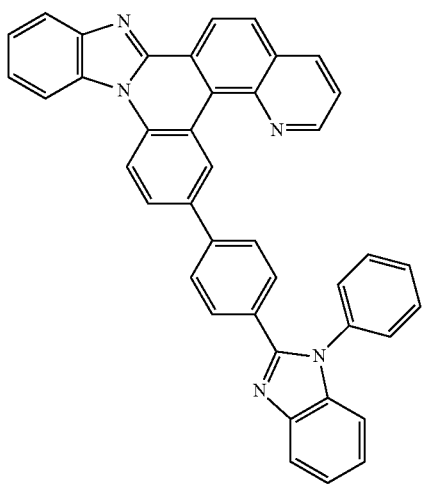
[Formula 3-9-2-13]
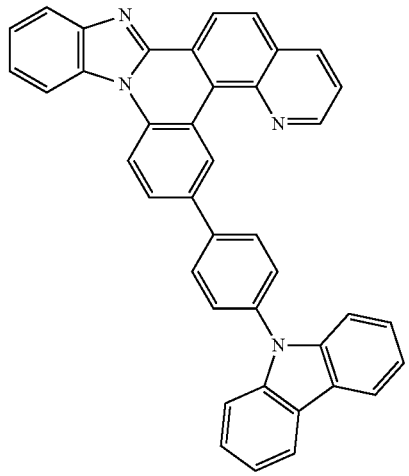
[Formula 3-9-2-14]
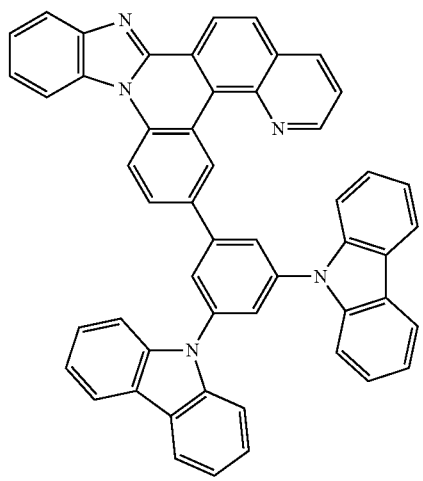
[Formula 3-9-2-15]
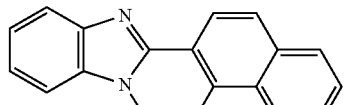
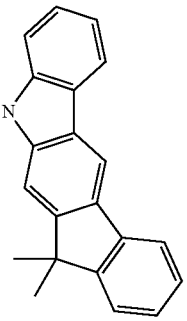

[Formula 3-9-2-16]
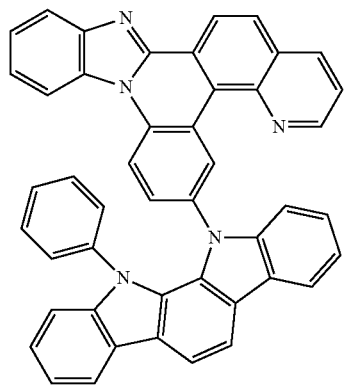
[Formula 3-9-2-17]
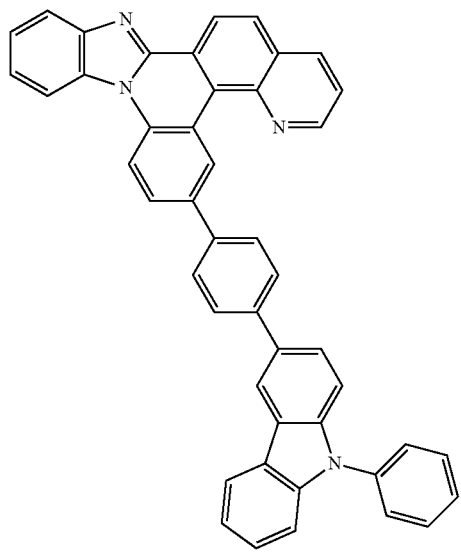
[Formula 3-9-2-18]
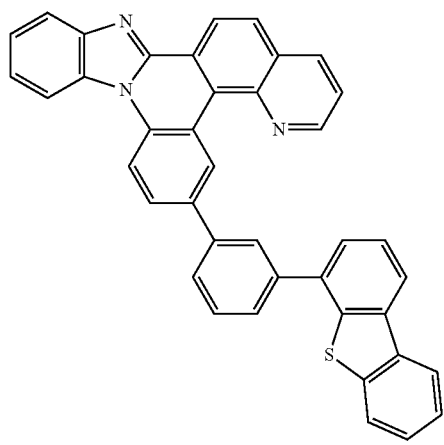
[Formula 3-9-2-19]
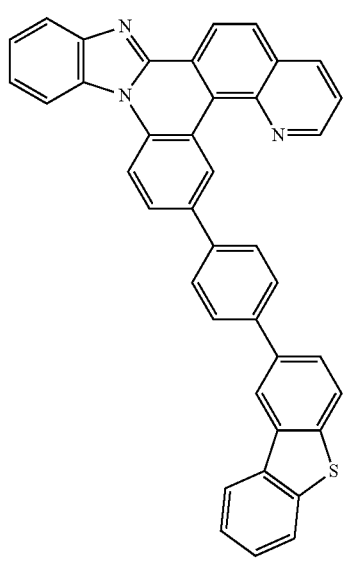
[Formula 3-9-2-20]
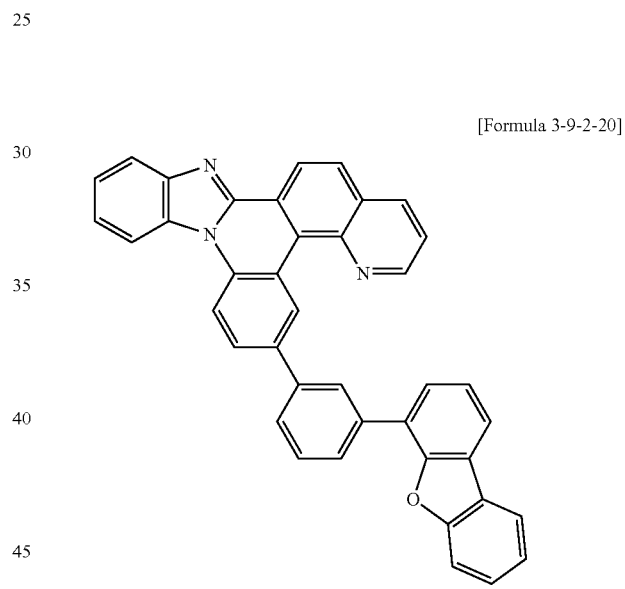
[Formula 3-9-2-21]
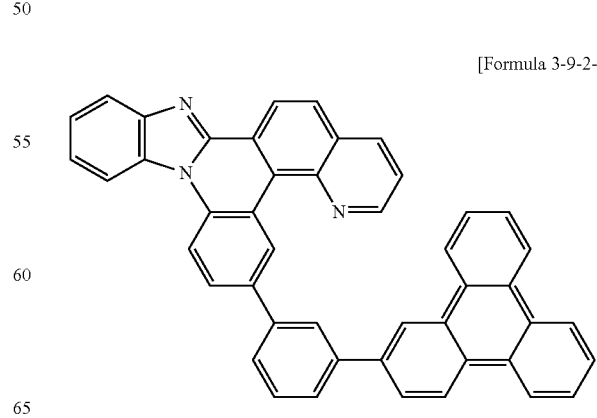

-continued
[Formula 3-9-2-22]
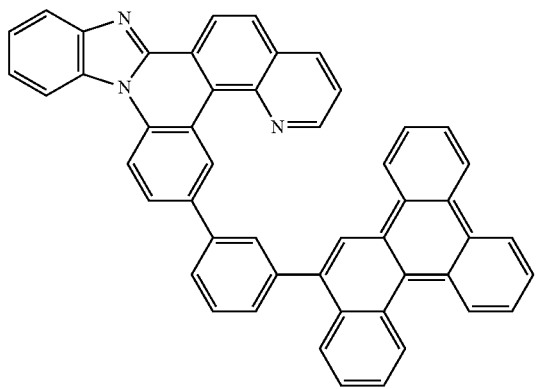
[Formula 3-9-2-23]
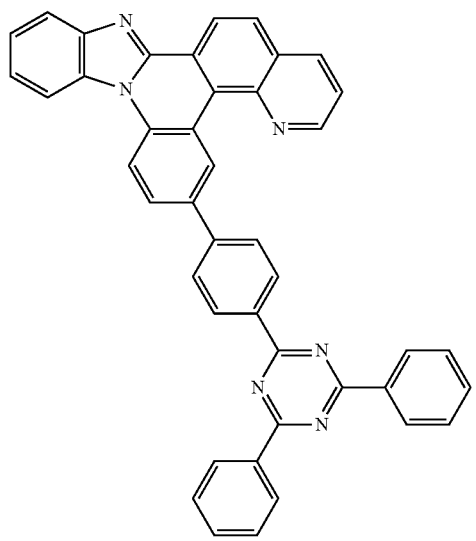
[Formula 3-9-2-24]
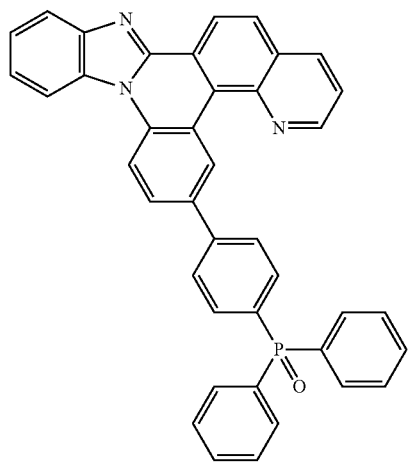
-continued
[Formula 3-9-2-25]
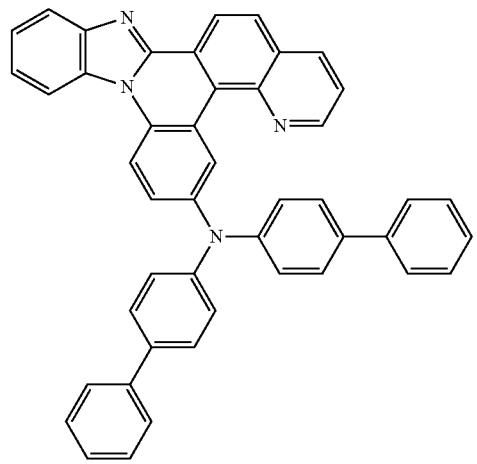
[Formula 3-9-2-26]
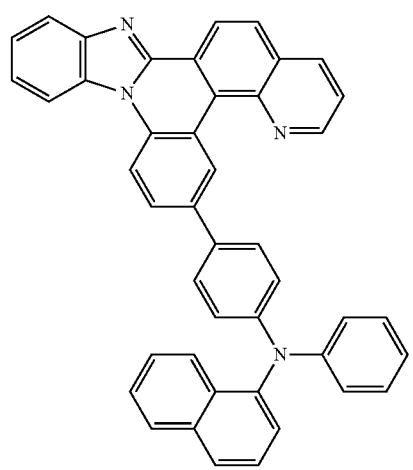
[Formula 3-9-2-27]
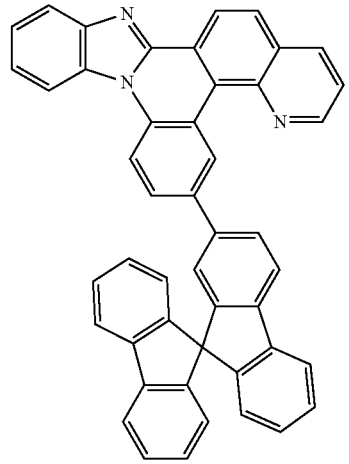

[Formula 3-9-2-28]

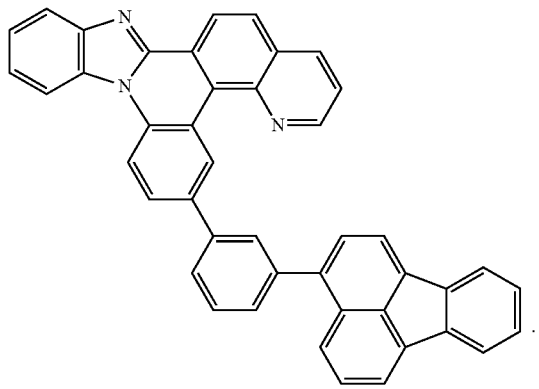

16. An organic electronic device comprising:

a first electrode;

a second electrode; and one or more organic material layers interposed between the first electrode and the second electrode, wherein one or more layers of the organic material layers comprise the compound of claim 1.

17. The organic electronic device of claim 16, wherein the organic material layer comprises one or more layers of a hole injection layer, a hole transport layer, and a layer injecting and transporting holes simultaneously, and one or more layers of the layers comprise a compound represented by Formula 1.

18. The organic electronic device of claim 16, wherein the organic material layer comprises a light emitting layer, and the light emitting layer comprises the compound represented by Formula 1.

19. The organic electronic device of claim 18, wherein the compound represented by Formula 1 is comprised as a host material in the light emitting layer, and the light emitting layer further comprises a dopant compound represented by the following Formula 7:

$$M_1L_{10}L_{11}L_{12}$$ [Formula 7]

wherein, $M_1$ is Ir or Os, $L_{10}$, $L_{11}$ and $L_{12}$ are ligands bonded to $M_1$, and are each independently selected from the following structures,

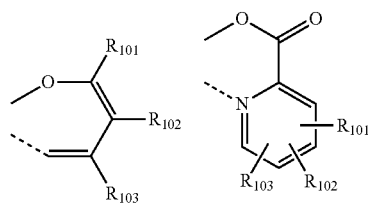

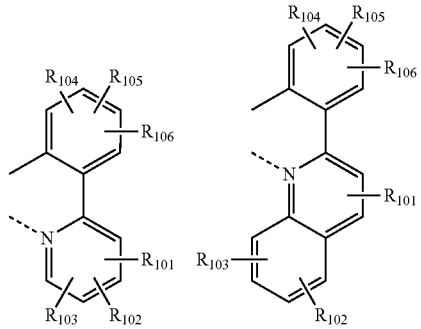

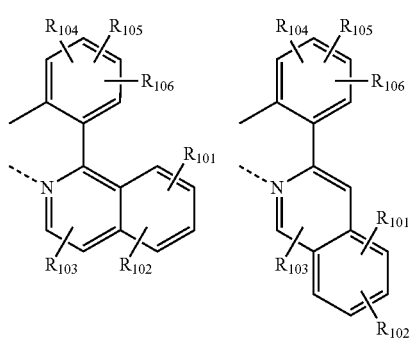

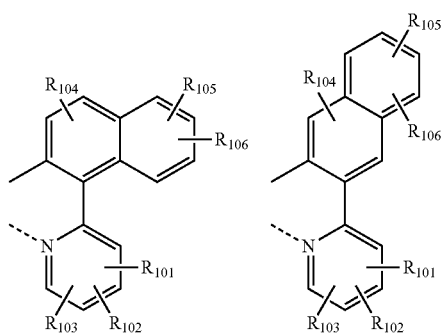

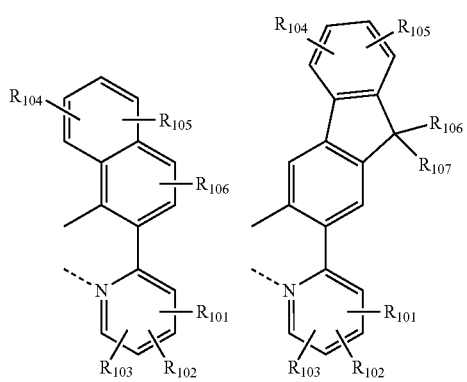

-continued

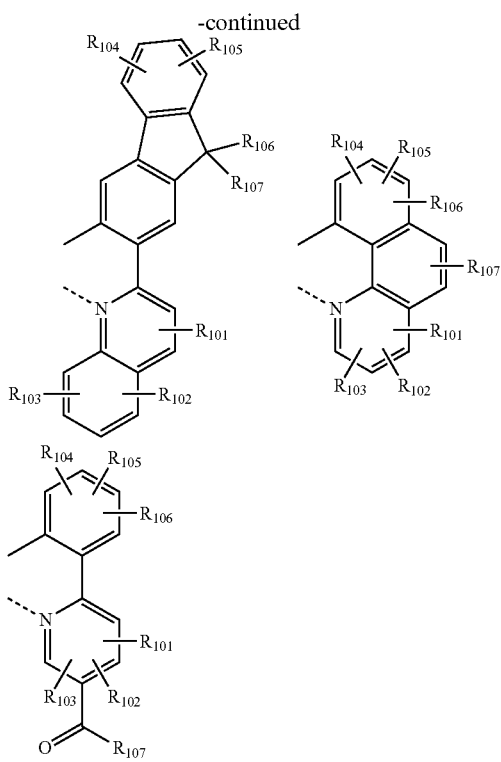

$R_{101}$ to $R_{107}$ are the same as or different from each other, and are each independently selected from the group consisting of hydrogen, heavy hydrogen, a halogen group, a cyano group, a substituted or unsubstituted alkylsilyl group having 2 to 10 carbon atoms, a substituted or unsubstituted arylsilyl group having 6 to 30 carbon atoms, a substituted or unsubstituted alkyl group having 1 to 10 carbon atoms, a substituted or unsubstituted alkenyl group having 2 to 10 carbon atoms, a substituted or unsubstituted alkoxy group having 1 to 10 carbon atoms, a substituted or unsubstituted aryl group having 6 to 20 carbon atoms, and a substituted or unsubstituted heteroaryl group having 5 to 20 carbon atoms, and the adjacent groups may be bonded to form an aromatic condensed ring group or a heteroaromatic condensed ring group.

20. The organic electronic device of claim 16, wherein the organic material layer comprises one or more layers of an electron transport layer, an electron injection layer, and a layer transporting and injecting electrons simultaneously, and one or more layers of the layers comprise the compound represented by Formula 1.

21. The organic electronic device of claim 20, wherein the organic material layer comprising the compound represented by Formula 1 further comprises alkali metal, an alkali metal compound, alkali earth metal, an alkali earth metal compound or a combination thereof.

22. The organic electronic device of claim 16, wherein the organic electronic device is selected from the group consisting of an organic light emitting device, an organic solar cell, an organic photoconductor (OPC) and an organic transistor.

* * * * *

UNITED STATES PATENT AND TRADEMARK OFFICE
CERTIFICATE OF CORRECTION

Page 1 of 1

PATENT NO.         : 9,000,169 B2
APPLICATION NO.    : 13/725170
DATED              : April 7, 2015
INVENTOR(S)        : Lee et al.

It is certified that error appears in the above-identified patent and that said Letters Patent is hereby corrected as shown below:

Title Page, Item (72) Inventor is corrected to read:
-- Dong Hoon Lee, Daejeon (KR);
   Tae Yoon Park, Daejeon (KR);
   Jungi Jang, Daejeon (KR);
   Sung Kil Hong, Daejeon (KR);
   Seong So Kim, Gyeonggi-do (KR);
   Boonjae Jang, Daejeon (KR);
   Sangbin Lee, Seoul (KR);
   Kidong Koo, Daejeon (KR) --.

Signed and Sealed this
Eleventh Day of August, 2015

Michelle K. Lee
*Director of the United States Patent and Trademark Office*